US012616807B2

(12) United States Patent
Lyman et al.

(10) Patent No.: US 12,616,807 B2
(45) Date of Patent: *May 5, 2026

(54) MEDICAL COUNTER MEASURES INCLUDING DRY POWDER FORMULATIONS AND ASSOCIATED METHODS

(71) Applicant: Belhaven BioPharma Inc., Raleigh, NC (US)

(72) Inventors: Scott Lyman, Raleigh, NC (US); Barry Bleske, Albuquerque, NM (US)

(73) Assignee: Belhaven BioPharma Inc., Ralrigh, NC (US)

( * ) Notice: Subject to any disclaimer, the term of this patent is extended or adjusted under 35 U.S.C. 154(b) by 135 days.

This patent is subject to a terminal disclaimer.

(21) Appl. No.: 18/669,046

(22) Filed: May 20, 2024

(65) Prior Publication Data

US 2024/0299680 A1 Sep. 12, 2024

Related U.S. Application Data

(63) Continuation of application No. 18/082,311, filed on Dec. 15, 2022, now Pat. No. 12,005,185.

(60) Provisional application No. 63/290,948, filed on Dec. 17, 2021.

(51) Int. Cl.
| | |
|---|---|
| *A61M 15/08* | (2006.01) |
| *A61K 9/00* | (2006.01) |
| *A61K 9/16* | (2006.01) |
| *A61K 31/13* | (2006.01) |
| *A61K 31/137* | (2006.01) |
| *A61K 31/277* | (2006.01) |
| *A61K 31/417* | (2006.01) |
| *A61K 31/4425* | (2006.01) |
| *A61K 31/46* | (2006.01) |
| *A61K 31/55* | (2006.01) |
| *A61K 31/5513* | (2006.01) |

(52) U.S. Cl.
CPC ........... *A61M 15/08* (2013.01); *A61K 9/0043* (2013.01); *A61K 9/1611* (2013.01); *A61K 9/1623* (2013.01); *A61K 9/1652* (2013.01); *A61K 31/13* (2013.01); *A61K 31/137* (2013.01); *A61K 31/277* (2013.01); *A61K 31/417* (2013.01); *A61K 31/4425* (2013.01); *A61K 31/46* (2013.01); *A61K 31/55* (2013.01); *A61K 31/5513* (2013.01); *A61M 2205/3327* (2013.01); *A61M 2209/06* (2013.01)

(58) Field of Classification Search
None
See application file for complete search history.

(56) References Cited

U.S. PATENT DOCUMENTS

| | | | |
|---|---|---|---|
| 4,548,922 | A | 10/1985 | Carey et al. |
| 4,746,508 | A | 5/1988 | Carey et al. |
| 5,023,252 | A | 6/1991 | Hseih |
| 5,240,149 | A | 8/1993 | Schmidt |
| 5,328,099 | A | 7/1994 | Petit et al. |
| 5,568,884 | A | 10/1996 | Bruna |
| 5,731,303 | A | 3/1998 | Hsieh |
| 5,901,883 | A | 5/1999 | Ritsche |
| 5,911,937 | A | 6/1999 | Hekal |
| 6,029,663 | A | 2/2000 | Eisele et al. |
| 6,080,350 | A | 6/2000 | Hekal |
| 6,124,006 | A | 9/2000 | Hekal |
| 6,130,263 | A | 10/2000 | Hekal |
| 6,174,952 | B1 | 1/2001 | Hekal et al. |
| 6,179,164 | B1 | 1/2001 | Fuchs |
| 6,194,079 | B1 | 2/2001 | Hekal |
| 6,209,760 | B1 | 4/2001 | Fuchs |
| 6,214,255 | B1 | 4/2001 | Hekal |
| 6,221,446 | B1 | 4/2001 | Hekal |
| 6,234,366 | B1 | 5/2001 | Fuchs |
| 6,261,274 | B1 | 7/2001 | Arghyris et al. |
| 6,264,065 | B1 | 7/2001 | Jouillat |
| 6,367,473 | B1 | 4/2002 | Käfer |
| 6,398,074 | B1 | 6/2002 | Bruna et al. |
| 6,425,499 | B1 | 7/2002 | Guiffray |
| 6,427,680 | B1 | 8/2002 | Oechsel |
| 6,450,216 | B1 | 9/2002 | Stradella |
| 6,461,322 | B1 | 10/2002 | Ritsche |
| 6,484,715 | B1 | 11/2002 | Ritsche et al. |

(Continued)

FOREIGN PATENT DOCUMENTS

| | | |
|---|---|---|
| WO | 1997032663 A1 | 9/1997 |
| WO | 2003037355 A1 | 5/2003 |

(Continued)

OTHER PUBLICATIONS

Chaturvedi, Mayank, Manish Kumar, and Kamla Pathak. "A review on mucoadhesive polymer used in nasal drug delivery system." J. Adv. Pharm. Tech. Res. 2.4 (2011): 215-222. (Year: 2011).*

(Continued)

*Primary Examiner* — Bethany P Barham
*Assistant Examiner* — Peter Anthopolos
(74) *Attorney, Agent, or Firm* — Neo IP

(57) ABSTRACT

Provided herein are dry powder formulations comprising at least one active pharmaceutical ingredient suitable for nasal application. Also provided are unit dose forms and devices comprising such formulations and methods of using such formulations for the treatment of various conditions including respiratory conditions, hemodynamic collapse, seizures, migraines, and other conditions.

20 Claims, 6 Drawing Sheets

(56) References Cited

U.S. PATENT DOCUMENTS

| | | |
|---|---|---|
| 6,486,231 B1 | 11/2002 | Hekal |
| 6,554,203 B2 | 4/2003 | Hess et al. |
| 6,626,379 B1 | 9/2003 | Ritsche et al. |
| 6,679,248 B2 | 1/2004 | Stadelhofer |
| 6,708,846 B1 | 3/2004 | Fuchs et al. |
| 6,725,857 B2 | 4/2004 | Ritsche |
| 6,877,672 B2 | 4/2005 | Stihl |
| 6,886,556 B2 | 5/2005 | Fuchs |
| 7,005,459 B2 | 2/2006 | Hekal |
| 7,011,234 B2 | 3/2006 | Stradella |
| 7,073,731 B2 | 7/2006 | Hess et al. |
| 7,100,601 B2 | 9/2006 | Bruna |
| 7,216,781 B2 | 5/2007 | Duquet et al. |
| 7,353,971 B2 | 4/2008 | Stradella |
| 7,387,265 B2 | 6/2008 | Hess et al. |
| 7,389,946 B2 | 6/2008 | Bruna et al. |
| 7,799,337 B2 | 9/2010 | Levin |
| 7,861,943 B2 | 1/2011 | Feriani et al. |
| 7,878,352 B2 | 2/2011 | Spreckelsen et al. |
| 7,946,455 B2 | 5/2011 | Ritsche et al. |
| 7,950,391 B2 | 5/2011 | Fuchs |
| 7,975,690 B2 | 7/2011 | Djupesland |
| 7,988,073 B2 | 8/2011 | Ligny et al. |
| 8,016,209 B2 | 9/2011 | Hess et al. |
| 8,224,438 B2 | 7/2012 | Levin |
| 8,263,581 B2 | 9/2012 | Du |
| 8,481,043 B2 | 7/2013 | Bergenhem et al. |
| 8,530,463 B2 | 9/2013 | Cartt et al. |
| 8,550,073 B2 | 10/2013 | Djupesland |
| 8,734,392 B2 | 5/2014 | Stadelhofer |
| 8,875,704 B2 | 11/2014 | Djupesland et al. |
| 9,156,048 B2 | 10/2015 | Maner |
| 9,205,208 B2 | 12/2015 | Djupesland |
| 9,227,031 B2 | 1/2016 | Shahaf et al. |
| 9,339,617 B2 | 5/2016 | Shahaf et al. |
| 9,550,036 B2 | 1/2017 | Hoekman et al. |
| 9,649,456 B2 | 5/2017 | Djupesland et al. |
| 9,682,205 B2 | 6/2017 | Shahaf et al. |
| 9,757,354 B2 | 9/2017 | Patterson et al. |
| 9,789,071 B2 | 10/2017 | Fleming |
| 9,808,818 B2 | 11/2017 | Maner |
| 9,834,341 B2 | 12/2017 | Giraud et al. |
| 9,902,788 B2 | 2/2018 | Klein et al. |
| 10,099,019 B2 | 10/2018 | Shahaf et al. |
| 10,124,132 B2 | 11/2018 | Djupesland |
| 10,172,870 B2 | 1/2019 | Reddy |
| 10,472,136 B2 | 11/2019 | Giraud et al. |
| 10,478,574 B2 | 11/2019 | Djupesland et al. |
| 10,507,295 B2 | 12/2019 | Hoekman et al. |
| 10,537,692 B2 | 1/2020 | Hoekman et al. |
| 10,549,052 B2 | 2/2020 | Shahaf et al. |
| 10,653,690 B1 | 5/2020 | Sävmarker et al. |
| 10,668,228 B2 | 6/2020 | Maner |
| 10,722,667 B2 | 7/2020 | Djupesland et al. |
| 10,806,870 B2 | 10/2020 | Maner |
| 10,814,079 B2 | 10/2020 | Francis et al. |
| 10,967,140 B2 | 4/2021 | Petit |
| 10,974,887 B2 | 4/2021 | Freedman et al. |
| 11,433,063 B1 | 9/2022 | Bleske et al. |
| 2001/0004644 A1 | 6/2001 | Levin |
| 2002/0079326 A1 | 6/2002 | Fuchs |
| 2004/0018989 A1* | 1/2004 | Jackson ............... A61K 9/0073 |
| | | 514/23 |
| 2004/0084554 A1 | 5/2004 | Milian |
| 2004/0176359 A1 | 9/2004 | Wermeling |
| 2004/0254146 A1 | 12/2004 | Quay et al. |
| 2005/0019411 A1 | 1/2005 | Colombo et al. |
| 2006/0003989 A1* | 1/2006 | Quay ..................... A61K 45/06 |
| | | 514/214.03 |
| 2007/0071687 A1 | 3/2007 | Wermeling |
| 2007/0129665 A1 | 6/2007 | Dickens et al. |
| 2007/0272764 A1 | 11/2007 | Poulard |
| 2008/0127972 A1 | 6/2008 | Morton |
| 2008/0279784 A1 | 11/2008 | Cartt et al. |
| 2009/0023706 A1 | 1/2009 | Albuquerque et al. |
| 2009/0220435 A1 | 9/2009 | Quay et al. |
| 2010/0055152 A1 | 3/2010 | Wahi |
| 2010/0078447 A1 | 4/2010 | Sauzade et al. |
| 2010/0113426 A1 | 5/2010 | Wermeling |
| 2011/0194110 A1 | 8/2011 | Langeard et al. |
| 2011/0233232 A1 | 9/2011 | Greiner-Perth et al. |
| 2012/0318677 A1 | 12/2012 | Bruna et al. |
| 2013/0018431 A1 | 1/2013 | Levin |
| 2013/0022750 A1 | 1/2013 | Bruna et al. |
| 2013/0081953 A1 | 4/2013 | Bruna et al. |
| 2013/0102998 A1 | 4/2013 | Coghill et al. |
| 2013/0149459 A1 | 6/2013 | Bruna et al. |
| 2013/0171330 A1 | 7/2013 | Sallak et al. |
| 2013/0171334 A1 | 7/2013 | Bruna et al. |
| 2013/0312740 A1 | 11/2013 | Pardonge |
| 2014/0000588 A1 | 1/2014 | Maner |
| 2014/0034663 A1 | 2/2014 | Königseder et al. |
| 2014/0050789 A1 | 2/2014 | Rogawski et al. |
| 2014/0103064 A1 | 4/2014 | Bruna et al. |
| 2014/0128379 A1 | 5/2014 | Bergenhem et al. |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0170220 A1 | 6/2014 | Cartt et al. |
| 2015/0053201 A1 | 2/2015 | Djupesland et al. |
| 2015/0144129 A1 | 5/2015 | Djupesland et al. |
| 2015/0216993 A1 | 8/2015 | Baker, Jr. et al. |
| 2015/0258287 A1 | 9/2015 | Shahaf et al. |
| 2015/0299846 A1 | 10/2015 | Bruna et al. |
| 2015/0313915 A1 | 11/2015 | Rogawski et al. |
| 2015/0367090 A1 | 12/2015 | Djupesland et al. |
| 2015/0367091 A1 | 12/2015 | Djupesland et al. |
| 2016/0045687 A1 | 2/2016 | Djupesland |
| 2016/0199296 A1 | 7/2016 | Bergenhem et al. |
| 2016/0279357 A1 | 9/2016 | Djupesland |
| 2016/0310421 A1 | 10/2016 | Cartt et al. |
| 2016/0318051 A1 | 11/2016 | Petit et al. |
| 2016/0367017 A1 | 12/2016 | Adams et al. |
| 2016/0367774 A1 | 12/2016 | Djupesland et al. |
| 2019/0091424 A1 | 3/2019 | Haruta |
| 2019/0134322 A1 | 5/2019 | Fabien |
| 2019/0142845 A1 | 5/2019 | Rogawski et al. |
| 2019/0269782 A1 | 9/2019 | Lowenthal et al. |
| 2019/0269867 A1 | 9/2019 | Djupesland |
| 2019/0358417 A1 | 11/2019 | Brouet et al. |
| 2020/0030304 A1 | 1/2020 | Rogawski et al. |
| 2020/0038320 A1 | 2/2020 | Cartt et al. |
| 2020/0101243 A1 | 4/2020 | Hoekman et al. |
| 2020/0155775 A1 | 5/2020 | Keppner et al. |
| 2020/0164164 A1 | 5/2020 | Helmlinger et al. |
| 2020/0246562 A1 | 8/2020 | Fabien |
| 2020/0276148 A1 | 9/2020 | Peterson et al. |
| 2020/0276401 A1 | 9/2020 | Djupesland et al. |
| 2020/0368156 A1 | 11/2020 | Temtsin-Krayz |
| 2020/0405983 A1 | 12/2020 | Haruta |
| 2021/0038671 A1 | 2/2021 | Farmer et al. |
| 2021/0069126 A1 | 3/2021 | Fleming |
| 2021/0077390 A1 | 3/2021 | Temtsin-Krayz et al. |
| 2021/0077392 A1 | 3/2021 | Temtsin-Krayz |
| 2021/0100817 A1 | 4/2021 | Rogawski et al. |
| 2021/0128462 A1 | 5/2021 | Temtsin-Krayz et al. |
| 2021/0161808 A1 | 6/2021 | Bobba et al. |
| 2021/0187216 A1 | 6/2021 | Djupesland et al. |
| 2021/0264716 A1 | 8/2021 | Norbeck et al. |
| 2021/0361770 A1 | 11/2021 | Lowenthal et al. |

(56) References Cited

U.S. PATENT DOCUMENTS

| 2022/0395457 A1 | 12/2022 | Lyman et al. |
| 2023/0191047 A1 | 6/2023 | Lyman et al. |

FOREIGN PATENT DOCUMENTS

| WO | 2015034822 A1 | 3/2015 |
| WO | 2019182908 A1 | 9/2019 |
| WO | 2019241401 A1 | 12/2019 |

OTHER PUBLICATIONS

Patel, S., et al. "Novel nasal microcapsular delivery system of galantamine hydrobromide." ARPB 2(III) (2012): 268-274. (Year: 2012).*

M. A. Malfatti et al., "The biodistribution and pharmacokinetics of the oxime acetylcholinesterase reactivator RS194B in guinea pigs," Chem. Biol. Interact., vol. 277, p. 159, Nov. 2017, doi: 10.1016/J.CBI.2017.09.016.

M. A. Turturro, P. M. Paris, and D. C. Seaberg, "Intramuscular ketorolac versus oral ibuprofen in acute musculoskeletal pain," Ann. Emerg. Med., vol. 26, No. 2, pp. 117-120, 1995, doi: 10.1016/S0196-0644(95)70138-9.

M. Brenner et al., "Sulfanegen sodium treatment in a rabbit model of sub-lethal cyanide toxicity," Toxicol. Appl. Pharmacol., vol. 248, No. 3, pp. 269-276, Nov. 2010, doi: 10.1016/J.TAAP.2010.08.002.

M. M. Koola and A. K. Parsaik, "Galantamine-memantine combination effective in dementia: Translate to dementia praecox?," Schizophr. Res. Cogn., vol. 12, p. 8, Jun. 2018, doi: 10.1016/J.SCOG.2017.11.001.

M. R. Sperling, P. Klein, and J. Tsai, "Randomized, double-blind, placebo-controlled phase 2 study of ganaxolone as add-on therapy in adults with uncontrolled partial-onset seizures," Epilepsia, vol. 58, No. 4, pp. 558-564, Apr. 2017, doi: 10.1111/EPI.13705.

M. W. Stutelberg et al., "Pharmacokinetics of next generation cyanide antidote sulfanegen in rabbits," http://dx.doi.org/10.4155/ipk-2016-0021, vol. 2, No. 2, pp. 105-111, Mar. 2017, doi: 10.4155/IPK-2016-0021.

Mihalek et al. "Attenuated sensitivity to neuroactive steroids in GABA-A receptor delta subunit, knockout mice" Proc Natl Acad Sci USA 96:12905-12910 (1999).

Nagasawa, H. T., et al., J. Med. Chem. 2007, 50, 6462-6464.

Nagelschmitz J, Blunck M, Kraetzschmar J, Ludwig M, Wensing G, Hohlfeld T. Pharmacokinetics and pharmacodynamics of acetylsalicylic acid after intravenous and oral administration to healthy volunteers. Clin Pharmacol. 2014;6:51-59. Published Mar. 19, 2014. doi:10.2147/CPAA.S47895.

NIH, "DailyMed—Prednisone—prednisone tablet." https://dailymed.nlm.nih.gov/dailymed/drugInfo.cfm?setid=931ceb82-23b9-46c6-a00b-4cd66ed6f88f (last accessed Nov. 15, 2021).

NIH, "Lidocaine HCL 2% 20 mg/mL Injection, USP 5 mL PreFilled Syringe." https://dailymed.nlm.nih.gov/dailymed/fda/fdaDrugXsl.cfm?setid=c1825011-6f51-42f2-9d85-6183cffe119a&type=display (last accessed Nov. 16, 2021).

Ousama Rachid, F. Estelle R. Simons, Mutasem Rawas-Qalaji, Stephen Lewis & Keith J. Simons (2016) Epinephrine doses delivered from auto-injectors stored at excessively high temperatures, Drug Development and Industrial Pharmacy, 42:1, 131-135, DOI: 10.3109/03639045.2015.1035283.

P. Dohare et al., "AMPA-Kainate Receptor Inhibition Promotes Neurologic Recovery in Premature Rabbits with Intraventricular Hemorrhage," J. Neurosci., vol. 36, No. 11, pp. 3363-3377, Mar. 2016, doi: 10.1523/JNEUROSCI.4329-15.2016.

Patel, S., et al. "Novel nasal microcapsular delivery system of galantamine hydrobromide." ARPB 2(111) (2012): 268-274. (Year: 2012).

Patterson, S. E., et al., J. Med. Chem. 2013, 56, 1346-1349.

R. K. Cady, S. Munjal, R. J. Cady, H. R. Manley, and E. Brand-Schieber, "Randomized, double-blind, crossover study comparing DFN-11 injection (3 mg subcutaneous sumatriptan) with 6 mg subcutaneous sumatriptan for the treatment of rapidly-escalating attacks of episodic migraine," J. Headache Pain, vol. 18, No. 1, Dec. 2017, doi: 10.1186/S10194-016-0717-7.

R. McDonald et al., "Pharmacokinetics of concentrated naloxone nasal spray for opioid overdose reversal: Phase I healthy volunteer study," Addiction, vol. 113, No. 3, pp. 484-493, Mar. 2018, doi: 10.1111/add.14033.

R. R. Taylor, K. L. Hoffman, B. Schniedewind, C. Clavijo, J. L. Galinkin, and U. Christians, "Comparison of the quantification of acetaminophen in plasma, cerebrospinal fluid and dried blood spots using high-performance liquidchromatography-tandem mass spectrometry," J. Pharm. Biomed. Anal., vol. 83, p. 1, Sep. 2013, doi: 10.1016/J.JPBA.2013.04.007.

Radic Z, Sit RK, Kovarik Z, et al. Refinement of structural leads for centrally acting oxime reactivators of phosphylated cholinesterases [published correction appears in J Biol Chem. Jun. 1, 2012;287(23):19337]. J Biol Chem. 2012;287(15):11798-11809. doi:10.1074/jbc.M111.333732.

Rawas-Qalaji M, Simons FE, Collins D, Simons KJ. Long-term stability of epinephrine dispensed in unsealed syringes for the first-aid treatment of anaphylaxis. Ann Allergy Asthma Immunol. Jun. 2009;102(6):500-3. doi: 10.1016/S1081-1206(10)60124-X. PMID: 19558009.

Recombinant human luteinizing hormone (LH) to support recombinant human follicle-stimulating hormone (FSH)-induced follicular development in LH- and FSH-deficient anovulatory women: a dose-finding study. The European Recombinant Human LH Study Group. J Clin Endocrinol Metab. May 1998;83(5):1507-14. doi: 10.1210/jcem.83.5.4770. PMID: 9589647.

Reddy "Role of anticonvulsant and antiepileptogenic neurosteroids in the pathophysiology and treatment of epilepsy" Frontiers Endocrinol 2 (38): 1-11 (2011).

Reddy et al. "Anticonvulsant activity of progesterone and neurosteroids in progesterone receptor knockout mice" J Pharmacol Exp Therap 310: 230-239 (2004).

Reddy et al. "Chronic treatment with the neuroactive steroid ganaxolone in the rat induces anticonvulsant tolerance to diazepam but not to itself" J Pharmacol Exp Therap 295: 1241-1248 (2000).

Robert J Good, Surface free energy of solids and liquids: Thermodynamics, molecular forces, and structure, J. Colloid Interface Sci., vol. 59, Issue 3, 1977, pp. 398-419, https://doi.org/10.1016/0021-9797(77)90034-0.

Robertson MJ, Hadzic G, Ambrus J, Pomè DY, Hyde E, Whiting A, Mariana A, von Kleist L, Chau N, Haucke V, Robinson PJ, McCluskey A. The Rhodadyns, a New Class of Small Molecule Inhibitors of Dynamin GTPase Activity. ACS Med Chem Lett. Mar. 26, 2012;3(5):352-6. doi: 10.1021/ml200284s. PMID: 24900478; PMCID: PMC4025782.

Rombauts L. Is there a recommended maximum starting dose of FSH in IVF?. J Assist Reprod Genet. 2007;24(8):343-349. doi:10.1007/s10815-007-9134-9.

Rosenberg YJ, Mao L, Jiang X, et al. Post-exposure treatment with the oxime RS194B rapidly reverses early and advanced symptoms in macaques exposed to sarin vapor. Chem Biol Interact. 2017;274:50-57. doi: 10.1016/j.cbi.2017.07.003.

Roth JV, Shields A. A dilemma: How does one treat anaphylaxis in the sulfite allergic patient since epinephrine contains sodium metabisulfite? Anesth Analg. May 2004;98(5):1499; author reply 1500. doi: 10.1213/01.ane.0000120092.39021.f2. PMID: 15105239.

S. D. George, A. J. George, P. A. Stein, P. F. Rolfe, B. C. Hosking, and W. Seewald, "The comparative efficacy of abamectin, monepantel and an abamectin/derquantel combination against fourth-stage larvae of a macrocyclic lactone-resistant Teladorsagia spp. isolate infecting sheep," Vet. Parasitol., vol. 188, No. 1-2, pp. 190-193, Aug. 2012, doi: 10.1016/J.VETPAR.2012.03.001.

S. E. Patterson et al., "Development of sulfanegen for mass cyanide casualties," Ann. N. Y. Acad. Sci., vol. 1374, No. 1, p. 202, 2016, doi: 10.1111/NYAS.13114.

S. K. Paul, K. Klein, B. L. Thorsted, M. L. Wolden, and K. Khunti, "Delay in treatment intensification increases the risks of cardiovas-

(56)     References Cited

OTHER PUBLICATIONS cular events in patients with type 2 diabetes," Cardiovasc. Diabetol., vol. 14, No. 1, p. 100, Aug. 2015, doi: 10.1186/S12933-015-0260-X.

S. Lähelmä et al., "Equivalent lung deposition of budesonide in vivo: a comparison of dry powder inhalers using a pharmacokinetic method," Br. J. Clin. Pharmacol., vol. 59, No. 2, p. 167, Feb. 2005, doi: 10.1111/J.1365-2125.2004.02238.X.

S. Lilienfeld, "Galantamine—a novel cholinergic drug with a unique dual mode of action for the treatment of patients with Alzheimer's disease," CNS Drug Rev., vol. 8, No. 2, pp. 159-176, 2002, doi: 10.1111/J.1527-3458.2002.TB00221.X.

S. M. Aquilonius, S. Å. Eckernas, P. Hartvig, B. Lindström, P. O. Osterman, and E. Stålbergt, "Clinical pharmacology of pyridostigmine and neostigmine in patients with myasthenia gravis," J. Neurol. Neurosurg. Psychiatry, vol. 46, No. 10, pp. 929-935, 1983, doi: 10.1136/JNNP.46.10.929.

S. Oltmanns, "[Pharmacokinetics of lidocaine after intramuscular injection in patients with acute myocardial infarction (author's transl)]—PubMed." https://pubmed.ncbi.nlm.nih.gov/442753/ (last accessed Nov. 16, 2021).

S. Schou et al., "Analgesic dose-response relationship of ibuprofen 50, 100, 200, and 400 mg after surgical removal of third molars: a single-dose, randomized, placebo-controlled, and double-blind study of 304 patients," J. Clin. Pharmacol., vol. 38, No. 5, pp. 447-454, 1998, doi: 10.1002/J.1552-4604.1998.TB04452.X.

S. W. Kirkland, E. Cross, S. Campbell, C. Villa-Roel, and B. H. Rowe, "Intramuscular versus oral corticosteroids to reduce relapses following discharge from the emergency department for acute asthma," Cochrane Database Syst. Rev., vol. 2018, No. 6, Jun. 2018, doi: 10.1002/14651858.CD012629.PUB2.

Simons FE, Gu X, Simons KJ. Epinephrine absorption in adults: intramuscular versus subcutaneous injection. J Allergy Clin Immunol. Nov. 2001;108(5):871-3. doi: 10.1067/mai.2001.119409. PMID: 11692118.

Stetcher, D., et.al., "Epinephrine Auto-injectors: Is Needle Length Adequate for Delivery of Epinephrine Intramuscularly?" Pediatrics, Jul. 2009, 124(1): 65-70, doi: 10.1542/peds.2008-3388.

Susan C. Smolinske (1992) Review of Parenteral Sulfite Reactions, Journal of Toxicology: Clinical Toxicology, 30:4, 597-606, DOI: 10.3109/15563659209017945.

T. Kongmalai, L. Preechasuk, S. Junnu, S. Manocheewa, C. Srisawat, and A. Sriwijitkamol, "The Effect of Temperature on the Stability of In-Use Insulin Pens," Exp. Clin. Endocrinol. Diabetes, vol. 129, No. 9, pp. 683-688, Sep. 2021, doi: 10.1055/a-1010-5466.

T. M. Shih, B. L. Oyler, B. R. Capacio, and I. Koplovitz, "The tertiary oxime monoisonitrosoacetone penetrates the brain, reactivates inhibited acetylcholinesterase, and reduces mortality and morbidity following lethal sarin intoxication in guinea pigs," Toxicol. Appl. Pharmacol., vol. 415, Mar. 2021, doi: 10.1016/J.TAAP.2021.115443.

T. V. Johnson, P. K. Gupta, D. K. Vudathala, I. A. Blair, and A. P. Tanna, "Thermal Stability of Bimatoprost, Latanoprost, and Travoprost Under Simulated Daily Use," J. Ocul. Pharmacol. Ther., vol. 27, No. 1, p. 51, Feb. 2011, doi: 10.1089/JOP.2010.0115.

T. Wu and T. Hanada, "Anti-Seizure Effects of Perampanel in Combination with Other Antiepileptic Drugs (AEDs) in a Rat Amygdala Kindling Model (P3.270)," Neurology, vol. 82, No. 10 Supplement, 2014.

Takeuchi H, Thongborisute J, Matsui Y, Sugihara H, Yamamoto H, Kawashima Y. Novel mucoadhesion tests for polymers and polymer-coated particles to design optimal mucoadhesive drug delivery systems. Adv Drug Deliv Rev. Nov. 3, 2005;57(11):1583-94. doi: 10.1016/j.addr.2005.07.008. Epub Sep. 16, 2005. PMID: 16169120.

Tiozzo Fasiolo L, Manniello MD, Tratta E, Buttini F, Rossi A, Sonvico F, Bortolotti F, Russo P, Colombo G. Opportunity and challenges of nasal powders: Drug formulation and delivery. Eur J Pharm Sci. Feb. 15, 2018;113:2-17. doi: 10.1016/j.ejps.2017.09.027. Epub Sep. 20, 2017. PMID: 28942007.

Van Asselt DZ, Merkus FW, Russel FG, Hoefnagels WH. Nasal absorption of hydroxocobalamin in healthy elderly adults. Br J Clin Pharmacol. 1998;45(1):83-86. doi:10.1046/j.1365-2125.1998.00642.x.

Wasserman, S., et. al. "Epinephrine Autoinjectors: New Data, New Problems," J Allergy Clin Immunol Pract., Sep.-Oct. 2017; 5(5):1180-1191, doi: 10.1016/j.jaip.2017.06.027.

A. C. Baakman et al., "An anti-nicotinic cognitive challenge model using mecamylamine in comparison with the anti-muscarinic cognitive challenge using scopolamine," Br. J. Clin. Pharmacol., vol. 83, No. 8, pp. 1676-1687, 2017, doi: 10.1111/BCP.13268.

A. Chan et al., "The combination of cobinamide and sulfanegen is highly effective in mouse models of cyanide poisoning," Clin. Toxicol. (Phila)., vol. 49, No. 5, pp. 366-373, Jun. 2011, doi: 10.3109/15563650.2011.584879.

A. S. Cornelissen, S. D. Klaassen, T. van Groningen, S. Bohnert, and M. J. A. Joosen, "Comparative physiology and efficacy of atropine and scopolamine in sarin nerve agent poisoning," Toxicol. Appl. Pharmacol., vol. 396, Jun. 2020, doi: 10.1016/j.taap.2020.114994.

American Osteopathic College of Dermatology (AOCD), "Antihistamines—American Osteopathic College of Dermatology (AOCD)." https://www.aocd.org/page/SteroidsOral (last accessed Nov. 15, 2021).

Aroniadou-Anderjaska V, Figueiredo TH, Apland JP, Braga MF. Targeting the glutamatergic system to counteract organophosphate poisoning: A novel therapeutic strategy. Neurobiol Dis. Jan. 2020;133:104406. doi: 10.1016/j.nbd.2019.02.017. Epub Feb. 21, 2019. PMID: 30798006.

Bakhrushina, Elena, et al. "Comparative study of the mucoadhesive properties of polymers for pharmaceutical use." Open Access Macedonian Journal of Medical Sciences 8.A (Sep. 2020): 639-645. (Year: 2020).

Belani, K. G., et al., Anesth. Analg. 2012, 114, 956-961.

Benedek, I.H., Joshi, A.S., Pieniaszek, H.J., King, S.-Y.P. and Kornhauser, D.M. (1995), Variability in the Pharmacokinetics and Pharmacodynamics of Low Dose Aspirin in Healthy Male Volunteers. The Journal of Clinical Pharmacology, 35: 1181-1186. https://doi.org/10.1002/j.1552-4604.1995.tb04044.x.

Bleske BE, Rice TL, Warren EW, Giacherio DA, Gilligan LJ, Massey KD, Tait AR. Effect of dose on the nasal absorption of epinephrine during cardiopulmonary resuscitation. Am J Emerg Med. Mar. 1996;14(2):133-8. doi: 10.1016/S0735-6757(96)90119-9. PMID: 8924133.

Bourganis V, Kammona O, Alexopoulos A, Kiparissides C. Recent advances in carrier mediated nose-to-brain delivery of pharmaceutics. Eur J Pharm Biopharm. Jul. 2018;128:337-362. doi: 10.1016/j.ejpb.2018.05.009. Epub May 4, 2018. PMID: 29733950.

C. Canton et al., "Monepantel pharmaco-therapeutic evaluation in cattle: Pattern of efficacy against multidrug resistant nematodes," Int. J. Parasitol. Drugs Drug Resist., vol. 15, p. 162, Apr. 2021, doi: 10.1016/J.IJPDDR.2021.03.003.

C. Duquesnoy, J. P. Mamet, D. Sumner, and E. Fuseau, "Comparative clinical pharmacokinetics of single doses of sumatriptan following subcutaneous, oral, rectal and intranasal administration," Eur. J. Pharm. Sci., vol. 6, No. 2, pp. 99-104, Apr. 1998, doi: 10.1016/S0928-0987(97)00073-0.

C. M. Wilhelm, T. H. Snider, M. C. Babin, D. A. Jett, G. E. Platoff, and D. T. Yeung, "Comparison of 2-PAM and pro-2-PAM containing treatment regimens as antagonists of nerve agent-induced lethality and incapacitation." Final report, Jun. 1981-Dec. 1985, Toxicol. Appl. Pharmacol., vol. 281, No. 3, pp. 254-265, Sep. 1986, doi: 10.1016/J.TAAP.2014.10.009.

Cambal LK, Swanson MR, Yuan Q, Weitz AC, Li HH, Pitt BR, Pearce LL, Peterson J. Acute, sublethal cyanide poisoning in mice is ameliorated by nitrite alone: complications arising from concomitant administration of nitrite and thiosulfate as an antidotal combination. Chem Res Toxicol. Jul. 18, 2011;24(7):1104-12. doi: 10.1021/tx2001042. Epub May 11, 2011. PMID: 21534623; PMCID: PMC5494963.

Carver et al. "Perimenstrual-like hormonal regulation of extrasynaptic δ-containing GABA-A receptors mediating tonic inhibition and neurosteroid sensitivity" J Neurosci 34(43):14181-14197 (2014).

(56) References Cited

OTHER PUBLICATIONS

Chatterjee, Bappaditya, et al. "Mucoadhesive polymers and their mode of action: A recent update." Journal of Applied Pharmaceutical Science 7.5 (2017): 195-203. (Year: 2017).

Chaturvedi, Mayank, Manish Kumar, and Kamla Pathak. "A review on mucoadhesive polymer used in nasal drug delivery system." Journal of advanced pharmaceutical technology & research 2.4 (2011): 215-222. (Year: 2011).

Clinicaltrials.gov, "Study to Assess the Safety, Tolerance and Efficacy of Tezampanel in Patients With Acute Migraine," https://clinicaltrials.gov/show/NCT00567086, 2007, Accessed: Nov. 15, 2021. [Online]. Available: https://clinicaltrials.gov/ct2/show/record/NCT00567086.

Costantino HR, Illum L, Brandt G, Johnson PH, Quay SC. Intranasal delivery: physicochemical and therapeutic aspects. Int J Pharm. Jun. 7, 2007;337(1-2):1-24. doi: 10.1016/j.ijpharm.2007.03.025. Epub Mar. 25, 2007. PMID: 17475423.

Costantino HR, Leonard AK, Brandt G, Johnson PH, Quay SC. Intranasal administration of acetylcholinesterase inhibitors. BMC Neurosci. Dec. 10, 2008;9 Suppl 3(Suppl 3):S6. doi: 10.1186/1471-2202-9-S3-S6. PMID: 19091003; PMCID: PMC2604884.

Crankshaw, D. L., et al., Toxicol. Lett. 2007, 175, 111-117.

Crowe TP, Greenlee MHW, Kanthasamy AG, Hsu WH. Mechanism of intranasal drug delivery directly to the brain. Life Sci. Feb. 15, 2018;195:44-52. doi: 10.1016/j.lfs.2017.12.025. Epub Dec. 22, 2017. PMID: 29277310.

D Tabor, Surface forces and surface interactions, J. Colloid Interface Sci., vol. 58, Issue 1, 1977, pp. 2-13, https://doi.org/10.1016/0021-9797(77)90366-6.

D. L. Seger and J. K. Loden, "Naloxone reversal of clonidine toxicity: dose, dose, dose," Clin. Toxicol., vol. 56, No. 10, pp. 873-879, Oct. 2018, doi: 10.1080/15563650.2018.1450986.

D. P. Wermeling, "A Response to the Opioid Overdose Epidemic: Naloxone Nasal Spray," Drug Deliv. Transl. Res., vol. 3, No. 1, p. 63, Feb. 2013, doi: 10.1007/S13346-012-0092-0.

D. P. Wermeling, G. M. Grant, A. Lee, N. Alexander, and A. C. Rudy, "Analgesic effects of intranasal butorphanol tartrate administered via a unit-dose device in the dental impaction pain model: a randomized, double-blind, placebo-controlled, parallel-group study," Clin. Ther., vol. 27, No. 4, pp. 430-440, Apr. 2005, doi: 10.1016/J.CLINTHERA.2005.04.002.

Davis SS, Illum L. Absorption enhancers for nasal drug delivery. Clin Pharmacokinet. 2003;42(13):1107-28. doi: 10.2165/00003088-200342130-00003. PMID: 14531723.

Fycompa, "Dosing Optimization & Drug Interactions | Fycompa (perampanel)." https://www.fycompa.com/hcp/dosing-and-half-life/dosing (last accessed Dec. 12, 2022).

G. Marucci, M. Buccioni, D. D. Ben, C. Lambertucci, R. Volpini, and F. Amenta, "Efficacy of acetylcholinesterase inhibitors in Alzheimer's disease," Neuropharmacology, vol. 190, p. 108352, Jun. 2021, doi: 10.1016/J.NEUROPHARM.2020.108352.

Ganger S, Schindowski K. Tailoring Formulations for Intranasal Nose-to-Brain Delivery: A Review on Architecture, Physico-Chemical Characteristics and Mucociliary Clearance of the Nasal Olfactory Mucosa. Pharmaceutics. Aug. 3, 2018;10(3):116. doi: 10.3390/pharmaceutics10030116. PMID: 30081536; PMCID: PMC6161189.

Gao, Mingyue, et al. "Effect of polysorbate 80 on the intranasal absorption and brain distribution of tetramethylpyrazine phosphate in rats." Drug delivery and translational research 9 (2019): 311-318. (Year: 2019).

Gundavarapu S, Zhuang J, Barrett EG, Xu F, Russell RG, Sopori ML. A critical role of acute bronchoconstriction in the mortality associated with high-dose sarin inhalation: effects of epinephrine and oxygen therapies. Toxicol Appl Pharmacol. Jan. 15, 2014;274(2):200-8. doi: 10.1016/j.taap.2013.11.007. Epub Nov. 19, 2013. PMID: 24269878.

Gundavarapu, Sravanthi, et al. "A critical role of acute bronchoconstriction in the mortality associated with high-dose sarin inhalation: effects of epinephrine and oxygen therapies." Toxicology and applied pharmacology 274.2 (2014): 200-208. (Year: 2014).

H. M. Hugel and N. Jackson, "Herbs and Dementia: A Focus on Chinese and Other Traditional Herbs," Diet Nutr. Dement. Cogn. Decline, pp. 795-804, 2015, doi: 10.1016/B978-0-12-407824-6. 00073-2.

H. Potschka and E. Trinka, "Perampanel: Does it have broad-spectrum potential?," Epilepsia, vol. 60 Suppl 1, No. S1, pp. 22-36, Mar. 2019, doi: 10.1111/EPI.14456.

H. Schuckman, D. P. DeJulius, M. Blanda, L. W. Gerson, A. J. DeJulius, and M. Rajaratman, "Comparison of intramuscular triamcinolone and oral prednisone in the outpatient treatment of acute asthma: a randomized controlled trial," Ann. Emerg. Med., vol. 31, No. 3, pp. 333-338, 1998, doi: 10.1016/S0196-0644(98)70343-9.

H. Soltaninejad and N. Vesal, "Plasma concentrations of lidocaine following laryngeal administration or laryngeal and intratesticular administration in cats," Am. J. Vet. Res., vol. 79, No. 6, pp. 614-620, Jun. 2018, doi: 10.2460/AJVR.79.6.614.

I. A. Ionita, K. Ogasawara, R. Y. Gohh, and F. Akhlaghi, "Pharmacokinetics of Total and Unbound Prednisone and Prednisolone in Stable Kidney Transplant Recipients with Diabetes Mellitus," Ther. Drug Monit., vol. 36, No. 4, p. 448, 2014, doi: 10.1097/FTD. 0000000000000045.

I. Bacher, B. Wu, D. R. Shytle, and T. P. George, "Mecamylamine—a nicotinic acetylcholine receptor antagonist with potential for the treatment of neuropsychiatric disorders," Expert Opin. Pharmacother., vol. 10, No. 16, pp. 2709-2721, 2009, doi: 10.1517/14656560903329102.

I. Rektor, "Perampanel, a novel, non-competitive, selective AMPA receptor antagonist as adjunctive therapy for treatment-resistant partial-onset seizures," http://dx.doi.org/10.1517/14656566.2013. 754883, vol. 14, No. 2, pp. 225-235, Feb. 2013, doi: 10.1517/14656566.2013.754883.

I. Tylleskar, A. K. Skulberg, T. Nilsen, and S. Skarra, "Naloksonnesespray—biotilgjengelighet og opptaksmønster i en fase 1-studie," Tidsskr. den Nor. Laegeforening, vol. 139, No. 13, Sep. 2019, doi: 10.4045/tidsskr.19.0162.

J. C. DeMar et al., "Pro-2-PAM Therapy for Central and Peripheral Cholinesterases," Chem. Biol. Interact., vol. 187, No. 1-3, p. 191, Sep. 2010, doi: 10.1016/J.CBI.2010.02.015.

J. I. Byun et al., "Efficacy of single or combined midodrine and pyridostigmine in orthostatic hypotension," Neurology, vol. 89, No. 10, pp. 1078-1086, Sep. 2017, doi: 10.1212/WNL.0000000000004340.

J. K. S. Krishnan et al., "Intranasal delivery of obidoxime to the brain prevents mortality and CNS damage from organophosphate poisoning," Neurotoxicology, vol. 53, pp. 64-73, Mar. 2016, doi: 10.1016/J.NEURO.2015.12.020.

J. R. Castillo, S. P. Peters, and W. W. Busse, "Asthma Exacerbations: Pathogenesis, Prevention, and Treatment," J. Allergy Clin. Immunol. Pract., vol. 5, No. 4, p. 918, Jul. 2017, doi: 10.1016/J. JAIP.2017.05.001.

K. Degeling et al., "An inverse stage-shift model to estimate the excess mortality and health economic impact of delayed access to cancer services due to the Covid-19 pandemic," Asia. Pac. J. Clin. Oncol., vol. 17, No. 4, pp. 359-367, Aug. 2021, doi: 10.1111/ajco. 13505.

K. Harris, C. B. Page, S. Samantray, L. Parker, A. J. A. Brier, and K. Z. Isoardi, "One single large intramuscular dose of naloxone is effective and safe in suspected heroin poisoning," EMA—Emerg. Med. Australas., vol. 32, No. 1, pp. 88-92, Feb. 2020, doi: 10.1111/1742-6723.13344.

Kokate et al. "Anticonvulsant activity of neurosteroids: Correlation with γ-aminobutyric acid-evoked chloride current potentiation" J Pharmacol Exp Ther 270:1223-1229 (1994).

Lacwik P, Bialas AJ, Wielanek M, Sklodowska M, Kupczyk M, Gorski P, Kuna P. Single, short-time exposure to heat in a car during sunny day can decrease epinephrine concentration in autoinjectors: a real-life pilot study. J Allergy Clin Immunol Pract. Apr. 2019;7(4):1362-1364. doi: 10.1016/j.jaip.2018.10.027. Epub Nov. 28, 2018. PMID: 30503198.

(56) References Cited

OTHER PUBLICATIONS

Iium L and Fisher AN (1997) Intranasal delivery of peptides and proteins, in Inhalation Delivery of Therapeutic Peptides and Proteins (Adjei AL and Gupta PK eds), Marcel Dekker, New York.

Wilhelm CM, Snider TH, Babin MC, Jett DA, Platoff GE Jr, Yeung DT. A comprehensive evaluation of the efficacy of leading oxime therapies in guinea pigs exposed to organophosphorus chemical warfare agents or pesticides. Toxicol Appl Pharmacol. Dec. 15, 2014;281(3):254-65. doi: 10.1016/j.taap.2014.10.009. Epub Oct. 31, 2014. PMID: 25448441; PMCID: PMC4255143.

Wohlfarth et al. "Enhanced neurosteroid potentiation of ternary GABA-A receptors containing the delta subunit" J Neurosci 22:1541-1549 (2002).

Y. Aracava, E. F. R. Pereira, M. Akkerman, M. Adler, and E. X. Albuquerque, "Effectiveness of donepezil, rivastigmine, and (+/−)huperzine A in counteracting the acute toxicity of organophosphorus nerve agents: comparison with galantamine," J. Pharmacol. Exp. Ther., vol. 331, No. 3, pp. 1014-1024, Dec. 2009, doi: 10.1124/JPET.109.160028.

Y. T. Lin, M. C. Chou, S. J. Wu, and Y. H. Yang, "Galantamine plasma concentration and cognitive response in Alzheimer's disease," PeerJ, vol. 2019, No. 5, 2019, doi: 10.7717/PEERJ.6887/SUPP-1.

Y. X. Li, R. Q. Zhang, C. R. Li, and X. H. Jiang, "Pharmacokinetics of huperzine A following oral administration to human volunteers," Eur. J. Drug Metab. Pharmacokinet., vol. 32, No. 4, pp. 183-187, 2007, doi: 10.1007/BF03191002.

Y. Yamamoto et al., "Pharmacokinetics, tolerability, and clinical effectiveness of perampanel in Japanese patients with epilepsy," Seizure, vol. 83, pp. 181-186, Dec. 2020, doi: 10.1016/j.seizure.2020.10.017.

Zhan et al. "Enhanced tonic GABA current in normotopic and hilar ectopic dentate granule cells after pilocarpine-reduced status epilepticus" J Neurophysiol 102:670-681 (2009).

* cited by examiner

100

102

104

106

108

110

112

100

220

210

200

MEDICAL COUNTER MEASURES INCLUDING DRY POWDER FORMULATIONS AND ASSOCIATED METHODS

CROSS REFERENCES TO RELATED APPLICATIONS

This application is related to and claims priority from the following U.S. patents and patent applications: this application is a continuation of U.S. application Ser. No. 18/082,311, filed on Dec. 15, 2022, which claims priority to and the benefit of U.S. Provisional Patent Application No. 63/290,948, filed Dec. 17, 2021. Each of the U.S. applications mentioned above is incorporated herein by reference in its entirety.

BACKGROUND OF THE INVENTION

1. Field of the Invention

The present invention relates to medical counter measures, and more specifically to dry powder formulations and methods of treatment of various conditions using the dry power formulations.

2. Description of the Prior Art

It is generally known in the prior art to provide medications for the treatment of various conditions. Medications are often delivered intravenously and by needle and syringe injection, which may be subcutaneous or intra-muscular. Increasingly, medications are delivered by auto-injectors, which may be used within medical facilities or in ambulatory settings by medical and non-medical personnel, caregivers, and patients themselves. Self-administration via auto-injector has dramatically improved the availability of treatment with medications in emergency situations. Alternatives that do not require a needle or syringe have been explored in the prior art.

Prior art patent documents include the following:

U.S. Pat. No. 10,099,019 for Nasal delivery device by inventors Shahaf, et al., filed Jan. 25, 2017 and issued Oct. 16, 2018, is directed to a method for delivering a substance to the nasal cavity of a subject in which drawing air from a mouthpiece triggers release of a substance to a subject's nasal cavities. The device comprises a container for containing the substance in fluid communication with a nosepiece, a valve with an active configuration and an inactive configuration, and a trigger mechanism to reconfigure the valve from its inactive configuration to its active configuration and vice versa. Drawing air from the mouthpiece, e.g., when the subject takes in air by mouth, activates the trigger mechanism, thereby reconfiguring the valve from its inactive configuration to its active configuration for a predetermined period of time and delivering the substance from the device to a nasal cavity of the subject.

U.S. Pat. No. 10,478,574 for Nasal administration by inventors Djupesland, et al., filed Jan. 19, 2006 and issued Nov. 19, 2019, is directed to delivery device for and method of providing for delivery of substance to the central nervous system (CNS) of a subject, the delivery device including a nosepiece unit for insertion into a nasal airway of a subject and including an outlet unit which includes a nozzle for delivering substance into the nasal airway of the subject; and a substance supply unit which is operable to deliver a dose of substance to the nozzle: wherein the delivery device is configured such that at least 30% of the dose as initially deposited in the nasal airway is deposited in an upper posterior region of the nasal airway, thereby providing a CNS concentration of the substance, and hence CNS effect, which is significantly greater than that which would be predicted from a counterpart blood plasma concentration of the substance.

U.S. Pat. No. 10,507,295 for Nasal drug delivery device by inventors Hoekman, et al., filed Oct. 28, 2016 and issued Dec. 17, 2019, is directed to a compound delivery device for delivering a plume derived from a propellant and a drug formulation. The drug formulation is in an intranasal dosage form in the form of powder, suspension, dispersion or liquid. The propelled intranasal dosage form is deposited within the olfactory region of the nasal cavity. The drug deposited within the olfactory region is delivered to the brain avoiding the blood-brain-barrier. Hydrofluoroalkane propellant from a pressurized canister is channeled to a diffuser and drug-containing chamber where the intra-nasal dosage form is aerosolized. The aerosolized intra-nasal dosage form passes through a nozzle thus delivering a plume to the olfactory region of a user's nasal cavity.

U.S. Pat. No. 10,549,052 for Nasal delivery device by inventors Shahaf, et al., filed Feb. 28, 2013 and issued Feb. 4, 2020, is directed to a two-step mechanism for delivering a flowable substance to the nasal passages, including: a. a nosepiece adapted to be in fluid connection with said nasal passages; b. at least one air-tight enclosure, including predetermined amount of compressed gas in the same; said compressed gas is pressurized to predetermined amount of pressure; c. a charging mechanism, fluidly connected with said air-tight enclosure, characterized by at least two configurations: a retracted position and an extended position; where, when said charging mechanism is transformed from said extended position to said retracted position, said charging mechanism is adapted to enable delivery of said pressurized and predetermined amount of compressed gas from at least one first predetermined position in said air-tight enclosure to at least one second predetermined position; d. an activation mechanism, adapted to entrain said flowable substance within said pressurized and predetermined amount of compressed gas.

U.S. Patent Publication No. 20050019411 for Powder for nasal administration of drugs by inventors Colombo, et al., filed Oct. 17, 2002 and published Jan. 27, 2005, is directed to drug formulae for nasal administration and insufflators filled with said formula. The publication also concerns methods for making said formulae available as well as primary particles for obtaining chimerical agglomerates that can be used in said formulae.

U.S. Patent Publication No. 20070129665 for Nasal drug delivery by inventors Dickens, et al., filed Apr. 8, 2004 and published Jun. 7, 2007, is directed to a method and device for delivering a drug aerosol to the turbinate region of the nasal passage. The drug is delivered to the nostril in a metered volume of gas such that it reaches the turbinates, and flow into the nostril is then prevented for sufficient time to allow the particles to settle. The particles have an aerodynamic diameter below about 12.5 $\mu m$ such that the majority pass the nasal valve.

U.S. Patent Publication No. 20130102998 for Holder and a method of using the holder by inventors Coghill, et al., filed Apr. 28, 2011 and published Apr. 25, 2013, is directed to a holder for a drug delivery device including a body portion, and a first flange extending from the holder, wherein the body portion includes a receiving portion for receiving a drug delivery device, and the flange extends from the body portion of the holder.

U.S. Patent Publication No. 20200038320 for Multimodal particulate formulations by inventors Cartt, et al., filed Oct. 7, 2019 and published Feb. 6, 2020, is directed to multimodal particulate formulations of medicaments and methods for their use, e.g., by nasal or pulmonary administration for the treatment of various medical conditions.

U.S. Patent Publication No. 20190091424 for Intranasal Delivery Devices by inventor Haruta, filed Sep. 21, 2018 and published Mar. 28, 2019, is directed to devices for delivery of powder formulations and methods of manufacture and use of such devices.

U.S. Patent Publication No. 20210077390 for Dry Powder Compositions for Intranasal Delivery by inventors Temtsin-Krayz, filed Dec. 1, 2020 and published Mar. 18, 2021, is directed to a pharmaceutical composition in a form of dry powder for intranasal administration including solid particles of at least one opioid receptor antagonist as active ingredient and two types of solid particles. A naloxone pharmaceutical composition in the form of dry powder for intranasal administration, including as active agent naloxone or a pharmaceutically acceptable salt thereof. A kit for intranasal administration of naloxone. A method of treating opioid overdose/intoxication and/or a symptom thereof in a patient in need thereof by intranasally administering a therapeutically effective amount of a composition including solid particles of at least one opioid receptor antagonist as active ingredient and two types of solid particles.

U.S. Patent Publication No. 20210361770 for Intranasal epinephrine formulations and methods for the treatment of disease by inventors Lowenthal, et al., filed Aug. 6, 2021 and published Nov. 25, 2021, is directed to drug products adapted for nasal delivery comprising formulations with epinephrine and devices comprising such formulations. Methods of treating anaphylaxis with epinephrine products are also provided.

SUMMARY OF THE INVENTION

The present invention relates to medical counter measures, and more specifically to dry powder formulations and methods of treatment of various conditions using the dry power formulations.

It is an object of this invention to provide therapeutic formulations for enabling the absorption and bioavailability of medications when sprayed into the human nasal passages.

In one embodiment, the present invention provides a device for intranasal administration of a pharmaceutical composition including a reservoir and a means for discharging one or more doses of the pharmaceutical composition, wherein the reservoir contains a quantity of the pharmaceutical composition, wherein the pharmaceutical composition is a dry powder including galantamine or a pharmaceutical salt thereof, wherein the pharmaceutical composition provides a dose of about 5 mg to about 75 mg of the galantamine or the pharmaceutical salt thereof, sodium chloride, wherein the pharmaceutical composition includes about 0.01 mg to about 5 mg of the sodium chloride, a polysorbate, wherein the pharmaceutical composition includes about 0.01% w/v to about 5% w/v of the polysorbate, and a carrier, wherein the carrier includes lactose and/or sodium carboxymethylcellulose, wherein a median particle diameter of the pharmaceutical composition is about 20 μm to about 75 μm, and wherein the device further includes a ball, an actuator, and a piston.

In another embodiment, the present invention provides a kit for intranasal administration of a pharmaceutical composition including at least one device, wherein each of the at least one device includes a reservoir and a means for discharging one or more doses of the pharmaceutical composition, wherein the reservoir contains a quantity of the pharmaceutical composition, and a pouch and/or a hard case, wherein the at least one device is enclosed in the pouch and/or the hard case, wherein the pharmaceutical composition is a dry powder including galantamine or a pharmaceutical salt thereof, wherein the pharmaceutical composition provides a dose of about 5 mg to about 75 mg of the galantamine or the pharmaceutical salt thereof, sodium chloride, wherein the pharmaceutical composition includes about 0.01 mg to about 5 mg of the sodium chloride, a polysorbate, wherein the pharmaceutical composition includes about 0.01% w/v to about 5% w/v of the polysorbate, and a carrier, and wherein the at least one device further includes a nasal probe, a ball, an actuator, and a piston.

In yet another embodiment, the present invention provides a device for intranasal administration of a pharmaceutical composition including a reservoir and a means for discharging one or more doses of the pharmaceutical composition, wherein the reservoir contains a quantity of the pharmaceutical composition, wherein the pharmaceutical composition is a spray-dried powder including galantamine or a pharmaceutical salt thereof, wherein the pharmaceutical composition provides a dose of about 5 mg to about 75 mg of the galantamine or the pharmaceutical salt thereof, memantine, wherein the pharmaceutical composition provides a dose of about 1 mg to about 30 mg of the memantine, sodium chloride, wherein the pharmaceutical composition includes about 0.01 mg to about 5 mg of the sodium chloride, polysorbate 80, wherein the pharmaceutical composition includes about 0.01% w/v to about 2% w/v of the polysorbate 80, and a carrier, wherein the carrier includes lactose and/or sodium carboxymethylcellulose, wherein a median particle diameter of the pharmaceutical composition is about 20 μm to about 40 μm, and wherein the device further includes a nasal probe, a ball, an actuator, and a piston.

These and other aspects of the present invention will become apparent to those skilled in the art after a reading of the following description of the preferred embodiment when considered with the drawings, as they support the claimed invention.

DETAILED DESCRIPTION

Figure 1:
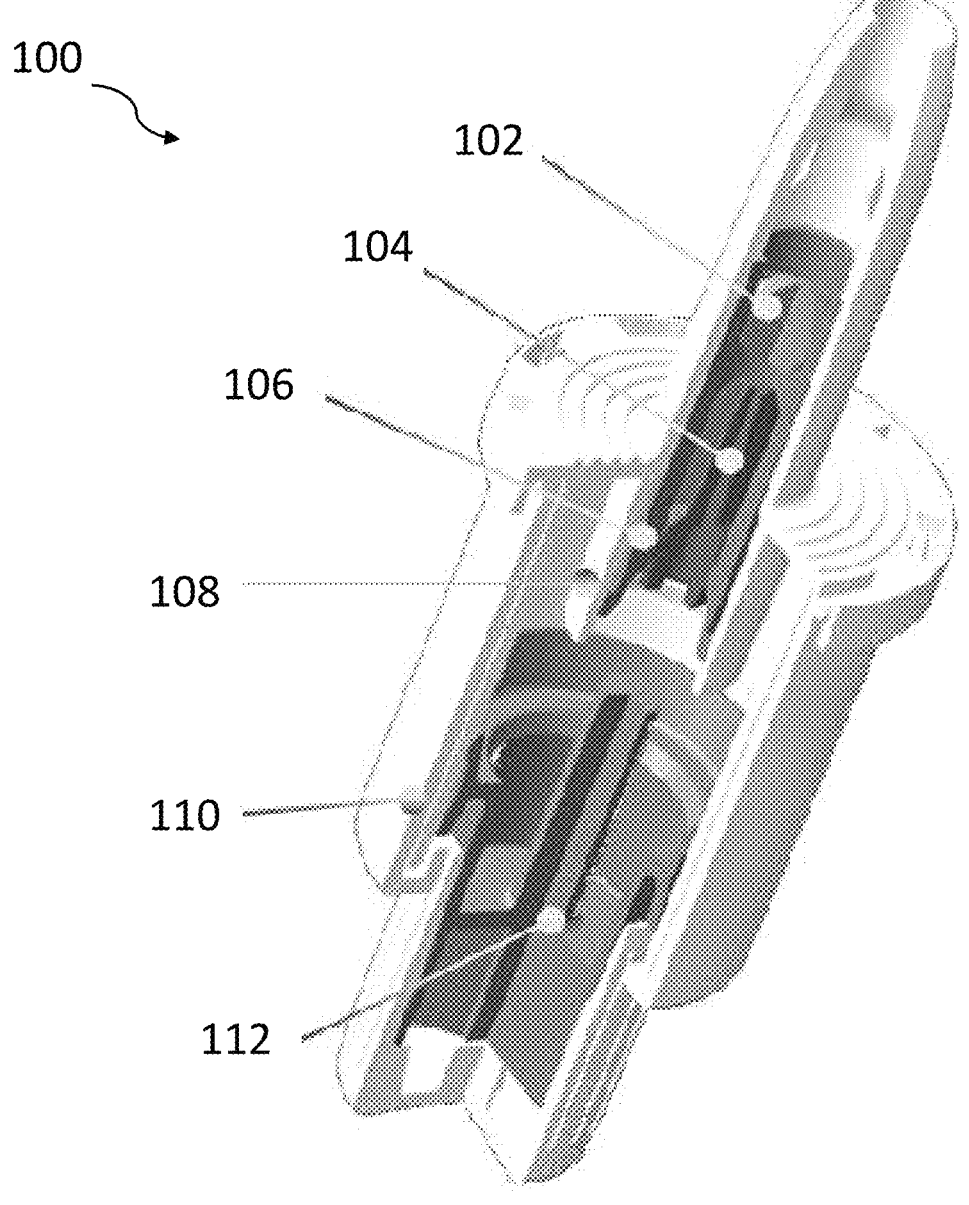
FIG. 1 illustrates one embodiment of a nasal delivery device according to the present invention.

The present invention is generally directed to medical counter measures, and more specifically to dry powder formulations and methods of treatment of various conditions using the dry power formulations.

In one embodiment, the present invention provides a device for intranasal administration of a pharmaceutical composition including a reservoir and a means for discharging one or more doses of the pharmaceutical composition, wherein the reservoir contains a quantity of the pharmaceutical composition, wherein the pharmaceutical composition is a dry powder including galantamine or a pharmaceutical salt thereof, wherein the pharmaceutical composition provides a dose of about 5 mg to about 75 mg of the galantamine or the pharmaceutical salt thereof, sodium chloride, wherein the pharmaceutical composition includes about 0.01 mg to about 5 mg of the sodium chloride, a polysorbate, wherein the pharmaceutical composition includes about 0.01% w/v to about 5% w/v of the polysorbate, and a carrier, wherein the carrier includes lactose and/or sodium carboxymethylcellulose, wherein a median particle diameter of the pharmaceutical composition is about 20 μm to about 75 μm, and wherein the device further includes a ball, an actuator, and a piston.

In one embodiment, the device includes a nasal probe, and wherein the nasal probe is constructed and configured to be replaced between discharges. In one embodiment, the pharmaceutical composition further includes a vasoactive agent, wherein the vasoactive agent is epinephrine or a pharmaceutically acceptable salt thereof, wherein the pharmaceutical composition provides a dose of about 0.01 mg to about 10 mg of the epinephrine or the pharmaceutically acceptable salt thereof. In one embodiment, the pharmaceutical composition further includes an anti-convulsant agent, wherein the anti-convulsant agent is diazepam or a pharmaceutically acceptable salt thereof, wherein the pharmaceutical composition provides a dose of about 0.1 mg to about 20 mg of the diazepam or the pharmaceutically acceptable salt thereof. In one embodiment, the pharmaceutical composition further includes at least one anticholinergic agent, wherein the at least one anticholinergic agent is atropine or a pharmaceutically acceptable salt thereof, wherein the pharmaceutical composition provides a dose of about 0.1 mg to about 10 mg of the atropine or the pharmaceutically acceptable salt thereof. In one embodiment, the pharmaceutical composition further includes a cholinesterase reactivator, wherein the cholinesterase reactivator is 2-pyridine aldoxime methyl chloride or a pharmaceutically acceptable salt thereof, wherein the pharmaceutical composition provides a dose of about 1 mg to about 1000 mg of the pyridine aldoxime methyl chloride or the pharmaceutically acceptable salt thereof. In one embodiment, the pharmaceutical composition further includes a vasodilator, wherein the vasodilator is phentolamine or a pharmaceutically acceptable salt thereof, wherein the pharmaceutical composition provides a dose of about 0.01 mg to about 10 mg of the phentolamine or the pharmaceutically acceptable salt thereof. In one embodiment, the pharmaceutical composition further includes a catechol-o-methyl transferase (COMT) inhibitor, wherein the COMT inhibitor is entacapone or a pharmaceutically acceptable salt thereof, wherein the pharmaceutical composition provides a dose of about 5 mg to about 20 mg of the entacapone or the pharmaceutically acceptable salt thereof. In one embodiment, the pharmaceutical composition further includes an N-Methyl-D-aspartate (NMDA) receptor antagonist, wherein the NMDA receptor antagonist is memantine, wherein the pharmaceutical composition provides a dose of about 1 mg to about 40 mg of the memantine. In one embodiment, the pharmaceutical composition further includes one or more agents selected from a group consisting of an anticaking agent, an excipient, a preservative, a humectant, a thickening agent, a solubilizing agent, a taste-masking agent, a scent-masking agent, an antioxidant enzyme, a viscosity enhancing agent, a dispersing agent, a surfactant, a chelator, an antihistamine, a colorant, or any combination thereof. In one embodiment, the pharmaceutical composition further includes one or more agents selected from a group consisting of a mucosal permeation or penetration enhancer, a mucoadhesive, a mucosal transit slowing agent, a mucosal transport enhancer, or any combination thereof. In one embodiment, the device has 360° functionality and is constructed and configured to dispense a dose from any position. In one embodiment, the pharmaceutical composition is a spray-dried powder. In one embodiment, the device further includes a sensor that is adapted to detect a displacement or a deformation of a portion of the delivery device when the dose is dispensed. In one embodiment, the device further includes a display, a power supply, a timer, a clock, and/or a printed circuit board, wherein the display is constructed and configured to display a time of dose dispensation. In one embodiment, the device further includes a communications interface, wherein the communications interface is constructed and configured to transmit data wirelessly to at least one remote device.

In another embodiment, the present invention provides a kit for intranasal administration of a pharmaceutical composition including at least one device, wherein each of the at least one device includes a reservoir and a means for discharging one or more doses of the pharmaceutical composition, wherein the reservoir contains a quantity of the pharmaceutical composition, and a pouch and/or a hard case, wherein the at least one device is enclosed in the pouch and/or the hard case, wherein the pharmaceutical composition is a dry powder including galantamine or a pharmaceutical salt thereof, wherein the pharmaceutical composition provides a dose of about 5 mg to about 75 mg of the galantamine or the pharmaceutical salt thereof, sodium chloride, wherein the pharmaceutical composition includes about 0.01 mg to about 5 mg of the sodium chloride, a polysorbate, wherein the pharmaceutical composition includes about 0.01% w/v to about 5% w/v of the polysorbate, and a carrier, and wherein the at least one device further includes a nasal probe, a ball, an actuator, and a piston.

In one embodiment, the hard case includes a desiccant plastic, wherein the desiccant plastic includes a base polymer, a channeling agent, and a desiccant. In one embodiment, the pouch and/or the hard case incorporates a pouch attachment ladder system (PALS).

In yet another embodiment, the present invention provides a device for intranasal administration of a pharmaceutical composition including a reservoir and a means for discharging one or more doses of the pharmaceutical composition, wherein the reservoir contains a quantity of the pharmaceutical composition, wherein the pharmaceutical composition is a spray-dried powder including galantamine or a pharmaceutical salt thereof, wherein the pharmaceutical composition provides a dose of about 5 mg to about 75 mg of the galantamine or the pharmaceutical salt thereof, memantine, wherein the pharmaceutical composition provides a dose of about 1 mg to about 30 mg of the memantine, sodium chloride, wherein the pharmaceutical composition includes about 0.01 mg to about 5 mg of the sodium chloride, polysorbate 80, wherein the pharmaceutical composition includes about 0.01% w/v to about 2% w/v of the polysorbate 80, and a carrier, wherein the carrier includes lactose and/or sodium carboxymethylcellulose, wherein a median particle diameter of the pharmaceutical composition is about 20 μm to about 40 μm, and wherein the device further includes a nasal probe, a ball, an actuator, and a piston.

Medications are often delivered intravenously and by needle and syringe injection, which may be subcutaneous or intra-muscular. Intravenous (IV) delivery has many drawbacks, including requiring administration by medical personnel (e.g., emergency medical technician, nurse, doctor). Medical personnel are often not immediately available in emergency situations, sometimes taking up to 20 minutes to arrive, which delays treatment. Further, placing an IV line can be difficult due to the nature of the medical emergency (e.g., if the patient is having a seizure). Additionally, many medications have poor stability in liquid, which means additional time required to dispense the medication because it has to be mixed just prior to delivery.

Increasingly, medications are delivered by auto-injectors, which may be used within medical facilities or in ambulatory settings by medical and non-medical personnel, caregivers, and patients themselves. Self-administration via auto-injector has dramatically improved the availability of medical treatment in emergency situations.

However, auto-injectors have a number of known disadvantages. These include widespread fear of needles and the size of the units themselves, which may be cumbersome to carry. For example, many patients and caregivers avoid carrying auto-injectors during hot weather or leaving them in automobiles or other places where aqueous formulations are liable to degrade and lose potency. These factors lead many patients or caregivers to not have medication available during emergency events, or if it is available, they may be reluctant to use the device. Delayed access and delayed use of medication has been associated with increased morbidity and mortality. For example, a 4-hour delay of treatment exacerbates the symptoms of an asthma attack, Type 2 diabetes patients whose medication is not administered punctually present a 45% higher mortality than the patients with a daily covered treatment, and having a stock of self-administered treatments can help to prevent the higher mortality reached in patients with infectious and autoimmune diseases during pandemics like COVID-19 due to inaccessibility. See, e.g., (1) J. R. Castillo, S. P. Peters, and W. W. Busse, "Asthma Exacerbations: Pathogenesis, Prevention, and Treatment," J. Allergy Clin. Immunol. Pract., vol. 5, no. 4, p. 918, July 2017, doi: 10.1016/J.JAIP.2017.05.001; (2) S. K. Paul, K. Klein, B. L. Thorsted, M. L. Wolden, and K. Khunti, "Delay in treatment intensification increases the risks of cardiovascular events in patients with type 2 diabetes," Cardiovasc. Diabetol., vol. 14, no. 1, p. 100, August 2015, doi: 10.1186/S12933-015-0260-X; (3) K. Degeling et al., "An inverse stage-shift model to estimate the excess mortality and health economic impact of delayed access to cancer services due to the COVID-19 pandemic," Asia. Pac. J. Clin. Oncol., vol. 17, no. 4, pp. 359-367, August 2021, doi: 10.1111/ajco.13505; and (4) Bleske B E, Rice T L, Warren E W, Giacherio D A, Gilligan L J, Massey K D, Tait A R. Effect of dose on the nasal absorption of epinephrine during cardiopulmonary resuscitation. Am J Emerg Med. 1996 March; 14(2): 133-8. doi: 10.1016/S0735-6757(96)90119-9. PMID: 8924133, each of which is incorporated herein by reference in its entirety.

In addition, studies have shown that many patients do not use auto-injectors correctly. For example, in one recent study of epinephrine auto-injector carriage and use practices among children, adolescents, and adults in the United States, the investigators reported that "Of the 242 patients, 54% were not able to recall all the steps for correct EAI use or completely failed to activate the device." Wasserman, S., et. al. "Epinephrine Autoinjectors: New Data, New Problems," J Allergy Clin Immunol Pract., September-October 2017; 5(5):1180-1191, doi: 10.1016/j.jaip.2017.06.027, which is incorporated herein by reference in its entirety.

Further, studies have shown that due to obesity many patients using auto-injectors do not receive the recommended dose via an intramuscular (IM) injection. One US study estimated that some thirty percent (30%) of both adults and children would not receive an IM injection. When injected, subcutaneously (SQ), a substantially lower plasma drug level and delayed delivery has been found. See, e.g., (1) Stecher, D., et. al., "Epinephrine Auto-injectors: Is Needle Length Adequate for Delivery of Epinephrine Intramuscularly?" Pediatrics, July 2009, 124(1): 65-70, doi:10.1542/peds.2008-3388 and (2) Simons F E, Gu X, Simons K J. Epinephrine absorption in adults: intramuscular versus subcutaneous injection. J Allergy Clin Immunol. 2001 November; 108(5):871-3. doi: 10.1067/mai.2001.119409. PMID: 11692118, each of which is incorporated herein by reference in its entirety. See also, e.g., Crowe T P, Greenlee M H W, Kanthasamy A G, Hsu W H. Mechanism of intranasal drug delivery directly to the brain. Life Sci. 2018 Feb. 15; 195:44-52. doi: 10.1016/j.lfs.2017.12.025. Epub 2017 Dec. 22. PMID: 29277310, which is incorporated herein by reference in its entirety.

The aforementioned drawbacks of auto-injectors have led to a search for new routes of delivering medications including pulmonary, sublingual, and nasal delivery. Pulmonary delivery may irritate the airways and produce a bronchial spasm. Further, sublingual and pulmonary delivery may be problematic for some patients. For example, patients suffering and anaphylactic event or seizure may clinch their jaw, making these routes unreliable for some patients. Additionally, pulmonary delivery requires an active participant, which may not be possible due to the patient's medical condition. Nasal delivery appears promising as it removes the needle-related concerns, provides a more portable device, and provides an easy-to-use delivery mechanism. Further, nasal mucosae are more tolerant to exposure to drugs due to their nature, and provide a large surface area. Additionally, the network of blood capillaries under the nasal mucosa allows for rapid and systemic absorption of drugs.

Nasal delivery of many drugs, however, retains some of the drawbacks of injection if an aqueous formulation is employed. Aqueous formulations typically have shorter shelf lives than powders. Aqueous formulations often have preservatives, such as sodium bisulfite, which itself can cause an allergic reaction in many individuals. Additionally, when aqueous formulations are delivered to the nasal passages, a significant portion of drug volume may be lost due to running down the back of the throat or back out the front of the nose when the device is removed. This may be exacerbated when a patient suffering an event is in a prone position. All of these factors lead to dose uncertainty for liquid nasal approaches. A particularly concerning drawback for aqueous formulations is that they are subject to degradation when exposed to high temperatures. When exposed to high temperature, even for short durations, as in outdoor summertime activity or when left in an automobile, many drugs can degrade and lose potency. Degradation of drugs and loss of potency is also a serious issue when traveling or living in areas where temperatures are elevated most of the year (e.g., the tropics). It has been reported that self-administered drugs in aqueous solution suffer a degradation rate. For example, a loss of 2.5% of effective drug was observed in insulin pens stored at 37° C. or below 8° C. and the degradation rate of ophthalmic drugs to treat hypertension increases from 0.15-0.46 µg/day when they are stored at 37° C. or above, which means that the ophthalmic solutions can lose approximately 10% of active drug over 30 days of storage if the temperature is not within storage parameters. See, e.g., (1) T. Kongmalai, L. Preechasuk, S. Junnu, S. Manocheewa, C. Srisawat, and A. Sriwijitkamol, "The Effect of Temperature on the Stability of In-Use Insulin Pens," Exp. Clin. Endocrinol. Diabetes, vol. 129, no. 9, pp. 683-688, September 2021, doi: 10.1055/a-1010-5466; (2) T. V. Johnson, P. K. Gupta, D. K. Vudathala, I. A. Blair, and A. P. Tanna, "Thermal Stability of Bimatoprost, Latanoprost, and Travoprost Under Simulated Daily Use," J. Ocul. Pharmacol. Ther., vol. 27, no. 1, p. 51, February 2011, doi: 10.1089/JOP.2010.0115; (3) Ousama Rachid, F. Estelle R. Simons, Mutasem Rawas-Qalaji, Stephen Lewis & Keith J. Simons (2016) Epinephrine doses delivered from auto-injectors stored at excessively high temperatures, Drug Development and Industrial Pharmacy, 42:1, 131-135, DOI: 10.3109/03639045.2015.1035283; (4) Lacwik P, Bialas A J, Wielanek M, Sklodowska M, Kupczyk M, Gorski P, Kuna P. Single, short-time exposure to heat in a car during sunny day can decrease epinephrine concentration in autoinjectors: a real-life pilot study. J Allergy Clin Immunol Pract. 2019 April; 7(4): 1362-1364. doi: 10.1016/j.jaip.2018.10.027. Epub 2018 Nov. 28. PMID: 30503198; and (5) Rawas-Qalaji M, Simons F E, Collins D, Simons K J. Long-term stability of epinephrine dispensed in unsealed syringes for the first-aid treatment of anaphylaxis. Ann Allergy Asthma Immunol. 2009 June; 102(6):500-3. doi: 10.1016/S1081-1206(10)60124-X. PMID: 19558009, each of which is incorporated herein by reference in its entirety.

Patients are aware of this issue and many will not carry medication at times or will not store medication in locations where high temperatures are likely. This behavior is due to both the concern over loss of potency and the concern about the cost of replacing the device that has gone bad. As a result, medication is not available during emergencies, leading to greater morbidity.

Additionally, dry powders nasal sprays appear to be more rapidly absorbed during the initial minutes after delivery than aqueous nasal sprays. This may reflect the fact that a greater portion of the volume stays on the nasal muscosa. Further, aqueous nasal sprays frequently shown a biphasic peak blood plasma level. This is thought to reflect the gastrologic absorption of a portion of the spray that is swallowed (runs down the throat).

Nasal delivery of drugs in a dry powder eliminates the significant disadvantages of intramuscular or subcutaneous injection as well as the major drawbacks of aqueous formulations of the drugs. The present invention describes dry powder formulations for delivery to the nasal passages by means of a nasal delivery device that may be handheld.

The present invention provides a dry powder formulation including at least one active pharmaceutical ingredient (API). The at least one active pharmaceutical ingredient includes, but is not limited to, at least one anticholinergic agent, at least one cholinesterase reactivator agent, at least one anticonvulsive agent, at least one antidote, at least one acetylcholinesterase inhibitor, at least one analgesic, at least one anesthetic, at least one anti-inflammatory, at least one migraine medication, at least one peptide, and/or at least one hormone.

In one embodiment, the API is formulated as a salt (e.g., an alkali metal salt, amine salt, acid salt, organic acid), an ester (e.g., low alkyl ester), and/or a solvate (e.g., hydrate). The salt includes, but is not limited to, magnesium, potassium, ammonium, hydrochloric, hydriodic, hydrobromic, phosphoric, metaphosphoric, nitric acid, sulfuric acid, tartaric, acetic, citric, malic, benzoic, gluconic, succinic, and/or arylsulfonic.

In one embodiment, the dry powder formulation further includes at least one enabling agent and/or at least one carrier. In a preferred embodiment, the dry powder formulation, the at least one enabling agent, and/or the at least one carrier is included in a delivery device (e.g., a nasal delivery device). The delivery device is operable to dispense at least one dose of the dry powder formulation.

As used herein, "therapeutically effective amount", "effective amount", or "effective dose" means an amount sufficient to provide a clinically beneficial result (e.g., reduction of symptoms) when the formulation is administered to a patient needing treatment. A skilled clinician will recognize that the therapeutically effective amount, effective amount, or effective dose depends on the patient, the indication, and the particular formulation administered to the patient.

As used herein, "Cmax" and "Tmax" have the ordinary meaning in the art with respect to a pharmacokinetic (PK) curve.

As used herein, the modifier "about" has its regularly recognized meaning of approximately. In one embodiment, "about" means±20%, ±10%, or ±5%

Referring now to the drawings in general, the illustrations are for the purpose of describing one or more preferred embodiments of the invention and are not intended to limit the invention thereto.

Anticholinergic Agents

In one aspect, provided herein is an intranasal dry powder composition comprising at least one anticholinergic agent. The at least one anticholinergic agent includes, but is not limited to, atropine, scopolamine, benztropine, oxybutynin, tolterodine, tiotropium, oxitropium, glycopyrrolate, ipratropium, tropicamide, trihexyphenidyl, pirenzepine, diphenhydramine, dimenhydrinate, dicyclomine, flavoxate, cyclopentolate, atropine methonitrate, solifenacin, darifenacin, mebeverine, or other agents with anticholinergic activity or anti-muscarinic activity or a pharmaceutically acceptable salt thereof. In a preferred embodiment, the at least one anticholinergic agent includes atropine or a pharmaceutically acceptable salt thereof.

In some embodiments, a single dose of the at least one anticholinergic agent is about 0.01 mg to about 10 mg. In another aspect, the amount of the at least one anticholinergic agent (e.g., atropine) is at least about: 0.01 mg, 0.05 mg, 1.0 mg, 2.0 mg, 5.0 mg, or 10 mg in the compositions. In some embodiments, the at least one anticholinergic agent (e.g., atropine) present in the compositions is about: 0.01 mg to 0.05 mg, 0.05 mg to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, or 9.0 to 10.0 mg. In some embodiments, the amount of the at least one anticholinergic agent (e.g., atropine) is about: 0.15, 0.3, 0.5, 0.75, 1, 1.5, 2, 3, 4, 5, 6, 7, 8, 9, or 10 mg in the compositions. In one instance, a single dose of the at least one anticholinergic agent is about 0.75 mg. In one instance, a single dose of the at least one anticholinergic agent is about 1.5 mg. In another instance, a single dose of the at least one anticholinergic agent is about 3.0 mg. In another related aspect, the dose of the at least one anticholinergic agent (e.g., atropine) is operable to be adjusted according to the weight of a patient at an increment of at least 0.01 mg/kg. Additionally or alternatively, the dose is operable to be repeated a number of times if the patient failed to improve patient symptoms. In one embodiment, the composition, in the form of a single dose, contains about 0.01 mg to about 10 mg of the at least one anticholinergic agent. In some embodiments, the composition, in the form of a single dose, contains about 0.75 mg, 1.5 mg, or 3.0 mg of the at least one anticholinergic agent.

In one embodiment, a unit dosage of the at least one anticholinergic agent ranges from about 0.01 mg to about 1 mg, for example about: 0.1, 0.2, 0.3, 0.4, 0.5, 0.6, 0.7, 0.8, 0.9, or 1 mg, of a composition. In another embodiment, the unit dosage is also operable to be at least about: 0.01 0.1, 0.5, or 1 mg of a composition. Administration of the compositions herein is operable to be repeated, e.g., every 5-20 minutes as necessary.

In some embodiments, the at least one anticholinergic agent is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the at least one anticholinergic agent is operable to be about 4%, about 7.5%, or about 15% w/w of the weight of the composition. In some embodiments, the at least one anticholinergic agent (e.g., atropine) is operable to be present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the at least one anticholinergic agent (e.g., atropine) is operable to be present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein are operable to increase the maximal blood concentration ($C_{max}$) of an anticholinergic agent (e.g., atropine) to about 13 ng/ml. In one embodiment, the compositions herein are operable to increase the blood concentration of the at least one anticholinergic agent (e.g., atropine) by about 1, 2, 3, 4, 5, 6, 7, 8, 9, 10, 11, 12, 13, 14, 15, 25, or 50 ng/mL.

In some embodiments, the dry powder composition disclosed herein when administered to a patient, reaches a maximal blood concentration of the at least one anticholinergic agent (e.g., atropine) in less than about 60 minutes ($T_{max}$) after administration. In some embodiments, the dry powder composition when administered to a patient, reaches a maximal blood concentration ($T_{max}$) of the at least one anticholinergic agent in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the at least one anticholinergic agent in less than about 30 minutes after administration. In some embodiments, the dry powder composition when administered to a patient, reaches a mean area under the curve $(AUC)_{(0\text{-}180\ minutes)}$ of the at least one anticholinergic agent which is at least 20%, 30%, 40%50%, 60%, 70%, 80%, 90%, 100%, 110%, 120%, 130%, 140%, or 150% of the mean $AUC_{(0\text{-}180\ minutes)}$ of an equivalent IV, IM, or SQ injected at least one anticholinergic agent. In some embodiments, the dry powder composition when administered to a patient, reaches a mean $AUC_{(0\text{-}\infty)}$ of the at least one anticholinergic agent which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected at least one anticholinergic agent. In some embodiments, the IV, IM, or SQ injected at least one anticholinergic agent contains 1 mg, 2 mg, 2.1 mg, 3 mg, 4 mg, 5 mg, 6 mg, 7 mg, 8 mg, 9 mg, or 10 mg of the at least one anticholinergic agent. For example, the dry powder composition when administered to a patient, reaches a mean $AUC_{(0\text{-}180\ minutes)}$ of the at least one anticholinergic agent, which is at least 80% of the mean $AUC_{(0\text{-}180\ minutes)}$ of an equivalent IM injected at least one anticholinergic agent (e.g., 2.1 mg IM injected at least one anticholinergic agent). In another instance, the dry powder composition when administered to a patient, reaches a mean $AUC_{(0\text{-}\infty)}$ of the at least one anticholinergic agent, which is at least 80% of the mean $AUC_{(0\text{-}\infty)}$ of an equivalent IM injected at least one anticholinergic agent (e.g., 2.1 mg IM injected at least one anticholinergic agent).

In certain embodiments, the dry powder compositions and/or dosage units herein are operable to raise the blood concentration of the at least one anticholinergic agent (e.g., atropine) to about 13 ng/ml within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the at least one anticholinergic agent (e.g., atropine) by about 13 ng/ml, for example 10 or 15 ng/ml, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the at least one anticholinergic agent in the dry powder compositions and/or dosage units given intranasally is bioequivalent (for example, in terms of peripheral blood levels, systemic exposure of atropine) to intravenously (IV), intramuscularly (IM) or subcutaneously (SQ) injected at least one anticholinergic agent (e.g., DUODOTE® autoinjector 2.1 mg atropine). For example, bioequivalence means that 90% confidence interval of a mean $T_{max}$ (e.g., the time to reach maximal blood concentration), a mean $C_{max}$ (e.g., maximal blood concentration), a mean $AUC_{(0\text{-}t)}$ (e.g., area under the plasma/serum/blood concentration-time curve from time zero to time t), and/or a mean $AUC_{(0\text{-}\infty)}$ (e.g., area under the plasma/serum/blood concentration-time curve from time zero to time infinity) of the test to reference are within 80.00% to 125.00%, optionally, in the fasting state.

Cholinesterase Reactivator Agents

In another aspect, provided herein is an intranasal dry powder composition comprising at least one cholinesterase reactivator agent. The at least one cholinesterase reactivator agent includes, but is not limited to, pralidoxime chloride (monopyridinium oxime pralidoxime-2-PAM), obidoxime, diacetylmonoxime, monoisonitrosoacetone, 1-methyl-1,6-dihydropyridine-2-carbaldoxime (pro-2-PAM), pralidoxime mesylate (1-methylpyridinium-2-aldoxime methanesulfonate-P2S), trimedoxime bromide (dipyroxime-TMB-4), asoxime chloride (HI-6), 4-formyl-1-methylpyridinium iodide oxime (4-PAM), hydroxamate, 1-(((4-(aminocarbonyl)pyridinio)methoxy)methyl)-2,4-bis((hydroxyimino) methyl)pyridinium dimethanesulfate (HLo7), 1,1'-Methyl-enebis(4-((hydroxyimino)methyl)-pyridinium) dimethanesulfonate (MMB4), a pharmaceutically acceptable salt thereof, and/or other agents with similar activity. In a preferred embodiment, the at least one cholinesterase reactivator agent is pralidoxime chloride (monopyridinium oxime pralidoxime-2-PAM), obidoxime, pro-2-PAM, and/or a pharmaceutically acceptable salt thereof. See, e.g., Wilhelm C M, Snider T H, Babin M C, Jett D A, Platoff G E Jr, Yeung D T. A comprehensive evaluation of the efficacy of leading oxime therapies in guinea pigs exposed to organophosphorus chemical warfare agents or pesticides. Toxicol Appl Pharmacol. 2014 Dec. 15; 281(3):254-65. doi: 10.1016/j.taap.2014.10.009. Epub 2014 Oct. 31. PMID: 25448441; PMCID: PMC4255143, which is incorporated herein by reference in its entirety.

In some embodiments, a single dose of the at least one cholinesterase reactivator agent is about 1 mg to about 1000 mg. In another aspect, the amount of the at least one cholinesterase reactivator agent is at least about: 1 mg, 10 mg, 100 mg, 500 mg, 600 mg, or 1000 mg in the compositions. In some embodiments, the at least one cholinesterase reactivator agent present in the compositions is about: 1 mg to 10 mg, 100 mg to 600 mg, or 600 mg to 1000 mg. In one instance, a single dose of the at least one cholinesterase reactivator agent is about 100 mg. In one instance, a single dose of the at least one cholinesterase reactivator agent is about 600 mg. In another related aspect, the dose of the at least one cholinesterase reactivator agent is operable to be adjusted according to the weight of the patient at an increment of at least 0.01 mg/kg. Additionally or alternatively, the dose is operable to be repeated a number of times if the patient failed to improve patient symptoms. In one embodiment, the composition, in the form of a single dose, contains about 10 mg to about 600 mg of the at least one cholinesterase reactivator agent. In some embodiments, the composition, in the form of a single dose, contains about 100 mg to about 600 mg of the at least one cholinesterase reactivator agent.

In one embodiment, a unit dosage of the at least one cholinesterase reactivator agent ranges from about 1 mg to about 1000 mg. In another embodiment, the unit dosage of the at least one cholinesterase reactivator agent is also operable to be at least about: 1, 50, 100, 600, or 1000 mg of a composition. Administration of the compositions herein is operable to be repeated, e.g., every 5-20 minutes, as necessary.

In some embodiments, the at least one cholinesterase reactivator agent is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the at least one cholinesterase reactivator agent is operable to be about 4%, about 7.5%, or about 15% w/w of the weight of the composition. In some embodiments, the at least one cholinesterase reactivator agent is operable to be present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the at least one cholinesterase reactivator agent is operable to be present in an amount of about:

0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein are operable to increase the maximal blood or CNS concentration (Cmax) of the at least one cholinesterase reactivator agent to about 7 mcg/mL. In one embodiment, the compositions herein are operable to increase the blood or CNS concentration of the at least one cholinesterase reactivator agent by about 0.01, 0.05, 1, 2, 3, 4, 5, 6, 7, 8, 9, 10, 11, 12, 13, 14, 15, 25, or 50 mcg/mL.

In some embodiments, the dry powder composition disclosed herein when administered to a patient, reaches a maximal blood or CNS concentration of the at least one cholinesterase reactivator agent in less than about 60 minutes (Tmax) after administration. In some embodiments, the dry powder composition when administered to a patient, reaches a maximal blood or CNS concentration (Tmax) of the at least one cholinesterase reactivator agent in less than about 60, 50, 40, 30, 20, 15, 10, 5, or 3 minutes (Tmax) after administration. In one embodiment, the dry powder composition when administered to a patient, reaches a maximal blood or CNS concentration (Tmax) of the at least one cholinesterase reactivator agent in less than about 30 minutes after administration. In some embodiments, the dry powder composition when administered to a patient, reaches a mean $AUC_{(0-180 \text{ minutes})}$ of the at least one cholinesterase reactivator agent which is at least 20%, 30%, 40% 50%, 60%, 70%, 80%, 90%, 100%, 110%, 120%, 130%, 140%, or 150% of the mean $AUC_{(0-180 \text{ minutes})}$ of an equivalent IV, IM, or SQ injected at least one cholinesterase reactivator agent. In some embodiments, the dry powder composition when administered to a patient, reaches a mean $AUC_{(0-\infty)}$ of the cholinesterase reactivator agent which is at least 20%, 30%, 40% 50%, 60%, 70%, 80%, 90%, 100%, 110%, 120%, 130%, 140%, or 150% of the mean $AUC_{(0-\infty)}$ of an equivalent IV, IM, or SQ injected at least one cholinesterase reactivator agent. In some embodiments, the IV, IM, or SQ injected cholinesterase reactivator agent contains about: 100 mg, 200 mg, 300 mg, 400 mg, 500 mg, or 600 mg of the at least one cholinesterase reactivator agent. For example, the dry powder composition when administered to a patient, reaches a mean $AUC_{(0-180 \text{ minutes})}$ of the at least one cholinesterase reactivator agent which is at least 80% of the mean $AUC_{(0-180 \text{ minutes})}$ of an equivalent IM injected at least one cholinesterase reactivator agent. In another instance, the dry powder composition when administered to a patient, reaches a mean $AUC_{(0-\infty)}$ of the at least one cholinesterase reactivator agent which is at least 80% of the mean $AUC_{(0-\infty)}$ of an equivalent IM injected at least one cholinesterase reactivator agent.

In certain embodiments, the dry powder compositions and/or dosage units herein are operable to raise the blood or CNS concentration of the at least one cholinesterase reactivator agent to about 7 mcg/mL within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood or CNS concentration of the at least one cholinesterase reactivator agent by about 7 mcg/mL, for example 8 or 10 mcg/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). In certain embodiments, the dry powder compositions and/or dosage units herein are operable to raise the blood or CNS concentration of the at least one cholinesterase reactivator agent to about 4 mcg/mL within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood or CNS concentration of the at least one cholinesterase reactivator agent by about 1 mcg/mL, for example 0.8 mcg/mL in brain and 0.9 mcg/mL in blood, in about 10-15 minutes (e.g., about: 10, 11, 12, 13, 14, or 15 minutes), or about 1.2 mcg/mL within about 3 to about 60 minutes (e.g., about: 60, 50, 40, 30, 20, 15, 10, 5, or 3 minutes), for example 1.15 mcg/mL in brain and 1.3 mcg/mL in blood. See, e.g., J. K. S. Krishnan et al., "Intranasal delivery of obidoxime to the brain prevents mortality and CNS damage from organophosphate poisoning," Neurotoxicology, vol. 53, pp. 64-73, March 2016, doi: 10.1016/J.NEURO.2015.12.020, which is incorporated herein by reference in its entirety.

In another aspect, a single dose of the at least one cholinesterase reactivator agent in the dry powder compositions and/or dosage units given intranasally is bioequivalent (for example, in terms of peripheral blood levels, systemic exposure of the at least one cholinesterase reactivator agent) to an equivalent intravenously (IV), intramuscularly (IM) or subcutaneously (SQ) injected at least one cholinesterase reactivator agent. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Pralidoxime

In one embodiment, the at least one cholinesterase reactivator agent is pralidoxime (e.g., pralidoxime chloride). In some embodiments, a single dose of the pralidoxime is about 1 mg to about 1000 mg. In another aspect, the amount of the pralidoxime is at least about: 1 mg, 10 mg, 100 mg, 500 mg, 600 mg, or 1000 mg in the compositions. In some embodiments, the pralidoxime present in the compositions is about: 1 mg to 10 mg, 100 mg to 600 mg, or 600 mg to 1000 mg. In one instance, a single dose of the pralidoxime is about 100 mg. In one instance, a single dose of the pralidoxime is about 600 mg. In another related aspect, the dose of the pralidoxime is operable to be adjusted according to the weight of the patient at an increment of at least 0.01 mg/kg. Additionally or alternatively, the dose is operable to be repeated a number of times if the patient failed to improve patient symptoms. In some embodiments, the composition, in the form of a single dose, contains about 100 mg to about 600 mg of the pralidoxime.

In one embodiment, a unit dosage of the pralidoxime ranges from about 1 mg to about 1000 mg. In another embodiment, the unit dosage of the pralidoxime is also operable to be at least about: 1, 50, 100, 600, or 1000 mg of a composition. Administration of the compositions herein is operable to be repeated, e.g., every 5-20 minutes, as necessary.

In some embodiments, the pralidoxime is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the pralidoxime is operable to be about 4%, about 7.5%, or about 15% w/w of the weight of the composition. In some embodiments, the pralidoxime is operable to be present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the pralidoxime is operable to be present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein are operable to increase the maximal blood or CNS concentration (Cmax) of the pralidoxime to about 7 mcg/mL. In one embodiment, the compositions herein are operable to increase the blood or CNS concentration of the pralidoxime by about 1, 2, 3, 4, 5, 6, 7, 8, 9, 10, 11, 12, 13, 14, 15, 25, or 50 mcg/mL.

In some embodiments, the dry powder composition disclosed herein when administered to a patient, reaches a maximal blood or CNS concentration of the pralidoxime (e.g., pralidoxime chloride) in less than about 60 minutes (Tmax) after administration. In some embodiments, the dry powder composition when administered to a patient, reaches a maximal blood or CNS concentration (Tmax) of the pralidoxime (e.g., pralidoxime chloride) in less than about 60, 50, 40, 30, 20, 15, 10, 5, or 3 minutes (Tmax) after administration. In one embodiment, the dry powder composition when administered to a patient, reaches a maximal blood or CNS concentration (Tmax) of the pralidoxime (e.g., pralidoxime chloride) in less than about 30 minutes after administration. In some embodiments, the dry powder composition when administered to a patient, reaches a mean $AUC_{(0\text{-}180\ minutes)}$ of the pralidoxime (e.g., pralidoxime chloride) which is at least 20%, 30%, 40%50%, 60%, 70%, 80%, 90%, 100%, 110%, 120%, 130%, 140%, or 150% of the mean $AUC_{(0\text{-}180\ minutes)}$ of an equivalent IV, IM, or SQ injected pralidoxime. In some embodiments, the dry powder composition when administered to a patient, reaches a mean $AUC_{(0\text{-}\infty)}$ of the pralidoxime which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected pralidoxime. In some embodiments, the IV, IM, or SQ injected pralidoxime contains 100 mg, 200 mg, 300 mg, 400 mg, 500 mg, or 600 mg of pralidoxime. For example, the dry powder composition when administered to a patient, reaches a mean $AUC_{(0\text{-}180\ minutes)}$ of the pralidoxime which is at least 80% of the mean $AUC_{(0\text{-}180\ minutes)}$ of an equivalent IM injected pralidoxime (e.g., 600 mg IM injected pralidoxime). In another instance, the dry powder composition when administered to a patient, reaches a mean $AUC_{(0\text{-}\infty)}$ of the pralidoxime which is at least 80% of the mean $AUC_{(0\text{-}\infty)}$ of an equivalent IM injected pralidoxime (e.g., 600 mg IM injected pralidoxime). In some embodiments, the IM injected pralidoxime is pralidoxime chloride injected by DUODOTE® autoinjector (atropine 2.1 mg/pralidoxime chloride 600 mg).

In certain embodiments, the dry powder compositions and/or dosage units herein are operable to raise the blood or CNS concentration of the pralidoxime to about 7 mcg/mL within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood or CNS concentration of the pralidoxime by about 7 mcg/mL, for example 8 or 10 mcg/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the pralidoxime in the dry powder compositions and/or dosage units given intra-nasally is bioequivalent (for example, in terms of peripheral blood levels, systemic exposure of the pralidoxime) to an equivalent intravenously (IV), intramuscularly (IM) or sub-cutaneously (SQ) injected pralidoxime. In one embodiment, the pralidoxime is pralidoxime chloride (e.g., DUODOTE® autoinjector 600 mg pralidoxime). For example, bioequiva-lence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Pro-2-PAM

In one embodiment, the at least one cholinesterase reac-tivator agent is pro-2-PAM. In some embodiments, a single dose of the pro-2-PAM is about 1 mg to about 1000 mg. In another aspect, the amount of the pro-2-PAM is at least about: 1 mg, 10 mg, 100 mg, 500 mg, 600 mg, or 1000 mg in the compositions. In some embodiments, the pro-2-PAM present in the compositions is about: 1 mg to 10 mg, 100 mg to 600 mg, or 600 mg to 1000 mg. In one instance, a single dose of the pro-2-PAM is about 100 mg. In one instance, a single dose of the pro-2-PAM is about 600 mg. In another related aspect, the dose of the pro-2-PAM is operable to be adjusted according to the weight of the patient at an incre-ment of at least 0.01 mg/kg. Additionally or alternatively, the dose is operable to be repeated a number of times if the patient failed to improve patient symptoms. In some embodiments, the composition, in the form of a single dose, contains about 100 mg to about 600 mg of the pro-2-PAM.

In one embodiment, a unit dosage of the pro-2-PAM ranges from about 1 mg to about 1000 mg. In another embodiment, the unit dosage of the pro-2-PAM is also operable to be at least about: 1, 50, 100, 600, or 1000 mg of a composition. In one embodiment, a unit dosage of the pro-2-PAM ranges from about 10 mg to about 30 mg, for example about: 10-30 mg, of a composition. In another embodiment, the unit dosage of the pro-2-PAM is at least about: 5-50 mg, of a composition. Administration of the compositions herein is operable to be repeated, e.g., every 5-20 minutes, as necessary. See, e.g., (1) J. C. DeMar et al., "Pro-2-PAM Therapy for Central and Peripheral Cholinest-erases," Chem. Biol. Interact., vol. 187, no. 1-3, p. 191, September 2010, doi: 10.1016/J.CBI.2010.02.015 and (2) C. M. Wilhelm, T. H. Snider, M. C. Babin, D. A. Jett, G. E. Platoff, and D. T. Yeung, "Comparison of 2-PAM and pro-2-PAM containing treatment regimens as antagonists of nerve agent-induced lethality and incapacitation." Final report, June 1981-December 1985, Toxicol. Appl. Pharma-col., vol. 281, no. 3, pp. 254-265, September 1986, doi: 10.1016/J.TAAP.2014.10.009, each of which is incorporated herein by reference in its entirety. Administration of the compositions herein is operable to be repeated, e.g., every 5-20 minutes, as necessary.

In some embodiments, the pro-2-PAM is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the pro-2-PAM is operable to be about 4%, about 7.5%, or about 15% w/w of the weight of the composition. In some embodiments, the pro-2-PAM is oper-able to be present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the pro-2-PAM is operable to be present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the pro-2-PAM to about 900 ng/ml (e.g., 880 ng/mL). In one embodiment, the compositions herein increase the blood concentration of the pro-2-PAM by about 1, 2, 3, 4, 5, 6, 7, 8, 9, 10, 11, 12, 13, 14, 15, 25, 50, 100, 200, 300, 400, 500, 600, 700, 800, 900, 1000, or 1250 ng/mL. See, e.g., T. M. Shih, B. L. Oyler, B. R. Capacio, and I. Koplovitz, "The tertiary oxime monoisonitrosoacetone penetrates the brain, reactivates inhibited acetylcholinesterase, and reduces mor-tality and morbidity following lethal sarin intoxication in guinea pigs," Toxicol. Appl. Pharmacol., vol. 415, March 2021, doi: 10.1016/J.TAAP.2021.115443, which is incorpo-rated herein by reference in its entirety.

In some embodiments, the dry powder composition dis-closed herein when administered to a patient, reaches a maximal blood concentration of the pro-2-PAM in less than about 60 minutes ($T_{max}$) after administration. In some embodiments, the dry powder composition when adminis-tered to a patient, reaches a maximal blood concentration ($T_{max}$) of the pro-2-PAM in less than about 60, 50, 40, 30, 20, 15, 10, 5, or 3 minutes ($T_{max}$) after administration. In one embodiment, the dry powder composition when adminis-tered to a patient, reaches a maximal blood concentration ($T_{max}$) of the pro-2-PAM in less than about 30 minutes after administration. In some embodiments, the dry powder com-position when administered to a patient, reaches a mean area under the curve $(AUC)_{(0-180 \ minutes)}$ of the pro-2-PAM which is at least 20%, 30%, 40%50%, 60%, 70%, 80%, 90%, 100%, 110%, 120%, 130%, 140%, or 150% of the mean $AUC_{(0-180 \ minutes)}$ of an equivalent IV, IM, or SQ injected pro-2-PAM. In some embodiments, the dry powder compo-sition when administered to a patient, reaches a mean $AUC_{(0-\infty)}$ of the pro-2-PAM which is at least 20%, 30%, 40%50%, 60%, 70%, 80%, 90%, 100%, 110%, 120%, 130%, 140%, or 150% of the mean $AUC_{(0-\infty)}$ of an equiva-lent IV, IM, or SQ injected pro-2-PAM. In some embodi-ments, the equivalent IV, IM, or SQ injected pro-2-PAM contains about 10 mg to about 30 mg (e.g., 13 mg) of the pro-2-PAM. For example, the dry powder composition when administered to a patient, reaches a mean $AUC_{(0-180 \ minutes)}$ of the pro-2-PAM, which is at least 80% of the mean $AUC_{(0-180 \ minutes)}$ of an equivalent IM injected pro-2-PAM (e.g., 13 mg IM injected pro-2-PAM). In another instance, the dry powder composition when administered to a patient, reaches a mean $AUC_{(0-\infty)}$ of the pro-2-PAM, which is at least 80% of the mean $AUC_{(0-\infty)}$ of an equivalent IM injected pro-2-PAM (e.g., 13 mg IM injected pro-2-PAM).

In certain embodiments, the dry powder compositions and/or dosage units herein are operable to raise the blood concentration of the pro-2-PAM to about 90 ng/ml (e.g., 88 ng/ml) within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the pro-2-PAM by about 900 ng/ml (e.g., 880 ng/ml), for example 400-1500 ng/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). See, e.g., (1) J. C. DeMar et al., "Pro-2-PAM Therapy for Central and Peripheral Cholinesterases," Chem. Biol. Interact., vol. 187, no. 1-3, p. 191, September 2010, doi: 10.1016/J.CBI.2010.02.015 and (2) T. M. Shih, B. L. Oyler, B. R. Capacio, and I. Koplovitz, "The tertiary oxime monoisonitrosoacetone penetrates the brain, reactivates inhibited acetylcholinesterase, and reduces mortality and morbidity following lethal sarin intoxication in guinea pigs," Toxicol. Appl. Pharmacol., vol. 415, March 2021, doi: 10.1016/J.TAAP.2021.115443, each of which is incorporated herein by reference in its entirety.

In another aspect, a single dose of the pro-2-PAM in the dry powder compositions and/or dosage units given intranasally is bioequivalent (for example, in terms of peripheral blood levels, systemic exposure of the pro-2-PAM) to an equivalent intravenously (IV), intramuscularly (IM) or subcutaneously (SQ) injected pro-2-PAM. For example, a single dose of the pro-2-PAM in the dry powder compositions and/or dosage units given intranasally is bioequivalent to an equivalent intravenously (IV), intramuscularly (IM) or subcutaneously (SQ) injected pro-2-PAM. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Obidoxime

In one embodiment, the at least one cholinesterase reactivator agent is obidoxime (e.g., obidoxime chloride). In some embodiments, a single dose of the obidoxime is about 1 mg to about 1000 mg. In another aspect, the amount of the obidoxime is at least about: 1 mg, 10 mg, 100 mg, 500 mg, 600 mg, or 1000 mg in the compositions. In some embodiments, the obidoxime present in the compositions is about: 1 mg to 10 mg, 100 mg to 600 mg, or 600 mg to 1000 mg. In one instance, a single dose of the obidoxime is about 100 mg. In one instance, a single dose of the obidoxime is about 600 mg. In another related aspect, the dose of the obidoxime is operable to be adjusted according to the weight of the patient at an increment of at least 0.01 mg/kg. Additionally or alternatively, the dose is operable to be repeated a number of times if the patient failed to improve patient symptoms. In some embodiments, the composition, in the form of a single dose, contains about 100 mg to about 600 mg of the obidoxime.

In one embodiment, a unit dosage of the obidoxime ranges from about 1 mg to about 1000 mg. In another embodiment, the unit dosage of the obidoxime is also operable to be at least about: 1, 50, 100, 600, or 1000 mg of a composition. Administration of the compositions herein is operable to be repeated, e.g., every 5-20 minutes, as necessary.

In some embodiments, the obidoxime is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the obidoxime is operable to be about 4%, about 7.5%, or about 15% w/w of the weight of the composition. In some embodiments, the obidoxime is operable to be present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the obidoxime is operable to be present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein are operable to increase the maximal blood or CNS concentration (Cmax) of the obidoxime to about 1-1.3 mcg/mL. In one embodiment, the compositions herein are operable to increase the blood or CNS concentration of the obidoxime by about 1, 2, 3, 4, 5, 6, 7, 8, 9, 10, 11, 12, 13, 14, 15, 25, or 50 mcg/mL.

In some embodiments, the dry powder composition disclosed herein when administered to a patient, reaches a maximal blood or CNS concentration of the obidoxime (e.g., obidoxime chloride) in less than about 60 minutes (Tmax) after administration. In some embodiments, the dry powder composition when administered to a patient, reaches a maximal blood or CNS concentration (Tmax) of the obidoxime (e.g., obidoxime chloride) in less than about 60, 50, 40, 30, 20, 15, 10, 5, or 3 minutes (Tmax) after administration. In one embodiment, the dry powder composition when administered to a patient, reaches a maximal blood or CNS concentration (Tmax) of the obidoxime (e.g., obidoxime chloride) in less than about 30 minutes after administration. In some embodiments, the dry powder composition when administered to a patient, reaches a mean $AUC_{(0-180\ minutes)}$ of the obidoxime (e.g., obidoxime chloride) which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected obidoxime. In some embodiments, the dry powder composition when administered to a patient, reaches a mean $AUC_{(0-\infty)}$ of the obidoxime which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected obidoxime. In some embodiments, the IV, IM, or SQ injected obidoxime contains about: 100 mg, 200 mg, 220 mg, 300 mg, 400 mg, 500 mg, or 600 mg of obidoxime. For example, the dry powder composition when administered to a patient, reaches a mean $AUC_{(0-180\ minutes)}$ of the obidoxime which is at least 80% of the mean $AUC_{(0-180\ minutes)}$ of an equivalent IM injected obidoxime (e.g., 220 mg IM injected obidoxime). In another instance, the dry powder composition when administered to a patient, reaches a mean $AUC_{(0-\infty)}$ of the obidoxime which is at least 80% of the mean $AUC_{(0-\infty)}$ of an equivalent IM injected obidoxime (e.g., 220 mg IM injected obidoxime). In some embodiments, the IM injected cholinesterase reactivator is obidoxime chloride injected by TROBIGARD® autoinjector (atropine sulfate 2 mg/obidoxime chloride 220 mg).

In certain embodiments, the dry powder compositions and/or dosage units herein are operable to raise the blood or CNS concentration of the obidoxime to about 1 mcg/mL within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood or CNS concentration of the obidoxime by about 1.2 mcg/mL, for example 1.15 mcg/mL in brain or 1.3 mcg/mL in blood mcg/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the obidoxime in the dry powder compositions and/or dosage units given intranasally is bioequivalent (for example, in terms of peripheral blood levels, systemic exposure of the obidoxime) to an equivalent intravenously (IV), intramuscularly (IM) or subcutaneously (SQ) injected obidoxime. In one embodiment, the at least one cholinesterase reactivator agent is obidoxime chloride (e.g., TROBIGARD® autoinjector 220 mg obidoxime). For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Combinations of Anticholinergic Agents and Cholinesterase Reactivator Agents

In one embodiment, the at least one active pharmaceutical ingredient includes the at least one anticholinergic agent and the at least one cholinesterase reactivator agent. In a preferred embodiment, the at least one pharmaceutical ingredient is selected from a group consisting of atropine, obidoxime, and a pharmaceutically acceptable salt thereof. In another preferred embodiment, the at least one pharmaceutical ingredient includes atropine, pralidoxime, and a pharmaceutically acceptable salt therefor. In one embodiment, the at least one active pharmaceutical ingredient further includes at least one vasoactive agent (e.g., epinephrine, vasopressin, phenylephrine, or a salt thereof), at least one anticonvulsive agent (e.g., diazepam, lorazepam, midazolam, clonazepam, temazepam, flunitrazepam, triazolam, alprazolam, zolpidem, eszopiclone, or a salt thereof), at least one vasodilator (e.g., phentolamine, prazosin, doxazosin, bosentan, a hydralazine and nitrate combination, a PDE3 inhibitor (e.g., milrinone), a PD5 inhibitor (e.g., sildenafil)), and/or at least one catechol-o-methyl transferase (COMT) inhibitor (e.g., entacapone, tolcapone). Additional details regarding the at least one vasoactive agent, the at least one anticonvulsive agent, the at least one vasodilator, and/or the at least one COMT inhibitor are included in U.S. patent application Ser. No. 17/349,507 and U.S. Provisional Patent Application No. 63/209,221, each which is incorporated herein by reference in its entirety.

Method of Treatment

Provided herein are methods of treating a patient by intranasally administrating the dry powder composition disclosed herein. Also provided herein are methods of treating a patient by using a kit or a product disclosed herein.

The methods, kits, compositions, doses, or products herein are useful for treating patients. In some instances, the patient has minimal to severe respiratory distress including bronchorrhea and bronchospasms. In some instances, the patient has excess sweating and salivation, seizures, and paralysis. In either case, the compositions described herein are operable to provide a fast onset time and are suitable for intranasal use.

In one embodiment, the patient has been exposed to at least one organophosphate compound. The at least one organophosphate compound includes, but is not limited to, sarin (GB), tabun (GA), soman (GD), cyclosarin (GF), VX, VR (Russian VX), diisopropyl-fluorophosphate, azinphosmethyl, chlorpyrifos, diazinon, dichlorvos, dimethoate, ethephon, malathion, methamidophos, naled, oxydemetonmethyl, parathion, fenthion, ethion, echothiophate, isofluro-phate, trichlorfon, and/or tribufos.

In some embodiments, the intranasal dry powder composition is sufficient to improve respiratory function and breathing in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to reduce bronchorrhea and bronchospasms in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to decrease excess sweating and salivation, seizures, and paralysis in the patient within 60 minutes, 50 minutes, 40 minutes, 30 minutes, 20 minutes, 10 minutes, 5 minutes, 3 minutes, 2 minutes, or 1 minute after administration.

Chemical warfare nerve agents and organophosphates work, in part, through irreversible inhibition of acetylcholinesterase, which affects the circulatory, respiratory, and neurological systems. This inhibition of acetylcholinesterase leads to accumulation of acetylcholine. Acetylcholine acts upon two receptor subtypes, the muscarinic and nicotinic receptors. Each receptor can mediate different adverse effects from acetylcholine excess (Table 1). For example, muscarinic effects can include bradycardia and bronchospasm and nicotinic effects may result in weakness. Most fatalities result from acute respiratory failure, which presents the opportunity for treatment. In addition, hypotension may often occur, which may be secondary to decreased sympathetic outflow from the medulla (sympatholysis). Vasoactive agents (e.g., epinephrine) are useful in these situations and where cardiorespiratory support is needed. Benzodiazepines are useful for seizure prevention and control when needed.

TABLE 1

| Clinical effects of organophosphate exposure | |
| --- | --- |
| Anatomic Site of Action | Signs and Symptoms |
| Muscarinic effects | |
| Sweat glands | Sweating |
| Pupils | Constricted pupils |
| Lacrimal glands | Lacrimation |
| Salivary glands | Excessive salivation |
| Bronchial tree | Wheezing |
| Gastrointestinal | Cramps, vomiting, diarrhea, tenesmus |
| Cardiovascular | Bradycardia, decrease in blood pressure |
| Ciliary body | Blurred vision |
| Bladder | Urinary incontinence |
| Nicotinic effects | |
| Striated muscle | Fasciculations, cramps, weakness, twitching, paralysis, respiratory embarrassment, cyanosis, arrest |
| Sympathetic ganglia | Tachycardia, elevated blood pressure |
| Central nervous system effects | Anxiety, restlessness, ataxia, convulsions, insomnia, coma, absent reflexes, Cheyne-Stokes respirations, respiratory and circulatory depression |

Activation of the muscarinic receptors results in series of symptoms that can be referred to by the mnemonic DUMBELS: diaphoresis and diarrhea, urination, miosis, bronchorrhea and bronchospasm, emesis, lacrimation, salivation and secretion. The most critical aspect related to chemical exposure is respiratory failure, which is highlighted by bronchorrhea and bronchoconstriction and can result in life-threatening pulmonary edema. Respiratory failure is the leading cause of death from nerve agents.

Activation of the nicotinic receptors can lead to a number of symptoms as highlighted in Table 1 and includes significant effects on the cardiovascular system. In one embodiment, these effects include bradycardia and hypotension. Additionally or alternatively, these cardiovascular effects are operable to contribute to death.

Also provided herein are methods for treating patients including applying to a mucosal surface(s) of the nasal cavity or cavities of an individual (e.g., the mucosal surfaces of the anterior regions of the nose, the frontal sinus, the maxillary sinuses, and/or on each of the mucosal surfaces which overlie the turbinates covering the conchas) any of the pharmaceutical compositions or dosage units herein by administering a nasal anticholinergic agent (e.g., atropine) loading dose (e.g., the amount of atropine administered nasally which results in the systemic blood bioequivalent of intravenously (IV), intramuscularly (IM) or subcutaneously (SQ) administered atropine for example, for the 2.1 mg atropine in DUODOTE®). In a related aspect, the method of treating a patient with nerve agent exposure in need of treatment from a nasal loading dose of about 1 mg to about 100 mg of an anticholinergic agent (e.g., atropine). In one embodiment, a method is employed to include as part of the packaging a cholinesterase reactivator (e.g., pralidoxime chloride, obidoxime chloride). For example, in some embodiments, a single dose of the cholinesterase reactivator is about 1 mg to about 1000 mg. In some embodiments, a single dose of the cholinesterase reactivator is about 300 mg or about 600 mg. In some embodiments, an acceptable carrier mixture is included in about 1 to about 50 mg, for example about 10 to about 30 mg, about 15 to about 20 mg, and optionally, an agent that reduces mucosal transit time, an agent that increases mucosal absorption and/or adhesion, an agent that enhances mucosal transport, (or the enantiomers, diastereoisomers, racemates, and the salts of such compounds with pharmaceutically acceptable counterions), wherein the amounts are operable to be synergistic for the treatment of respiratory distress. When used in such low doses, compositions herein are operable to provide a sufficiently high peak blood plasma concentration of an anticholinergic agent (e.g., atropine), to blood levels at least 10-20 ng/ml within about: 60, 50, 40, 30, 20, 15, 10, 5, or 3 minutes, to be effective in the treatment or reducing the symptoms (e.g., of nerve agent exposure).

In another aspect, the methods, kits, compositions doses or products herein are useful for treating patients. In some embodiments, the patient is not in a hospital. In some embodiments, the patient is in a hospital. In some embodiments, the patient is in a combat setting. In some embodiments, the patient is in a civil emergency setting. In one embodiment, the patient is in or near an ambulance. In some embodiments, the patient has a wound.

Advantageously, the dry powder compositions and/or dosage units provided in the present invention are given intranasally, and do not require IV infusion. Placement of an IV line during an emergency or during a combat situation is time consuming and difficult given the environment and nature of the emergency (e.g., organophosphate exposure), which includes attempting IV placement in patients experiencing a seizure, respiratory collapse, and/or circulatory collapse. Additionally, the dry powder compositions and/or dosage units provided are not via an autoinjector, which is subject to failure due to obesity and/or misuse. Further, this allows for untrained and/or non-medical personnel to attend to the patient (e.g., troops in combat). Advantageously, the nasal delivery device has a substantially smaller form factor than an autoinjector, which allows for easier incorporation in field kits and easier for an individual to carry at all times. There are no needles, glass, or aqueous dosage forms. Further, the dry powder compositions of the present invention are a more stable product and are operable to withstand a wider range of environmental conditions than conventional aqueous preparations.

Anticonvulsive Agents

In one embodiment, the at least one active pharmaceutical ingredient includes at least one anticonvulsive agent. The at least one anticonvulsive agent includes, but is not limited to, an aldehyde (e.g., paraldehyde), an aromatic allylic alcohol (e.g., stiripentol), a barbiturate (e.g., phenobarbital, methylphenobarbital, barbexaclone), a benzodiazepine (e.g., diazepam, midazolam, lorazepam, nitrazepam, temazepam, nimetazepam, clobazam, clonazepam, clorazepate), a bromide (e.g., potassium bromide), a carbamate (e.g., felbamate), a carboxamide (e.g., carbamazepine, oxcarbazepine, eslicarbazepine acetate), a fatty acid (e.g., vigabatrin, prograbide, tiagabine, valproic acid, sodium valproate, divalproex sodium), a fructose derivative (e.g., topiramate), a hydantoin (e.g., ethotoin, phenytoin, mephenytoin, fosphenytoin), an oxazolidinedione (e.g., paramethadoine, trimethadione, ethadione), a propionate (e.g., beclamide), a pyrimidinedione (e.g., primidone), a pyrrolidine (e.g., brivaracetam, etiracetam, levetiracetam, sletracetam), a succinimide (e.g., ethosuximide, phensuximide, mesuximide), a sulfonamide (e.g., acetazolamide, sultiame, methazolamide, zonisamide), a triazine (e.g., lamotrigine), a urea (e.g., pheneturide, phenacemide), and/or a valproylamide (e.g., valpromide, valoctamide). In one embodiment, the at least one anticonvulsive agent includes, but is not limited to, diazepam, lorazepam, midazolam, clonazepam, temazepam, flunitrazepam, nitrazepam, clobazam, triazolam, alprazolam, zolpidem, eszopiclone, perampanel, stiripentol, pyridoxine, chlordiazepoxide, brotizolam, clorazepam, demoxazepam, flumazenil, flurazepam, halazepam, nordazepam, medazepam, oxazepam, midazepam, prazepam, quazepam, loprazolam, or a pharmaceutically acceptable salt thereof. In one embodiment, the at least one anticonvulsive agent has agonist activity at the benzodiazepine site on the GABA receptor. In one embodiment, the at least one anticonvulsive agent is a single anticonvulsive agent.

In one embodiment, a single dose of the at least one anticonvulsive agent is about 0.1 mg to about 30 mg. In one embodiment, an amount of the at least one anticonvulsive agent is at least about: 0.1 mg, 0.25 mg, 0.5 mg, 1.0 mg, 2.0 mg, 5.0 mg, 10 mg, 15 mg, 20 mg, 25 mg, or 30 mg. In another embodiment, the amount of the at least one anticonvulsive agent is at least about 0.1 mg to 0.5 mg, 0.5 mg to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, 9.0 to 10.0 mg, 10 to 20 mg, or 20 to 30 mg. In yet another embodiment, the amount of the at least one anticonvulsive agent is about: 0.15, 0.3, 0.5, 0.75, 1, 1.5, 2, 3, 4, 5, 6, 7, 8, 9, 10, 15, 20, 25, or 3 mg. In one embodiment, a single dose of the at least one anticonvulsive agent is about: 0.15, 0.3, 0.5, 0.75, 1, 1.5, 2, 3, 4, 5, 6, 7, 8, 9, 10, 15, 20, 25, or 30 mg. In one embodiment, a single dose of the at least one anticonvulsive agent is about 0.75 mg. In another embodiment, a single dose of the at least one anticonvulsive agent is about 1.5 mg. In another embodiment, a single dose of the at least one anticonvulsive agent is about 3.0 mg.

In one embodiment, a dose of the at least one anticonvulsive agent is adjusted according to a weight of a patient. In one embodiment, the dose of the at least one anticonvulsive agent is adjusted according to the weight of the patient at an increment of at least 0.01 mg/kg. In another embodiment, a dose of the at least one anticonvulsive agent is operable to be repeated a number of times if patient symptoms fail to improve. For example, administration of a dose of the at least one anticonvulsive agent is repeated, e.g., every 5 to 20 minutes as necessary.

In some embodiments, the at least one anticonvulsive agent is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, e.g., based on the weight of the dry powder formulation and/or the dose. For example, the at least one anticonvulsive agent is about 4%, about 7.5%, or about 15% w/w of the weight of the composition. In one embodiment, the at least one anticonvulsive agent is present in an amount of at least about: 0.25% w/w, 1% w/w, 5% w/w, 10% w/w, 20% w/w, 30% w/w, 40% w/w, or 50% w/w based on the weight of the dry powder formulation and/or the dose. In yet another embodiment, the at least one anticonvulsive agent (e.g., diazepam) is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the dry powder formulation and/or the dose.

In one embodiment, the dry powder formulations herein increase the blood concentration of the at least one anticonvulsive agent (e.g., diazepam) to about 0.2-2.5 µg/mL. In one embodiment, the dry powder formulations herein increase the blood concentration of the at least one anticonvulsive agent (e.g., diazepam) by about 0.05, 0.1, 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, or 4.0 µg/mL.

In one embodiment, the dry powder formulation disclosed herein, when administered to a patient, reaches a maximal blood concentration of the at least one anticonvulsive agent (e.g., diazepam) in less than about 60 minutes ($T_{max}$) after administration. In one embodiment, the dry powder formulation, when administered to a patient, reaches a maximal blood concentration ($T_{max}$) of the at least one anticonvulsive agent in less than about 60, 50, 40, 30, 20, 15, 10, 5, or 3 minutes ($T_{max}$) after administration. In one embodiment, the dry powder formulation, when administered to a patient, reaches a maximal blood concentration ($T_{max}$) of the at least one anticonvulsive agent in less than about 30 minutes after administration. In one embodiment, the dry powder formulation, when administered to a patient, reaches a mean $AUC_{(0-180\ minutes)}$ of the at least one anticonvulsive agent which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected at least one anticonvulsive agent. For example, the at least one anticonvulsive agent includes a first anticonvulsive agent and a second anticonvulsive agent. The first anticonvulsive agent is at least 20%, 30%, 40%50%, 60%, 70%, 80%, 90%, 100%, 110%, 120%, 130%, 140%, or 150% of the mean $AUC_{(0-180\ minutes)}$ of an IV, IM, or SQ injected first anticonvulsive agent, and the second anticonvulsive agent is at least 20%, 30%, 40%50%, 60%, 70%, 80%, 90%, 100%, 110%, 120%, 130%, 140%, or 150% of the mean $AUC_{(0-180\ minutes)}$ of an IV, IM, or SQ injected second anticonvulsive agent. In one embodiment, the dry powder formulation, when administered to a patient, reaches a mean $AUC_{(0-\infty)}$ of the anticonvulsive agent which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected at least one anticonvulsive agent. For example, the at least one anticonvulsive agent includes a first anticonvulsive agent and a second anticonvulsive agent. The first anticonvulsive agent is at least 20%, 30%, 40%50%, 60%, 70%, 80%, 90%, 100%, 110%, 120%, 130%, 140%, or 150% of the mean $AUC_{(0-\infty)}$ of an IV, IM, or SQ injected first anticonvulsive agent, and the second anticonvulsive agent is at least 20%, 30%, 40%50%, 60%, 70%, 80%, 90%, 100%, 110%, 120%, 130%, 140%, or 150% of the mean $AUC_{(0-\infty)}$ of an IV, IM, or SQ injected second anticonvulsive agent. In one embodiment, the IV, IM, or SQ injected at least one anticonvulsive agent contains 0.25 mg, 0.5 mg, 1 mg, 2 mg, 2.1 mg, 3 mg, 4 mg, 5 mg, 6 mg, 7 mg, 8 mg, 9 mg, 10 mg, 15 mg, 20 mg, 25 mg, or 30 mg of each of the at least one anticonvulsive agent. For example, the dry powder formulation when administered to a patient, reaches a mean $AUC_{(0-180\ minutes)}$ of the at least one anticonvulsive agent that is at least 80% of the mean $AUC_{(0-180\ minutes)}$ of an equivalent IV injected at least one anticonvulsive agent (e.g., 5 mg IV injected at least one anticonvulsive agent). For example, the at least one anticonvulsive agent includes a first anticonvulsive agent and a second anticonvulsive agent. The first anticonvulsive agent reaches a mean $AUC_{(0-180\ minutes)}$ that is at least 80% of the mean $AUC_{(0-180\ minutes)}$ of an equivalent IV injected first anticonvulsive agent (e.g., 5 mg IV injected at least one first anticonvulsive agent), and the second anticonvulsive agent reaches a mean $AUC_{(0-180\ minutes)}$ that is at least 80% of the mean $AUC_{(0-180\ minutes)}$ of an equivalent IV injected second anticonvulsive agent (e.g., 5 mg IV injected at least one second anticonvulsive agent). In another embodiment, the dry powder formulation, when administered to a patient, reaches a mean $AUC_{(0-\infty)}$ of the at least one anticonvulsive agent that is at least 80% of the mean $AUC_{(0-\infty)}$ of an equivalent IV injected at least one anticonvulsive agent (e.g., 5 mg IV injected at least one anticonvulsive agent). For example, the at least one anticonvulsive agent includes a first anticonvulsive agent and a second anticonvulsive agent. The first anticonvulsive agent reaches a mean $AUC_{(0-\infty)}$ that is at least 80% of the mean $AUC_{(0-\infty)}$ of an equivalent IV injected first anticonvulsive agent (e.g., 5 mg IV injected at least one first anticonvulsive agent), and the second anticonvulsive agent reaches a mean $AUC_{(0-\infty)}$ that is at least 80% of the mean $AUC_{(0-\infty)}$ of an equivalent IV injected second anticonvulsive agent (e.g., 5 mg IV injected at least one second anticonvulsive agent).

In one embodiment, the dry powder formulation and/or the dose is operable to raise the blood concentration of one or more of the at least one anticonvulsive agent (e.g., diazepam) to about 2 µg/mL within about 3 minutes to about 60 minutes (e.g., about: 60, 50, 40, 30, 20, 15, 10, 5, or 3 minutes), or about 10 minutes to about 15 minutes (e.g., about: 10, 11, 12, 13, 14, or 15 minutes) of intranasal administration. In one embodiment, the dry powder formulation and/or the dose is operable to increase the blood concentration of one or more of the at least one anticonvulsive agent (e.g., diazepam) by about 2 µg/mL in about 10 minutes to about 15 minutes (e.g., about: 10, 11, 12, 13, 14, or 15 minutes). Alternatively, the dry powder formulation and/or the dose is operable to increase the blood concentration of one or more of the at least one anticonvulsive agent (e.g., diazepam) by about 2 µg/mL in about 3 to about 60 minutes (e.g., about: 60, 50, 40, 30, 20, 15, 10, 5, or 3 minutes).

In a preferred embodiment, a single dose of the at least one anticonvulsive agent in the dry powder formulation and/or the dose given intranasally is bioequivalent (for example, in terms of peripheral blood levels, systemic exposure of the at least one anticonvulsive agent) to an intravenously (IV), intramuscularly (IM) or subcutaneously (SQ) injected at least one anticonvulsive agent. For example, in one embodiment, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Diazepam

In one embodiment, the at least one anticonvulsive agent is diazepam. In one embodiment, a single dose of the diazepam is about 0.1 mg to about 30 mg. In one embodiment, an amount of the diazepam is at least about: 0.1 mg, 0.25 mg, 0.5 mg, 1.0 mg, 2.0 mg, 5.0 mg, 10 mg, 15 mg, 20 mg, 25 mg, or 30 mg. In another embodiment, the amount of the diazepam is at least about 0.1 mg to 0.5 mg, 0.5 mg to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, 9.0 to 10.0 mg, 10 to 20 mg, or 20 to 30 mg. In yet another embodiment, the amount of the diazepam is about: 0.15, 0.3, 0.5, 0.75, 1, 1.5, 2, 3, 4, 5, 6, 7, 8, 9, 10, 15, 20, 25, or 3 mg. In one embodiment, a single dose of the diazepam is about: 0.15, 0.3, 0.5, 0.75, 1, 1.5, 2, 3, 4, 5, 6, 7, 8, 9, 10, 15, 20, 25, or 30 mg. In one embodiment, a single dose of the diazepam is about 0.75 mg. In another embodiment, a single dose of the diazepam is about 1.5 mg. In another embodiment, a single dose of the diazepam is about 3.0 mg.

In one embodiment, a dose of the diazepam is adjusted according to a weight of a patient. In one embodiment, the dose of the diazepam is adjusted according to the weight of the patient at an increment of at least 0.01 mg/kg. In another embodiment, a dose of the diazepam is operable to be repeated a number of times if patient symptoms fail to improve. For example, administration of a dose of the diazepam is repeated, e.g., every 5 to 20 minutes as necessary.

In some embodiments, the diazepam is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, e.g., based on the weight of the dry powder formulation and/or the dose. For example, the diazepam is about 4%, about 7.5%, or about 15% w/w of the weight of the composition. In one embodiment, the diazepam is present in an amount of at least about: 0.25% w/w, 1% w/w, 5% w/w, 10% w/w, 20% w/w, 30% w/w, 40% w/w, or 50% w/w based on the weight of the dry powder formulation and/or the dose. In yet another embodiment, the diazepam is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the dry powder formulation and/or the dose.

In one embodiment, the dry powder formulations herein increase the blood concentration of the diazepam to about 0.2-2.5 µg/mL. In one embodiment, the dry powder formulations herein increase the blood concentration of the diazepam by about 0.05, 0.1, 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, or 4.0 µg/mL.

In one embodiment, the dry powder formulation disclosed herein, when administered to a patient, reaches a maximal blood concentration of the diazepam in less than about 60 minutes ($T_{max}$) after administration. In one embodiment, the dry powder formulation, when administered to a patient, reaches a maximal blood concentration ($T_{max}$) of the diazepam in less than about 60, 50, 40, 30, 20, 15, 10, 5, or 3 minutes ($T_{max}$) after administration. In one embodiment, the dry powder formulation, when administered to a patient, reaches a maximal blood concentration ($T_{max}$) of the diazepam in less than about 30 minutes after administration. In one embodiment, the dry powder formulation, when administered to a patient, reaches a mean $AUC_{(0-180\ minutes)}$ of the diazepam which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected diazepam. In one embodiment, the dry powder formulation, when administered to a patient, reaches a mean $AUC_{(0-\infty)}$ of the diazepam which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected diazepam. In one embodiment, the IV, IM, or SQ injected diazepam contains 0.25 mg, 0.5 mg, 1 mg, 2 mg, 2.1 mg, 3 mg, 4 mg, 5 mg, 6 mg, 7 mg, 8 mg, 9 mg, 10 mg, 15 mg, 20 mg, 25 mg, or 30 mg. For example, the dry powder formulation when administered to a patient, reaches a mean $AUC_{(0-180\ minutes)}$ of the diazepam that is at least 80% of the mean $AUC_{(0-180\ minutes)}$ of an equivalent IV injected diazepam (e.g., 5 mg IV injected diazepam). In another embodiment, the dry powder formulation, when administered to a patient, reaches a mean $AUC_{(0-\infty)}$ of the diazepam that is at least 80% of the mean $AUC_{(0-\infty)}$ of an equivalent IV injected diazepam (e.g., 5 mg IV injected diazepam).

In one embodiment, the dry powder formulation and/or the dose is operable to raise the blood concentration of the diazepam to about 2 µg/mL within about 3 minutes to about 60 minutes (e.g., about: 60, 50, 40, 30, 20, 15, 10, 5, or 3 minutes), or about 10 minutes to about 15 minutes (e.g., about: 10, 11, 12, 13, 14, or 15 minutes) of intranasal administration. In one embodiment, the dry powder formulation and/or the dose is operable to increase the blood concentration of the diazepam by about 2 µg/mL in about 10 minutes to about 15 minutes (e.g., about: 10, 11, 12, 13, 14, or 15 minutes). Alternatively, the dry powder formulation and/or the dose is operable to increase the blood concentration of the diazepam by about 2 µg/mL in about 3 to about 60 minutes (e.g., about: 60, 50, 40, 30, 20, 15, 10, 5, or 3 minutes).

In a preferred embodiment, a single dose of the diazepam in the dry powder formulation and/or the dose given intranasally is bioequivalent (for example, in terms of peripheral blood levels, systemic exposure of the diazepam) to an intravenously (IV), intramuscularly (IM) or subcutaneously (SQ) injected diazepam. For example, in one embodiment, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Lorazepam

In one embodiment, the at least one anticonvulsive agent is lorazepam. In one embodiment, a single dose of the lorazepam is about 0.1 mg to about 30 mg. In one embodiment, an amount of the lorazepam is at least about: 0.1 mg, 0.25 mg, 0.5 mg, 1.0 mg, 2.0 mg, 5.0 mg, 10 mg, 15 mg, 20 mg, 25 mg, or 30 mg. In another embodiment, the amount of the lorazepam is at least about 0.1 mg to 0.5 mg, 0.5 mg to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, 9.0 to 10.0 mg, 10 to 20 mg, or 20 to 30 mg. In yet another embodiment, the amount of the lorazepam is about: 0.15, 0.3, 0.5, 0.75, 1, 1.5, 2, 3, 4, 5, 6, 7, 8, 9, 10, 15, 20, 25, or 3 mg. In one embodiment, a single dose of the lorazepam is about: 0.15, 0.3, 0.5, 0.75, 1, 1.5, 2, 3, 4, 5, 6, 7, 8, 9, 10, 15, 20, 25, or 30 mg. In one embodiment, a single dose of the lorazepam is about 0.75 mg. In another embodiment, a single dose of the lorazepam is about 1.5 mg. In another embodiment, a single dose of the lorazepam is about 3.0 mg.

In one embodiment, a dose of the lorazepam is adjusted according to a weight of a patient. In one embodiment, the dose of the lorazepam is adjusted according to the weight of the patient at an increment of at least 0.01 mg/kg. In another embodiment, a dose of the lorazepam is operable to be repeated a number of times if patient symptoms fail to improve. For example, administration of a dose of the lorazepam is repeated, e.g., every 5 to 20 minutes as necessary.

In some embodiments, the lorazepam is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, e.g., based on the weight of the dry powder formulation and/or the dose. For example, the lorazepam is about 4%, about 7.5%, or about 15% w/w of the weight of the composition. In one embodiment, the lorazepam is present in an amount of at least about: 0.25% w/w, 1% w/w, 5% w/w, 10% w/w, 20% w/w, 30% w/w, 40% w/w, or 50% w/w based on the weight of the dry powder formulation and/or the dose. In yet another embodiment, the lorazepam is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the dry powder formulation and/or the dose.

In one embodiment, the dry powder formulations herein increase the blood concentration of the lorazepam to about 0.2-2.5 µg/mL. In one embodiment, the dry powder formulations herein increase the blood concentration of the lorazepam by about 0.5, 0.1, 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, or 4.0 µg/mL.

In one embodiment, the dry powder formulation disclosed herein, when administered to a patient, reaches a maximal blood concentration of the lorazepam in less than about 60 minutes ($T_{max}$) after administration. In one embodiment, the dry powder formulation, when administered to a patient, reaches a maximal blood concentration ($T_{max}$) of the lorazepam in less than about 60, 50, 40, 30, 20, 15, 10, 5, or 3 minutes ($T_{max}$) after administration. In one embodiment, the dry powder formulation, when administered to a patient, reaches a maximal blood concentration ($T_{max}$) of the lorazepam in less than about 30 minutes after administration. In one embodiment, the dry powder formulation, when administered to a patient, reaches a mean $AUC_{(0-180\ minutes)}$ of the lorazepam which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected lorazepam. In one embodiment, the dry powder formulation, when administered to a patient, reaches a mean $AUC_{(0-\infty)}$ of the anticonvulsive agent which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected lorazepam. In one embodiment, the IV, IM, or SQ injected lorazepam contains 0.25 mg, 0.5 mg, 1 mg, 2 mg, 2.1 mg, 3 mg, 4 mg, 5 mg, 6 mg, 7 mg, 8 mg, 9 mg, 10 mg, 15 mg, 20 mg, 25 mg, or 30 mg. For example, the dry powder formulation when administered to a patient, reaches a mean $AUC_{(0-180\ minutes)}$ of the lorazepam that is at least 80% of the mean $AUC_{(0-180\ minutes)}$ of an equivalent IV injected lorazepam (e.g., 5 mg IV injected lorazepam). In another embodiment, the dry powder formulation, when administered to a patient, reaches a mean $AUC_{(0-\infty)}$ of the lorazepam that is at least 80% of the mean $AUC_{(0-\infty)}$ of an equivalent IV injected lorazepam (e.g., 5 mg IV injected lorazepam).

In one embodiment, the dry powder formulation and/or the dose is operable to raise the blood concentration of the lorazepam to about 2 µg/mL within about 3 minutes to about 60 minutes (e.g., about: 60, 50, 40, 30, 20, 15, 10, 5, or 3 minutes), or about 10 minutes to about 15 minutes (e.g., about: 10, 11, 12, 13, 14, or 15 minutes) of intranasal administration. In one embodiment, the dry powder formulation and/or the dose is operable to increase the blood concentration of the lorazepam by about 2 µg/mL in about 10 minutes to about 15 minutes (e.g., about: 10, 11, 12, 13, 14, or 15 minutes). Alternatively, the dry powder formulation and/or the dose is operable to increase the blood concentration of the lorazepam by about 2 µg/mL in about 3 to about 60 minutes (e.g., about: 60, 50, 40, 30, 20, 15, 10, 5, or 3 minutes).

In a preferred embodiment, a single dose of the lorazepam in the dry powder formulation and/or the dose given intranasally is bioequivalent (for example, in terms of peripheral blood levels, systemic exposure of the lorazepam) to an intravenously (IV), intramuscularly (IM) or subcutaneously (SQ) injected lorazepam. For example, in one embodiment, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Midazolam

In one embodiment, the at least one anticonvulsive agent is midazolam. In one embodiment, a single dose of the midazolam is about 0.1 mg to about 30 mg. In one embodiment, an amount of the midazolam is at least about: 0.1 mg, 0.25 mg, 0.5 mg, 1.0 mg, 2.0 mg, 5.0 mg, 10 mg, 15 mg, 20 mg, 25 mg, or 30 mg. In another embodiment, the amount of the midazolam is at least about 0.1 mg to 0.5 mg, 0.5 mg to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, 9.0 to 10.0 mg, 10 to 20 mg, or 20 to 30 mg. In yet another embodiment, the amount of the midazolam is about: 0.15, 0.3, 0.5, 0.75, 1, 1.5, 2, 3, 4, 5, 6, 7, 8, 9, 10, 15, 20, 25, or 3 mg. In one embodiment, a single dose of the midazolam is about: 0.15, 0.3, 0.5, 0.75, 1, 1.5, 2, 3, 4, 5, 6, 7, 8, 9, 10, 15, 20, 25, or 30 mg. In one embodiment, a single dose of the midazolam is about 0.75 mg. In another embodiment, a single dose of the midazolam is about 1.5 mg. In another embodiment, a single dose of the midazolam is about 3.0 mg.

In one embodiment, a dose of the midazolam is adjusted according to a weight of a patient. In one embodiment, the dose of the midazolam is adjusted according to the weight of the patient at an increment of at least 0.01 mg/kg. In another embodiment, a dose of the midazolam is operable to be repeated a number of times if patient symptoms fail to improve. For example, administration of a dose of the midazolam is repeated, e.g., every 5 to 20 minutes as necessary.

In some embodiments, the midazolam is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, e.g., based on the weight of the dry powder formulation and/or the dose. For example, the midazolam is about 4%, about 7.5%, or about 15% w/w of the weight of the composition. In one embodiment, the midazolam is present in an amount of at least about: 0.25% w/w, 1% w/w, 5% w/w, 10% w/w, 20% w/w, 30% w/w, 40% w/w, or 50% w/w based on the weight of the dry powder formulation and/or the dose. In yet another embodiment, the midazolam is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the dry powder formulation and/or the dose.

In one embodiment, the dry powder formulations herein increase the blood concentration of the midazolam to about 0.2-2.5 μg/mL. In one embodiment, the dry powder formulations herein increase the blood concentration of the midazolam by about 0.05, 0.1, 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, or 4.0 μg/mL.

In one embodiment, the dry powder formulation disclosed herein, when administered to a patient, reaches a maximal blood concentration of the midazolam in less than about 60 minutes ($T_{max}$) after administration. In one embodiment, the dry powder formulation, when administered to a patient, reaches a maximal blood concentration ($T_{max}$) of the midazolam in less than about 60, 50, 40, 30, 20, 15, 10, 5, or 3 minutes ($T_{max}$) after administration. In one embodiment, the dry powder formulation, when administered to a patient, reaches a maximal blood concentration ($T_{max}$) of the midazolam in less than about 30 minutes after administration. In one embodiment, the dry powder formulation, when administered to a patient, reaches a mean $AUC_{(0-180 \ minutes)}$ of the midazolam which is at least 20%, 30%, 40%50%, 60%, 70%, 80%, 90%, 100%, 110%, 120%, 130%, 140%, or 150% of the mean $AUC_{(0-180 \ minutes)}$ of an equivalent IV, IM, or SQ injected midazolam. In one embodiment, the dry powder formulation, when administered to a patient, reaches a mean $AUC_{(0-\infty)}$ of the anticonvulsive agent which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected midazolam. In one embodiment, the IV, IM, or SQ injected midazolam contains 0.25 mg, 0.5 mg, 1 mg, 2 mg, 2.1 mg, 3 mg, 4 mg, 5 mg, 6 mg, 7 mg, 8 mg, 9 mg, 10 mg, 15 mg, 20 mg, 25 mg, or 30 mg. For example, the dry powder formulation when administered to a patient, reaches a mean $AUC_{(0-180 \ minutes)}$ of the midazolam that is at least 80% of the mean $AUC_{(0-180 \ minutes)}$ of an equivalent IV injected midazolam (e.g., 5 mg IV injected midazolam). In another embodiment, the dry powder formulation, when administered to a patient, reaches a mean $AUC_{(0-\infty)}$ of the midazolam that is at least 80% of the mean $AUC_{(0-\infty)}$ of an equivalent IV injected midazolam (e.g., 5 mg IV injected midazolam).

In one embodiment, the dry powder formulation and/or the dose is operable to raise the blood concentration of the midazolam to about 2 μg/mL within about 3 minutes to about 60 minutes (e.g., about: 60, 50, 40, 30, 20, 15, 10, 5, or 3 minutes), or about 10 minutes to about 15 minutes (e.g., about: 10, 11, 12, 13, 14, or 15 minutes) of intranasal administration. In one embodiment, the dry powder formulation and/or the dose is operable to increase the blood concentration of the midazolam by about 2 μg/mL in about 10 minutes to about 15 minutes (e.g., about: 10, 11, 12, 13, 14, or 15 minutes). Alternatively, the dry powder formulation and/or the dose is operable to increase the blood concentration of the midazolam by about 2 μg/mL in about 3 to about 60 minutes (e.g., about: 60, 50, 40, 30, 20, 15, 10, 5, or 3 minutes).

In a preferred embodiment, a single dose of the midazolam in the dry powder formulation and/or the dose given intranasally is bioequivalent (for example, in terms of peripheral blood levels, systemic exposure of the midazolam) to an intravenously (IV), intramuscularly (IM) or subcutaneously (SQ) injected midazolam. For example, in one embodiment, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one active pharmaceutical ingredient includes the at least one anticonvulsive agent. In one embodiment, the at least one active pharmaceutical ingredient further includes at least one anticholinergic agent (e.g., atropine), at least one cholinesterase reactivator agent (e.g., pralidoxime, obidoxime), at least one vasoactive agent (e.g., epinephrine, vasopressin, phenylephrine, or a salt thereof), at least one vasodilator (e.g., phentolamine, prazosin, doxazosin, bosentan, a hydralazine and nitrate combination, a PDE3 inhibitor (e.g., milrinone), a PD5 inhibitor (e.g., sildenafil)), and/or at least one catechol-o-methyl transferase (COMT) inhibitor (e.g., entacapone). Additional details regarding the at least one anticholinergic agent, at least one cholinesterase reactivator agent, the at least one vasoactive agent, the at least one anticonvulsive agent, the at least one vasodilator, and/or the at least one COMT inhibitor are included in U.S. patent application Ser. No. 17/349,507 and U.S. Provisional Patent Application No. 63/209,221, each which is incorporated herein by reference in its entirety.

Method of Treatment

Provided herein are methods of treating a patient by intranasally administrating the dry powder composition disclosed herein. Also provided herein are methods of treating a patient by using the kit disclosed herein.

The methods, kits, compositions doses or products herein are useful for treating patients. In some instances, the patient has risk for seizures, signs of seizure, or status epilepticus. The compositions described herein are operable to provide a fast onset time and are suitable for intranasal use.

In some embodiments, the intranasal dry powder composition is operable to prevent, limit, or eliminate seizure activity in the patient within 60 minutes, 50 minutes, 40 minutes, 30 minutes, 20 minutes, 10 minutes, 5 minutes, 3 minutes, 2 minutes, or 1 minute after administration. In another embodiment, the intranasal dry powder composition is operable to increase a duration between a first seizure and a second seizure.

Also provided herein are methods for treating patients by applying to a mucosal surface(s) of the nasal cavity or cavities of an individual (e.g., the mucosal surfaces of the anterior regions of the nose, the frontal sinus, the maxillary sinuses, and/or on each of the mucosal surfaces which overlie the turbinates covering the conchas) any of the pharmaceutical compositions or dosage units herein by administering a nasal anticonvulsive agent (e.g., diazepam) loading dose (e.g., the amount of diazepam administered nasally which results in the systemic blood bioequivalent of intravenously (IV), intramuscularly (IM) or subcutaneously (SQ) administered diazepam). In a related aspect, the method of treating a patient in need of treatment from a nasal loading dose of about 0.1 mg to about 20 mg of an anticonvulsive agent (e.g., diazepam).

In one embodiment, the at least one anticonvulsive agent is administered following at least one aura event. The at least one aura event includes audible, visual, olfactory, and/or tactile sensations that precede a seizure. Advantageously, providing the at least one anticonvulsive agent during the at least one aura prevents or reduces the severity of the seizure.

In another aspect, the methods, kits, compositions doses or products herein are useful for treating patients. In some embodiments, the patient is not in a hospital. In some embodiments, the patient is in a hospital. In some embodiments, the patient is in a combat setting. In some embodiments, the patient is in a civil emergency setting. In one embodiment, the patient is in or near an ambulance. In some embodiments, the patient has a wound.

Advantageously, the dry powder compositions and/or dosage units provided in the present invention are given intranasally, and do not require IV infusion. Placement of an IV line during an emergency or during a combat situation is time consuming and difficult given the environment and nature of the emergency (e.g., organophosphate exposure), which includes attempting IV placement in patients experiencing a seizure, respiratory collapse, and/or circulatory collapse. Additionally, the dry powder compositions and/or dosage units provided are not via an autoinjector, which is subject to failure due to obesity and/or misuse. Further, this allows for untrained and/or non-medical personnel to attend to the patient (e.g., troops in combat). Advantageously, the nasal delivery device has a substantially smaller form factor than an autoinjector, which allows for easier incorporation in field kits and easier for an individual to carry at all times. There are no needles, glass, or aqueous dosage forms. Further, the dry powder compositions of the present invention are a more stable product and are operable to withstand a wider range of environmental conditions than conventional aqueous preparations.

Antidotes

In one embodiment, the at least one active pharmaceutical ingredient includes at least one antidote to at least one poison. The at least one antidote includes, but is not limited to, a 3-mercaptopyruvic acid (3-MP) prodrug (e.g., sulfanegen), a cobalt compound (e.g., dicobalt edetate), 4-dimethylaminophenol (4-DMAP), a vitamer (e.g., hydroxocobalamin), a nitrite (e.g., sodium nitrite), a thiosulfate (e.g., sodium thiosulfate), a steroid (e.g., ganaxolone), an α-amino-3-hydroxy-5-methyl-4-isoxazolepropionic acid (AMPA) receptor antagonist (e.g., teazampanel), a noncompetitive nicotinic antagonist (e.g., 1,1-(propane-1,3-diyl)bis (4-tert-butylpyridinium) diiodide), glucose, amyl nitrite, sodium nitrite, sodium thiosulfate, an anticholinergic agent (e.g., atropine), a cholinesterase reactivator agent (e.g., 2-PAM, obidoxime), and/or an anticonvulsive agent (e.g., diazepam). The at least one poison includes, but is not limited to an organophosphate and/or cyanide. The organophosphate includes, but is not limited to, an insecticide (e.g., malathion, parathion, diazinon, fenthion, dichlorvos, chlorpyrifos, ethion, trichlorfon), a nerve agent (e.g., soman, sarin, tabun, O-ethyl S-[2-(diisopropylamino) ethyl] methylphosphonothioate) (VX)), and/or an herbicide (e.g., tribufos, merphos). See, e.g., van Asselt D Z, Merkus F W, Russel F G, Hoefnagels W H. Nasal absorption of hydroxocobalamin in healthy elderly adults. Br J Clin Pharmacol. 1998; 45(1):83-86. doi: 10.1046/j.1365-2125.1998.00642.x, which is incorporated herein by reference in its entirety.

Antidotes are often given via intravenous (IV) infusion, which restricts use to healthcare professionals. This may delay treatment, especially when a victim is convulsing. Advantageously, the dry powder compositions and/or dosage units provided in the present invention are given intranasally, and do not require IV infusion. Placement of an IV line during an emergency or during a combat situation is time consuming and difficult given the environment and nature of the emergency (e.g., organophosphate exposure), which includes attempting IV placement in patients experiencing a seizure, respiratory collapse, and/or circulatory collapse. Additionally, the dry powder compositions and/or dosage units provided are not via an autoinjector, which is subject to failure due to obesity and/or misuse. Further, this allows for untrained and/or non-medical personnel to attend to the patient (e.g., troops in combat). Advantageously, the nasal delivery device has a substantially smaller form factor than an autoinjector, which allows for easier incorporation in field kits and easier for an individual to carry at all times. There are no needles, glass, or aqueous dosage forms. Further, the dry powder compositions of the present invention are a more stable product and are operable to withstand a wider range of environmental conditions than conventional aqueous preparations.

In one embodiment, a unit dosage of the at least one antidote ranges from about 2 mg to about 10 mg, for example about: 2-10 mg, of a composition. In another embodiment, the unit dosage of the at least one antidote is at least about: 0.5 mg to about 20 mg, of a composition. Administration of the compositions herein is operable to be repeated, e.g., every 5-20 minutes, as necessary. See, e.g., D. L. Seger and J. K. Loden, "Naloxone reversal of clonidine toxicity: dose, dose, dose," Clin. Toxicol., vol. 56, no. 10, pp. 873-879, October 2018, doi: 10.1080/15563650.2018.1450986, which is incorporated herein by reference in its entirety.

In some embodiments, the at least one antidote is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the at least one antidote is about 4%, about 7.5%, or about 15% w/w of the weight of the composition. In some embodiments, the at least one antidote is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the at least one antidote is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of one or more of the at least one antidote to about 4 ng/ml (e.g., 4.2 ng/ml).

In one embodiment, the compositions herein increase the blood concentration of one or more of the at least one antidote by about 1, 2, 3, 4, 5, 6, 7, 8, 9, 10, 11, 12, 13, 14, 15, 20, 25, 30, 35, 40, 45, or 50 ng/ml. See, e.g., I. Tylleskar, A. K. Skulberg, T. Nilsen, and S. Skarra, "Naloksonnesespray—biotilgjengelighet og opptaksmønster i en fase 1-studie," Tidsskr. den Nor. Laegeforening, vol. 139, no. 13, September 2019, doi: 10.4045/tidsskr. 19.0162, which is incorporated herein by reference in its entirety.

In some embodiments, the dry powder composition disclosed herein when administered to a patient, reaches a maximal blood concentration of the at least one antidote in less than about 60 minutes ($T_{max}$) after administration. In some embodiments, the dry powder composition when administered to a patient, reaches a maximal blood concentration ($T_{max}$) of the at least one antidote in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the at least one antidote in less than about 30 minutes after administration. In some embodiments, the dry powder composition when administered to a patient, reaches a mean area under the curve ($AUC_{(0-180\ minutes)}$) of the at least one antidote which is at least 20%, 30%, 40% 50%, 60%, 70%, 80%, 90%, 100%, 110%, 120%, 130%, 140%, or 150% of the mean $AUC_{(0-180\ minutes)}$ of an equivalent IV, IM, or SQ injected at least one antidote. In some embodiments, the dry powder composition when administered to a patient, reaches a mean $AUC_{(0-\infty)}$ of the at least one antidote which is at least 20%, 30%, 40% 50%, 60%, 70%, 80%, 90%, 100%, 110%, 120%, 130%, 140%, or 150% of the mean $AUC_{(0-\infty)}$ of an equivalent IV, IM, or SQ injected at least one antidote. In some embodiments, the equivalent IV, IM, or SQ injected at least one antidote contains about 1 mg to about 10 mg of the at least one antidote. For example, the dry powder composition when administered to a patient, reaches a mean $AUC_{(0-180\ minutes)}$ of the at least one antidote, which is at least 80% of the mean $AUC_{(0-180\ minutes)}$ of an equivalent IM injected at least one antidote (e.g., 1.6 mg IM injected at least one antidote, 2 mg IM injected at least one antidote). In another instance, the dry powder composition when administered to a patient, reaches a mean $AUC_{(0-\infty)}$ of the at least one antidote, which is at least 80% of the mean $AUC_{(0-\infty)}$ of an equivalent IM injected at least one antidote (e.g., 1.6 mg IM injected at least one antidote, 2 mg IM injected at least one antidote). See, e.g., (1) A. S. Cornelissen, S. D. Klaassen, T. van Groningen, S. Bohnert, and M. J. A. Joosen, "Comparative physiology and efficacy of atropine and scopolamine in sarin nerve agent poisoning," Toxicol. Appl. Pharmacol., vol. 396, June 2020, doi: 10.1016/j.taap.2020.114994; (2) D. L. Seger and J. K. Loden, "Naloxone reversal of clonidine toxicity: dose, dose, dose," Clin. Toxicol., vol. 56, no. 10, pp. 873-879, October 2018, doi: 10.1080/15563650.2018.1450986; and (3) K. Harris, C. B. Page, S. Samantray, L. Parker, A. J. A. Brier, and K. Z. Isoardi, "One single large intramuscular dose of naloxone is effective and safe in suspected heroin poisoning," EMA-Emerg. Med. Australas., vol. 32, no. 1, pp. 88-92, February 2020, doi: 10.1111/1742-6723.13344, each of which is incorporated herein by reference in its entirety.

In certain embodiments, the dry powder compositions and/or dosage units herein are operable to raise the blood concentration of the at least one antidote to about 4 ng/mL (e.g., about 0.5 ng/ml to about 8 ng/ml) within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the at least one antidote by about 4 ng/ml, for example about 2 to about 6 ng/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). See, e.g., R. McDonald et al., "Pharmacokinetics of concentrated naloxone nasal spray for opioid overdose reversal: Phase I healthy volunteer study," Addiction, vol. 113, no. 3, pp. 484-493, March 2018, doi: 10.1111/add. 14033, which is incorporated herein by reference in its entirety.

In another aspect, a single dose of the at least one antidote in the dry powder compositions and/or dosage units given intranasally is bioequivalent (for example, in terms of peripheral blood levels, systemic exposure of the at least one antidote) to an equivalent intravenously (IV), intramuscularly (IM) or subcutaneously (SQ) injected at least one antidote. For example, a single dose of the at least one antidote in the dry powder compositions and/or dosage units given intranasally is bioequivalent to an equivalent intravenously (IV), intramuscularly (IM) or subcutaneously (SQ) injected at least one antidote. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

In a further embodiment, the intranasal dry powder composition is present in amounts of up to 100 mg, for example about: 1 to 5 mg, 5 to 10 mg, 10 to 20 mg, 20 to 40 mg, 40 to 60 mg, 60 to 80 mg, or 80 to 100 mg. In some embodiments, the compositions herein are present in about: 1, 5, 10, 15, 20, 25, 30, 35, 40, 45, or 50 mg.

In one embodiment, the at least one active pharmaceutical ingredient includes the at least one antidote. In one embodiment, the at least one active pharmaceutical ingredient further includes at least one anticholinergic agent (e.g., atropine), at least one cholinesterase reactivator agent (e.g., pralidoxime, obidoxime), at least one anticonvulsive agent (e.g., diazepam, lorazepam, midazolam, clonazepam, temazepam, flunitrazepam, triazolam, alprazolam, zolpidem, eszopiclone, or a salt thereof), at least one vasoactive agent (e.g., epinephrine, vasopressin, phenylephrine, or a salt thereof), at least one vasodilator (e.g., phentolamine, prazosin, doxazosin, bosentan, a hydralazine and nitrate combination, a PDE3 inhibitor (e.g., milrinone), a PD5 inhibitor (e.g., sildenafil)), and/or at least one catechol-o-methyl transferase (COMT) inhibitor (e.g., entacapone). Additional details regarding the at least one anticholinergic agent, the at least one cholinesterase reactivator agent, the at least one anticonvulsive agent, the at least one vasoactive agent, the at least one vasodilator, and/or the at least one COMT inhibitor are included in U.S. patent application Ser. No. 17/349,507 and U.S. Provisional Patent Application No. 63/209,221, each which is incorporated herein by reference in its entirety. See also, e.g., Gundavarapu S, Zhuang J, Barrett E G, Xu F, Russell R G, Sopori M L. A critical role of acute bronchoconstriction in the mortality associated with high-dose sarin inhalation: effects of epinephrine and oxygen therapies. Toxicol Appl Pharmacol. 2014 Jan. 15; 274 (2):200-8. doi: 10.1016/j.taap.2013.11.007. Epub 2013 Nov. 19. PMID: 24269878, which is incorporated herein by reference in its entirety.

AMPA Receptor Antagonists

In one embodiment, the at least one antidote includes at least one AMPA receptor antagonist. The at least one AMPA receptor antagonist includes, but is not limited to, tezampanel, perampanel, selurampanel, talampanel, fanapanel, irampanel, kynurenic acid, 1-(4'-aminophenyl)-3,5-dihydro-7,8-dimethoxy-4H-2,3-benzodiazepin-4-one (CFM-2), 6-cyano-7-nitroquinoxaline-2,3-dione (CNQX), 6-cyano-7-nitroquinoxaline-2,3-dione disodium (CNQX disodium salt), CP 465022 hydrochloride, 6,7-dinitroquinoxaline-2,3-dione (DNQX), 6,7-dinitroquinoxaline-2,3-dione disodium salt (DNQX disodium salt), 6,6-[(3,3'-dimethyl[1,1'-biphenyl]-4,4'-diyl)bis(azo)bis[4-amino-5-hydroxy-1,3-naphthalenedisulphonic acid] tetrasodium salt (Evans Blue tetrasodium salt), 4-(8-chloro-2-methyl-11H-imidazo[1,2-c][2,3]benzodiazepin-6-benzeneamine dihydrochloride (GYKI 47261 dihydrochloride), 4-(8-methyl-9H-1,3-dioxolo[4,5-h][2,3]benzodiazepin-5-yl)-benzenamine dihydrochloride (GYKI 52466 dihydrochloride), 1-(4-aminophenyl)-3-methylcarbamyl-4-methyl-3,4-dihydro-7,8-methylenedioxy-5H-2,3-benzodiazepine hydrochloride (GYKI 53655 hydrochloride), N-(1-phenylcyclohexyl)-1,5-pentanediamine dihydrobromide (IEM 1925 dihydrobromide), N-[3-[[4-[(3-aminopropyl)amino]butyl]amino]propyl]-1-naphthaleneacetamide trihydrochloride (naspm trihydrochloride), 2,3-dioxo-6-nitro-1,2,3,4-tetrahydrobenzo[f]quinoxaline-7-sulfonamide (NBQX), 2,3-dioxo-6-nitro-1,2,3,4-tetrahydrobenzo[f]quinoxaline-7-sulfonamide disodium salt (NBQX disodium salt), (S)-N-[7-[(4-aminobutyl)amino]heptyl]-4-hydroxy-α-[(1-oxobutyl)amino]benzenepropanamide dihydrochloride (philanthotoxin 74), 1,4-dihydro-6-(1H-imidazol-1-yl)-7-nitro-2,3-quinoxalinedione hydrochloride (YM 90K hydrochloride), [[3,4-dihydro-7-(4-morpholinyl)-2,3-dioxo-6-(trifluoromethyl)-1(2H)-quinoxalinyl]methyl]phosphonic acid (ZK 200775), (+)-4-(4-Aminophenyl)-1,2-dihydro-1-methyl-2-propylcarbamoyl-6,7-methylenedioxyphthalazine (SYM 2206), and/or (αS)-α-Amino-3-[(4-carboxyphenyl)methyl]-3,4-dihydro-2,4-dioxo-1(2H)-pyrimidinepropanoic acid (UBP 282).

In one embodiment, a unit dosage of the at least one AMPA receptor antagonist ranges from about 2 mg to about 12 mg, for example about: 4-6 mg, of a composition. In another embodiment, the unit dosage of the at least one AMPA receptor antagonist is at least about: 40-100 mg, of a composition. In one embodiment, a unit dosage of the at least one AMPA receptor antagonist ranges from about 2 mg to about 100 mg, for example about: 2-100 mg, of a composition. Administration of the compositions herein is operable to be repeated, e.g., every 5-20 minutes, as necessary. See, e.g., (1) H. Potschka and E. Trinka, "Perampanel: Does it have broad-spectrum potential?," Epilepsia, vol. 60 Suppl 1, no. S1, pp. 22-36, March 2019, doi: 10.1111/EPI. 14456; (2) FYCOMPA, "Dosing Optimization & Drug Interactions|FYCOMPA (perampanel)." https://www.fycompa.com/hcp/dosing-and-half-life/dosing (last accessed Nov. 15, 2021); and (3) Clinicaltrials.gov, "Study to Assess the Safety, Tolerance and Efficacy of Tezampanel in Patients With Acute Migraine," https://clinicaltrials.gov/show/NCT00567086, 2007, Accessed: Nov. 15, 2021. [Online], each of which is incorporated herein by reference in its entirety.

In some embodiments, the at least one AMPA receptor antagonist is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the at least one AMPA receptor antagonist is about 4%, about 7.5%, or about 15% w/w of the weight of the composition. In some embodiments, the at least one AMPA receptor antagonist is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the at least one AMPA receptor antagonist is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of one or more of the at least one AMPA receptor antagonist to about 350 ng/ml (e.g., from about 200 ng/mL to about 600 ng/mL). In one embodiment, the compositions herein increase the blood concentration of one or more of the at least one AMPA receptor antagonist by about 1, 2, 3, 4, 5, 6, 7, 8, 9, 10, 11, 12, 13, 14, 15, 25, 50, 100, 200, 300, 350, 400, 500, or 600 ng/ml. See, e.g., Y. Yamamoto et al., "Pharmacokinetics, tolerability, and clinical effectiveness of perampanel in Japanese patients with epilepsy," Seizure, vol. 83, pp. 181-186, December 2020, doi: 10.1016/j.seizure.2020.10.017, which is incorporated herein by reference in its entirety.

In some embodiments, the dry powder composition disclosed herein when administered to a patient, reaches a maximal blood concentration of the at least one AMPA receptor antagonist in less than about 60 minutes ($T_{max}$) after administration. In some embodiments, the dry powder composition when administered to a patient, reaches a maximal blood concentration ($T_{max}$) of the at least one AMPA receptor antagonist in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the at least one AMPA receptor antagonist in less than about 30 minutes after administration. In some embodiments, the dry powder composition when administered to a patient, reaches a mean area under the curve $(AUC)_{(0-180\ minutes)}$ of the at least one AMPA receptor antagonist which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected at least one AMPA receptor antagonist. In some embodiments, the dry powder composition when administered to a patient, reaches a mean $AUC_{(0-\infty)}$ of the at least one AMPA receptor antagonist which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected at least one AMPA receptor antagonist. In some embodiments, the equivalent IV, IM, or SQ injected at least one AMPA receptor antagonist contains about 10 mg to about 100 mg of the at least one AMPA receptor antagonist. For example, the dry powder composition when administered to a patient, reaches a mean $AUC_{(0-180\ minutes)}$ of the at least one AMPA receptor antagonist, which is at least 80% of the mean $AUC_{(0-180\ minutes)}$ of an equivalent IM injected at least one AMPA receptor antagonist (e.g., 15 mg IM injected at least one AMPA receptor antagonist, 40 mg IM injected at least one AMPA receptor antagonist, 80 mg IM injected at least one AMPA receptor antagonist). In another instance, the dry powder composition when administered to a patient, reaches a mean $AUC_{(0-\infty)}$ of the at least one AMPA receptor antagonist, which is at least 80% of the mean $AUC_{(0-\infty)}$ of an equivalent IM injected at least one AMPA receptor antagonist (e.g., 15 mg IM injected at least one AMPA receptor antagonist, 40 mg IM injected at least one AMPA receptor antagonist, 80 mg IM injected at least one AMPA receptor antagonist). See, e.g., (1) P. Dohare et al., "AMPA-Kainate Receptor Inhibition Promotes Neurologic Recovery in Premature Rabbits with Intraventricular Hemorrhage," J. Neurosci., vol. 36, no. 11, pp. 3363-3377 March 2016, doi: 10.1523/JNEUROSCI.4329-15.2016 and (2) Clinicaltrials.gov, "Study to Assess the Safety, Tolerance and Efficacy of Tezampanel in Patients With Acute Migraine," https://clinicaltrials.gov/show/NCT00567086, 2007, Accessed: Nov. 15, 2021. [Online], each of which is incorporated herein by reference in its entirety.

In certain embodiments, the dry powder compositions and/or dosage units herein are operable to raise the blood concentration of the at least one AMPA receptor antagonist to about 400 ng/ml (e.g., about 413 ng/ml) within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the at least one AMPA receptor antagonist by about 150 ng/ml, for example about 50 to about 250 ng/ml, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). In another embodiment, the compositions herein increase the blood concentration of the at least one AMPA receptor antagonist by about 350 ng/mL, for example about 200 to about 600 ng/ml, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). See, e.g., I. Rektor, "Perampanel, a novel, non-competitive, selective AMPA receptor antagonist as adjunctive therapy for treatment-resistant partial-onset seizures," http://dx.doi.org/10.1517/14656566.2013.754883, vol. 14, no. 2, pp. 225-235, February 2013, doi: 10.1517/14656566.2013.754883, which is incorporated herein by reference in its entirety.

In another aspect, a single dose of the at least one AMPA receptor antagonist in the dry powder compositions and/or dosage units given intranasally is bioequivalent (for example, in terms of peripheral blood levels, systemic exposure of the at least one AMPA receptor antagonist) to an equivalent intravenously (IV), intramuscularly (IM) or subcutaneously (SQ) injected at least one AMPA receptor antagonist. For example, a single dose of the at least one AMPA receptor antagonist in the dry powder compositions and/or dosage units given intranasally is bioequivalent to an equivalent intravenously (IV), intramuscularly (IM) or subcutaneously (SQ) injected at least one AMPA receptor antagonist. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one active pharmaceutical ingredient includes at least one AMPA receptor antagonist (e.g., tezampanel). In one embodiment, the at least one active pharmaceutical ingredient includes at least one AMPA receptor antagonist (e.g., tezampanel) and at least one anticonvulsant agent (e.g., carbamazepine, lamotrigine, levitiracetam, sodium valporate). See, e.g., T. Wu and T. Hanada, "Anti-Seizure Effects of Perampanel in Combination with Other Antiepileptic Drugs (AEDs) in a Rat Amygdala Kindling Model (P3.270)," Neurology, vol. 82, no. 10 Supplement, 2014, which is incorporated herein by reference in its entirety. In one embodiment, the at least one pharmaceutical ingredient includes at least one AMPA receptor antagonist (e.g., tezampanel) and at least one NMDA receptor antagonist. See, e.g., Aroniadou-Anderjaska V, Figueiredo T H, Apland J P, Braga M F. Targeting the glutamatergic system to counteract organophosphate poisoning: A novel therapeutic strategy. Neurobiol Dis. 2020 January; 133:104406. doi: 10.1016/j.nbd.2019.02.017. Epub 2019 Feb. 21. PMID: 30798006, which is incorporated herein by reference in its entirety. In one embodiment, the at least one active pharmaceutical ingredient further includes at least one anticholinergic agent (e.g., atropine), at least one cholinesterase reactivator agent (e.g., pralidoxime, obidoxime), at least one vasoactive agent (e.g., epinephrine, vasopressin, phenylephrine, or a salt thereof), at least one vasodilator (e.g., phentolamine, prazosin, doxazosin, bosentan, a hydralazine and nitrate combination, a PDE3 inhibitor (e.g., milrinone), a PD5 inhibitor (e.g., sildenafil)), and/or at least one catechol-o-methyl transferase (COMT) inhibitor (e.g., entacapone). Additional details regarding the at least one anticholinergic agent, at least one cholinesterase reactivator agent, the at least one vasoactive agent, the at least one anticonvulsive agent, the at least one vasodilator, and/or the at least one COMT inhibitor are included in U.S. patent application Ser. No. 17/349,507 and U.S. Provisional Patent Application No. 63/209,221, each which is incorporated herein by reference in its entirety.

Steroids

In one embodiment, the at least one antidote includes at least one steroid. In one embodiment, the at least one steroid includes a synthetic pregnane steroid. The synthetic pregnane steroid includes, but is not limited to ganaxolone, alfadolone, alfaxolone, allopregnanolone, hydroxydione, minaxolone, pregnanolone, and/or renanolone. See, e.g., (1) Kokate et al. "Anticonvulsant activity of neurosteroids: Correlation with γ-aminobutyric acid-evoked chloride current potentiation" *J Pharmacol Exp Ther* 270:1223-1229 (1994); (2) Reddy et al. "Chronic treatment with the neuroactive steroid ganaxolone in the rat induces anticonvulsant tolerance to diazepam but not to itself" *J Pharmacol Exp Therap* 295: 1241-1248 (2000); (3) Reddy et al. "Anticonvulsant activity of progesterone and neurosteroids in progesterone receptor knockout mice" *J Pharmacol Exp Therap* 310: 230-239 (2004); (4) Reddy "Role of anticonvulsant and antiepileptogenic neurosteroids in the pathophysiology and treatment of epilepsy" *Frontiers Endocrinol* 2 (38): 1-11 (2011); (5) Wohlfarth et al. "Enhanced neurosteroid potentiation of ternary GABA-A receptors containing the delta subunit" *J Neurosci* 22:1541-1549 (2002); (6) Mihalek et al. "Attenuated sensitivity to neuroactive steroids in GABA-A receptor delta subunit, knockout mice" *Proc Natl Acad Sci USA* 96:12905-12910 (1999); (7) Zhan et al. "Enhanced tonic GABA current in normotopic and hilar ectopic dentate granule cells after pilocarpine-reduced status epilepticus" *J Neurophysiol* 102:670-681 (2009); and (8) Carver et al. "Perimenstrual-like hormonal regulation of extrasynaptic δ-containing GABA-A receptors mediating tonic inhibition and neurosteroid sensitivity" *J Neurosci* 34 (43): 14181-14197 (2014), each of which is incorporated herein by reference in its entirety.

In one embodiment, a unit dosage of the at least one steroid ranges from about 5 mg to about 50 mg, for example about: 7.5-40 mg, of a composition. In another embodiment, the unit dosage of the at least one steroid is at least about: 5-10 mg, of a composition. Administration of the compositions herein is operable to be repeated, e.g., every 5-20 minutes, as necessary. See, e.g., (1) American Osteopathic College of Dermatology (AOCD), "Antihistamines-American Osteopathic College of Dermatology (AOCD)." https://www.aocd.org/page/SteroidsOral (last accessed Nov. 15, 2021) and (2) NIH, "DailyMed-PREDNISONE-prednisone tablet." https://dailymed.nlm.nih.gov/dailymed/drugInfo.cfm?setid=931ceb82-23b9-46c6-a00b-4cd66ed6f88f (last accessed Nov. 15, 2021), each of which is incorporated herein by reference in its entirety.

In some embodiments, the at least one steroid is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the at least one steroid is about 4%, about 7.5%, or about 15% w/w of the weight of the composition. In some embodiments, the at least one steroid is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the at least one steroid is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of one or more of the at least one steroid to about 150 ng/ml. In one embodiment, the compositions herein increase the blood concentration of one or more of the at least one steroid by about 1, 2, 3, 4, 5, 6, 7, 8, 9, 10, 11, 12, 13, 14, 15, 25, 50, 75, 100, 125, 150, 200, or 250 ng/ml. See, e.g., I. A. Ionita, K. Ogasawara, R. Y. Gohh, and F. Akhlaghi, "Pharmacokinetics of Total and Unbound Prednisone and Prednisolone in Stable Kidney Transplant Recipients with Diabetes Mellitus," Ther. Drug Monit., vol. 36, no. 4, p. 448, 2014, doi: 10.1097/FTD.0000000000000045, which is incorporated herein by reference in its entirety.

In some embodiments, the dry powder composition disclosed herein when administered to a patient, reaches a maximal blood concentration of the at least one steroid in less than about 60 minutes ($T_{max}$) after administration. In some embodiments, the dry powder composition when administered to a patient, reaches a maximal blood concentration ($T_{max}$) of the at least one steroid in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the at least one steroid in less than about 30 minutes after administration. In some embodiments, the dry powder composition when administered to a patient, reaches a mean area under the curve $(AUC)_{(0\text{-}180 \ minutes)}$ of the at least one steroid which is at least 20%, 30%, 40% 50%, 60%, 70%, 80%, 90%, 100%, 110%, 120%, 130%, 140%, or 150% of the mean $AUC_{(0\text{-}180 \ minutes)}$ of an equivalent IV, IM, or SQ injected at least one steroid. In some embodiments, the dry powder composition when administered to a patient, reaches a mean $AUC_{(0\text{-}\infty)}$ of the at least one steroid which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected at least one steroid. In some embodiments, the equivalent IV, IM, or SQ injected at least one steroid contains about 40 mg to about 120 mg of the at least one steroid. For example, the dry powder composition when administered to a patient, reaches a mean $AUC_{(0\text{-}180 \ minutes)}$ of the at least one steroid, which is at least 80% of the mean $AUC_{(0\text{-}180 \ minutes)}$ of an equivalent IM injected at least one steroid (e.g., 50 mg IM injected at least one steroid, 78 mg IM injected at least one steroid). In another instance, the dry powder composition when administered to a patient, reaches a mean $AUC_{(0\text{-}\infty)}$ of the at least one steroid, which is at least 80% of the mean $AUC_{(0\text{-}\infty)}$ of an equivalent IM injected at least one steroid (e.g., 50 mg IM injected at least one steroid, 78 mg IM injected at least one steroid). See, e.g., (1) H. Schuckman, D. P. DeJulius, M. Blanda, L. W. Gerson, A. J. DeJulius, and M. Rajaratman, "Comparison of intramuscular triamcinolone and oral prednisone in the outpatient treatment of acute asthma: a randomized controlled trial," Ann. Emerg. Med., vol. 31, no. 3, pp. 333-338, 1998, doi: 10.1016/S0196-0644(98)70343-9 and (2) S. W. Kirkland, E. Cross, S. Campbell, C. Villa-Roel, and B. H. Rowe, "Intramuscular versus oral corticosteroids to reduce relapses following discharge from the emergency department for acute asthma," Cochrane Database Syst. Rev., vol. 2018, no. 6, June 2018, doi: 10.1002/14651858.CD012629.PUB2, each of which is incorporated herein by reference in its entirety.

In certain embodiments, the dry powder compositions and/or dosage units herein are operable to raise the blood concentration of the at least one steroid to about 1.3 ng/ml (e.g., 1.29 ng/ml) within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the at least one steroid by about 150 ng/ml, for example about 100 ng/ml to about 200 ng/ml, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). In another embodiment, the compositions herein increase the blood concentration of the at least one steroid by about 1.25 ng/mL, for example about 1.2 ng/ml to about 1.3 ng/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). See, e.g., S. Lähelmä et al., "Equivalent lung deposition of budesonide in vivo: a comparison of dry powder inhalers using a pharmacokinetic method," Br. J. Clin. Pharmacol., vol. 59, no. 2, p. 167, February 2005, doi: 10.1111/J.1365-2125.2004.02238.X, which is incorporated herein by reference in its entirety.

In another aspect, a single dose of the at least one steroid in the dry powder compositions and/or dosage units given intranasally is bioequivalent (for example, in terms of peripheral blood levels, systemic exposure of the at least one steroid) to an equivalent intravenously (IV), intramuscularly (IM) or subcutaneously (SQ) injected at least one steroid. For example, a single dose of the at least one steroid in the dry powder compositions and/or dosage units given intranasally is bioequivalent to an equivalent intravenously (IV), intramuscularly (IM) or subcutaneously (SQ) injected at least one steroid. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one steroid (e.g., ganaxolone) is combined with at least one anticonvulsive agent (e.g., lamotrigine, levetiracetam, carbamazepine). See, e.g., M. R. Sperling, P. Klein, and J. Tsai, "Randomized, double-blind, placebo-controlled phase 2 study of ganaxolone as add-on therapy in adults with uncontrolled partial-onset seizures," Epilepsia, vol. 58, no. 4, pp. 558-564, April 2017, doi: 10.1111/EPI.13705, which is incorporated herein by reference in its entirety. In one embodiment, the at least one active pharmaceutical ingredient further includes at least one anticholinergic agent (e.g., atropine), at least one cholinesterase reactivator agent (e.g., pralidoxime, obidoxime), at least one vasoactive agent (e.g., epinephrine, vasopressin, phenylephrine, or a salt thereof), at least one vasodilator (e.g., phentolamine, prazosin, doxazosin, bosentan, a hydralazine and nitrate combination, a PDE3 inhibitor (e.g., milrinone), a PD5 inhibitor (e.g., sildenafil)), and/or at least one catechol-o-methyl transferase (COMT) inhibitor (e.g., entacapone). Additional details regarding the at least one anticholinergic agent, at least one cholinesterase reactivator agent, the at least one vasoactive agent, the at least one anticonvulsive agent, the at least one vasodilator, and/or the at least one COMT inhibitor are included in U.S. patent application Ser. No. 17/349,507 and U.S. Provisional Patent Application No. 63/209,221, each which is incorporated herein by reference in its entirety.

3-MP Prodrugs

In one embodiment, the at least one antidote includes at least one 3-mercaptopyruvic acid (3-MP) prodrug. 3-MP is an intermediate in cysteine metabolism that has been examined as a possible treatment for cyanide poisoning, but its half-life is too short to be clinically effective. In one embodiment, the at least one 3-MP prodrug includes sulfanegen or a pharmaceutically acceptable salt thereof (e.g., sulfanegen sodium, sulfanegen triethanolamine (TEA)). Advantageously, sulfanegen or the pharmaceutically acceptable salt thereof does not require IV infusion. Further, sulfanegen has poor long-term stability in solution. See, e.g., (1) Nagasawa, H. T., et al., *J. Med. Chem.* 2007, 50, 6462-6464; (2) Belani, K. G., et al., *Anesth. Analg.* 2012, 114, 956-961; (3) Crankshaw, D. L., et al., Toxicol. Lett. 2007, 175, 111-117; and (4) Patterson, S. E., et al., *J. Med. Chem.* 2013, 56, 1346-1349, each of which is incorporated herein by reference in its entirety.

In one embodiment, a unit dosage of the at least one 3-MP prodrug ranges from about 15 mg to about 75 mg, for example about: 15-75 mg, of a composition. In another embodiment, the unit dosage of the at least one 3-MP prodrug is at least about: 50 mg (e.g., 67.5 mg) of a composition. Administration of the compositions herein is operable to be repeated, e.g., every 5-20 minutes, as necessary. See, e.g., (1) M. Brenner et al., "Sulfanegen sodium treatment in a rabbit model of sub-lethal cyanide toxicity," Toxicol. Appl. Pharmacol., vol. 248, no. 3, pp. 269-276, November 2010, doi: 10.1016/J.TAAP.2010.08.002 and (2) S. E. Patterson et al., "Development of sulfanegen for mass cyanide casualties," Ann. N. Y. Acad. Sci., vol. 1374, no. 1, p. 202, 2016, doi: 10.1111/NYAS.13114, each of which is incorporated herein by reference in its entirety.

In some embodiments, the at least one 3-MP prodrug is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the at least one 3-MP prodrug is about 4%, about 7.5%, or about 15% w/w of the weight of the composition. In some embodiments, the at least one 3-MP prodrug is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the at least one 3-MP prodrug is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration $(C_{max})$ of one or more of the at least one 3-MP prodrug to about 350 µg/mL (e.g., about 360 µg/mL). In one embodiment, the compositions herein increase the blood concentration of one or more of the at least one 3-MP prodrug by about 1, 2, 3, 4, 5, 6, 7, 8, 9, 10, 11, 12, 13, 14, 15, 25, or 50 ng/mL. In another embodiment, the compositions herein increase the blood concentration of one or more of the at least one 3-MP prodrug by about 1, 2, 3, 4, 5, 6, 7, 8, 9, 10, 11, 12, 13, 14, 15, 25, 50, 75, 100, 200, 300, 350, 400, or 500 µg/mL. See, e.g., M. W. Stutelberg et al., "Pharmacokinetics of next generation cyanide antidote sulfanegen in rabbits," http://dx.doi.org/10.4155/ipk-2016-0021, vol. 2, no. 2, pp. 105-111, March 2017, doi: 10.4155/IPK-2016-0021, which is incorporated herein by reference in its entirety.

In some embodiments, the dry powder composition disclosed herein when administered to a patient, reaches a maximal blood concentration of the at least one 3-MP prodrug in less than about 60 minutes $(T_{max})$ after administration. In some embodiments, the dry powder composition when administered to a patient, reaches a maximal blood concentration $(T_{max})$ of the at least one 3-MP prodrug in less than about 60, 50, 40, 30, 20, 15, 10, 5, or 3 minutes $(T_{max})$ after administration. In one embodiment, the dry powder composition when administered to a patient, reaches a maximal blood concentration $(T_{max})$ of the at least one 3-MP prodrug in less than about 30 minutes after administration. In some embodiments, the dry powder composition when administered to a patient, reaches a mean area under the curve $(AUC)_{(0-180\ minutes)}$ of the at least one 3-MP prodrug which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected at least one 3-MP prodrug. In some embodiments, the dry powder composition when administered to a patient, reaches a mean $AUC_{(0-\infty)}$ of the at least one 3-MP prodrug which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected at least one 3-MP prodrug. In some embodiments, the equivalent IV, IM, or SQ injected at least one 3-MP prodrug contains about 150 mg (e.g., 149 mg) of the at least one 3-MP prodrug. For example, the dry powder composition when administered to a patient, reaches a mean $AUC_{(0-180\ minutes)}$ of the at least one 3-MP prodrug, which is at least 80% of the mean $AUC_{(0-180\ minutes)}$ of an equivalent IM injected at least one 3-MP prodrug (e.g., 149 mg IM injected at least one 3-MP prodrug). In another instance, the dry powder composition when administered to a patient, reaches a mean $AUC_{(0-\infty)}$ of the at least one 3-MP prodrug, which is at least 80% of the mean $AUC_{(0-\infty)}$ of an equivalent IM injected at least one 3-MP prodrug (e.g., 149 mg IM injected at least one 3-MP prodrug).

In certain embodiments, the dry powder compositions and/or dosage units herein are operable to raise the blood concentration of the at least one 3-MP prodrug to about 350 µg/mL (e.g., 360 µg/mL) within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the at least one 3-MP prodrug by about 20 to about 30 µg/mL, for example about 24 µg/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the at least one 3-MP prodrug in the dry powder compositions and/or dosage units given intranasally is bioequivalent (for example, in terms of peripheral blood levels, systemic exposure of the at least one 3-MP prodrug) to an equivalent intravenously (IV), intramuscularly (IM) or subcutaneously (SQ) injected at least one 3-MP prodrug. For example, a single dose of the at least one 3-MP prodrug in the dry powder compositions and/or dosage units given intranasally is bioequivalent to an equivalent intravenously (IV), intramuscularly (IM) or subcutaneously (SQ) injected at least one 3-MP prodrug. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one 3-MP prodrug (e.g., sulfanegen) is used in combination with a Vitamin B12 analogue (e.g., cobinamide, hydroxocobalamin). See, e.g., A. Chan et al., "The combination of cobinamide and sulfanegen is highly effective in mouse models of cyanide poisoning," Clin. Toxicol. (Phila)., vol. 49, no. 5, pp. 366-373, June 2011, doi: 10.3109/15563650.2011.584879, which is incorporated herein by reference in its entirety.

Noncompetitive Nicotinic Antagonist

In one embodiment, the at least one antidote includes at least one noncompetitive nicotinic antagonist. In one embodiment, the at least one noncompetitive nicotinic antagonist is a type of anticholinergic agent that is effective against organophosphate poisoning. The at least one noncompetitive nicotinic antagonist includes, but is not limited to, 1,1-(propane-1,3-diyl)bis(4-tert-butylpyridinium) diiodide (MB327) and its di(methanesulfonate) salt (MB399). See, e.g., Robertson M J, Hadzic G, Ambrus J, Pomè DY, Hyde E, Whiting A, Mariana A, von Kleist L, Chau N, Haucke V, Robinson P J, Mccluskey A. The Rhodadyns, a New Class of Small Molecule Inhibitors of Dynamin GTPase Activity. ACS Med Chem Lett. 2012 Mar. 26; 3(5):352-6. doi: 10.1021/ml200284s. PMID: 24900478; PMCID: PMC4025782, which is incorporated herein by reference in its entirety.

In one embodiment, a unit dosage of the at least one noncompetitive nicotinic antagonist ranges from about 20 mg to about 100 mg, for example about: 25-90 mg, of a composition. In another embodiment, the unit dosage of the at least one noncompetitive nicotinic antagonist is at least about: 20 mg to 100 mg of a composition. Administration of the compositions herein is operable to be repeated, e.g., every 5-20 minutes, as necessary. See, e.g., I. Bacher, B. Wu, D. R. Shytle, and T. P. George, "Mecamylamine—a nicotinic acetylcholine receptor antagonist with potential for the treatment of neuropsychiatric disorders," Expert Opin. Pharmacother., vol. 10, no. 16, pp. 2709-2721, 2009, doi: 10.1517/14656560903329102, which is incorporated herein by reference in its entirety.

In some embodiments, the at least one noncompetitive nicotinic antagonist is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the at least one noncompetitive nicotinic antagonist is about 4%, about 7.5%, or about 15% w/w of the weight of the composition. In some embodiments, the at least one noncompetitive nicotinic antagonist is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the at least one noncompetitive nicotinic antagonist is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of one or more of the at least one noncompetitive nicotinic antagonist to about 65 ng/ml (e.g., 64.5 ng/mL). In one embodiment, the compositions herein increase the blood concentration of one or more of the at least one noncompetitive nicotinic antagonist by about 1, 2, 3, 4, 5, 6, 7, 8, 9, 10, 11, 12, 13, 14, 15, 25, 50, 65, 70, 75, or 100 ng/ml. See, e.g., A. C. Baakman et al., "An anti-nicotinic cognitive challenge model using mecamylamine in comparison with the antimuscarinic cognitive challenge using scopolamine," Br. J. Clin. Pharmacol., vol. 83, no. 8, pp. 1676-1687, 2017, doi: 10.1111/BCP.13268, which is incorporated herein by reference in its entirety.

In some embodiments, the dry powder composition disclosed herein when administered to a patient, reaches a maximal blood concentration of the at least one noncompetitive nicotinic antagonist in less than about 60 minutes ($T_{max}$) after administration. In some embodiments, the dry powder composition when administered to a patient, reaches a maximal blood concentration ($T_{max}$) of the at least one noncompetitive nicotinic antagonist in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the at least one noncompetitive nicotinic antagonist in less than about 30 minutes after administration. In some embodiments, the dry powder composition when administered to a patient, reaches a mean area under the curve $(AUC)_{(0-180\ minutes)}$ of the at least one noncompetitive nicotinic antagonist which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected at least one noncompetitive nicotinic antagonist. In some embodiments, the dry powder composition when administered to a patient, reaches a mean $AUC_{(0-\infty)}$ of the at least one noncompetitive nicotinic antagonist which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected at least one noncompetitive nicotinic antagonist. In some embodiments, the equivalent IV, IM, or SQ injected at least one noncompetitive nicotinic antagonist contains about 0.1 mg to about 5 mg (e.g., about 0.2 mg to about 3.75 mg) of the at least one noncompetitive nicotinic antagonist. For example, the dry powder composition when administered to a patient, reaches a mean $AUC_{(0-180\ minutes)}$ of the at least one noncompetitive nicotinic antagonist, which is at least 80% of the mean $AUC_{(0-180\ minutes)}$ of an equivalent IM injected at least one noncompetitive nicotinic antagonist (e.g., 3.75 mg IM injected at least one noncompetitive nicotinic antagonist). In another instance, the dry powder composition when administered to a patient, reaches a mean $AUC_{(0-\infty)}$ of the at least one noncompetitive nicotinic antagonist, which is at least 80% of the mean $AUC_{(0-\infty)}$ of an equivalent IM injected at least one noncompetitive nicotinic antagonist (e.g., 3.75 mg IM injected at least one noncompetitive nicotinic antagonist). See, e.g., C. Canton et al., "Monepantel pharmacotherapeutic evaluation in cattle: Pattern of efficacy against multidrug resistant nematodes," Int. J. Parasitol. Drugs Drug Resist., vol. 15, p. 162, April 2021, doi: 10.1016/ J.IJPDDR.2021.03.003, which is incorporated herein by reference in its entirety.

In certain embodiments, the dry powder compositions and/or dosage units herein are operable to raise the blood concentration of the at least one noncompetitive nicotinic antagonist to about 65 ng/ml within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the at least one noncompetitive nicotinic antagonist by about 20 to about 60 ng/ml, for example about 40 ng/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). See, e.g., A. C. Baakman et al., "An anti-nicotinic cognitive challenge model using mecamylamine in comparison with the anti-muscarinic cognitive challenge using scopolamine," Br. J. Clin. Pharmacol., vol. 83, no. 8, pp. 1676-1687, 2017, doi: 10.1111/BCP.13268, which is incorporated herein by reference in its entirety.

In another aspect, a single dose of the at least one noncompetitive nicotinic antagonist in the dry powder compositions and/or dosage units given intranasally is bioequivalent (for example, in terms of peripheral blood levels, systemic exposure of the at least one noncompetitive nicotinic antagonist) to an equivalent intravenously (IV), intramuscularly (IM) or subcutaneously (SQ) injected at least one noncompetitive nicotinic antagonist. For example, a single dose of the at least one noncompetitive nicotinic antagonist in the dry powder compositions and/or dosage units given intranasally is bioequivalent to an equivalent intravenously (IV), intramuscularly (IM) or subcutaneously (SQ) injected at least one noncompetitive nicotinic antagonist. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/ serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one pharmaceutical ingredient includes at least one noncompetitive nicotinic antagonist. In one embodiment, the at least one active pharmaceutical ingredient includes at least one noncompetitive nicotinic antagonist and at least one avermectin (e.g., ivermectin, selamectin, doramectin, eprinomectin, abamectin). See, e.g., S. D. George, A. J. George, P. A. Stein, P. F. Rolfe, B. C. Hosking, and W. Seewald, "The comparative efficacy of abamectin, monepantel and an abamectin/derquantel combination against fourth-stage larvae of a macrocyclic lactone-resistant Teladorsagia spp. isolate infecting sheep," Vet. Parasitol., vol. 188, no. 1-2, pp. 190-193, August 2012, doi: 10.1016/J.VETPAR.2012.03.001, which is incorporated herein by reference in its entirety. In one embodiment, the at least one active pharmaceutical ingredient further includes at least one anticholinergic agent (e.g., atropine), at least one cholinesterase reactivator agent (e.g., pralidoxime, obidoxime), at least one vasoactive agent (e.g., epinephrine, vasopressin, phenylephrine, or a salt thereof), at least one anticonvulsive agent (e.g., diazepam, lorazepam, midazolam, clonazepam, temazepam, flunitrazepam, triazolam, alprazolam, zolpidem, eszopiclone, or a salt thereof), at least one vasodilator (e.g., phentolamine, prazosin, doxazosin, bosentan, a hydralazine and nitrate combination, a PDE3 inhibitor (e.g., milrinone), a PD5 inhibitor (e.g., sildenafil)), and/or at least one catechol-o-methyl transferase (COMT) inhibitor (e.g., entacapone). Additional details regarding the at least one vasoactive agent, the at least one anticonvulsive agent, the at least one vasodilator, and/or the at least one COMT inhibitor are included in U.S. patent application Ser. No. 17/349,507 and U.S. Provisional Patent Application No. 63/209,221, each which is incorporated herein by reference in its entirety.

Sodium Nitrite

In one embodiment, the at least one antidote includes sodium nitrite. In one embodiment, a unit dosage of the sodium nitrite ranges from about 160 mg to about 12,000 mg, for example about: 500-10,000 mg, of a composition. Administration of the compositions herein is operable to be repeated, e.g., every 5-20 minutes, as necessary. See, e.g., Cambal L K, Swanson M R, Yuan Q, Weitz A C, Li H H, Pitt B R, Pearce L L, Peterson J. Acute, sublethal cyanide poisoning in mice is ameliorated by nitrite alone: complications arising from concomitant administration of nitrite and thiosulfate as an antidotal combination. Chem Res Toxicol. 2011 Jul. 18; 24(7):1104-12. doi: 10.1021/ tx2001042. Epub 2011 May 11. PMID: 21534623; PMCID: PMC5494963, which is incorporated herein by reference in its entirety.

In some embodiments, the sodium nitrite is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the sodium nitrite is about 4%, about 7.5%, or about 15% w/w of the weight of the composition. In some embodiments, the sodium nitrite is present in an amount of at least about: 0.25% w/w, 1% w/w, 5% w/w, 10% w/w, 20% w/w, 30% w/w, 40% w/w, or 50% w/w based on the weight of the formulations and/or dosage units. In some embodiments, the sodium nitrite is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In some embodiments, the dry powder composition disclosed herein when administered to a patient, reaches a maximal blood concentration of the sodium nitrite in less than about 60 minutes ($T_{max}$) after administration. In some embodiments, the dry powder composition when administered to a patient, reaches a maximal blood concentration ($T_{max}$) of the sodium nitrite in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the sodium nitrite in less than about 30 minutes after administration. In some embodiments, the dry powder composition when administered to a patient, reaches a mean area under the curve $(AUC)_{(0\text{-}180\ minutes)}$ of the sodium nitrite which is at least 20%, 30%, 40%50%, 60%, 70%, 80%, 90%, 100%, 110%, 120%, 130%, 140%, or 150% of the mean $AUC_{(0\text{-}180\ minutes)}$ of an equivalent IV, IM, or SQ injected sodium nitrite. In some embodiments, the dry powder composition when administered to a patient, reaches a mean $AUC_{(0\text{-}\infty)}$ of the sodium nitrite which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected sodium nitrite.

In another aspect, a single dose of the sodium nitrite in the dry powder compositions and/or dosage units given intranasally is bioequivalent (for example, in terms of peripheral blood levels, systemic exposure of the sodium nitrite) to an equivalent intravenously (IV), intramuscularly (IM) or subcutaneously (SQ) injected sodium nitrite. For example, a single dose of the sodium nitrite in the dry powder compositions and/or dosage units given intranasally is bioequivalent to an equivalent intravenously (IV), intramuscularly (IM) or subcutaneously (SQ) injected sodium nitrite. For example, bioequivalence means a 90% confidence interval of a mean $T_{max}$ (e.g., the time to reach maximal blood concentration), a mean $C_{max}$ (e.g., maximal blood concentration), a mean $AUC_{(0\text{-}t)}$ (e.g., area under the plasma/serum/ blood concentration-time curve from time zero to time t), and/or a mean $AUC_{(0\text{-}\infty)}$ (e.g., area under the plasma/serum/ blood concentration-time curve from time zero to time infinity) of the test to reference are within 80.00% to 125.00%. In one embodiment, bioequivalence is measured in a fasting state.

In one embodiment, the at least one pharmaceutical ingredient includes sodium nitrite. In one embodiment, the at least one active pharmaceutical ingredient includes amyl nitrite, sodium nitrite, and/or sodium thiosulfate. In one embodiment, the at least one active pharmaceutical ingredient further includes at least one anticholinergic agent (e.g., atropine), at least one cholinesterase reactivator agent (e.g., pralidoxime, obidoxime), at least one vasoactive agent (e.g., epinephrine, vasopressin, phenylephrine, or a salt thereof), at least one anticonvulsive agent (e.g., diazepam, lorazepam, midazolam, clonazepam, temazepam, flunitrazepam, triazolam, alprazolam, zolpidem, eszopiclone, or a salt thereof), at least one vasodilator (e.g., phentolamine, prazosin, doxazosin, bosentan, a hydralazine and nitrate combination, a PDE3 inhibitor (e.g., milrinone), a PD5 inhibitor (e.g., sildenafil)), and/or at least one catechol-o-methyl transferase (COMT) inhibitor (e.g., entacapone). Additional details regarding the at least one vasoactive agent, the at least one anticonvulsive agent, the at least one vasodilator, and/or the at least one COMT inhibitor are included in U.S. patent application Ser. No. 17/349,507 and U.S. Provisional Patent Application No. 63/209,221, each which is incorporated herein by reference in its entirety.

In one embodiment, the present invention provides a kit including amyl nitrite, sodium nitrite, and/or sodium thiosulfate. For example, and not limitation, the kit includes at least one ampule of amyl nitrite, a first nasal delivery device for sodium nitrite, and/or a second nasal delivery device for sodium thiosulfate. In another example, the kit includes at least one ampule of amyl nitrite, a nasal delivery device for sodium nitrite and/or sodium thiosulfate. In still another example, the kit includes a delivery device for sodium nitrite and/or sodium thiosulfate.

Sodium Thiosulfate

In one embodiment, the at least one antidote includes sodium thiosulfate. In one embodiment, a unit dosage of the sodium thiosulfate ranges from about 0.1 mg to about 50 mg, for example about: 5-20 mg, of a composition. Administration of the compositions herein is operable to be repeated, e.g., every 5-20 minutes, as necessary.

In some embodiments, the sodium thiosulfate is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the sodium thiosulfate is about 4%, about 7.5%, or about 15% w/w of the weight of the composition. In some embodiments, the sodium thiosulfate is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the sodium thiosulfate is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In some embodiments, the dry powder composition disclosed herein when administered to a patient, reaches a maximal blood concentration of the sodium thiosulfate in less than about 60 minutes ($T_{max}$) after administration. In some embodiments, the dry powder composition when administered to a patient, reaches a maximal blood concentration ($T_{max}$) of the sodium thiosulfate in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the sodium thiosulfate in less than about 30 minutes after administration. In some embodiments, the dry powder composition when administered to a patient, reaches a mean area under the curve $(AUC)_{(0\text{-}180\ minutes)}$ of the sodium thiosulfate which is at least 20%, 30%, 40% 50%, 60%, 70%, 80%, 90%, 100%, 110%, 120%, 130%, 140%, or 150% of the mean $AUC_{(0\text{-}180\ minutes)}$ of an equivalent IV, IM, or SQ injected sodium thiosulfate. In some embodiments, the dry powder composition when administered to a patient, reaches a mean $AUC_{(0\text{-}\infty)}$ of the sodium thiosulfate which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected sodium thiosulfate. In some embodiments, the equivalent IV, IM, or SQ injected sodium thiosulfate contains about 5 mg to about 20 mg of the sodium thiosulfate.

In another aspect, a single dose of the sodium thiosulfate in the dry powder compositions and/or dosage units given intranasally is bioequivalent (for example, in terms of peripheral blood levels, systemic exposure of the sodium thiosulfate) to an equivalent intravenously (IV), intramuscularly (IM) or subcutaneously (SQ) injected sodium thiosulfate. For example, a single dose of the sodium thiosulfate in the dry powder compositions and/or dosage units given intranasally is bioequivalent to an equivalent intravenously (IV), intramuscularly (IM) or subcutaneously (SQ) injected sodium thiosulfate. For example, bioequivalence means a 90% confidence interval of a mean $T_{max}$ (e.g., the time to reach maximal blood concentration), a mean $C_{max}$ (e.g., maximal blood concentration), a mean $AUC_{(0\text{-}t)}$ (e.g., area under the plasma/serum/blood concentration-time curve from time zero to time t), and/or a mean $AUC_{(0\text{-}\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one pharmaceutical ingredient includes sodium nitrite. In one embodiment, the at least one active pharmaceutical ingredient includes amyl nitrite, sodium nitrite, and/or sodium thiosulfate. In one embodiment, the at least one active pharmaceutical ingredient further includes at least one anticholinergic agent (e.g., atropine), at least one cholinesterase reactivator agent (e.g., pralidoxime, obidoxime), at least one vasoactive agent (e.g., epinephrine, vasopressin, phenylephrine, or a salt thereof), at least one anticonvulsive agent (e.g., diazepam, lorazepam, midazolam, clonazepam, temazepam, flunitrazepam, triazolam, alprazolam, zolpidem, eszopiclone, or a salt thereof), at least one vasodilator (e.g., phentolamine, prazosin, doxazosin, bosentan, a hydralazine and nitrate combination, a PDE3 inhibitor (e.g., milrinone), a PD5 inhibitor (e.g., sildenafil)), and/or at least one catechol-o-methyl transferase (COMT) inhibitor (e.g., entacapone). Additional details regarding the at least one vasoactive agent, the at least one anticonvulsive agent, the at least one vasodilator, and/or the at least one COMT inhibitor are included in U.S. patent application Ser. No. 17/349,507 and U.S. Provisional Patent Application No. 63/209,221, each which is incorporated herein by reference in its entirety.

In one embodiment, the present invention provides a kit including amyl nitrite, sodium nitrite, and/or sodium thiosulfate. For example, and not limitation, the kit includes at least one ampule of amyl nitrite, a first nasal delivery device for sodium nitrite, and/or a second nasal delivery device for sodium thiosulfate. In another example, the kit includes at least one ampule of amyl nitrite, a nasal delivery device for sodium nitrite and/or sodium thiosulfate. In still another example, the kit includes a delivery device for sodium nitrite and/or sodium thiosulfate.

Method of Treatment

Provided herein are methods of treating a patient by intranasally administrating the dry powder composition disclosed herein. Also provided herein are methods of treating a patient by using the kit disclosed herein.

The methods, kits, compositions, doses, or products herein are useful for treating patients. In some instances, the patient has minimal to severe respiratory distress including bronchorrhea and bronchospasms. In some instances, the patient has excess sweating and salivation, seizures, and paralysis. In some instances, the patient has bronchoconstriction, hypotension, or cardiac arrest. The compositions described herein are operable to provide a fast onset time and are suitable for intranasal use.

In some embodiments, the intranasal dry powder composition is sufficient to improve respiratory function and breathing in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to reduce bronchorrhea and bronchospasms in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to decrease excess sweating and salivation, seizures, and paralysis in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to reverse or decrease bronchoconstriction, increase blood pressure, and increase coronary perfusion pressure in the patient within 60 minutes, 50 minutes, 40 minutes, 30 minutes, 20 minutes, 10 minutes, 5 minutes, 3 minutes, 2 minutes, or 1 minute after administration.

Also provided herein are methods for treating patients by applying to a mucosal surface(s) of the nasal cavity or cavities of an individual (e.g., the mucosal surfaces of the anterior regions of the nose, the frontal sinus, the maxillary sinuses, and/or on each of the mucosal surfaces which overlie the turbinates covering the conchas) any of the pharmaceutical compositions or dosage units herein by administering at least one antidote loading dose (e.g., the amount of the at least one antidote administered nasally which results in the systemic blood bioequivalent of intravenously (IV), intramuscularly (IM) or subcutaneously (SQ) administered the at least one antidote). In a related aspect, the method of treating a patient in need of treatment from a nasal loading dose of about 2 mg to about 10 mg of the at least one antidote. See, e.g., D. P. Wermeling, "A Response to the Opioid Overdose Epidemic: Naloxone Nasal Spray," Drug Deliv. Transl. Res., vol. 3, no. 1, p. 63, February 2013, doi: 10.1007/S13346-012-0092-0, which is incorporated herein by reference in its entirety.

In one embodiment, the at least one antidote is provided prior to exposure to the at least one poison (e.g., 60 minutes before exposure). In another aspect, the methods, kits, compositions doses or products herein are useful for treating patients. In some embodiments, the patient is not in a hospital. In some embodiments, the patient is in a hospital. In some embodiments, the patient is in a combat setting. In some embodiments, the patient is in a civil emergency setting. In one embodiment, the patient is in or near an ambulance. In some embodiments, the patient has a wound.

Advantageously, the dry powder compositions and/or dosage units provided in the present invention are given intranasally, and do not require IV infusion. Placement of an IV line during an emergency or during a combat situation is time consuming and difficult given the environment and nature of the emergency (e.g., organophosphate exposure), which includes attempting IV placement in patients experiencing a seizure, respiratory collapse, and/or circulatory collapse. Additionally, the dry powder compositions and/or dosage units provided are not via an autoinjector, which is subject to failure due to obesity and/or misuse. Further, this allows for untrained and/or non-medical personnel to attend to the patient (e.g., troops in combat). Advantageously, the nasal delivery device has a substantially smaller form factor than an autoinjector, which allows for easier incorporation in field kits and easier for an individual to carry at all times. There are no needles, glass, or aqueous dosage forms. Further, the dry powder compositions of the present invention are a more stable product and are operable to withstand a wider range of environmental conditions than conventional aqueous preparations.

53

54

Acetylcholinesterase Inhibitors

In one embodiment, the at least one active pharmaceutical ingredient includes at least one acetylcholinesterase inhibitor. The at least one acetylcholinesterase inhibitor includes, but is not limited to, pyridostigmine, galantamine, 1-methyl-1,6-dihydropyridine-2-carbaldoxime (pro-2-PAM), and/or RS194B.

In one embodiment, a unit dosage of the at least one acetylcholinesterase inhibitor ranges from about 15 mg to about 25 mg, for example about: 15-25 mg, of a composition. In another embodiment, the unit dosage of the at least one acetylcholinesterase inhibitor is at least about: 15-25 mg, of a composition. Administration of the compositions herein is operable to be repeated, e.g., every 5-20 minutes, as necessary. See, e.g., S. Lilienfeld, "Galantamine—a novel cholinergic drug with a unique dual mode of action for the treatment of patients with Alzheimer's disease," CNS Drug Rev., vol. 8, no. 2, pp. 159-176, 2002, doi: 10.1111/J.1527-3458.2002.TB00221.X, which is incorporated herein by reference in its entirety.

In some embodiments, the at least one acetylcholinesterase inhibitor is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the at least one acetylcholinesterase inhibitor is about 4%, about 7.5%, or about 15% w/w of the weight of the composition. In some embodiments, the at least one acetylcholinesterase inhibitor is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the at least one acetylcholinesterase inhibitor is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of one or more of the at least one acetylcholinesterase inhibitor to about 85 ng/ml (e.g., 83.7 ng/mL). In one embodiment, the compositions herein increase the blood concentration of one or more of the at least one acetylcholinesterase inhibitor by about 1, 2, 3, 4, 5, 6, 7, 8, 9, 10, 11, 12, 13, 14, 15, 25, 50, 60, 70, 80, 85, 90, 100, or 125 ng/mL. See, e.g., Y. T. Lin, M. C. Chou, S. J. Wu, and Y. H. Yang, "Galantamine plasma concentration and cognitive response in Alzheimer's disease," PeerJ, vol. 2019, no. 5, 2019, doi: 10.7717/PEERJ.6887/SUPP-1, which is incorporated herein by reference in its entirety.

In some embodiments, the dry powder composition disclosed herein when administered to a patient, reaches a maximal blood concentration of the at least one acetylcholinesterase inhibitor in less than about 60 minutes ($T_{max}$) after administration. In some embodiments, the dry powder composition when administered to a patient, reaches a maximal blood concentration ($T_{max}$) of the at least one acetylcholinesterase inhibitor in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the at least one acetylcholinesterase inhibitor in less than about 30 minutes after administration. In some embodiments, the dry powder composition when administered to a patient, reaches a mean area under the curve $(AUC)_{(0\text{-}180\ minutes)}$ of the at least one acetylcholinesterase inhibitor which is at least 20%, 30%, 40%50%, 60%, 70%, 80%, 90%, 100%, 110%, 120%, 130%, 140%, or 150% of the mean $AUC_{(0\text{-}180\ minutes)}$ of an equivalent IV, IM, or SQ injected at least one acetylcholinesterase inhibitor. In some embodiments, the dry powder composition when administered to a patient, reaches a mean $AUC_{(0\text{-}\infty)}$ of the at least one acetylcholinesterase inhibitor which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected at least one acetylcholinesterase inhibitor. In some embodiments, the equivalent IV, IM, or SQ injected at least one acetylcholinesterase inhibitor contains about 5 mg to about 10 mg (e.g., about 6 mg to about 8 mg) of the at least one acetylcholinesterase inhibitor. For example, the dry powder composition when administered to a patient, reaches a mean $AUC_{(0\text{-}180\ minutes)}$ of the at least one acetylcholinesterase inhibitor, which is at least 80% of the mean $AUC_{(0\text{-}180\ minutes)}$ of an equivalent IM injected at least one acetylcholinesterase inhibitor (e.g., 8 mg IM injected at least one acetylcholinesterase inhibitor). In another instance, the dry powder composition when administered to a patient, reaches a mean $AUC_{(0\text{-}\infty)}$ of the at least one acetylcholinesterase inhibitor, which is at least 80% of the mean $AUC_{(0\text{-}\infty)}$ of an equivalent IM injected at least one acetylcholinesterase inhibitor (e.g., 8 mg IM injected at least one acetylcholinesterase inhibitor). See, e.g., Y. Aracava, E. F. R. Pereira, M. Akkerman, M. Adler, and E. X. Albuquerque, "Effectiveness of donepezil, rivastigmine, and (+/−)huperzine A in counteracting the acute toxicity of organophosphorus nerve agents: comparison with galantamine," J. Pharmacol. Exp. Ther., vol. 331, no. 3, pp. 1014-124 December 2009, doi: 10.1124/JPET.109.160028, which is incorporated herein by reference in its entirety.

In certain embodiments, the dry powder compositions and/or dosage units herein are operable to raise the blood concentration of the at least one acetylcholinesterase inhibitor to about 150 ng/ml within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the at least one acetylcholinesterase inhibitor by about 10-150 ng/ml, for example about 84 ng/ml, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the at least one acetylcholinesterase inhibitor in the dry powder compositions and/or dosage units given intranasally is bioequivalent (for example, in terms of peripheral blood levels, systemic exposure of the at least one acetylcholinesterase inhibitor) to an equivalent intravenously (IV), intramuscularly (IM) or subcutaneously (SQ) injected at least one acetylcholinesterase inhibitor. For example, a single dose of the at least one acetylcholinesterase inhibitor in the dry powder compositions and/or dosage units given intranasally is bioequivalent to an equivalent intravenously (IV), intramuscularly (IM) or subcutaneously (SQ) injected at least one acetylcholinesterase inhibitor. For example, bioequivalence means a 90% confidence interval of a mean $T_{max}$ (e.g., the time to reach maximal blood concentration), a mean $C_{max}$ (e.g., maximal blood concentration), a mean $AUC_{(0\text{-}t)}$ (e.g., area under the plasma/serum/blood concentration-time curve from time zero to time t), and/or a mean $AUC_{(0\text{-}\infty)}$ (e.g., area under the plasma/serum/blood concentration-time curve from time zero to time infinity) of the test to reference are within 80.00% to 125.00%. In one embodiment, bioequivalence is measured in a fasting state.

In a further embodiment, the intranasal dry powder composition is present in amounts of up to 100 mg, for example about: 1 to 5 mg, 5 to 10 mg, 10 to 20 mg, 20 to 40 mg, 40 to 60 mg, 60 to 80 mg, or 80 to 100 mg. In some embodiments, the compositions herein are present in about: 1, 5, 10, 15, 20, 25, 30, 35, 40, 45, or 50 mg.

In one embodiment, the at least one active pharmaceutical ingredient includes the at least one acetylcholinesterase inhibitor. In one embodiment, the at least one active pharmaceutical ingredient further includes at least one anticholinergic agent (e.g., atropine), at least one cholinesterase reactivator agent (e.g., pralidoxime, obidoxime), at least one anticonvulsive agent (e.g., diazepam, lorazepam, midazolam, clonazepam, temazepam, flunitrazepam, triazolam, alprazolam, zolpidem, eszopiclone, or a salt thereof), at least one vasoactive agent (e.g., epinephrine, vasopressin, phenylephrine, or a salt thereof), at least one vasodilator (e.g., phentolamine, prazosin, doxazosin, bosentan, a hydralazine and nitrate combination, a PDE3 inhibitor (e.g., milrinone), a PD5 inhibitor (e.g., sildenafil)), and/or at least one catechol-o-methyl transferase (COMT) inhibitor (e.g., entacapone). Additional details regarding the at least one anticholinergic agent, the at least one cholinesterase reactivator agent, the at least one anticonvulsive agent, the at least one vasoactive agent, the at least one vasodilator, and/or the at least one COMT inhibitor are included in U.S. patent application Ser. No. 17/349,507 and U.S. Provisional Patent Application No. 63/209,221, each which is incorporated herein by reference in its entirety.

Pyridostigmine

In one embodiment, the at least one acetylcholinesterase inhibitor includes pyridostigmine. In one embodiment, a unit dosage of the pyridostigmine ranges from about 30 mg to about 60 mg, for example about: 30-60 mg, of a composition. In another embodiment, the unit dosage of the pyridostigmine is at least about: 15-75 mg, of a composition. Administration of the compositions herein is operable to be repeated, e.g., every 5-20 minutes, as necessary. See, e.g., (1) F. Schumm, H. J. Gaertner, G. Wiatr, and J. Dichgans, "[Serum levels of pyridostigmine in myasthenia gravis: methods and clinical significance]," Fortschr. Neurol. Psychiatr., vol. 53, no. 6, pp. 201-211, 1985, doi: 10.1055/S-2007-1001967 and (2) S. M. Aquilonius, S. Å. Eckernas, P. Hartvig, B. Lindström, P. O. Osterman, and E. Stålbergt, "Clinical pharmacology of pyridostigmine and neostigmine in patients with myasthenia gravis," J. Neurol. Neurosurg. Psychiatry, vol. 46, no. 10, pp. 929-935, 1983, doi: 10.1136/JNNP.46.10.929, each of which is incorporated herein by reference in its entirety.

In some embodiments, the pyridostigmine is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the pyridostigmine is about 4%, about 7.5%, or about 15% w/w of the weight of the composition. In some embodiments, the pyridostigmine is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the pyridostigmine is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the pyridostigmine to about 40 ng/mL. In one embodiment, the compositions herein increase the blood concentration of the pyridostigmine by about 1, 2, 3, 4, 5, 6, 7, 8, 9, 10, 11, 12, 13, 14, 15, 20, 25, 30, 35, 40, 45, 50, or 75 ng/mL.

In some embodiments, the dry powder composition disclosed herein when administered to a patient, reaches a maximal blood concentration of the pyridostigmine in less than about 60 minutes ($T_{max}$) after administration. In some embodiments, the dry powder composition when administered to a patient, reaches a maximal blood concentration ($T_{max}$) of the pyridostigmine in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the pyridostigmine in less than about 30 minutes after administration. In some embodiments, the dry powder composition when administered to a patient, reaches a mean area under the curve $(AUC)_{(0\text{-}180\ minutes)}$ of the pyridostigmine which is at least 20%, 30%, 40%50%, 60%, 70%, 80%, 90%, 100%, 110%, 120%, 130%, 140%, or 150% of the mean $AUC_{(0\text{-}180\ minutes)}$ of an equivalent IV, IM, or SQ injected pyridostigmine. In some embodiments, the dry powder composition when administered to a patient, reaches a mean $AUC_{(0\text{-}\infty)}$ of the pyridostigmine which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected pyridostigmine. In some embodiments, the equivalent IV, IM, or SQ injected pyridostigmine contains about 5 mg to about 75 mg of the pyridostigmine. For example, the dry powder composition when administered to a patient, reaches a mean $AUC_{(0\text{-}180\ minutes)}$ of the pyridostigmine, which is at least 80% of the mean $AUC_{(0\text{-}180\ minutes)}$ of an equivalent IM injected pyridostigmine (e.g., 5 mg IM injected pyridostigmine, 60 mg IM injected pyridostigmine). In another instance, the dry powder composition when administered to a patient, reaches a mean $AUC_{(0\text{-}\infty)}$ of the pyridostigmine, which is at least 80% of the mean $AUC_{(0\text{-}\infty)}$ of an equivalent IM injected pyridostigmine (e.g., 5 mg IM injected pyridostigmine, 60 mg IM injected pyridostigmine,).

In certain embodiments, the dry powder compositions and/or dosage units herein are operable to raise the blood concentration of the pyridostigmine to about 40 ng/ml within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the pyridostigmine by about 40 ng/ml, for example about 20 ng/mL to about 60 ng/ml, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). See, e.g., S. M. Aquilonius, S. Å. Eckernas, P. Hartvig, B. Lindström, P. O. Osterman, and E. Stålbergt, "Clinical pharmacology of pyridostigmine and neostigmine in patients with myasthenia gravis," J. Neurol. Neurosurg. Psychiatry, vol. 46, no. 10, pp. 929-935, 1983, doi: 10.1136/JNNP.46.10.929, which is incorporated herein by reference in its entirety.

In another aspect, a single dose of the pyridostigmine in the dry powder compositions and/or dosage units given intranasally is bioequivalent (for example, in terms of peripheral blood levels, systemic exposure of the pyridostigmine) to an equivalent intravenously (IV), intramuscularly (IM) or subcutaneously (SQ) injected pyridostigmine. For example, a single dose of the pyridostigmine in the dry powder compositions and/or dosage units given intranasally is bioequivalent to an equivalent intravenously (IV), intramuscularly (IM) or subcutaneously (SQ) injected pyridostigmine. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one acetylcholinesterase inhibitor (e.g., pyridostigmine) is combined with at least one alpha-adrenergic agonist (e.g., midodrine). See, e.g., J. I. Byun et al., "Efficacy of single or combined midodrine and pyridostigmine in orthostatic hypotension," Neurology, vol. 89, no. 10, pp. 1078-186 September 2017, doi: 10.1212/WNL.0000000000004340, which is incorporated herein by reference in its entirety. In one embodiment, the at least one acetylcholinesterase inhibitor (e.g., pyridostigmine) is combined with at least one vasoactive agent (e.g., epinephrine, vasopressin, phenylephrine, or a salt thereof).

Galantamine

In one embodiment, the at least one acetylcholinesterase inhibitor includes galantamine. In one embodiment, a unit dosage of the galantamine ranges from about 15 mg to about 25 mg, for example about: 15-25 mg, of a composition. In another embodiment, the unit dosage of the galantamine is at least about: 5-75 mg, of a composition. Administration of the compositions herein is operable to be repeated, e.g., every 5-20 minutes, as necessary. See, e.g., S. Lilienfeld, "Galantamine—a novel cholinergic drug with a unique dual mode of action for the treatment of patients with Alzheimer's disease," CNS Drug Rev., vol. 8, no. 2, pp. 159-176, 2002, doi: 10.1111/J.1527-3458.2002.TB00221.X, which is incorporated herein by reference in its entirety.

In some embodiments, the galantamine is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the galantamine is about 4%, about 7.5%, or about 15% w/w of the weight of the composition. In some embodiments, the galantamine is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the galantamine is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the galantamine to about 85 ng/ml (e.g., 84 ng/ml). In one embodiment, the compositions herein increase the blood concentration of the galantamine by about 1, 2, 3, 4, 5, 6, 7, 8, 9, 10, 11, 12, 13, 14, 15, 20, 25, 30, 40, 50, 60, 70, 80, 85, 90, 100, or 125 ng/mL. See, e.g., Y. T. Lin, M. C. Chou, S. J. Wu, and Y. H. Yang, "Galantamine plasma concentration and cognitive response in Alzheimer's disease," PeerJ, vol.

2019, no. 5, 2019, doi: 10.7717/PEERJ.6887/SUPP-1, which is incorporated herein by reference in its entirety.

In some embodiments, the dry powder composition disclosed herein when administered to a patient, reaches a maximal blood concentration of the galantamine in less than about 60 minutes ($T_{max}$) after administration. In some embodiments, the dry powder composition when administered to a patient, reaches a maximal blood concentration ($T_{max}$) of the galantamine in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the galantamine in less than about 30 minutes after administration. In some embodiments, the dry powder composition when administered to a patient, reaches a mean area under the curve ($AUC_{(0-180\ minutes)}$) of the galantamine which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected galantamine. In some embodiments, the dry powder composition when administered to a patient, reaches a mean $AUC_{(0-\infty)}$ of the galantamine which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected galantamine. In some embodiments, the equivalent IV, IM, or SQ injected galantamine contains about 6 to about 8 mg of the galantamine. For example, the dry powder composition when administered to a patient, reaches a mean $AUC_{(0-180\ minutes)}$ of the galantamine, which is at least 80% of the mean $AUC_{(0-180\ minutes)}$ of an equivalent IM injected galantamine (e.g., 8 mg IM injected galantamine). In another instance, the dry powder composition when administered to a patient, reaches a mean $AUC_{(0-\infty)}$ of the galantamine, which is at least 80% of the mean $AUC_{(0-\infty)}$ of an equivalent IM injected galantamine (e.g., 8 mg IM injected galantamine). See, e.g., Y. Aracava, E. F. R. Pereira, M. Akkerman, M. Adler, and E. X. Albuquerque, "Effectiveness of donepezil, rivastigmine, and (+/−)huperzine A in counteracting the acute toxicity of organophosphorus nerve agents: comparison with galantamine," J. Pharmacol. Exp. Ther., vol. 331, no. 3, pp. 1014-124 December 2009, doi: 10.1124/JPET.109.160028, which is incorporated herein by reference in its entirety.

In certain embodiments, the dry powder compositions and/or dosage units herein are operable to raise the blood concentration of the galantamine to about 150 ng/mL within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the galantamine by about 80 ng/ml, for example 15-150 ng/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the galantamine in the dry powder compositions and/or dosage units given intranasally is bioequivalent (for example, in terms of peripheral blood levels, systemic exposure of the galantamine) to an equivalent intravenously (IV), intramuscularly (IM) or subcutaneously (SQ) injected galantamine. For example, a single dose of the galantamine in the dry powder compositions and/or dosage units given intranasally is bioequivalent to an equivalent intravenously (IV), intramuscularly (IM) or subcutaneously (SQ) injected galantamine. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one acetylcholinesterase inhibitor is used in combination with an N-Methyl-D-aspartate (NMDA) receptor antagonist (e.g., memantine). In one embodiment, the pharmaceutical composition provides a dose of about 1 mg to about 40 mg of the memantine. See, e.g., M. M. Koola and A. K. Parsaik, "Galantamine-memantine combination effective in dementia: Translate to dementia praecox?," Schizophr. Res. Cogn., vol. 12, p. 8, June 2018, doi: 10.1016/J.SCOG.2017.11.001, which is incorporated herein by reference in its entirety.

RS194B

In one embodiment, the at least one acetylcholinesterase reactivator includes RS194B. In one embodiment, a unit dosage of the RS194B ranges from about 10 mg to about 150 mg, for example about: 60 mg (e.g., 62.5 mg), of a composition. In another embodiment, the unit dosage of the RS194B is at least about: 40-80 mg, of a composition. Administration of the compositions herein is operable to be repeated, e.g., every 5-20 minutes, as necessary. See, e.g., (1) Rosenberg Y J, Mao L, Jiang X, et al. Post-exposure treatment with the oxime RS194B rapidly reverses early and advanced symptoms in macaques exposed to sarin vapor. *Chem Biol Interact.* 2017; 274:50-57. doi: 10.1016/j.cbi.2017.07.003; (2) Radić Z, Sit R K, Kovarik Z, et al. Refinement of structural leads for centrally acting oxime reactivators of phosphylated cholinesterases [published correction appears in J Biol Chem. 2012 Jun. 1; 287(23): 19337]. J Biol Chem. 2012; 287(15): 11798-11809. doi: 10.1074/jbc.M111.333732; and (3) Y. J. Rosenberg et al., "Post-exposure treatment with the oxime RS194B rapidly reverses early and advanced symptoms in macaques exposed to sarin vapor," Chem. Biol. Interact., vol. 274, pp. 50-57, August 2017, doi: 10.1016/J.CBI.2017.07.003, each of which is incorporated herein by reference in its entirety.

In some embodiments, the RS194B is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the RS194B is about 4%, about 7.5%, or about 15% w/w of the weight of the composition. In some embodiments, the RS194B is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the RS194B is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the RS194B to about 10 ng/mL. In one embodiment, the compositions herein increase the blood concentration of the RS194B by about 1, 2, 3, 4, 5, 6, 7, 8, 9, 10, 11, 12, 13, 14, 15, 25, or 50 ng/mL. See, e.g., M. A. Malfatti et al., "The biodistribution and pharmacokinetics of the oxime acetylcholinesterase reactivator RS194B in guinea pigs," Chem.

Biol. Interact., vol. 277, p. 159, November 2017, doi: 10.1016/J.CBI.2017.09.016, which is incorporated herein by reference in its entirety.

In some embodiments, the dry powder composition disclosed herein when administered to a patient, reaches a maximal blood concentration of the RS194B in less than about 60 minutes ($T_{max}$) after administration. In some embodiments, the dry powder composition when administered to a patient, reaches a maximal blood concentration ($T_{max}$) of the RS194B in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the RS194B in less than about 30 minutes after administration. In some embodiments, the dry powder composition when administered to a patient, reaches a mean area under the curve $(AUC)_{(0-180\ minutes)}$ of the RS194B which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected RS194B. In some embodiments, the dry powder composition when administered to a patient, reaches a mean $AUC_{(0-\infty)}$ of the RS194B which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected RS194B. In some embodiments, the equivalent IV, IM, or SQ injected RS194B contains about 60 mg (e.g., 62.5 mg) of the RS194B. For example, the dry powder composition when administered to a patient, reaches a mean $AUC_{(0-180\ minutes)}$ of the RS194B, which is at least 80% of the mean $AUC_{(0-180\ minutes)}$ of an equivalent IM injected RS194B (e.g., 62.5 mg IM injected RS194B). In another instance, the dry powder composition when administered to a patient, reaches a mean $AUC_{(0-\infty)}$ of the RS194B, which is at least 80% of the mean $AUC_{(0-\infty)}$ of an equivalent IM injected RS194B (e.g., 62.5 mg IM injected RS194B).

In certain embodiments, the dry powder compositions and/or dosage units herein are operable to raise the blood concentration of the RS194B to about 10 ng/ml within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the RS194B by about 10 ng/ml, for example 1-20 ng/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the RS194B in the dry powder compositions and/or dosage units given intranasally is bioequivalent (for example, in terms of peripheral blood levels, systemic exposure of the RS194B) to an equivalent intravenously (IV), intramuscularly (IM) or subcutaneously (SQ) injected RS194B. For example, a single dose of the RS194B in the dry powder compositions and/or dosage units given intranasally is bioequivalent to an equivalent intravenously (IV), intramuscularly (IM) or subcutaneously (SQ) injected RS194B. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one active pharmaceutical ingredient includes RS194B. In one embodiment, the at least one active pharmaceutical ingredient further includes at least one cholinesterase reactivator agent, at least one vasoactive agent (e.g., epinephrine, vasopressin, phenylephrine, or a salt thereof), at least one anticonvulsive agent (e.g., diazepam, lorazepam, midazolam, clonazepam, temazepam, flunitrazepam, triazolam, alprazolam, zolpidem, eszopiclone, or a salt thereof), at least one vasodilator (e.g., phentolamine, prazosin, doxazosin, bosentan, a hydralazine and nitrate combination, a PDE3 inhibitor (e.g., milrinone), a PD5 inhibitor (e.g., sildenafil)), and/or at least one catechol-o-methyl transferase (COMT) inhibitor (e.g., entacapone, tolcapone). Additional details regarding the at least one vasoactive agent, the at least one anticonvulsive agent, the at least one vasodilator, and/or the at least one COMT inhibitor are included in U.S. patent application Ser. No. 17/349,507 and U.S. Provisional Patent Application No. 63/209,221, each which is incorporated herein by reference in its entirety.

Huperizine A

In one embodiment, the at least one acetylcholinesterase reactivator includes huperizine A. In one embodiment, a unit dosage of the huperizine A ranges from about 0.2 mg to about 0.4 mg, for example about: 0.2-0.4 mg, of a composition. In another embodiment, the unit dosage of the huperizine A is at least about: 0.05-2 mg, of a composition. Administration of the compositions herein is operable to be repeated, e.g., every 5-20 minutes, as necessary. See, e.g., H. M. Hügel and N. Jackson, "Herbs and Dementia: A Focus on Chinese and Other Traditional Herbs," Diet Nutr. Dement. Cogn. Decline, pp. 795-804, 2015, doi: 10.1016/B978-0-12-407824-6.00073-2, which is incorporated herein by reference in its entirety.

In some embodiments, the huperizine A is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the huperizine A is about 4%, about 7.5%, or about 15% w/w of the weight of the composition. In some embodiments, the huperizine A is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the huperizine A is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the huperizine A to about 2.5 ng/ml (e.g., 2.59 ng/mL). In one embodiment, the compositions herein increase the blood concentration of the huperizine A by about 1, 2, 3, 4, 5, 6, 7, 8, 9, 10, 11, 12, 13, 14, 15, 25, or 50 ng/mL. See, e.g., Y. X. Li, R. Q. Zhang, C. R. Li, and X. H. Jiang, "Pharmacokinetics of huperzine A following oral administration to human volunteers," Eur. J. Drug Metab. Pharmacokinet., vol. 32, no. 4, pp. 183-187, 2007, doi: 10.1007/BF03191002, which is incorporated herein by reference in its entirety.

In some embodiments, the dry powder composition disclosed herein when administered to a patient, reaches a maximal blood concentration of the huperizine A in less than about 60 minutes ($T_{max}$) after administration. In some embodiments, the dry powder composition when administered to a patient, reaches a maximal blood concentration ($T_{max}$) of the huperizine A in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the huperizine A in less than about 30 minutes after administration. In some embodiments, the dry powder composition when administered to a patient, reaches a mean area under the curve $(AUC)_{(0\text{-}180 \ minutes)}$ of the huperizine A which is at least 20%, 30%, 40%50%, 60%, 70%, 80%, 90%, 100%, 110%, 120%, 130%, 140%, or 150% of the mean $AUC_{(0\text{-}180 \ minutes)}$ of an equivalent IV, IM, or SQ injected huperizine A. In some embodiments, the dry powder composition when administered to a patient, reaches a mean $AUC_{(0\text{-}\infty)}$ of the huperizine A which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected huperizine A. In some embodiments, the equivalent IV, IM, or SQ injected huperizine A contains about 0.05 mg to 10 mg (e.g., 0.1-0.2 mg) of the huperizine A. For example, the dry powder composition when administered to a patient, reaches a mean $AUC_{(0\text{-}180 \ minutes)}$ of the huperizine A, which is at least 80% of the mean $AUC_{(0\text{-}180 \ minutes)}$ of an equivalent IM injected huperizine A (e.g., 0.2 mg IM injected huperizine A). In another instance, the dry powder composition when administered to a patient, reaches a mean $AUC_{(0\text{-}\infty)}$ of the huperizine A, which is at least 80% of the mean $AUC_{(0\text{-}\infty)}$ of an equivalent IM injected huperizine A (e.g., 0.2 mg IM injected huperizine A).

In certain embodiments, the dry powder compositions and/or dosage units herein are operable to raise the blood concentration of the huperizine A to about 1.0-5 ng/ml (e.g., 2.59 ng/ml) within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the huperizine A by about 2.6 ng/ml, for example 2.0-3.5 ng/ml, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the huperizine A in the dry powder compositions and/or dosage units given intranasally is bioequivalent (for example, in terms of peripheral blood levels, systemic exposure of the huperizine A) to an equivalent intravenously (IV), intramuscularly (IM) or subcutaneously (SQ) injected huperizine A. For example, a single dose of the huperizine A in the dry powder compositions and/or dosage units given intranasally is bioequivalent to an equivalent intravenously (IV), intramuscularly (IM) or subcutaneously (SQ) injected huperizine A. For example, bioequivalence means a 90% confidence interval of a mean $T_{max}$ (e.g., the time to reach maximal blood concentration), a mean $C_{max}$ (e.g., maximal blood concentration), a mean $AUC_{(0\text{-}t)}$ (e.g., area under the plasma/serum/blood concentration-time curve from time zero to time t), and/or a mean $AUC_{(0\text{-}\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one active pharmaceutical ingredient includes huperizine A. In one embodiment, the at least one active pharmaceutical ingredient further includes at least one cholinesterase reactivator agent, at least one vasoactive agent (e.g., epinephrine, vasopressin, phenylephrine, or a salt thereof), at least one anticonvulsive agent (e.g., diazepam, lorazepam, midazolam, clonazepam, temazepam, flunitrazepam, triazolam, alprazolam, zolpidem, eszopiclone, or a salt thereof), at least one vasodilator (e.g., phentolamine, prazosin, doxazosin, bosentan, a hydralazine and nitrate combination, a PDE3 inhibitor (e.g., milrinone), a PD5 inhibitor (e.g., sildenafil)), and/or at least one catechol-o-methyl transferase (COMT) inhibitor (e.g., entacapone, tolcapone). Additional details regarding the at least one vasoactive agent, the at least one anticonvulsive agent, the at least one vasodilator, and/or the at least one COMT inhibitor are included in U.S. patent application Ser. No. 17/349,507 and U.S. Provisional Patent Application No. 63/209,221, each which is incorporated herein by reference in its entirety.

Method of Treatment

Provided herein are methods of treating a patient by intranasally administrating the dry powder composition disclosed herein. Also provided herein are methods of treating a patient by using the kit disclosed herein.

The methods, kits, compositions, doses, or products herein are useful for treating patients. In some instances, the patient has minimal to severe respiratory distress including bronchorrhea and bronchospasms. In some instances, the patient has excess sweating and salivation, seizures, and paralysis. In some instances, the patient has bronchoconstriction, hypotension, or cardiac arrest. The compositions described herein are operable to provide a fast onset time and are suitable for intranasal use.

In some embodiments, the intranasal dry powder composition is sufficient to improve respiratory function and breathing in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to reduce bronchorrhea and bronchospasms in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to decrease excess sweating and salivation, seizures, and paralysis in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to reverse or decrease bronchoconstriction, increase blood pressure, and increase coronary perfusion pressure in the patient within 60 minutes, 50 minutes, 40 minutes, 30 minutes, 20 minutes, 10 minutes, 5 minutes, 3 minutes, 2 minutes, or 1 minute after administration.

Also provided herein are methods for treating patients by applying to a mucosal surface(s) of the nasal cavity or cavities of an individual (e.g., the mucosal surfaces of the anterior regions of the nose, the frontal sinus, the maxillary sinuses, and/or on each of the mucosal surfaces which overlie the turbinates covering the conchas) any of the pharmaceutical compositions or dosage units herein by administering at least one acetylcholinesterase inhibitor loading dose (e.g., the amount of the at least one acetylcholinesterase inhibitor administered nasally which results in the systemic blood bioequivalent of intravenously (IV), intramuscularly (IM) or subcutaneously (SQ) administered the at least one acetylcholinesterase inhibitor). In a related aspect, the method of treating a patient in need of treatment from a nasal loading dose of about 1 mg to about 40 mg (e.g., about 4 mg to about 25 mg) of the at least one acetylcholinesterase inhibitor. See, e.g., G. Marucci, M.

Buccioni, D. D. Ben, C. Lambertucci, R. Volpini, and F. Amenta, "Efficacy of acetylcholinesterase inhibitors in Alzheimer's disease," Neuropharmacology, vol. 190, p. 108352, June 2021, doi: 10.1016/J.NEURO-PHARM.2020.108352, which is incorporated herein by reference in its entirety.

In one embodiment, the at least one acetylcholinesterase inhibitor is provided prior to exposure to the at least one poison (e.g., 60 minutes before exposure). In another aspect, the methods, kits, compositions doses or products herein are useful for treating patients. In some embodiments, the patient is not in a hospital. In some embodiments, the patient is in a hospital. In some embodiments, the patient is in a combat setting. In some embodiments, the patient is in a civil emergency setting. In one embodiment, the patient is in or near an ambulance. In some embodiments, the patient has a wound.

Advantageously, the dry powder compositions and/or dosage units provided in the present invention are given intranasally, and do not require IV infusion. Placement of an IV line during an emergency or during a combat situation is time consuming and difficult given the environment and nature of the emergency (e.g., organophosphate exposure), which includes attempting IV placement in patients experiencing a seizure, respiratory collapse, and/or circulatory collapse. Additionally, the dry powder compositions and/or dosage units provided are not via an autoinjector, which is subject to failure due to obesity and/or misuse. Further, this allows for untrained and/or non-medical personnel to attend to the patient (e.g., troops in combat). Advantageously, the nasal delivery device has a substantially smaller form factor than an autoinjector, which allows for easier incorporation in field kits and easier for an individual to carry at all times. There are no needles, glass, or aqueous dosage forms. Further, the dry powder compositions of the present invention are a more stable product and are operable to withstand a wider range of environmental conditions than conventional aqueous preparations.

Analgesics, Anesthetics, Anti-Inflammatory Agents, and/or Migraine Medication

In one embodiment, the at least one active pharmaceutical ingredient includes at least one analgesic, at least one anesthetic, at least one anti-inflammatory agent, and/or at least one migraine medication. The at least one analgesic, the at least one anesthetic, the at least one anti-inflammatory agent, and/or the at least one migraine medication includes, but is not limited to, benzocaine, bupivacaine, lidocaine, prilocaine, procaine, ropivacaine, tetracaine, codeine, diphenoxylate, heroin, dihydromorphine, ergotamine, fentanyl, hydrocodone, 1-alpha-acetyl-methadol, levomethadyl acetate, loperamide, meperidine, methadone, oxycodone, d-propoxyphene, tramadol, buprenorphine, butorphanol, nalbuphine, nalorphine, naloxone, acetaminophen, acetylsalicylic acid, caffeine, tramadol, sumatriptan, rizatriptan, naratriptan, eletriptan, donitriptan, almotriptan, frovatriptan, avitriptan, zolmitriptan dihydroergotamine, and/or butorphanol.

In one embodiment, a unit dosage of the at least one analgesic, the at least one anesthetic, the at least one anti-inflammatory agent, and/or the at least one migraine medication ranges from about 50 mg to about 500 mg, for example about: 50-500 mg, of a composition. In another embodiment, the unit dosage of the at least one analgesic, the at least one anesthetic, the at least one anti-inflammatory agent, and/or the at least one migraine medication is at least about: 10 mg to about 1 g, of a composition. Administration of the compositions herein is operable to be repeated, e.g., every 5-20 minutes, as necessary. See, e.g., S. Schou et al., "Analgesic dose-response relationship of ibuprofen 50, 100, 200, and 400 mg after surgical removal of third molars: a single-dose, randomized, placebo-controlled, and double-blind study of 304 patients," J. Clin. Pharmacol., vol. 38, no. 5, pp. 447-454, 1998, doi: 10.1002/J.1552-4604.1998.TB04452.X, which is incorporated herein by reference in its entirety.

In some embodiments, the at least one analgesic, the at least one anesthetic, the at least one anti-inflammatory agent, and/or the at least one migraine medication is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the at least one analgesic, the at least one anesthetic, the at least one anti-inflammatory agent, and/or the at least one migraine medication is about 4%, about 7.5%, or about 15% w/w of the weight of the composition. In some embodiments, the at least one analgesic, the at least one anesthetic, the at least one anti-inflammatory agent, and/or the at least one migraine medication is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the at least one analgesic, the at least one anesthetic, the at least one anti-inflammatory agent, and/or the at least one migraine medication is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the at least one analgesic, the at least one anesthetic, the at least one anti-inflammatory agent, and/or the at least one migraine medication to about 20 g/mL. In one embodiment, the compositions herein increase the blood concentration of the at least one analgesic, the at least one anesthetic, the at least one anti-inflammatory agent, and/or the at least one migraine medication by about 1, 2, 3, 4, 5, 6, 7, 8, 9, 10, 11, 12, 13, 14, 15, 20, 25, 30, 40, or 50 µg/mL. In another embodiment, the dry powder compositions herein increase the maximal blood concentration ($C_{max}$) of the at least one analgesic, the at least one anesthetic, the at least one anti-inflammatory agent, and/or the at least one migraine medication to about 180 ng/mL. In one embodiment, the compositions herein increase the blood concentration of the at least one analgesic, the at least one anesthetic, the at least one anti-inflammatory agent, and/or the at least one migraine medication by about 1, 2, 3, 4, 5, 6, 7, 8, 9, 10, 11, 12, 13, 14, 15, 25, 50, 75, 100, 125, 150, 175, 200, or 250 ng/ml. See, e.g., R. R. Taylor, K. L. Hoffman, B. Schniedewind, C. Clavijo, J. L. Galinkin, and U. Christians, "Comparison of the quantification of acetaminophen in plasma, cerebrospinal fluid and dried blood spots using high-performance liquid chromatography-tandem mass spectrometry," J. Pharm. Biomed. Anal., vol. 83, p. 1, September 2013, doi: 10.1016/J.JPBA.2013.04.007, which is incorporated herein by reference in its entirety.

In some embodiments, the dry powder composition disclosed herein when administered to a patient, reaches a maximal blood concentration of the at least one analgesic, the at least one anesthetic, the at least one anti-inflammatory agent, and/or the at least one migraine medication in less than about 60 minutes ($T_{max}$) after administration. In some embodiments, the dry powder composition when administered to a patient, reaches a maximal blood concentration ($T_{max}$) of the at least one analgesic, the at least one anesthetic, the at least one anti-inflammatory agent, and/or the at least one migraine medication in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the at least one analgesic, the at least one anesthetic, the at least one anti-inflammatory agent, and/or the at least one migraine medication in less than about 30 minutes after administration. In some embodiments, the dry powder composition when administered to a patient, reaches a mean area under the curve $(AUC)_{(0\text{-}180\ minutes)}$ of the at least one analgesic, the at least one anesthetic, the at least one anti-inflammatory agent, and/or the at least one migraine medication which is at least 20%, 30%, 40%50%, 60%, 70%, 80%, 90%, 100%, 110%, 120%, 130%, 140%, or 150% of the mean $AUC_{(0\text{-}180\ minutes)}$ of an equivalent IV, IM, or SQ injected at least one analgesic, at least one anesthetic, at least one anti-inflammatory agent, and/or at least one migraine medication. In some embodiments, the dry powder composition when administered to a patient, reaches a mean $AUC_{(0\text{-}\infty)}$ of the at least one analgesic, the at least one anesthetic, the at least one anti-inflammatory agent, and/or the at least one migraine medication which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected at least one analgesic, at least one anesthetic, at least one anti-inflammatory agent, and/or at least one migraine medication. In some embodiments, the equivalent IV, IM, or SQ injected at least one analgesic, at least one anesthetic, at least one anti-inflammatory agent, and/or at least one migraine medication contains about 25 mg to about 75 mg (e.g., about 30 mg to about 60 mg) of the at least one analgesic, the at least one anesthetic, the at least one anti-inflammatory agent, and/or the at least one migraine medication. For example, the dry powder composition when administered to a patient, reaches a mean $AUC_{(0\text{-}180\ minutes)}$ of the at least one analgesic, the at least one anesthetic, the at least one anti-inflammatory agent, and/or the at least one migraine medication, which is at least 80% of the mean $AUC_{(0\text{-}180\ minutes)}$ of an equivalent IM injected at least one analgesic, the at least one anesthetic, the at least one anti-inflammatory agent, and/or the at least one migraine medication (e.g., 60 mg IM injected at least one analgesic, the at least one anesthetic, the at least one anti-inflammatory agent, and/or the at least one migraine medication). In another instance, the dry powder composition when administered to a patient, reaches a mean $AUC_{(0\text{-}\infty)}$ of the at least one analgesic, the at least one anesthetic, the at least one anti-inflammatory agent, and/or the at least one migraine medication, which is at least 80% of the mean $AUC_{(0\text{-}\infty)}$ of an equivalent IM injected at least one analgesic, the at least one anesthetic, the at least one anti-inflammatory agent, and/or the at least one migraine medication (e.g., 60 mg IM injected at least one analgesic, the at least one anesthetic, the at least one anti-inflammatory agent, and/or the at least one migraine medication). See, e.g., M. A. Turturro, P. M. Paris, and D. C. Seaberg, "Intramuscular ketorolac versus oral ibuprofen in acute musculoskeletal pain," Ann. Emerg. Med., vol. 26, no. 2, pp. 117-120, 1995, doi: 10.1016/S0196-0644(95)70138-9, which is incorporated herein by reference in its entirety.

In certain embodiments, the dry powder compositions and/or dosage units herein are operable to raise the blood concentration of the at least one analgesic, the at least one anesthetic, the at least one anti-inflammatory agent, and/or the at least one migraine medication to about 10 μg/mL within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the at least one analgesic, the at least one anesthetic, the at least one anti-inflammatory agent, and/or the at least one migraine medication by about 10 μg/mL, for example 1-20 μg/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the at least one analgesic, the at least one anesthetic, the at least one anti-inflammatory agent, and/or the at least one migraine medication in the dry powder compositions and/or dosage units given intranasally is bioequivalent (for example, in terms of peripheral blood levels, systemic exposure of the at least one analgesic, the at least one anesthetic, the at least one anti-inflammatory agent, and/or the at least one migraine medication) to an equivalent intravenously (IV), intramuscularly (IM) or subcutaneously (SQ) injected at least one analgesic, at least one anesthetic, at least one anti-inflammatory agent, and/or at least one migraine medication. For example, a single dose of the at least one analgesic, the at least one anesthetic, the at least one anti-inflammatory agent, and/or the at least one migraine medication in the dry powder compositions and/or dosage units given intranasally is bioequivalent to an equivalent intravenously (IV), intramuscularly (IM) or subcutaneously (SQ) injected at least one analgesic, at least one anesthetic, at least one anti-inflammatory agent, and/or at least one migraine medication. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Lidocaine

In one embodiment, the at least one analgesic, the at least one anesthetic, the at least one anti-inflammatory agent, and/or the at least one migraine medication includes lidocaine. In one embodiment, a unit dosage of the lidocaine ranges from about 25 mg to about 200 mg, for example about: 50-100 mg, of a composition. In another embodiment, the unit dosage of the lidocaine is at least about: 25-50 mg, of a composition. Administration of the compositions herein is operable to be repeated, e.g., every 5-20 minutes, as necessary. See, e.g., NIH, "Lidocaine HCL 2%20 mg/mL Injection, USP 5 mL PreFilled Syringe." https://dailymed.nlm.nih.gov/dailymed/fda/fdaDrugXsl.cfm?setid=c1825011-6f51-42f2-9d85-6183cffe119a&type=display (last accessed Nov. 16, 2021), which is incorporated herein by reference in its entirety.

In some embodiments, the lidocaine is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the lidocaine is about 4%, about 7.5%, or about 15% w/w of the weight of the composition. In some embodiments, the lidocaine is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the lidocaine is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the lidocaine to about 1-8 μg/mL (e.g., about 1-5 μg/mL). In one embodiment, the compositions herein increase the blood concentration of the lidocaine by about 25, 50, 100, 150, 200, 250, 300, 400, 500, 600, 700, 750, 800, or 900 ng/mL. In another embodiment, the compositions herein increase the blood concentration of the lidocaine by about 1, 2, 3, 4, 5, 6, 7, or 8 μg/mL. See, e.g., H. Soltaninejad and N. Vesal, "Plasma concentrations of lidocaine following laryngeal administration or laryngeal and intratesticular administration in cats," Am. J. Vet. Res., vol. 79, no. 6, pp. 614-620, June 2018, doi: 10.2460/AJVR.79.6.614, which is incorporated herein by reference in its entirety.

In some embodiments, the dry powder composition disclosed herein when administered to a patient, reaches a maximal blood concentration of the lidocaine in less than about 60 minutes ($T_{max}$) after administration. In some embodiments, the dry powder composition when administered to a patient, reaches a maximal blood concentration ($T_{max}$) of the lidocaine in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the lidocaine in less than about 30 minutes after administration. In some embodiments, the dry powder composition when administered to a patient, reaches a mean area under the curve $(AUC)_{(0-180\ minutes)}$ of the lidocaine which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected lidocaine. In some embodiments, the dry powder composition when administered to a patient, reaches a mean $AUC_{(0-\infty)}$ of the lidocaine which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected lidocaine. In some embodiments, the equivalent IV, IM, or SQ injected lidocaine contains about 50 mg to about 500 mg (e.g., 300 mg) of the lidocaine. For example, the dry powder composition when administered to a patient, reaches a mean $AUC_{(0-180\ minutes)}$ of the lidocaine, which is at least 80% of the mean $AUC_{(0-180\ minutes)}$ of an equivalent IM injected lidocaine (e.g., 300 mg IM injected lidocaine). In another instance, the dry powder composition when administered to a patient, reaches a mean $AUC_{(0-\infty)}$ of the lidocaine, which is at least 80% of the mean $AUC_{(0-\infty)}$ of an equivalent IM injected lidocaine (e.g., 300 mg IM injected lidocaine).

In certain embodiments, the dry powder compositions and/or dosage units herein are operable to raise the blood concentration of the lidocaine to about 1-5 μg/mL (e.g., about 3.6 μg/mL) within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the lidocaine by about 3.6 μg/mL, for example 1-5 μg/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). See, e.g., S. Oltmanns, "[Pharmacokinetics of lidocaine after intramuscular injection in patients with acute myocardial infarction (author's transl)]-PubMed." https://pubmed.ncbi.nlm.nih.gov/442753/(last accessed Nov. 16, 2021), which is incorporated herein by reference in its entirety.

In another aspect, a single dose of the lidocaine in the dry powder compositions and/or dosage units given intranasally is bioequivalent (for example, in terms of peripheral blood levels, systemic exposure of the lidocaine) to an equivalent intravenously (IV), intramuscularly (IM) or subcutaneously (SQ) injected lidocaine. For example, a single dose of the lidocaine in the dry powder compositions and/or dosage units given intranasally is bioequivalent to an equivalent intravenously (IV), intramuscularly (IM) or subcutaneously (SQ) injected lidocaine. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Triptan

In one embodiment, the at least one analgesic, the at least one anesthetic, the at least one anti-inflammatory agent, and/or the at least one migraine medication includes a triptan or a pharmaceutical salt thereof. The triptan includes, but is not limited to, sumatriptan, rizatriptan, naratriptan, eletriptan, donitriptan, almotriptan, frovatriptan, avitriptan, and/or zolmitriptan or a pharmaceutical salt thereof. In one embodiment, a unit dosage of the triptan ranges from about 1 mg to about 10 mg, for example about: 3-6 mg, of a composition. In another embodiment, the unit dosage of the triptan is at least about: 1-3 mg, of a composition. Administration of the compositions herein is operable to be repeated, e.g., every 5-20 minutes, as necessary. See, e.g., R. K. Cady, S. Munjal, R. J. Cady, H. R. Manley, and E. Brand-Schieber, "Randomized, double-blind, crossover study comparing DFN-11 injection (3 mg subcutaneous sumatriptan) with 6 mg subcutaneous sumatriptan for the treatment of rapidly-escalating attacks of episodic migraine," J. Headache Pain, vol. 18, no. 1, December 2017, doi: 10.1186/S10194-016-0717-7, which is incorporated herein by reference in its entirety.

In some embodiments, the triptan is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the triptan is about 4%, about 7.5%, or about 15% w/w of the weight of the composition. In some embodiments, the triptan is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the triptan is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the triptan to about 50-100 ng/mL (e.g., 69.5 ng/ml). In one embodiment, the compositions herein increase the blood concentration of the triptan by about 1, 2, 3, 4, 5, 6, 7, 8, 9, 10, 11, 12, 13, 14, 15, 25, 50, 75, 100, 125, 150, or 200 ng/ml. See, e.g., C. Duquesnoy, J. P. Mamet, D. Sumner, and E. Fuseau, "Comparative clinical pharmacokinetics of single doses of sumatriptan following subcutaneous, oral, rectal and intranasal administration," Eur. J. Pharm. Sci., vol. 6, no. 2, pp. 99-104, April 1998, doi: 10.1016/S0928-0987(97)00073-0, which is incorporated herein by reference in its entirety.

In some embodiments, the dry powder composition disclosed herein when administered to a patient, reaches a maximal blood concentration of the triptan in less than about 60 minutes ($T_{max}$) after administration. In some embodiments, the dry powder composition when administered to a patient, reaches a maximal blood concentration ($T_{max}$) of the triptan in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the triptan in less than about 30 minutes after administration. In some embodiments, the dry powder composition when administered to a patient, reaches a mean area under the curve (AUC)(0-180 minutes) of the triptan which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected triptan. In some embodiments, the dry powder composition when administered to a patient, reaches a mean $AUC_{(0-\infty)}$ of the triptan which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected triptan. In some embodiments, the equivalent IV, IM, or SQ injected triptan contains about 1 mg to about 10 mg (e.g., about 3 mg to about 6 mg) of the triptan. For example, the dry powder composition when administered to a patient, reaches a mean $AUC_{(0-180\ minutes)}$ of the triptan, which is at least 80% of the mean $AUC_{(0-180\ minutes)}$ of an equivalent IM injected triptan (e.g., 6 mg IM injected triptan). In another instance, the dry powder composition when administered to a patient, reaches a mean $AUC_{(0-\infty)}$ of the triptan, which is at least 80% of the mean $AUC_{(0-\infty)}$ of an equivalent IM injected triptan (e.g., 6 mg IM injected triptan). See, e.g., R. K. Cady, S. Munjal, R. J. Cady, H. R. Manley, and E. Brand-Schieber, "Randomized, double-blind, crossover study comparing DFN-11 injection (3 mg subcutaneous sumatriptan) with 6 mg subcutaneous sumatriptan for the treatment of rapidly-escalating attacks of episodic migraine," J. Headache Pain, vol. 18, no. 1, December 2017, doi: 10.1186/S10194-016-0717-7, which is incorporated herein by reference in its entirety.

In certain embodiments, the dry powder compositions and/or dosage units herein are operable to raise the blood concentration of the triptan to about 70 ng/ml (e.g., 69.5 ng/ml) within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the triptan by about 50-100 ng/ml (e.g., 69.5 ng/ml), for example 60-80 ng/ml, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). See, e.g., C. Duquesnoy, J. P. Mamet, D. Sumner, and E. Fuseau, "Comparative clinical pharmacokinetics of single doses of sumatriptan following subcutaneous, oral, rectal and intranasal administration," Eur. J. Pharm. Sci., vol. 6, no. 2, pp. 99-104, April 1998, doi: 10.1016/S0928-0987(97)00073-0, which is incorporated herein by reference in its entirety.

In another aspect, a single dose of the triptan in the dry powder compositions and/or dosage units given intranasally is bioequivalent (for example, in terms of peripheral blood levels, systemic exposure of the triptan) to an equivalent intravenously (IV), intramuscularly (IM) or subcutaneously (SQ) injected triptan. For example, a single dose of the triptan in the dry powder compositions and/or dosage units given intranasally is bioequivalent to an equivalent intravenously (IV), intramuscularly (IM) or subcutaneously (SQ) injected triptan. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Acetylsalicylic Acid

In one embodiment, the at least one analgesic, the at least one anesthetic, the at least one anti-inflammatory agent, and/or the at least one migraine medication includes acetylsalicylic acid. In one embodiment, a unit dosage of the acetylsalicylic acid ranges from about 50 mg to about 1300 mg, for example about: 325-650 mg, of a composition. In another embodiment, the unit dosage of the acetylsalicylic acid is at least about: 200-300, of a composition. Administration of the compositions herein is operable to be repeated, e.g., every 5-20 minutes, as necessary. Oral administration of acetylsalicylic acid may cause stomach ulcers and/or gastrointestinal problems. Advantageously, nasal administration of acetylsalicylic acid bypasses the gastrointestinal system. Further, some patients may have dysphagia (e.g., following a stroke), and nasal administration of acetylsalicylic acid advantageously does not require swallowing.

In some embodiments, the acetylsalicylic acid is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the acetylsalicylic acid is about 4%, about 7.5%, or about 15% w/w of the weight of the composition. In some embodiments, the acetylsalicylic acid is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the acetylsalicylic acid is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the acetylsalicylic acid to about 1-5 μg/mL. In one embodiment, the compositions herein increase the blood concentration of the acetylsalicylic acid to about 0.5, 1, 2, 3, 4, 5, 6, 7, 8, 9, 10, 11, 12, 13, 14, 15, 25, or 50 μg/mL. See, e.g., (1) Benedek, I. H., Joshi, A. S., Pieniaszek, H. J., King, S.-Y. P. and Kornhauser, D. M. (1995), Variability in the Pharmacokinetics and Pharmacodynamics of Low Dose Aspirin in Healthy Male Volunteers. The Journal of Clinical Pharmacology, 35: 1181-1186. https://doi.org/10.1002/j.1552-4604.1995.tb04044.x and (2) Nagelschmitz J, Blunck M, Kraetzschmar J, Ludwig M, Wensing G, Hohlfeld T. Pharmacokinetics and pharmacodynamics of acetylsalicylic acid after intravenous and oral administration to healthy volunteers. *Clin Pharmacol.* 2014; 6:51-59. Published 2014 Mar. 19. doi: 10.2147/CPAA.S47895, each of which is incorporated herein by reference in its entirety.

In some embodiments, the dry powder composition disclosed herein when administered to a patient, reaches a maximal blood concentration of the acetylsalicylic acid in less than about 60 minutes ($T_{max}$) after administration. In some embodiments, the dry powder composition when administered to a patient, reaches a maximal blood concentration ($T_{max}$) of the acetylsalicylic acid in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the acetylsalicylic acid in less than about 30 minutes after administration. In some embodiments, the dry powder composition when administered to a patient, reaches a mean area under the curve ($AUC_{(0-180\ minutes)}$) of the acetylsalicylic acid which is at least 20%, 30%, 40% 50%, 60%, 70%, 80%, 90%, 100%, 110%, 120%, 130%, 140%, or 150% of the mean $AUC_{(0-180\ minutes)}$ of an equivalent IV, IM, or SQ injected acetylsalicylic acid. In some embodiments, the dry powder composition when administered to a patient, reaches a mean $AUC_{(0-\infty)}$ of the acetylsalicylic acid which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected acetylsalicylic acid.

In certain embodiments, the dry powder compositions and/or dosage units herein are operable to raise the blood concentration of the acetylsalicylic acid to about 1-5 μg/mL within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the acetylsalicylic acid by about 0.5-10 μg/mL, for example 1-5 μg/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the acetylsalicylic acid in the dry powder compositions and/or dosage units given intranasally is bioequivalent (for example, in terms of peripheral blood levels, systemic exposure of the acetylsalicylic acid) to an equivalent intravenously (IV), intramuscularly (IM) or subcutaneously (SQ) injected acetylsalicylic acid. For example, a single dose of the acetylsalicylic acid in the dry powder compositions and/or dosage units given intranasally is bioequivalent to an equivalent intravenously (IV), intramuscularly (IM) or subcutaneously (SQ) injected acetylsalicylic acid. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Method of Treatment

Provided herein are methods of treating a patient by intranasally administrating the dry powder composition disclosed herein. Also provided herein are methods of treating a patient by using the kit disclosed herein.

The methods, kits, compositions, doses, or products herein are useful for treating patients. In some instances, the patient has minimal to severe pain. In some instances, the patient has a migraine. In some instances, the patient is suffering from or has previously suffered from a heart attack, a stroke, a transient ischemic attack (TIA), a blood clot, a clotting disorder, and/or a deep vein thrombosis (DVT) (e.g., and requires treatment with acetylsalicylic acid). In some instances, the patient is suffering from inflammation and/or an inflammatory condition (e.g., pericarditis, rheumatoid arthritis, Kawasaki disease). In some instances, the patient is suffering from a fever. The compositions described herein are operable to provide a fast onset time and are suitable for intranasal use.

In some embodiments, the intranasal dry powder composition is sufficient to reduce pain in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to reduce migraine symptoms in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to reduce symptoms from the heart attack, the stroke, the TIA, the blood clot, the clotting disorder, and/or the DVT in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to reduce fever symptoms in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to reduce symptoms from the inflammation and/or the inflammatory condition in the patient within 60 minutes, 50 minutes, 40 minutes, 30 minutes, 20 minutes, 10 minutes, 5 minutes, 3 minutes, 2 minutes, or 1 minute after administration.

Also provided herein are methods for treating patients by applying to a mucosal surface(s) of the nasal cavity or cavities of an individual (e.g., the mucosal surfaces of the anterior regions of the nose, the frontal sinus, the maxillary sinuses, and/or on each of the mucosal surfaces which overlie the turbinates covering the conchas) any of the pharmaceutical compositions or dosage units herein by administering at least one analgesic, at least one anesthetic, at least one anti-inflammatory agent, and/or at least one migraine medication loading dose (e.g., the amount of the at least one analgesic, the at least one anesthetic, the at least one anti-inflammatory agent, and/or the at least one migraine medication administered nasally which results in the systemic blood bioequivalent of intravenously (IV), intramuscularly (IM) or subcutaneously (SQ) administered the at least one analgesic, the at least one anesthetic, the at least one anti-inflammatory agent, and/or the at least one migraine medication). In a related aspect, the method of treating a patient in need of treatment from a nasal loading dose of about 0.1 mg to about 10 mg (e.g., about 1 mg to about 2 mg) of the at least one analgesic, the at least one anesthetic, the at least one anti-inflammatory agent, and/or the at least one migraine medication. See, e.g., D. P. Wermeling, G. M. Grant, A. Lee, N. Alexander, and A. C. Rudy, "Analgesic effects of intranasal butorphanol tartrate administered via a unit-dose device in the dental impaction pain model: a randomized, double-blind, placebo-controlled, parallel-group study," Clin. Ther., vol. 27, no. 4, pp. 430-440, April 2005, doi: 10.1016/J.CLINTHERA.2005.04.002, which is incorporated herein by reference in its entirety.

In another aspect, the methods, kits, compositions doses or products herein are useful for treating patients. In some embodiments, the patient is not in a hospital. In some embodiments, the patient is in a hospital. In some embodiments, the patient is in a combat setting. In some embodiments, the patient is in a civil emergency setting. In one embodiment, the patient is in or near an ambulance. In some embodiments, the patient has a wound.

Advantageously, the dry powder compositions and/or dosage units provided in the present invention are given intranasally, and do not require IV infusion, injection, or oral administration. Placement of an IV line during an emergency or during a combat situation is time consuming and difficult given the environment and nature of the emergency, which may include attempting IV placement in patients experiencing a seizure, respiratory collapse, and/or circulatory collapse. Additionally, the dry powder compositions and/or dosage units provided are not via an autoinjector or syringe, which is subject to failure due to obesity and/or misuse. Further, this allows for untrained and/or non-medical personnel to attend to the patient and/or self-administer the at least one analgesic, the at least one anesthetic, the at least one anti-inflammatory agent, and/or the at least one migraine medication. Advantageously, the nasal delivery device has a substantially smaller form factor than an autoinjector or a syringe, which allows for easier incorporation in field kits and easier for an individual to carry at all times. There are no needles, glass, or aqueous dosage forms. Further, the dry powder compositions of the present invention are a more stable product and are operable to withstand a wider range of environmental conditions than conventional aqueous preparations.

Peptides and Hormones

In one embodiment, the at least one active pharmaceutical ingredient includes at least one peptide and/or at least one hormone. The at least one peptide and/or the at least one hormone includes, but is not limited to, at least one androgen (e.g., testosterone), at least one estrogen (e.g., estradiol), at least one progestogen (e.g., progesterone), and/or at least one gonadotropin (e.g., follicle stimulating hormone (FSH), luteinizing hormone (LH)).

In some embodiments, the at least one peptide and/or the at least one hormone is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the at least one peptide and/or the at least one hormone is about 4%, about 7.5%, or about 15% w/w of the weight of the composition. In some embodiments, the at least one peptide and/or the at least one hormone is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the at least one peptide and/or the at least one hormone is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In some embodiments, the dry powder composition disclosed herein when administered to a patient, reaches a maximal blood concentration of the a at least one peptide and/or the at least one hormone in less than about 60 minutes ($T_{max}$) after administration. In some embodiments, the dry powder composition when administered to a patient, reaches a maximal blood concentration ($T_{max}$) of the at least one peptide and/or the at least one hormone in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the at least one peptide and/or the at least one hormone in less than about 30 minutes after administration. In some embodiments, the dry powder composition when administered to a patient, reaches a mean area under the curve ($AUC_{(0\text{-}180\ minutes)}$) of the at least one peptide and/or the at least one hormone which is at least 20%, 30%, 40%50%, 60%, 70%, 80%, 90%, 100%, 110%, 120%, 130%, 140%, or 150% of the mean $AUC_{(0\text{-}180\ minutes)}$ of an equivalent IV, IM, or SQ injected at least one peptide and/or at least one hormone. In some embodiments, the dry powder composition when administered to a patient, reaches a mean $AUC_{(0\text{-}\infty)}$ of the at least one peptide and/or the at least one hormone which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected at least one peptide and/or at least one hormone.

In another aspect, a single dose of the at least one peptide and/or the at least one hormone in the dry powder compositions and/or dosage units given intranasally is bioequivalent (for example, in terms of peripheral blood levels, systemic exposure of the at least one peptide and/or the at least one hormone) to an equivalent intravenously (IV), intramuscularly (IM) or subcutaneously (SQ) injected at least one peptide and/or at least one hormone. For example, a single dose of the at least one peptide and/or the at least one hormone in the dry powder compositions and/or dosage units given intranasally is bioequivalent to an equivalent intravenously (IV), intramuscularly (IM) or subcutaneously (SQ) injected at least one peptide and/or at least one hormone. For example, bioequivalence means a 90% confidence interval of a mean $T_{max}$ (e.g., the time to reach maximal blood concentration), a mean $C_{max}$ (e.g., maximal blood concentration), a mean $AUC_{(0\text{-}t)}$ (e.g., area under the plasma/serum/blood concentration-time curve from time zero to time t), and/or a mean $AUC_{(0\text{-}\infty)}$ (e.g., area under the plasma/serum/blood concentration-time curve from time zero to time infinity) of the test to reference are within 80.00% to 125.00%. In one embodiment, bioequivalence is measured in a fasting state.

Progesterone

In one embodiment, the at least one peptide and/or the at least one hormone includes a progesterone (e.g., medroxy-progesterone, megestrol, norethindrone). In one embodiment, a unit dosage of the progesterone equivalent ranges from about 5 mg to about 400 mg, for example about: 10-250 mg, of a composition. Administration of the compositions herein is operable to be repeated, e.g., daily, as necessary.

In some embodiments, the progesterone is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the progesterone is about 4%, about 7.5%, or about 15% w/w of the weight of the composition. In some embodiments, the progesterone is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the progesterone is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the progesterone to about 7-50 ng/mL. In one embodiment, the compositions herein increase the blood concentration of the progesterone by about 1, 2, 3, 4, 5, 6, 7, 8, 9, 10, 11, 12, 13, 14, 15, 25, or 50 ng/mL.

In some embodiments, the dry powder composition disclosed herein when administered to a patient, reaches a maximal blood concentration of the progesterone in less than about 60 minutes ($T_{max}$) after administration. In some embodiments, the dry powder composition when administered to a patient, reaches a maximal blood concentration ($T_{max}$) of the progesterone in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the progesterone in less than about 30 minutes after administration. In some embodiments, the dry powder composition when administered to a patient, reaches a mean area under the curve (AUC)(0-180 minutes) of the progesterone which is at least 20%, 30%, 40%50%, 60%, 70%, 80%, 90%, 100%, 110%, 120%, 130%, 140%, or 150% of the mean $AUC_{(0\text{-}180\ minutes)}$ of an equivalent IV, IM, or SQ injected progesterone. In some embodiments, the dry powder composition when administered to a patient, reaches a mean $AUC_{(0\text{-}\infty)}$ of the progesterone which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected progesterone.

In certain embodiments, the dry powder compositions and/or dosage units herein are operable to raise the blood concentration of the progesterone to about 7-50 ng/ml within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the progesterone by about 2-100 ng/mL, for example 5-75 ng/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes). See, e.g., PROGESTERONE INJECTION USP, available at https://www.accessdata.fda-.gov/drugsatfda_docs/label/2007/017362s104lbl.pdf, which is incorporated herein by reference in its entirety.

In another aspect, a single dose of the progesterone in the dry powder compositions and/or dosage units given intranasally is bioequivalent (for example, in terms of peripheral blood levels, systemic exposure of the progesterone) to an equivalent intravenously (IV), intramuscularly (IM) or subcutaneously (SQ) injected progesterone. For example, a single dose of the progesterone in the dry powder compositions and/or dosage units given intranasally is bioequivalent to an equivalent intravenously (IV), intramuscularly (IM) or subcutaneously (SQ) injected progesterone. For example, bioequivalence means a 90% confidence interval of a mean $T_{max}$ (e.g., the time to reach maximal blood concentration), a mean $C_{max}$ (e.g., maximal blood concentration), a mean $AUC_{(0\text{-}t)}$ (e.g., area under the plasma/serum/blood concentration-time curve from time zero to time t), and/or a mean $AUC_{(0\text{-}\infty)}$ (e.g., area under the plasma/serum/blood concentration-time curve from time zero to time infinity) of the test to reference are within 80.00% to 125.00%. In one embodiment, bioequivalence is measured in a fasting state.

Estrogen

In one embodiment, the at least one peptide and/or the at least one hormone includes an estrogen (e.g., estradiol, estradiol cypionate, estradio valerate, estrone, estropipate, norethindrone, esterified estrogens, conjugated estrogens). In one embodiment, a unit dosage of the estrogen (e.g., estradiol) ranges from about 100 μg to about 400 μg, for example about: 200-300 μg, of a composition. Administration of the compositions herein is operable to be repeated, e.g., daily, as necessary.

In some embodiments, the estrogen is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the estrogen is about 4%, about 7.5%, or about 15% w/w of the weight of the composition. In some embodiments, the estrogen is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the estrogen is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In some embodiments, the dry powder composition disclosed herein when administered to a patient, reaches a maximal blood concentration of the estrogen in less than about 60 minutes ($T_{max}$) after administration. In some embodiments, the dry powder composition when administered to a patient, reaches a maximal blood concentration ($T_{max}$) of the estrogen in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the estrogen in less than about 30 minutes after administration. In some embodiments, the dry powder composition when administered to a patient, reaches a mean area under the curve ($AUC$)$_{(0-180\ minutes)}$ of the estrogen which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected estrogen. In some embodiments, the dry powder composition when administered to a patient, reaches a mean $AUC_{(0-\infty)}$ of the estrogen which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected estrogen.

In another aspect, a single dose of the estrogen in the dry powder compositions and/or dosage units given intranasally is bioequivalent (for example, in terms of peripheral blood levels, systemic exposure of the estrogen) to an equivalent intravenously (IV), intramuscularly (IM) or subcutaneously (SQ) injected estrogen. For example, a single dose of the estrogen in the dry powder compositions and/or dosage units given intranasally is bioequivalent to an equivalent intravenously (IV), intramuscularly (IM) or subcutaneously (SQ) injected estrogen. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Testosterone

In one embodiment, the at least one peptide and/or the at least one hormone includes a testosterone (e.g., testosterone undecanoate, testosterone enanthate, testosterone cypionate). In one embodiment, a unit dosage of the testosterone (e.g., testosterone enanthate) ranges from about 50 mg to about 400 mg, for example about: 100-300 mg, of a composition. Administration of the compositions herein is operable to be repeated, e.g., daily, as necessary.

In some embodiments, the testosterone is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the testosterone is about 4%, about 7.5%, or about 15% w/w of the weight of the composition. In some embodiments, the testosterone is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the testosterone is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the testosterone to about 300-1050 ng/dL. In one embodiment, the compositions herein increase the blood concentration of the testosterone by about 50, 100, 200, 300, 400, 500, 600, 700, 800, 900, or 1000 ng/dL.

In some embodiments, the dry powder composition disclosed herein when administered to a patient, reaches a maximal blood concentration of the testosterone in less than about 60 minutes ($T_{max}$) after administration. In some embodiments, the dry powder composition when administered to a patient, reaches a maximal blood concentration ($T_{max}$) of the testosterone in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the testosterone in less than about 30 minutes after administration. In some embodiments, the dry powder composition when administered to a patient, reaches a mean area under the curve ($AUC$)$_{(0-180\ minutes)}$ of the testosterone which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected testosterone. In some embodiments, the dry powder composition when administered to a patient, reaches a mean $AUC_{(0-\infty)}$ of the testosterone which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected testosterone.

In certain embodiments, the dry powder compositions and/or dosage units herein are operable to raise the blood concentration of the testosterone to about 300-1050 ng/dL within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the testosterone by about 50-1000 ng/dL, for example 200-500 ng/dL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the testosterone in the dry powder compositions and/or dosage units given intranasally is bioequivalent (for example, in terms of peripheral blood levels, systemic exposure of the testosterone) to an equivalent intravenously (IV), intramuscularly (IM) or subcutaneously (SQ) injected testosterone. For example, a single dose of the testosterone in the dry powder compositions and/or dosage units given intranasally is bioequivalent to an equivalent intravenously (IV), intramuscularly (IM) or subcutaneously (SQ) injected testosterone. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

Follicle Stimulating Hormone

In one embodiment, the at least one peptide and/or the at least one hormone includes follicle stimulating hormone (FSH). In one embodiment, a unit dosage of the FSH ranges from about 100 IU to about 600 IU, for example about: 300-450 IU, of a composition. Administration of the compositions herein is operable to be repeated, e.g., daily, as necessary. See, e.g., Rombauts L. Is there a recommended maximum starting dose of FSH in IVF?. *J Assist Reprod Genet.* 2007,24(8): 343-349. doi: 10.1007/s10815-007-9134-9, which is incorporated herein by reference in its entirety.

In some embodiments, the FSH is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the FSH is about 4%, about 7.5%, or about 15% w/w of the weight of the composition. In some embodiments, the FSH is present in an amount of at least about: 0.25% w/w, 1% w/w, 5% w/w, 10% w/w, 20% w/w, 30% w/w, 40% w/w, or 50% w/w based on the weight of the formulations and/or dosage units. In some embodiments, the FSH is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the FSH to about 0.3 to 25 mIU/mL. In one embodiment, the compositions herein increase the blood concentration of the FSH by about 0.5, 1, 2, 3, 4, 5, 6, 7, 8, 9, 10, 11, 12, 13, 14, 15, 20, or 25 mIU/mL.

In some embodiments, the dry powder composition disclosed herein when administered to a patient, reaches a maximal blood concentration of the FSH in less than about 60 minutes ($T_{max}$) after administration. In some embodiments, the dry powder composition when administered to a patient, reaches a maximal blood concentration ($T_{max}$) of the FSH in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the FSH in less than about 30 minutes after administration. In some embodiments, the dry powder composition when administered to a patient, reaches a mean area under the curve $(AUC)_{(0-180\ minutes)}$ of the FSH which is at least 20%, 30%, 40%50%, 60%, 70%, 80%, 90%, 100%, 110%, 120%, 130%, 140%, or 150% of the mean $AUC_{(0-180\ minutes)}$ of an equivalent IV, IM, or SQ injected FSH. In some embodiments, the dry powder composition when administered to a patient, reaches a mean $AUC_{(0-\infty)}$ of the FSH which is at least 20%, 30%, 40%50%, 60%, 70%, 80%, 90%, 100%, 110%, 120%, 130%, 140%, or 150% of the mean $AUC_{(0-\infty)}$ of an equivalent IV, IM, or SQ injected FSH.

In certain embodiments, the dry powder compositions and/or dosage units herein are operable to raise the blood concentration of the FSH to about 0.3-25 mIU/mL within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the FSH by about 3-20 mIU/mL, for example 5-15 mIU/mL, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the FSH in the dry powder compositions and/or dosage units given intranasally is bioequivalent (for example, in terms of peripheral blood levels, systemic exposure of the FSH) to an equivalent intravenously (IV), intramuscularly (IM) or subcutaneously (SQ) injected FSH. For example, a single dose of the FSH in the dry powder compositions and/or dosage units given intranasally is bioequivalent to an equivalent intravenously (IV), intramuscularly (IM) or subcutaneously (SQ) injected FSH. For example, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one active pharmaceutical ingredient includes FSH and LH.

Luteinizing Hormone

In one embodiment, the at least one peptide and/or the at least one hormone includes luteinizing hormone (LH) (e.g., recombinant human luteinizing hormone (rhLH)). In one embodiment, a unit dosage of the LH ranges from about 25 IU to about 225 IU, for example about: 50-175 IU, of a composition. Administration of the compositions herein is operable to be repeated, e.g., daily, as necessary. See, e.g., Recombinant human luteinizing hormone (LH) to support recombinant human follicle-stimulating hormone (FSH)-induced follicular development in LH- and FSH-deficient anovulatory women: a dose-finding study. The European Recombinant Human LH Study Group. J Clin Endocrinol Metab. 1998 May; 83(5):1507-14. doi: 10.1210/jcem.83.5.4770. PMID: 9589647, which is incorporated herein by reference in its entirety.

In some embodiments, the LH is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w, based on the weight of the formulations and/or dosage units. For example, the LH is about 4%, about 7.5%, or about 15% w/w of the weight of the composition. In some embodiments, the LH is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, the LH is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the formulations and/or dosage units.

In one embodiment, the dry powder compositions herein increase the maximal blood concentration ($C_{max}$) of the LH to between about 1 IU/L and about 100 IU/L. In one embodiment, the compositions herein increase the equivalent blood concentration of the LH by about 1, 2, 3, 4, 5, 6, 7, 8, 9, 10, 11, 12, 13, 14, 15, 25, 50, 75, or 100 IU/L.

In some embodiments, the dry powder composition disclosed herein when administered to a patient, reaches a maximal blood concentration of the LH in less than about 60 minutes ($T_{max}$) after administration. In some embodiments, the dry powder composition when administered to a patient, reaches a maximal blood concentration ($T_{max}$) of the LH in less than about 60, 50, 40, 30, 20, 15, 10, 5, or 3 minutes ($T_{max}$) after administration. In one embodiment, the dry powder composition when administered to a patient, reaches a maximal blood concentration ($T_{max}$) of the LH in less than about 30 minutes after administration. In some embodiments, the dry powder composition when administered to a patient, reaches a mean area under the curve $(AUC)_{(0\text{-}180\ minutes)}$ of the LH which is at least 20%, 30%, 40%50%, 60%, 70%, 80%, 90%, 100%, 110%, 120%, 130%, 140%, or 150% of the mean $AUC_{(0\text{-}180\ minutes)}$ of an equivalent IV, IM, or SQ injected LH. In some embodiments, the dry powder composition when administered to a patient, reaches a mean $AUC_{(0\text{-}\infty)}$ of the LH which is at least 20%, 30%, 40%50%, 60%, 70%, 80%, 90%, 100%, 110%, 120%, 130%, 140%, or 150% of the mean $AUC_{(0\text{-}\infty)}$ of an equivalent IV, IM, or SQ injected LH.

In certain embodiments, the dry powder compositions and/or dosage units herein are operable to raise the blood concentration of the LH to about 1-100 IU/L within about 3 to about 60 minutes (e.g., about: 60, 50, 40, 30, 20, 15, 10, 5, or 3 minutes), or about 10 to about 15 minutes (e.g., about: 10, 11, 12, 13, 14, or 15 minutes) of intranasal administration. In one embodiment, the compositions herein increase the blood concentration of the LH by about 1-20 IU/L, for example 1-10 IU/L, in about 10-15 minutes (e.g., about: 10, 11, 12, 13, 14, or 15 minutes), or about 3 to about 60 minutes (e.g., about: 60, 50, 40, 30, 20, 15, 10, 5, or 3 minutes).

In another aspect, a single dose of the LH in the dry powder compositions and/or dosage units given intranasally is bioequivalent (for example, in terms of peripheral blood levels, systemic exposure of the LH) to an equivalent intravenously (IV), intramuscularly (IM) or subcutaneously (SQ) injected LH. For example, a single dose of the LH in the dry powder compositions and/or dosage units given intranasally is bioequivalent to an equivalent intravenously (IV), intramuscularly (IM) or subcutaneously (SQ) injected LH. For example, bioequivalence means a 90% confidence interval of a mean $T_{max}$ (e.g., the time to reach maximal blood concentration), a mean $C_{max}$ (e.g., maximal blood concentration), a mean $AUC_{(0\text{-}t)}$ (e.g., area under the plasma/serum/blood concentration-time curve from time zero to time t), and/or a mean $AUC_{(0\text{-}\infty)}$ (e.g., area under the plasma/serum/blood concentration-time curve from time zero to time infinity) of the test to reference are within 80.00% to 125.00%. In one embodiment, bioequivalence is measured in a fasting state.

In one embodiment, the at least one active pharmaceutical ingredient includes FSH and LH.

Method of Treatment

Provided herein are methods of treating a patient by intranasally administrating the dry powder composition disclosed herein. Also provided herein are methods of treating a patient by using the kit disclosed herein.

The methods, kits, compositions, doses, or products herein are useful for treating patients. In some instances, the patient is suffering from low testosterone levels. In some instances, the patient is suffering from symptoms of menopause (e.g., hot flashes). In some instances, the patient is suffering from infertility. The compositions described herein are operable to provide a fast onset time and are suitable for intranasal use.

In some embodiments, the intranasal dry powder composition is sufficient to improve levels of the at least one peptide and/or the at least one hormone in the patient within 60 minutes, 50 minutes, 40 minutes, 30 minutes, 20 minutes, 10 minutes, 5 minutes, 3 minutes, 2 minutes, or 1 minute after administration.

Also provided herein are methods for treating patients by applying to a mucosal surface(s) of the nasal cavity or cavities of an individual (e.g., the mucosal surfaces of the anterior regions of the nose, the frontal sinus, the maxillary sinuses, and/or on each of the mucosal surfaces which overlie the turbinates covering the conchas) any of the pharmaceutical compositions or dosage units herein by administering at least one peptide and/or at least one hormone loading dose (e.g., the amount of the at least one peptide and/or the at least one hormone administered nasally which results in the systemic blood bioequivalent of intravenously (IV), intramuscularly (IM) or subcutaneously (SQ) administered the at least one peptide and/or the at least one hormone).

In another aspect, the methods, kits, compositions doses or products herein are useful for treating patients. In some embodiments, the patient is not in a hospital. In some embodiments, the patient is in a hospital. In some embodiments, the patient is in a combat setting. In some embodiments, the patient is in a civil emergency setting. In one embodiment, the patient is in or near an ambulance. In some embodiments, the patient is in a residential setting.

Advantageously, the dry powder compositions and/or dosage units provided in the present invention are given intranasally, and do not require IV infusion or injections. Additionally, the dry powder compositions and/or dosage units provided are not via an autoinjector or a syringe, which is subject to failure due to obesity and/or misuse. Further, this allows for untrained and/or non-medical personnel to attend to the patient and/or self-administer the at least one peptide and/or the at least one hormone. There are no needles, glass, or aqueous dosage forms. Further, the dry powder compositions of the present invention are a more stable product and are operable to withstand a wider range of environmental conditions than conventional aqueous preparations. Advantageously, the present invention allows for patients to receive treatment without fear of needles.

Enabling Agents

In one embodiment, the intranasal dry powder formulations and/or unit doses include at least one enabling agent. The at least one enabling agent includes, but is not limited to, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

Additional details regarding nasal delivery of drugs, including information regarding enabling agents, are disclosed in (1) Bourganis V, Kammona O, Alexopoulos A, Kiparissides C. Recent advances in carrier mediated nose-to-brain delivery of pharmaceutics. Eur J Pharm Biopharm. 2018 July; 128:337-362. doi: 10.1016/j.ejpb.2018.05.009. Epub 2018 May 4. PMID: 29733950; (2) Davis S S, Illum L. Absorption enhancers for nasal drug delivery. Clin Pharmacokinet. 2003; 42(13): 1107-28. doi: 10.2165/00003088-200342130-00003. PMID: 14531723; (3) Gänger S, Schindowski K. Tailoring Formulations for Intranasal Nose-to-Brain Delivery: A Review on Architecture, Physico-Chemical Characteristics and Mucociliary Clearance of the Nasal Olfactory Mucosa. Pharmaceutics. 2018 Aug. 3; 10(3): 116. doi: 10.3390/pharmaceutics 10030116. PMID: 30081536; PMCID: PMC6161189; and (4) Tiozzo Fasiolo L, Manniello M D, Tratta E, Buttini F, Rossi A, Sonvico F, Bortolotti F, Russo P, Colombo G. Opportunity and challenges of nasal powders: Drug formulation and delivery. Eur J Pharm Sci. 2018 Feb. 15; 113:2-17. doi: 10.1016/j.ejps.2017.09.027. Epub 2017 Sep. 20. PMID: 28942007, each of which is incorporated herein by reference in its entirety.

In one embodiment, the intranasal dry powder formulations and/or unit doses include at least one mucoadhesive. In one embodiment, the at least one mucoadhesive includes a starch, crystalline cellulose, a cellulose derivative, a polymer (e.g., chitosan, a carbopol (e.g., carbopol 943), carbophil, carbomer), a polyacrylic acid or polyacrylic acid derivative, a protein (e.g., mucin, lactoferrin, transferrin), and/or lecithin. See, e.g., (1) Takeuchi H, Thongborisute J, Matsui Y, Sugihara H, Yamamoto H, Kawashima Y. Novel mucoadhesion tests for polymers and polymer-coated particles to design optimal mucoadhesive drug delivery systems. Adv Drug Deliv Rev. 2005 Nov. 3; 57(11): 1583-94. doi: 10.1016/j.addr.2005.07.008. Epub 2005 Sep. 16. PMID: 16169120; (2) D Tabor, Surface forces and surface interactions, J. Colloid Interface Sci., Volume 58, Issue 1, 1977, Pages 2-13, https://doi.org/10.1016/0021-9797(77)90366-6; and (3) Robert J Good, Surface free energy of solids and liquids: Thermodynamics, molecular forces, and structure, J. Colloid Interface Sci., Volume 59, Issue 3, 1977, Pages 398-419, https://doi.org/10.1016/0021-9797(77)90034-0, each of which is incorporated herein by reference in its entirety.

In one embodiment, the intranasal dry powder formulations and/or unit doses include at least one absorption enhancer. In one embodiment, the at least one absorption enhancer includes a flavonoid (e.g., Vitamin P-like compound), vasopressin, methylphenidate, tropolone, desmethyl papaverine, pyrogallol, an amino acid (e.g., histidine), an antihistamine, an amphetamine, a local anesthetic, norepinephrine, isoproterenol, hydrocortisone, tripelennamine, bufotenine, harmine, methergine, a ganglionic blocker, guanethidine, mescaline, cocaine, lysergic acid diethylamide (LSD), or an enantiomer, diastereoisomer, racemate, prodrug, or salt of such compounds.

In one embodiment, the intranasal dry powder formulations and/or unit doses include at least one permeability enhancer and/or at least one mucosal permeation enhancer. In one embodiment, the at least one permeability enhancer and/or at least one mucosal permeation enhancer increases a fraction of the at least one active pharmaceutical ingredient that reaches circulation by at least about 10%, at least about 25%, preferably at least 50%, and most preferably at least 100%. In one embodiment, the at least one permeability enhancer includes a bile salt, alkyl glycoside, a polymer, a tight junction modulation peptide, a lipid, a surfactant, a cyclodextrin, a chelator (e.g., EDTA), a Hsieh enhancer, a cyclic lactone, a cyclic diester, a cyclic ketone, a fatty acid, a salicylate, and/or an amphiphilic steroid (e.g., a fusidic acid derivative). Tight junction modulating peptides are described in U.S. Patent Publication No. 20090220435, which is incorporated herein by reference in its entirety. In one embodiment, the cyclodextrin includes alpha-cyclodextrin, beta-cyclodextrin, gamma-cyclodextrin, hydroxypropyl-beta-cyclodextrin, and/or sulfobutylether beta-cyclodextrin. In one embodiment, the lipid includes 1,2-Dioleoyl-sn-Glycero-3 Ethylphosphocholine, 1,2-di-O-phytanyl-glycero-3-phosphocholine, 1-O-hexadecyl-2-acetoyl-sn-glycerol, 1-O-octadecyl-2-O-methyl-glycerol-3-phosphocholine, 16:0-09:0(ALDO)PC, 16:0-09:0(COOH) PC, 3-beta-hydroxy-5alpha-cholest-8(14)-en-15-one, C10 sucrose, C12 maltose, C12 sucrose, C14 maltose, C16-09:0, C6 glucose, C6 maltose, C7 glucose, C8 glucose, Cardiolipin (sodium salt), Ceramide (brain porcine), Ceramide C10:0, Ceramide C12:0, Ceramide C14:0, Ceramide C16:0, Ceramide C17:0, Ceramide C18:0, Ceramide C18:1, Ceramide C20:0, Ceramide C24:0, Ceramide C24:1, Ceramide C2:0, Ceramide C4:0, Ceramide C6:0, Ceramide C8:0, Cerebroside (brain porcine), Cerebroside Sulfatide (porcine), Dimethylsphingosine, Egg Ceramide, Galactosyl sphingosine, Glucosyl-sphingosine, Lactosyl(B) Sphingosine, Lyso-PAF, N-acetoyl ceramide-1-phosphate, N-octanoyl ceramide-1-phosphate, PGPC1, POVPC, Phosphatidylinositol (Soy), Phosphatidylinositol (bovine), Platelet-Activation Factor, Porcine brain ganglioside, Sphingomyelin (brain porcine), Sphingosine-1-phosphate, and trimethylsphingosine. The lipid is preferably a glycosylated sphingosine, an alkylglucoside, an oxidized lipid, and/or an ether lipid (PAF). In one embodiment, the fatty acid is sodium caprate, sodium laurate, sodium caprylate, capric acid, lauric acid, caprylic acid, and/or an acyl carnitine (e.g., palmitoyl carnitine, stearoyl carnitine, myristoyl carnitine, lauroyl carnitine). In one embodiment, the salicylate is sodium salicylate, 5-methoxy salicylate, and methyl salicylate. Hsieh enhancers are described in U.S. Pat. Nos. 5,023,252 and 5,731,303, each of which is incorporated herein by reference in its entirety. Cyclic lactones, cyclic diesters, and cyclic ketones are described in U.S. Pat. No. 8,481,043, which is incorporated herein by reference in its entirety. Amphipihilic steroids are discussed in U.S. Pat. Nos. 4,548,922 and 4,746,508, each of which is incorporated herein by reference in its entirety. In one preferred embodiment, the at least one permeability enhancer and/or the at least one mucosal permeation enhancer is a generally accepted as safe (GRAS) pharmaceutical excipient. Alternatively, the at least one permeability enhancer and/or the at least one mucosal permeation enhancer is a near-GRAS excipient and/or a non-GRAS excipient. In one embodiment, the at least one permeation enhancer and/or the at least one mucosal permeation enhancer is about 1% to about 30% w/w of the weight of the composition.

In one embodiment, the intranasal dry powder formulations and/or unit doses include at least one surfactant. The at least one surfactant is a non-ionic surfactant, an ionic surfactant, a cationic surfactant, an anionic surfactant, and/or a zwitterionic surfactant. Examples of the at least one surfactant compatible with the present invention include, but are not limited to, sodium glycocholate, sodium taurocholate, polyoxyethylene lauryl ether, polyacrylic acid gel, sodium lauryl sulfate, polysorbate, and/or sodium deoxycholate.

In a preferred embodiment, the intranasal dry powder formulations and/or unit doses do not include a surfactant. Some liquid formulations of drugs require a surfactant to prevent aggregation of the active ingredient. Advantageously, dry powder formulations do not require a surfactant.

In one embodiment, the intranasal dry powder formulations and/or unit doses include at least one surface modifier. In one embodiment, the at least one surface modifier includes a lubricant (e.g., magnesium stearate), a fluidizing agent (e.g., talc, silicon dioxide), a nitric oxide (NO) stimulator, chitosan, and/or a chitosan derivative.

In one embodiment, the intranasal dry powder formulations and/or unit doses include at least one sustained release agent. In one embodiment, the at least one sustained release agent is achieved by manipulating one or more of the at least one active pharmaceutical ingredient to control its dissolution and/or the composition in which the at least one active pharmaceutical ingredient is suspended. In one embodiment, excipients with mucoadhesive and/or viscosity enhancing characteristics are incorporated. Additionally or alternatively, the composition is operable to reversibly diminish mucocilliary clearance.

In one embodiment, the intranasal dry powder formulations and/or unit doses include at least one anticaking agent. The at least one anticaking agent includes, but is not limited to, tribasic calcium phosphate. In one embodiment, the at least one anticaking agent is about 0.5% to about 5% w/w of the weight of the composition. In some embodiments, the at least one anticaking agent has an average particle diameter of about 100 μm or less, for example about: 90 to 100 μm, 80 to 90 μm, 70 to 80 μm, 60 to 70 μm, 50 to 60 μm, 40 to 50 μm, 30 to 40 μm, 20 to 30 μm, or 10 to 20 μm. In some embodiments, the at least one anticaking agent has an average particle diameter of about 30 μm to 100 μm.

In one embodiment, the intranasal dry powder formulations and/or unit doses include at least one systemic vasodilator and/or at least one nasal mucosal vasodilator. In one embodiment, the at least one systemic vasodilator and/or the at least one nasal mucosal vasodilator includes an angiotensin-converting enzyme (ACE) inhibitor (e.g., Benazepril (Lotensin), Captopril (Capoten), Enalopril (Vasotec), Fosinopril (Monopril), Lisinopril (Prinivil, Zestril), Minoxidil (Loniten), Meoexipril (Univasc), Perindopril (Aceon), Quinapril (Accupril), Ramipril (Altace), Trandolaptril (Mavik)), an angiotensin II receptor antagonist (e.g., Losartan, Candesatran, Valsartan, Irbesartan, Telmisartan, Eprosartan, Olmesartan, Azilsartan), phentolamine, nitroglycerine, hydralazine, isosorbide mononitrate, isosorbide dinitrate, papaverine hydrochloride or mesylate, cocaine, ethyl nitrate, diltiazem, urapidil, nicorandil, sodium nitroprusside, glyceryl trinitrate-verapamil, phenoxybenzamine, dopexamine, chloropromazine, propiverine hydrochloride, or an enantiomer, diastereoisomer, racemate, prodrug, or salt of such compounds. In a preferred embodiment, the at least one systemic vasodilator and/or the at least one nasal mucosal vasodilator is phentolamine.

In one embodiment, the intranasal dry powder formulations and/or unit doses include at least one agent that reduces mucosal transit time. In one embodiment, the at least one agent that reduces mucosal transit time includes a polyacrylate mucoadhesive agent and/or a peptide. See, e.g., WIPO Publication No. WO2003037355, which is incorporated herein by reference in its entirety.

In one embodiment, the intranasal dry powder formulations and/or unit doses include at least one agent that increases mucosal absorption or adhesion or transport. In one embodiment, the at least one agent that increases mucosal absorption or adhesion or transport includes a surfactant, gelling microsphere, chitosan, sodium lauryl sulfate, sodium salicylate, oleic acid, lecithin, dehydrated alcohol, Tween, polyoxyl 40 stearate, polyoxyl ethylene 40 stearate, propylene glycol, hydroxyl fatty acid ester of polyethylene glycol, glycerol monooleate, fusieates, a bile salt, octoxynol, polysorbate 20, polysorbate 80, DDPC, DPPC, a chelator (e.g., EDTA, EGTA, citrate), and/or a surfactant. See, e.g., (1) Ilium L and Fisher A N (1997) Intranasal delivery of peptides and proteins, in Inhalation Delivery of Therapeutic Peptides and Proteins (Adjei A L and Gupta P K eds), Marcel Dekker, New York and (2) Costantino H R, Illum L, Brandt G, Johnson P H, Quay S C. Intranasal delivery: physicochemical and therapeutic aspects. Int J Pharm. 2007 Jun. 7; 337(1-2): 1-24. doi: 10.1016/j.ijpharm.2007.03.025. Epub 2007 Mar. 25. PMID: 17475423, each of which is incorporated herein by reference in its entirety.

In one embodiment, the intranasal dry powder formulations and/or unit doses include at least one chelator. In one embodiment, the at least one chelator includes ethylenediaminetetraacetic acid (EDTA), ethylene glycol-bis(B-aminoethyl ether)-N,N,N',N'-tetraacetic acid (EGTA), and/or citrate.

In one embodiment, the intranasal dry powder formulations and/or unit doses include at least one non-sulfite stabilizer. In one embodiment, the at least one non-sulfite stabilizer is ascorbic acid.

In one embodiment, the intranasal dry powder formulations and/or unit doses include at least one preservative. The at least one preservative includes, but is not limited to a paraben, benzalkonium chloride, phenyl ethyl alcohol, ethylenediaminetetraacetic acid (EDTA), benzoyl alcohol, a thiol, glutathione, glutathione reductase, glutathione peroxidase, hydroquinone, amikasin sulfate, apomorphine hydrochloride, metaraminol, levobunonol, levobunonol hydrochloride, acamprosate calcium, fenoldopam, hydrocortisone/neomycin sulfate/polymyxin B, dexamethasone sodium phosphate, hydromorphone, dobutamine, epinephrine, etidicaine/epinephrine bitartrate, gentamycin, tinzaparin, isoproternerol, ketoconazole, sodium sulfacetamide, norepinephrine, bupivacaine/epinephrine bitartrate, morphine, tobramycin, rotigotine, orphenadrine, procaine, nalbuphine, oxytetracycline, nortriptyline, perphenazine, promethazine hydrochloride, prednisolone acetate, propofol, mesalamine, trimethoprim/sulfamethoxazole, carisoprodol/aspirin/codeine, streptomycin, mafenide acetate, tetracycline hydrochloride, pentazocine lactate, chlorpromazine, triethylperazine maleate, fluorinolone acetonide/hydroquinone/tretinoin, acetaminophen/codeine, doxycline calcium, and/or lidocaine/epinephrine. In one embodiment, the at least one preservative is about 0.01% to about 5% w/w of the weight of the composition, for example about: 0.01%, 0.05%, 0.1%, 0.2%, 0.5%, 1%, 2%, 3%, 4%, or 5% w/w, based on the weight of the formulations and/or dosage units. In one embodiment, the at least one preservative is about 0.01% to 5%, 0.02% to 4%, or 0.05% to 2.5% w/w, based on the weight of the formulations and/or dosage units. In a preferred embodiment, the at least one preservative is sulfite-free.

In a preferred embodiment, the intranasal dry powder formulations and/or unit doses do not include a preservative. Preservatives (e.g., sodium bisulfite, which is present in EpiPen® and other autoinjectors) can cause an allergic reaction in some individuals. Because aqueous formulations of drugs are often sensitive to light and heat, they generally include a preservative to improve stability. The intranasal dry powder formulations and/or unit doses of the present invention advantageously do not require a preservative. Additionally, not including a preservative in the intranasal dry powder formulations and/or unit doses reduces the risk of further allergic reaction(s) and/or sensitivities. "Despite documentation of sensitivity, sulfites should not be withheld from patients experiencing a life-threatening emergency. Non-sulfited alternatives are often available, and should be used preferentially." See, e.g., Roth J V, Shields A. A dilemma: How does one treat anaphylaxis in the sulfite allergic patient since epinephrine contains sodium metabisulfite? Anesth Analg. 2004 May; 98(5): 1499; author reply 1500. doi: 10.1213/01.ane.0000120092.39021.f2. PMID: 15105239, which is incorporated herein by reference in its entirety. Also see, e.g., Susan C. Smolinske (1992) Review of Parenteral Sulfite Reactions, Journal of Toxicology: Clinical Toxicology, 30:4, 597-606, DOI: 10.3109/15563659209017945, which is incorporated herein by reference in its entirety. Drugs without sulfites are often available in a medical setting (e.g., hospital, clinic) because environmental conditions can be controlled. Aqueous preparations and auto-injectors generally contain preservatives because they are intended for ambient use. There is a long-standing, unmet need for dry powder formulations that do not contain a preservative.

In one embodiment, the intranasal dry powder formulations and/or unit doses include at least one thickening agent. In one embodiment, the at least one thickening agent includes microcrystalline cellulose and/or carboxymethylcellulose sodium.

In one embodiment, the intranasal dry powder formulations and/or unit doses include at least one humectant. The at least one humectant includes, but is not limited to, glycerine, glycerol, sorbitol, mannitol, and/or vegetable oil.

In one embodiment, the intranasal dry powder formulations and/or unit doses include at least one antihistamine. In one embodiment, the at least one antihistamine includes loratadine, desloratadine, diphenhydramine, fexofenadine, chlorpheniramine, hydroxyzine, cetirizine, levocetrizine, brompheniramine, clemastine, carbinoxamine, azelastine, emadastine, and/or levocabastine. Additional information regarding antihistamines are disclosed in U.S. Patent Publication No. 20100055152 and U.S. Pat. No. 8,263,581, each of which is incorporated herein by reference in its entirety.

In one embodiment, the intranasal dry powder formulations and/or unit doses include at least one solubilizing agent. The at least one solubilizing agent includes, but is not limited to, a glycol, an alcohol, 2-(2-ethoxyethoxy)ethanol, a cyclodextrin, and/or a glyceride (e.g., a medium chain glyceride, LABRASOL®).

In one embodiment, the intranasal dry powder formulations and/or unit doses include at least one masking agent (e.g., taste, smell). In a preferred embodiment, the at least one masking agent includes, but is not limited to, at least one sweetener and/or at least one flavoring agent. The at least one sweetener includes, but is not limited to, saccharin (e.g., sodium salt, calcium salt), fructose, dextrose, aspartame, acesulfame potassium, glycerin, sucralose, maltodextrin, sucrose, glucose, maltose, xylitol, sorbitol, erythritol, and/or mannitol. In one embodiment, the at least one masking agent includes phenethyl alcohol, vanilla, cherry, cinnamon, lavender, lemon, menthol, orange, peppermint, spearmint, raspberry, strawberry, grape, ethyl vanillin, coriander, ginger, nutmeg, cardamom, butterscotch, cocoa, acacia syrup, anethole, anise oil, benzaldehyde, ethyl acetate, methyl salicylate, and/or tolu. In one embodiment, the at least one masking agent is about 0.001% to about 1% w/w of the weight of the composition, for example about: 0.001%, 0.005%, 0.01%, 0.02%, 0.05%, 0.1%, 0.2%, 0.3%, 0.4%, 0.5%, 0.6%, 0.7%, 0.8%, 0.9%, or 1% w/w, based on the weight of the formulations and/or dosage units. In one embodiment, the at least one masking agent is about 0.01% to 0.5%, 0.02% to 0.2%, or 0.015% to 0.15% w/w, based on the weight of the formulations and/or dosage units.

In one embodiment, the intranasal dry powder formulations and/or unit doses include at least one antioxidant. The at least one antioxidant includes, but is not limited to, sodium metabisulfite, sodium bisulfate, butylated hydroxytoluene, tocopherol, ascorbic acid (Vitamin C), glutathione, glutathione reductase, glutathione peroxidase, superoxide dismutase (CuZn—SOD), superoxide reductase, carnosine, ergothionene, ovothiol, lipoic acid, thioctic acid, thioredoxin peroxidase, and/or recombinant thermostable variants thereof. In one embodiment, the at least one antioxidant is about 0.0001% to about 10% w/w of the weight of the composition, for example about: 0.0001%, 0.0005%, 0.001%, 0.005%, 0.01%, 0.02%, 0.05%, 0.1%, 0.5%, 1%, 2%, 3%, 4%, 5%, 6%, 7%, 8%, 9%, or 10% w/w, based on the weight of the formulations and/or dosage units. In one embodiment, the at least one antioxidant is about 0.001% to 5%, 0.05% to 2%, or 0.1% to 1% w/w, based on the weight of the formulations and/or dosage units.

In one embodiment, the intranasal dry powder formulations and/or unit doses include at least one viscosity enhancing agent. The at least one viscosity enhancing agent includes, but is not limited to, a cellulose derivative (e.g., crystalline cellulose, amorphous cellulose, methylcellulose, carboxymethylcellulose, ethylcellulose, hypromellose, hydroxylpropyle cellulose, or a salt thereof), carrageenan, guar gum, an alginate, a carbomer, a polyethylene glycol, propylene glycol, a polyvinyl alcohol, xanthan gum, a polyvinylpyrrolidone (PVP), chitosan, a polysaccharide, a starch, and/or carbopol. In one embodiment, the at least one viscosity enhancing agent is about 0.1% to about 10% w/w of the weight of the composition, for example about: 0.1%, 0.5%, 1%, 2%, 3%, 4%, 5%, 6%, 7%, 7.5%, 8%, 9%, or 10% w/w, based on the weight of the formulations and/or dosage units.

In one embodiment, the intranasal dry powder formulations and/or unit doses include at least one dispersing agent. In one embodiment, the at least one dispersing agent includes citric acid.

In one embodiment, the intranasal dry powder formulations and/or unit doses include at least one colorant. In a preferred embodiment, the at least one colorant is non-allergenic.

In one embodiment, the intranasal dry powder formulations and/or unit doses include at least one buffering agent. The at least one buffering agent includes, but is not limited to, a phosphate, a citrate, a succinate, histidine, glycine, arginine, malic acid, tartaric acid, acetic acid, benzoic acid, lactic acid, ascorbic acid, ammonium chloride, sodium chloride, potassium chloride, zinc chloride, calcium chloride, sodium acetate trihydrate, and/or triethanolamine. In one embodiment, the at least one buffering agent is about 0.10% to about 3% w/w of the weight of the composition, for example about: 0.01%, 0.05%, 0.1%, 0.2%, 0.3%, 0.4%, 0.5%, 0.6%, 0.7%, 0.8%, 0.9%, 1%, 1.5%, 2%, 2.5%, or 3% w/w, based on the weight of the formulations and/or dosage units. In one embodiment, the at least one buffering agent is about 0.05% to 2.5% w/w, based on the weight of the formulations and/or dosage units.

In one embodiment, the formulations of the present invention do not include a pH buffer. For example, the most stable pH for many drugs is below 7. A pH buffer (e.g., hydrochloric acid) is often to liquid formulations to reduce the pH. However, a low pH (e.g., between 2.5 and 5) may cause some discomfort for patients. Advantageously, the formulations of the present invention do not require a pH buffer.

Carriers and Excipients

In some embodiments, the dry powder formulation further includes at least one carrier and/or excipient (e.g., at least one pharmaceutically acceptable carrier and/or excipient). In one embodiment, the at least one carrier and/or excipient includes, but is not limited to, lactose (e.g., D-lactose, lactose monohydrate), sucrose, glucose, dextrose, trehalose, sodium carboxymethylcellulose (CMC), mannitol, sorbitol, malitol, xylitol, maltose, cellulose and derivatives, starch and derivatives, microcrystalline cellulose, hypromellose acetate succinate (HPMCAS), a cyclodextrin (e.g., dimethyl-beta-cyclodextrin), calcium carbonate, citric acid, tartaric acid, glycine, leucine, polyvinyl pyrrolidone (PVP), a polyethylene glycol, polysorbate (e.g., Polysorbate 80 (e.g., TWEEN® 80)), chitosan, hyaluronic acid (e.g., sodium hyaluronate), sodium carboxymethyl cellulose (NaCMC), magnesium stearate, calcium stearate, an alkyl saccharide (e.g., n-Dodecyl ß-D-Maltoside (DDM)), niacin, ethanol (e.g., dried ethanol), caffeine, benzalkonium chloride, ubiquinone (i.e., coenzyme Q10), magnesium oxide, sodium chloride, dodecylphosphocholine (DPC), silicone, gelatin, a polyacrylic acid polymer (e.g., CARBOPOL® 934), sodium taurocholate, carnitine hydrochloride, Poloxamer 188, histidine, arginine, crospovidone, ethylenediaminetetraacetic acid (EDTA), sodium starch glycolate, and/or a mixture of mannitol and hydroxypropyl methylcellulose (HPMC). In one embodiment, the at least one carrier and/or excipient includes at least one carbohydrate. In one embodiment, the at least one carbohydrate includes at least one monosaccharide, at least one disaccharide, at least one cyclodextrin, at least one polysaccharide, at least one starch, and/or at least one cellulose. In one embodiment, the at least one carrier and/or excipient includes at least one salt. The at least one salt includes, but is not limited to, sodium chloride, potassium chloride, sodium phosphate, calcium phosphate, calcium sulfate, and/or magnesium sulfate.

In one embodiment, the at least one carrier and/or excipient includes particles having an average diameter of 1 μm to 100 μm. This is applicable to unimodal or multimodal formulations. In a preferred embodiment, the at least one carrier and/or excipient includes particles having an average diameter of at least 15 μm. Advantageously, an average diameter greater than 15 μm prevents particles from entering the lungs. In a preferred embodiment, the at least one carrier and/or excipient includes particles having an average diameter of about 50 μm. In one embodiment, the at least one carrier and/or excipient includes particles having an average diameter of about 25 μm to about 75 μm.

The formulations of the present invention preferably do not include any liquid carriers (e.g., water, alcohol, and/or propylene glycol). Liquid carriers often require additional preservatives to improve stability. Advantageously, dry powder formulations do not require a preservative, which reduces the risk for allergic reactions.

Particle Characteristics

The at least one active pharmaceutical ingredient, the at least one enabling agent, and/or the at least one carrier are operable to be individually substantially amorphous or crystalline. In some embodiments, the formulations and/or unit doses provided herein are in the form of particles, and the shapes of the particles are operable to be individually, e.g., cylindrical, discoidal, spherical, tabular, ellipsoidal, angular, and/or irregular.

In some embodiments, the average particle diameter of the at least one active pharmaceutical ingredient, the at least one enabling agent, and/or the at least one carrier and/or excipient are, individually, up to 100 μm, up to 50 μm, or up to 30 μm. In a preferred embodiment, the average particle diameter of the at least one active pharmaceutical ingredient, the at least one enabling agent, and/or the at least one carrier and/or excipient are, individually, less than or equal to 50 μm. In one embodiment, the average particle diameter of the at least one active pharmaceutical ingredient, the at least one enabling agent, and/or the at least one carrier and/or excipient are, individually, about: 10-20, 20-30, 30-40, 40-50, 50-60, 60-70, 70-80, 80-90, or 90-100 μm. In another embodiment, the average particle diameter of the at least one active pharmaceutical ingredient, the at least one enabling agent, and/or the at least one carrier and/or excipient are, individually, about: 10, 15, 20, 25, 30, 35, 40, 45, 50, 55, 60, 65, 70, 75, 80, 85, 90, 95, or 100 μm.

In some embodiments, the median particle diameter of the at least one active pharmaceutical ingredient herein is about 30 μm (e.g., 28.7 μm). In some embodiments, the median particle diameter of the at least one active pharmaceutical ingredient herein is about: 10-50, 20-40, or 25-35 μm. In one embodiment, 90% of particles of the at least one active pharmaceutical ingredient herein have a particle diameter under about 50 μm (e.g., about 45.5 μm). In another embodiment, 90% of particles of the at least one active pharmaceutical ingredient herein have a particle diameter under about: 40, 45, 35, 30, 25, or 20 μm. In yet another embodiment, about 10% of particles of the at least one active pharmaceutical ingredient herein have a particle diameter under about 20 μm (e.g., about 17.3 μm). In still another embodiment, about 10% of particles of the at least one active pharmaceutical ingredient herein have a particle diameter under about: 19, 18, 17, 16, 15, 14, 13, 12, 11, or 10 μm.

In a preferred embodiment, the average particle size, and/or the mean particle size is greater than 15 μm. Advantageously, an average particle size and/or a mean particle size greater than 15 μm avoids any entry of the particles into the lungs. In a preferred embodiment, the average particle size and/or the mean particle size is about 50 μm. In one embodiment, the average particle size and/or the mean particle size is between about 25 μm and about 75 μm.

Delivery Devices and Packaging

In one embodiment, provided herein is therapeutic product including: (a) a dose of an intranasal dry powder formulations disclosed herein; (b) a dry powder nasal delivery device; and/or (c) a secondary packaging for the device that provides protection against humidity, light, or oxygen or other gases that may reduce the stability or physical characteristics of the dry powder formulations disclosed herein. An example of such a delivery device is the UDS-P nasal delivery device manufactured by Aptar Pharma.

Nasal devices are disclosed in U.S. Pat. Nos. 10,814,079; 10,806,870; 10,668,228; 9,808,818; 9,156,048; 8,734,392; 8,016,209; 7,988,073; 7,950,391; 7,946,455; 7,878,352; 7,389,946; 7,387,265; 7,353,971; 7,216,781; 7,100,601; 7,073,731; 7,011,234; 6,877,672; 6,725,857; 6,708,846; 6,679,248; 6,626,379; 6,554,203; 6,484,715; 6,461,322; 6,450,216; 6,427,680; 6,425,499; 6,398,074; 6,367,473; 6,264,065; 6,261,274; 6,234,366; 6,209,760; 6,179,164; 6,029,663; 5,901,883; 5,568,884; 5,328,099; and 5,240,149, U.S. Publication Nos. 20190358417, 20160318051, 20150299846, 20140103064, 20140034663, 20140000588, 20130312740, 20130171334, 20130171330, 20130149459, 20130081953, 20130022750, 20120318677, 20110233232, 20110194110, 20100078447, 20070272764, 20040084554, and 20020079326, and U.S. application Ser. No. 16/814, 997, each of which is incorporated herein by reference in its entirety.

In one embodiment, the delivery device includes at least one nasal probe that is operable to be replaced between discharges, so that the device is operable to be used to treat two or more individuals. The packaging of the delivery device includes with a plurality of replaceable nasal probes (e.g., corresponding to a number of doses in the device). In contrast to the existing injectors, wherein the needle comes in contact with tissue and blood of each individual, this embodiment of the delivery device advantageously enables the more rapid treatment of a plurality of patients. Additionally, this embodiment of the delivery device and the set of replaceable nasal probes reduces the physical space required for carriage or storage of the quantity of pharmaceutical agent needed to respond to a plurality of patients (e.g., on a battlefield, in an ambulance, etc.).

In one embodiment, the delivery device includes a reservoir that holds the dry powder composition. The delivery device preferably includes a reservoir and means for expelling a pharmaceutical dose in the form of a spray. The reservoir is operable to contain a plurality of pharmaceutical doses (e.g., at least 4 doses, at least 8 doses, at least 20 doses, at least 50 doses, etc.). In one embodiment, the reservoir has a fill weight of at least 10 mg. In another embodiment, the reservoir has a fill weight of between about 10 mg and about 80 mg (e.g., about 10 mg, 20 mg, 30 mg, 40 mg, 50 mg, 60 mg, 70 mg, or 80 mg). In one embodiment, the reservoir has a fill volume of at least 50 mm$^3$. In another embodiment, the reservoir has a fill volume of between about 50 mm$^3$ and about 300 mm$^3$ (e.g., about 50 mm$^3$, 80 mm$^3$, 100 mm$^3$, 130 mm$^3$, 150 mm$^3$, 175 mm$^3$, 200 mm$^3$, 225 mm$^3$, 250 mm$^3$, 275 mm$^3$, or 300 mm$^3$). In one embodiment, the delivery device includes a plurality of individual reservoirs, each containing a pharmaceutical dose (e.g., blisters). In some embodiments, the delivery device is disposable. In some embodiments, the delivery device is reusable. In some embodiments, the delivery device is recyclable. In some embodiments, the package further includes one intranasal delivery device.

In a preferred embodiment, the delivery device does not require priming or shaking. The delivery device is preferably operable to dispense a dose from any position (i.e., 360° functionality).

FIG. 1 illustrates one embodiment of a nasal delivery device according to the present invention. The nasal delivery device 100 includes a plurality of components. In a preferred embodiment, the plurality of components includes a ball 102, a center piece 104, a container or reservoir 106, an actuator 108, a bottom 110, and a piston 112. In one embodiment, the plurality of components is formed of at least one plastic. The at least one plastic includes, but is not limited to, polypropylene (e.g., high density polypropylene (HDPE), linear low-density polyethylene (LLDPE)) and/or polyethylene. In one embodiment, one or more of the plurality of components further includes a dye or a colorant. The piston 112 is operable to push upward into the center piece 104. The center piece 104 comes into contact with the ball 102. Movement pushes the piston 112, the center piece 104, and the ball 102 upwards, which dispenses the dry powder composition from a tip or nasal probe of the delivery device 100.

Figures 2A, 2B, 2C, 2D:
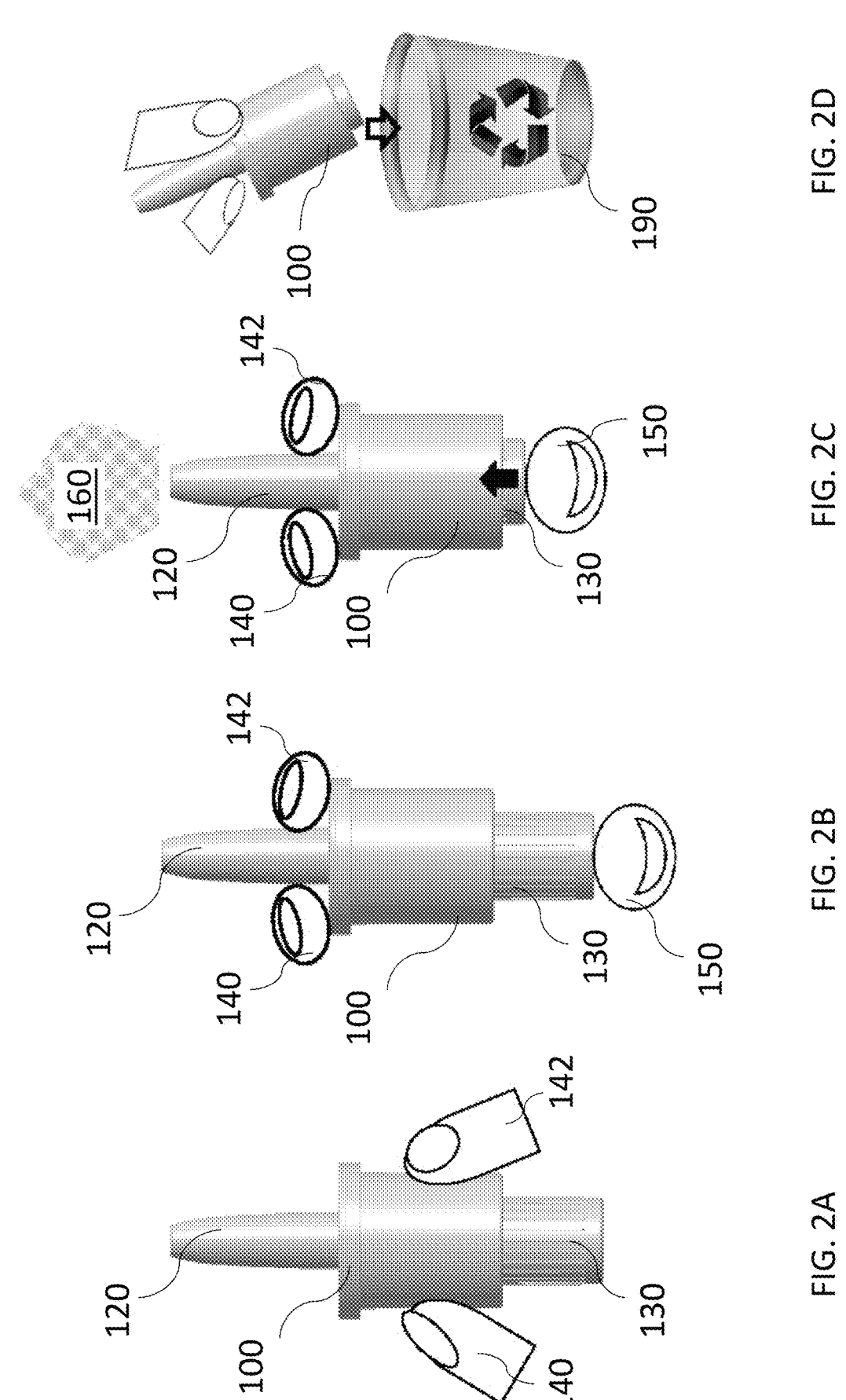
FIG. 2A illustrates a nasal delivery device at rest according to one embodiment of the present invention.
FIG. 2B illustrates positioning of fingers and a thumb on the nasal delivery device according to one embodiment of the present invention.
FIG. 2C illustrates discharge of the nasal delivery device according to one embodiment of the present invention.
FIG. 2D illustrates disposal of the nasal delivery device following use according to one embodiment of the present invention.

FIGS. 2A-2D illustrate one embodiment of a method of using a nasal delivery device according to the present invention. FIG. 2A illustrates one embodiment of the nasal delivery device 100 at rest. The nasal delivery device 100 includes a nasal probe 120 and a push button 130. FIG. 2B illustrates positioning of a first finger 140 and a second finger 142 on the nasal delivery device 100 according to one embodiment of the present invention. A thumb 150 is positioned on the push button 130 of the nasal delivery device 100. To discharge the nasal delivery device 100, the thumb 150 presses up on the push button 130 of the nasal delivery device 100 as shown in FIG. 2C. Discharge causes particles 160 to be expelled from the nasal delivery device 100 (e.g., into a nasal passage). The nasal delivery device 100 is preferably operable to be disposed of (e.g., in a recycling can 190) following use as shown in FIG. 2D.

Figure 3:
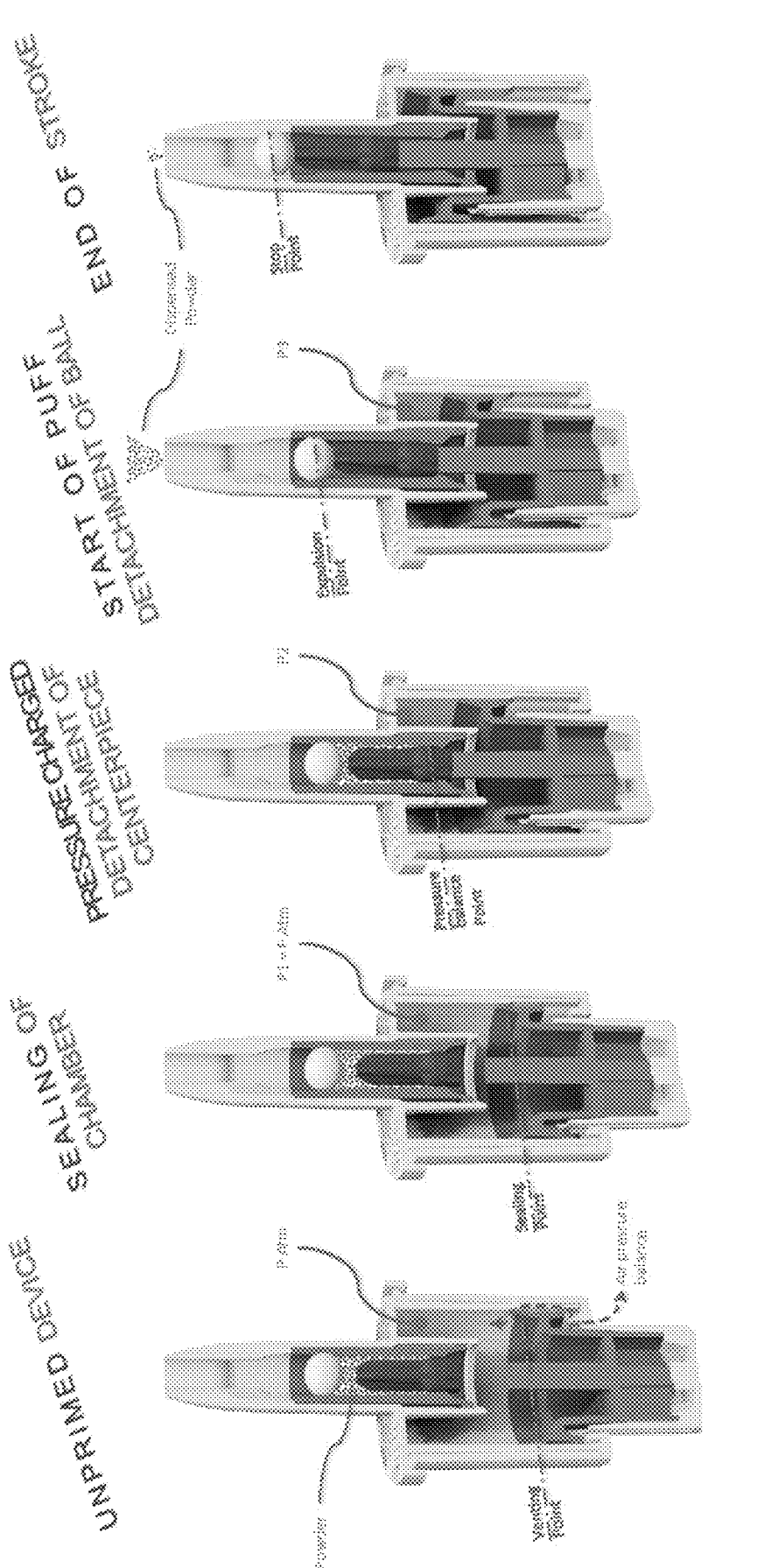
FIG. 3 illustrates the nasal delivery device in an unprimed state, with a sealed chamber, pressure charged detachment of a centerpiece, a start of a discharge, and an end of a stroke according to one embodiment of the present invention.

FIG. 3 illustrates the nasal delivery device in an unprimed state, with a sealed chamber, pressure charged detachment of a centerpiece, a start of a discharge, and an end of a stroke according to one embodiment of the present invention.

In one embodiment, the delivery device includes a counter or indicator. In one embodiment, the counter or the indicator is mechanical. Alternatively, the counter or indicator is electronic. In one embodiment, the electronic counter or indicator includes a sensor that is adapted to detect a displacement or a deformation of a portion of the delivery device (e.g., when the dry powder formulation is dispensed). In one embodiment, the electronic counter or indicator includes a display (e.g., LCD screen), a power supply (e.g., battery, rechargeable battery), a timer, a clock, at least one processor, at least one memory, a communication interface, and/or a printed circuit board (PCB). The sensor preferably transmits a signal to the PCB that causes the display to change when the delivery device is actuated. The at least one memory is operable to store information generated by the delivery device and/or the sensor. In one embodiment, the communications interface is operable to transmit data wirelessly (e.g., via BLUETOOTH®). In one embodiment, the data is transmitted wirelessly to at least one remote device (e.g., smartphone, tablet, etc.). The at least one remote device preferably includes a mobile application with a graphical user interface (GUI). In one embodiment, the mobile application tracks an expiration date of a delivery device, tracks use of the delivery device (e.g., remaining doses), and/or prompts ordering of another delivery device after use of the delivery device. In one embodiment, the at least one remote device is operable to provide messaging and/or notifications between a user and a third party (e.g., healthcare provider, parent, caregiver, emergency services, pharmacy). For example, the at least one remote device provides a notification to the third party when the delivery device dispenses a dose and/or provides a notification on a screen of the at least one remote device. In one embodiment, the notification includes instructions and/or a video for how to use the delivery device. In one embodiment, the delivery device displays a time of dose dispensation on the display (e.g., from the timer or the clock). Advantageously, this alerts the third party to the emergency situation (e.g., allergic reaction, anaphylaxis, cardiac arrest, poisoning, seizure) and/or use of the device (e.g., to order a new delivery device). In the case of an emergency situation, conveying to the third party the time of dose dispensation is significant, as in many medical events a second dose is required. Thus, the knowledge of how much time has passed since the initial dosing is operable to guide the decision of whether to administer subsequent doses. In one embodiment, the at least one remote device is operable to transmit the data to at least one remote server. In another embodiment, the delivery device further includes an accelerometer and/or a gyroscope to detect movement of the delivery device. In one embodiment, the remote device is operable to transmit location data (e.g., to the third party) after the delivery device is discharged. In one embodiment, the location data is obtained from the remote device. Additionally or alternatively, the device further includes a global positioning system (GPS) device or is coupled to a GPS device operable to provide location data. Advantageously, this alerts the third party to the emergency situation (e.g., allergic reaction, anaphylaxis, cardiac arrest, poisoning, seizure). In one example, a third party (e.g., emergency services, a parent, and/or a healthcare provider) is alerted when the delivery device is discharged. In a preferred embodiment, the location of the delivery device is provided to the third party. Wireless communication in delivery devices is disclosed in U.S. Pat. Nos. 10,967,140; 7,861,943; and 6,886,556 and U.S. Patent Publication Nos. 20200164164, 20200246562, 20200155775, and 20190134322, each of which is incorporated herein by reference in its entirety.

The delivery device is preferably packaged in at least one secondary packaging. The at least one secondary packaging is operable to protect the delivery device from external elements (e.g., light, humidity, oxygen or other gases). The at least one secondary package includes, but is not limited to, a vial, a tube, a container, a bottle, a box, and/or a carton. In one embodiment, the at least one secondary package includes a desiccant or other agents that assist with stability of the formulation (e.g., by preventing effects of temperature, light, humidity, oxygen or other gases). In one embodiment, the desiccant is included as a liner (e.g., a tube liner). In one embodiment, the at least one secondary package is formed of a plastic. In one embodiment, the plastic is a desiccant plastic. In one embodiment, the desiccant plastic includes a base polymer, a channeling agent, and a desiccant. Such materials are described in, for example U.S. Pat. Nos. 5,911,937; 6,080,350; 6,124,006; 6,130,263; 6,174,952; 6,194,079; 6,214,255; 6,221,446; 6,486,231; 7,005,459; and 9,902,788, each of which is incorporated herein by reference in its entirety. Advantageously, the desiccant removes moisture within the packaging and improves the stability of the API in the delivery device.

In one embodiment, the delivery device and/or one or more of the at least one secondary packaging includes a tamper resistant seal. In one embodiment, the one or more of the at least one secondary packaging and/or the delivery device includes a sensor to detect if the tamper resistant seal is removed. For example, the one or more of the at least one secondary packaging and/or the delivery device includes a smart sticker with a sensor that sends an alert (e.g., to a remote device) when a signal within the sensor is broken. In one embodiment, a notification that the sensor detected the removal of the tamper resistant seal is transmitted to the mobile application and/or a third party. Advantageously, this provides notification that the delivery device is exposed to external elements (e.g., humidity). Additionally or alternatively, one or more of the at least one secondary packaging is child resistant.

In one embodiment, one or more of the at least one secondary packaging includes an authentication method to ensure that the delivery device enclosed in the at least one secondary packaging is from the manufacturer (e.g., and not counterfeit). In one embodiment, the authentication method includes, but is not limited to, at least one code (e.g., serial number, bar code), at least one image, at least one text, and/or at least one tracker (e.g., RFID chip). In one embodiment, the at least one authentication method is verifiable via the mobile application.

Figure 4:
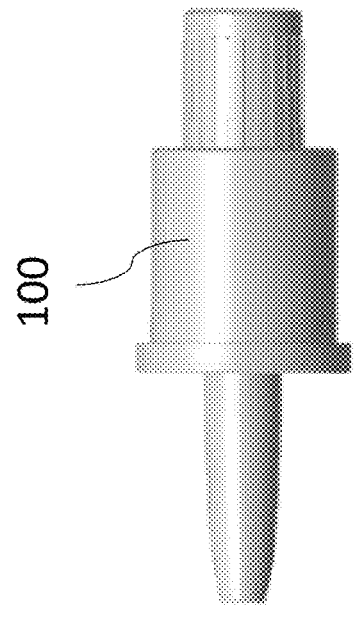
FIG. 4 illustrates a delivery device and a secondary packaging in the form of a container according to one embodiment of the present invention.
Figure 4:
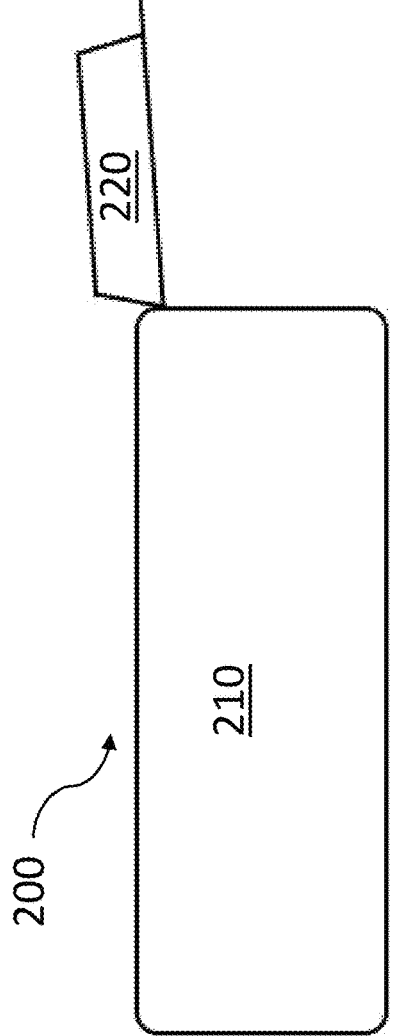

FIG. 4 illustrates one embodiment of a delivery device 100 and a secondary packaging in the form of a container 200. The delivery device 100 is operable to be stored in the container 200. The container 200 includes a base 210 and a lid 220. In one embodiment, the lid 220 is connected and/or attached to the base 210. Alternatively, the lid 220 is not connected and/or attached to the base 210 (e.g., screw on lid). Examples of a container compatible with the present invention include, but are not limited to, those disclosed in U.S. Pat. Nos. 9,834,341; 10,472,136; and 10,974,887, each of which is incorporated herein by reference in its entirety.

Figure 5:
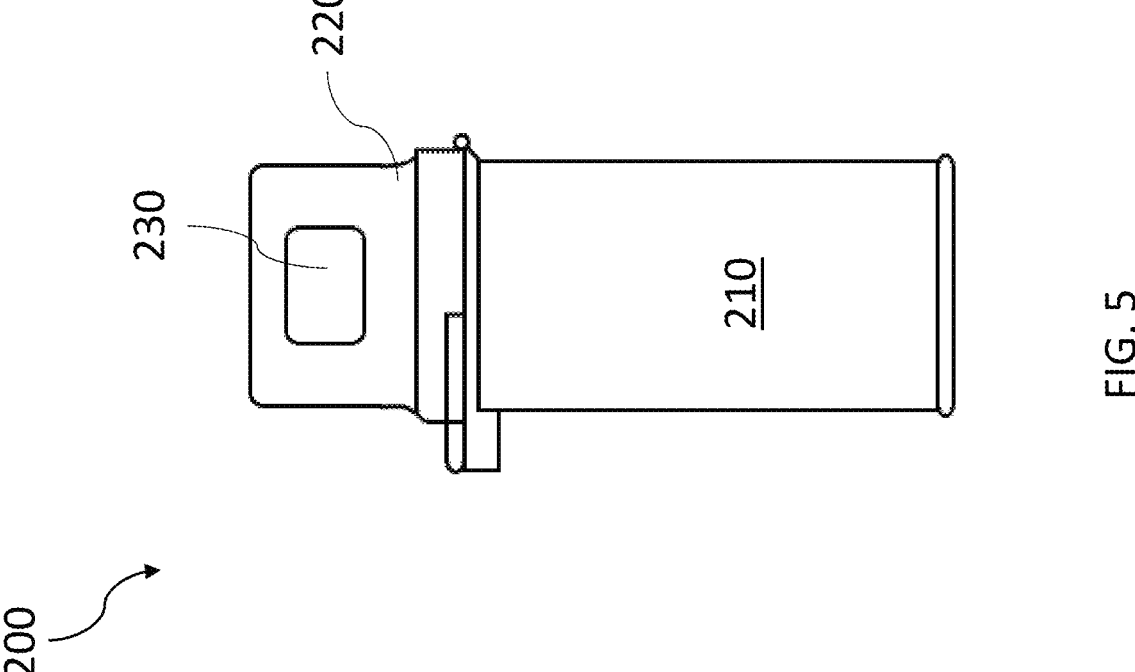
FIG. 5 illustrates a secondary packaging in the form of a container according to one embodiment of the present invention.

FIG. 5 illustrates one embodiment of a secondary packaging in the form of a container 200. The container 200 includes a base 210 and a lid 220. The container 200 is operable to store the delivery device (not shown). The lid 220 further includes a hole 230. The hole 230 is operable to attach the container 200 to a ring. The ring is further operable to attach the container 200 to a keychain or a set of keys, a backpack, a purse, or other personal item. Advantageously, this helps to ensure that the delivery device is conveniently located at all times.

In one embodiment, the at least one secondary package (e.g., carton) includes a first delivery device and a second delivery device. When providing medications, the lowest effective dose is desired. If a patient does not adequately respond to delivery of a first dose from the first delivery device, the second delivery device is operable to provide a second dose. Advantageously, this also ensures that a second dose is available if the first delivery device is not used properly. However, unlike auto-injectors, the nasal delivery device is not subject to a syringe misfiring.

The nasal delivery device preferably meets regulatory conditions described in Guidance for Industry, FDA, July 2002: Nasal Spray and Inhalation Solution, Suspension and Spray Drug Products: Chemistry, Manufacturing, and Controls Documentation; EMEA-Guideline on the Pharmaceutical Quality of Inhalation and Nasal Products (2006); Guidance for Industry, FDA, July 2002: Nasal Spray and Inhalation Solution, Suspension and Spray Drug Products: Drug Product Characterization Study; ISO 11608-1:2014 Needle-based injection systems for medical use—Requirements and test methods; ISO 20072:2009 Aerosol drug delivery device design verification—Requirements and test methods; ASTM D999-08(2015), Standard Test Methods for Vibration Testing of Shipping Containers, ASTM International, West Conshohocken, P A, 2015; ASTM D4169-16, Standard Practice for Performance Testing of Shipping Containers and Systems, ASTM International, West Conshohocken, P A, 2016; and/or EMEA-ICH Topic Q 1 A (R2)

Stability Testing of new Drug Substances and Products (2003), each of which is incorporated herein by reference in its entirety.

Training Device

In one embodiment, the present invention includes a training device. Advantageously, the training device educates a patient on proper use of the nasal delivery device, providing the patient with a greater level of confidence in the event of an emergency situation when the delivery device must be used. Patients with auto-injectors routinely receive training with a training device. such as in a prescribing physician office or at a dispensing pharmacy. This creates familiarity with the device operation and is intended to reduce errors in usage and hesitancy to use the device in an emergency. Delay in administering medications is associated with increased morbidity. However, many patients fear needles despite the training for auto-injectors. There is a long-standing, unmet need for a training device for medication delivery that provides confidence in device operation while not invoking a fear of needles.

Example Combinations

The following are examples of embodiments used in combination. However, the present disclosure is not limited to the example embodiments provided below. The intranasal dry powder compositions and/or unit doses are operable to include any combination of the at least one active pharmaceutical ingredient, the at least one enabling agent, and/or the at least one carrier and/or excipient.

Example 1: In one embodiment, the pharmaceutical composition includes pro-2-PAM.

Example 2: In one embodiment, the pharmaceutical composition includes (1) pro-2-PAM and (2) at least one additional cholinesterase reactivator agent (e.g., obidoxime, 2-PAM).

Example 3: In one embodiment, the pharmaceutical composition includes (1) pro-2-PAM and (2) at least one vasoactive agent (e.g., epinephrine, vasopressin, phenylephrine, or a salt thereof).

Example 4: In one embodiment, the pharmaceutical composition includes (1) pro-2-PAM and (2) at least one anticholinergic agent (e.g., atropine).

Example 5: In one embodiment, the pharmaceutical composition includes (1) pro-2-PAM and (2) at least one anticonvulsive agent (e.g., diazepam, lorazepam, midazolam).

Example 6: In one embodiment, the pharmaceutical composition includes (1) pro-2-PAM and (2) at least one vasodilator (e.g., phentolamine, caffeine).

Example 7: In one embodiment, the pharmaceutical composition includes (1) pro-2-PAM and (2) at least one COMT inhibitor (e.g., entacapone).

Example 8: In one embodiment, the pharmaceutical composition includes (1) pro-2-PAM, (2) at least one additional cholinesterase reactivator agent (e.g., obidoxime, 2-PAM), and (3) at least one vasoactive agent (e.g., epinephrine, vasopressin, phenylephrine, or a salt thereof).

Example 9: In one embodiment, the pharmaceutical composition includes (1) pro-2-PAM, (2) at least one additional cholinesterase reactivator agent (e.g., obidoxime, 2-PAM), and (3) at least one anticholinergic agent (e.g., atropine).

Example 10: In one embodiment, the pharmaceutical composition includes (1) pro-2-PAM, (2) at least one additional cholinesterase reactivator agent (e.g., obidoxime, 2-PAM), and (3) at least one anticonvulsive agent (e.g., diazepam, lorazepam, midazolam).

Example 11: In one embodiment, the pharmaceutical composition includes (1) pro-2-PAM, (2) at least one additional cholinesterase reactivator agent (e.g., obidoxime, 2-PAM), and (3) at least one vasodilator (e.g., phentolamine, caffeine).

Example 12: In one embodiment, the pharmaceutical composition includes (1) pro-2-PAM, (2) at least one additional cholinesterase reactivator agent (e.g., obidoxime, 2-PAM), and (3) at least one COMT inhibitor (e.g., entacapone).

Example 13: In one embodiment, the pharmaceutical composition includes (1) pro-2-PAM, (2) at least one vasoactive agent (e.g., epinephrine, vasopressin, phenylephrine, or a salt thereof), and (3) at least one anticholinergic agent (e.g., atropine).

Example 14: In one embodiment, the pharmaceutical composition includes (1) pro-2-PAM, (2) at least one vasoactive agent (e.g., epinephrine, vasopressin, phenylephrine, or a salt thereof), and (3) at least one anticonvulsive agent (e.g., diazepam, lorazepam, midazolam).

Example 15: In one embodiment, the pharmaceutical composition includes (1) pro-2-PAM, (2) at least one vasoactive agent (e.g., epinephrine, vasopressin, phenylephrine, or a salt thereof), and (3) at least one vasodilator (e.g., phentolamine, caffeine).

Example 16: In one embodiment, the pharmaceutical composition includes (1) pro-2-PAM, (2) at least one vasoactive agent (e.g., epinephrine, vasopressin, phenylephrine, or a salt thereof), and (3) at least one COMT inhibitor (e.g., entacapone).

Example 17: In one embodiment, the pharmaceutical composition includes (1) pro-2-PAM, (2) at least one anticholinergic agent (e.g., atropine), and (3) at least one anticonvulsive agent (e.g., diazepam, lorazepam, midazolam).

Example 18: In one embodiment, the pharmaceutical composition includes (1) pro-2-PAM, (2) at least one anticholinergic agent (e.g., atropine), and (3) at least one vasodilator (e.g., phentolamine, caffeine).

Example 19: In one embodiment, the pharmaceutical composition includes (1) pro-2-PAM, (2) at least one anticholinergic agent (e.g., atropine), and (3) at least one COMT inhibitor (e.g., entacapone).

Example 20: In one embodiment, the pharmaceutical composition includes (1) pro-2-PAM, (2) at least one anticonvulsive agent (e.g., diazepam, lorazepam, midazolam), and (3) at least one vasodilator (e.g., phentolamine, caffeine).

Example 21: In one embodiment, the pharmaceutical composition includes (1) pro-2-PAM, (2) at least one anticonvulsive agent (e.g., diazepam, lorazepam, midazolam), and (3) at least one COMT inhibitor (e.g., entacapone).

Example 22: In one embodiment, the pharmaceutical composition includes (1) pro-2-PAM, (2) at least one vasodilator (e.g., phentolamine, caffeine), and (3) at least one COMT inhibitor (e.g., entacapone).

Example 23: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), and (4) at least one anticholinergic agent (e.g., atropine).

Example 24: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), and (4) at least one anticonvulsive agent (e.g., diazepam, lorazepam, midazolam).

Example 25: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), and (4) at least one vasodilator (e.g., phentolamine, caffeine).

Example 26: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), and (4) at least one COMT inhibitor (e.g., entacapone).

Example 27: In one embodiment, the pharmaceutical composition includes (1) pro-2-PAM, (2) at least one additional cholinesterase reactivator agent (e.g., obidoxime, 2-PAM), (3) at least one anticholinergic agent (e.g., atropine), and (4) at least one anticonvulsive agent (e.g., diazepam, lorazepam, midazolam).

Example 28: In one embodiment, the pharmaceutical composition includes (1) pro-2-PAM, (2) at least one additional cholinesterase reactivator agent (e.g., obidoxime, 2-PAM), (3) at least one anticholinergic agent (e.g., atropine), and (4) at least one vasodilator (e.g., phentolamine, caffeine).

Example 29: In one embodiment, the pharmaceutical composition includes (1) pro-2-PAM, (2) at least one additional cholinesterase reactivator agent (e.g., obidoxime, 2-PAM), (3) at least one anticholinergic agent (e.g., atropine), and (4) at least one COMT inhibitor (e.g., entacapone).

Example 30: In one embodiment, the pharmaceutical composition includes (1) pro-2-PAM, (2) at least one additional cholinesterase reactivator agent (e.g., obidoxime, 2-PAM), (3) at least one anticonvulsive agent (e.g., diazepam, lorazepam, midazolam), and (4) at least one vasodilator (e.g., phentolamine, caffeine).

Example 31: In one embodiment, the pharmaceutical composition includes (1) pro-2-PAM, (2) at least one additional cholinesterase reactivator agent (e.g., obidoxime, 2-PAM), (3) at least one anticonvulsive agent (e.g., diazepam, lorazepam, midazolam), and (4) at least one COMT inhibitor (e.g., entacapone).

Example 32: In one embodiment, the pharmaceutical composition includes (1) pro-2-PAM, (2) at least one additional cholinesterase reactivator agent (e.g., obidoxime, 2-PAM), (3) at least one vasodilator (e.g., phentolamine, caffeine), and (4) at least one COMT inhibitor (e.g., entacapone).

Example 33: In one embodiment, the pharmaceutical composition includes (1) pro-2-PAM, (2) at least one vasoactive agent (e.g., epinephrine, vasopressin, phenylephrine, or a salt thereof), (3) at least one anticholinergic agent (e.g., atropine), and (4) at least one anticonvulsive agent (e.g., diazepam, lorazepam, midazolam).

Example 34: In one embodiment, the pharmaceutical composition includes (1) pro-2-PAM, (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 35: In one embodiment, the pharmaceutical composition includes (1) pro-2-PAM, (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 36: In one embodiment, the pharmaceutical composition includes (1) pro-2-PAM, (2) at least one vasoactive agent (e.g., epinephrine, vasopressin, phenylephrine, or a salt thereof), (3) at least one anticonvulsive agent (e.g., diazepam, lorazepam, midazolam), and (4) at least one vasodilator (e.g., phentolamine, caffeine).

Example 37: In one embodiment, the pharmaceutical composition includes (1) pro-2-PAM, (2) at least one vasoactive agent (e.g., epinephrine, vasopressin, phenylephrine, or a salt thereof), (3) at least one anticonvulsive agent (e.g., diazepam, lorazepam, midazolam), and (4) at least one COMT inhibitor (e.g., entacapone).

Example 38: In one embodiment, the pharmaceutical composition includes (1) pro-2-PAM, (2) at least one vasoactive agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 39: In one embodiment, the pharmaceutical composition includes (1) pro-2-PAM, (2) at least one anticholinergic agent (e.g., atropine), (3) at least one anticonvulsive agent (e.g., diazepam, lorazepam, midazolam), and (4) at least one vasodilator (e.g., phentolamine, caffeine).

Example 40: In one embodiment, the pharmaceutical composition includes (1) pro-2-PAM, (2) at least one anticholinergic agent (e.g., atropine), (3) at least one anticonvulsive agent (e.g., diazepam, lorazepam, midazolam), and (4) at least one COMT inhibitor (e.g., entacapone).

Example 41: In one embodiment, the pharmaceutical composition includes (1) pro-2-PAM, (2) at least one anticholinergic agent (e.g., atropine), (3) at least one vasodilator (e.g., phentolamine, caffeine), and (4) at least one COMT inhibitor (e.g., entacapone).

Example 42: In one embodiment, the pharmaceutical composition includes (1) pro-2-PAM, (2) at least one anticonvulsive agent (e.g., diazepam, lorazepam, midazolam), (3) at least one vasodilator (e.g., phentolamine, caffeine), and (4) at least one COMT inhibitor (e.g., entacapone).

Example 43: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), (4) at least one anticholinergic agent (e.g., atropine), and (5) at least one anticonvulsive agent (e.g., diazepam, lorazepam, midazolam).

Example 44: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 45: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 46: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), (4) at least one anticonvulsive agent (e.g., diazepam, lorazepam, midazolam), and (5) at least one vasodilator (e.g., phentolamine, caffeine).

Example 47: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), (4) at least one anticonvulsive agent (e.g., diazepam, lorazepam, midazolam), and (5) at least one COMT inhibitor (e.g., entacapone).

Example 48: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 49: In one embodiment, the pharmaceutical composition includes (1) pro-2-PAM, (2) at least one additional cholinesterase reactivator agent (e.g., obidoxime, 2-PAM), (3) at least one anticholinergic agent (e.g., atropine), (4) at least one anticonvulsive agent (e.g., diazepam, lorazepam, midazolam), and (5) at least one vasodilator (e.g., phentolamine, caffeine).

Example 50: In one embodiment, the pharmaceutical composition includes (1) pro-2-PAM, (2) at least one additional cholinesterase reactivator agent (e.g., obidoxime, 2-PAM), (3) at least one anticholinergic agent (e.g., atropine), (4) at least one anticonvulsive agent (e.g., diazepam, lorazepam, midazolam), and (5) at least one COMT inhibitor (e.g., entacapone).

Example 51: In one embodiment, the pharmaceutical composition includes (1) pro-2-PAM, (2) at least one additional cholinesterase reactivator agent (e.g., obidoxime, 2-PAM), (3) at least one anticholinergic agent (e.g., atropine), (4) at least one vasodilator (e.g., phentolamine, caffeine), and (5) at least one COMT inhibitor (e.g., entacapone).

Example 52: In one embodiment, the pharmaceutical composition includes (1) pro-2-PAM, (2) at least one additional cholinesterase reactivator agent (e.g., obidoxime, 2-PAM), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 53: In one embodiment, the pharmaceutical composition includes (1) pro-2-PAM, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), and (5) at least one vasodilator (e.g., phentolamine, caffeine).

Example 54: In one embodiment, the pharmaceutical composition includes (1) pro-2-PAM, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), and (5) at least one COMT inhibitor (e.g., entacapone).

Example 55: In one embodiment, the pharmaceutical composition includes (1) pro-2-PAM, (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 56: In one embodiment, the pharmaceutical composition includes (1) pro-2-PAM, (2) at least one vasoactive agent (e.g., epinephrine, vasopressin, phenylephrine, or a salt thereof), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 57: In one embodiment, the pharmaceutical composition includes (1) pro-2-PAM, (2) at least one anticholinergic agent (e.g., atropine), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 58: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), and (6) at least one vasodilator (e.g., phentolamine, caffeine)
.

Example 59: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), and (6) at least one COMT inhibitor (e.g., entacapone).

Example 60: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 61: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 62: In one embodiment, the pharmaceutical composition includes (1) pro-2-PAM, (2) at least one additional cholinesterase reactivator agent (e.g., obidoxime, 2-PAM), (3) at least one anticholinergic agent (e.g., atropine), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 63: In one embodiment, the pharmaceutical composition includes (1) pro-2-PAM, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 64: In one embodiment, the pharmaceutical composition includes (1) pro-2-PAM, (2) at least one additional cholinesterase reactivator agent (e.g., obidoxime, 2-PAM), (3) at least one vasoactive agent (e.g., epinephrine, vasopressin, phenylephrine, or a salt thereof), (4) at least one anticholinergic agent (e.g., atropine), (5) at least one anti-convulsive agent (e.g., diazepam, lorazepam, midazolam), (6) at least one vasodilator (e.g., phentolamine, caffeine), and (7) at least one COMT inhibitor (e.g., entacapone).

Example 65: In one embodiment, the pharmaceutical composition includes 2-PAM.

Example 66: In one embodiment, the pharmaceutical composition includes (1) 2-PAM and (2) at least one additional cholinesterase reactivator agent (e.g., obidoxime, pro-2-PAM).

Example 67: In one embodiment, the pharmaceutical composition includes (1) 2-PAM and (2) at least one vaso-active agent (e.g., epinephrine, vasopressin, phenylephrine, or a salt thereof).

Example 68: In one embodiment, the pharmaceutical composition includes (1) 2-PAM and (2) at least one anticholinergic agent (e.g., atropine).

Example 69: In one embodiment, the pharmaceutical composition includes (1) 2-PAM and (2) at least one anti-convulsive agent (e.g., diazepam, lorazepam, midazolam).

Example 70: In one embodiment, the pharmaceutical composition includes (1) 2-PAM and (2) at least one vaso-dilator (e.g., phentolamine, caffeine).

Example 71: In one embodiment, the pharmaceutical composition includes (1) 2-PAM and (2) at least one COMT inhibitor (e.g., entacapone).

Example 72: In one embodiment, the pharmaceutical composition includes (1) 2-PAM, (2) at least one additional cholinesterase reactivator agent (e.g., obidoxime, pro-2-PAM), and (3) at least one vasoactive agent (e.g., epineph-rine, vasopressin, phenylephrine, or a salt thereof).

Example 73: In one embodiment, the pharmaceutical composition includes (1) 2-PAM, (2) at least one additional cholinesterase reactivator agent (e.g., obidoxime, pro-2-PAM), and (3) at least one anticholinergic agent (e.g., atropine).

Example 74: In one embodiment, the pharmaceutical composition includes (1) 2-PAM, (2) at least one additional cholinesterase reactivator agent (e.g., obidoxime, pro-2-PAM), and (3) at least one anticonvulsive agent (e.g., diazepam, lorazepam, midazolam).

Example 75: In one embodiment, the pharmaceutical composition includes (1) 2-PAM, (2) at least one additional cholinesterase reactivator agent (e.g., obidoxime, pro-2-PAM), and (3) at least one vasodilator (e.g., phentolamine, caffeine).

Example 76: In one embodiment, the pharmaceutical composition includes (1) 2-PAM, (2) at least one additional cholinesterase reactivator agent (e.g., obidoxime, pro-2-PAM), and (3) at least one COMT inhibitor (e.g., entaca-pone).

Example 77: In one embodiment, the pharmaceutical composition includes (1) 2-PAM, (2) at least one vasoactive agent (e.g., epinephrine, vasopressin, phenylephrine, or a salt thereof), and (3) at least one anticholinergic agent (e.g., atropine).

Example 78: In one embodiment, the pharmaceutical composition includes (1) 2-PAM, (2) at least one vasoactive agent (e.g., epinephrine, vasopressin, phenylephrine, or a salt thereof), and (3) at least one anticonvulsive agent (e.g., diazepam, lorazepam, midazolam).

Example 79: In one embodiment, the pharmaceutical composition includes (1) 2-PAM, (2) at least one vasoactive agent (e.g., epinephrine, vasopressin, phenylephrine, or a salt thereof), and (3) at least one vasodilator (e.g., phen-tolamine, caffeine).

Example 80: In one embodiment, the pharmaceutical composition includes (1) 2-PAM, (2) at least one vasoactive agent (e.g., epinephrine, vasopressin, phenylephrine, or a salt thereof), and (3) at least one COMT inhibitor (e.g., entacapone).

Example 81: In one embodiment, the pharmaceutical composition includes (1) 2-PAM, (2) at least one anticho-linergic agent (e.g., atropine), and (3) at least one anticon-vulsive agent (e.g., diazepam, lorazepam, midazolam).

Example 82: In one embodiment, the pharmaceutical composition includes (1) 2-PAM, (2) at least one anticho-linergic agent (e.g., atropine), and (3) at least one vasodilator (e.g., phentolamine, caffeine).

Example 83: In one embodiment, the pharmaceutical composition includes (1) 2-PAM, (2) at least one anticho-linergic agent (e.g., atropine), and (3) at least one COMT inhibitor (e.g., entacapone).

Example 84: In one embodiment, the pharmaceutical composition includes (1) 2-PAM, (2) at least one anticon-vulsive agent (e.g., diazepam, lorazepam, midazolam), and (3) at least one vasodilator (e.g., phentolamine, caffeine).

Example 85: In one embodiment, the pharmaceutical composition includes (1) 2-PAM, (2) at least one anticon-vulsive agent (e.g., diazepam, lorazepam, midazolam), and (3) at least one COMT inhibitor (e.g., entacapone).

Example 86: In one embodiment, the pharmaceutical composition includes (1) 2-PAM, (2) at least one vasodilator (e.g., phentolamine, caffeine), and (3) at least one COMT inhibitor (e.g., entacapone).

Example 87: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), and (4) at least one anticholinergic agent (e.g., atropine).

Example 88: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), and (4) at least one anticonvulsive agent (e.g., diazepam, lorazepam, mida-zolam).

Example 89: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), and (4) at least one vasodilator (e.g., phentolamine, caffeine).

Example 90: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), and (4) at least one COMT inhibitor (e.g., entacapone).

Example 91: In one embodiment, the pharmaceutical composition includes (1) 2-PAM, (2) at least one additional cholinesterase reactivator agent (e.g., obidoxime, pro-2-PAM), (3) at least one anticholinergic agent (e.g., atropine), and (4) at least one anticonvulsive agent (e.g., diazepam, lorazepam, midazolam).

Example 92: In one embodiment, the pharmaceutical composition includes (1) 2-PAM, (2) at least one additional cholinesterase reactivator agent (e.g., obidoxime, pro-2-PAM), (3) at least one anticholinergic agent (e.g., atropine), and (4) at least one vasodilator (e.g., phentolamine, caffeine).

Example 93: In one embodiment, the pharmaceutical composition includes (1) 2-PAM, (2) at least one additional cholinesterase reactivator agent (e.g., obidoxime, pro-2-PAM), (3) at least one anticholinergic agent (e.g., atropine), and (4) at least one COMT inhibitor (e.g., entacapone).

Example 94: In one embodiment, the pharmaceutical composition includes (1) 2-PAM, (2) at least one additional cholinesterase reactivator agent (e.g., obidoxime, pro-2-PAM), (3) at least one anticonvulsive agent (e.g., diazepam, lorazepam, midazolam), and (4) at least one vasodilator (e.g., phentolamine, caffeine).

Example 95: In one embodiment, the pharmaceutical composition includes (1) 2-PAM, (2) at least one additional cholinesterase reactivator agent (e.g., obidoxime, pro-2-PAM), (3) at least one anticonvulsive agent (e.g., diazepam, lorazepam, midazolam), and (4) at least one COMT inhibitor (e.g., entacapone).

Example 96: In one embodiment, the pharmaceutical composition includes (1) 2-PAM, (2) at least one additional cholinesterase reactivator agent (e.g., obidoxime, pro-2-PAM), (3) at least one vasodilator (e.g., phentolamine, caffeine), and (4) at least one COMT inhibitor (e.g., entacapone).

Example 97: In one embodiment, the pharmaceutical composition includes (1) 2-PAM, (2) at least one vasoactive agent (e.g., epinephrine, vasopressin, phenylephrine, or a salt thereof), (3) at least one anticholinergic agent (e.g., atropine), and (4) at least one anticonvulsive agent (e.g., diazepam, lorazepam, midazolam).

Example 98: In one embodiment, the pharmaceutical composition includes (1) 2-PAM, (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 99: In one embodiment, the pharmaceutical composition includes (1) 2-PAM, (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 100: In one embodiment, the pharmaceutical composition includes (1) 2-PAM, (2) at least one vasoactive agent (e.g., epinephrine, vasopressin, phenylephrine, or a salt thereof), (3) at least one anticholinergic agent (e.g., diazepam, lorazepam, midazolam), and (4) at least one vasodilator (e.g., phentolamine, caffeine).

Example 101: In one embodiment, the pharmaceutical composition includes (1) 2-PAM, (2) at least one vasoactive agent (e.g., epinephrine, vasopressin, phenylephrine, or a salt thereof), (3) at least one anticonvulsive agent (e.g., diazepam, lorazepam, midazolam), and (4) at least one COMT inhibitor (e.g., entacapone).

Example 102: In one embodiment, the pharmaceutical composition includes (1) 2-PAM, (2) at least one vasoactive agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 103: In one embodiment, the pharmaceutical composition includes (1) 2-PAM, (2) at least one anticholinergic agent (e.g., atropine), (3) at least one anticonvulsive agent (e.g., diazepam, lorazepam, midazolam), and (4) at least one vasodilator (e.g., phentolamine, caffeine).

Example 104: In one embodiment, the pharmaceutical composition includes (1) 2-PAM, (2) at least one anticholinergic agent (e.g., atropine), (3) at least one anticonvulsive agent (e.g., diazepam, lorazepam, midazolam), and (4) at least one COMT inhibitor (e.g., entacapone).

Example 105: In one embodiment, the pharmaceutical composition includes (1) 2-PAM, (2) at least one anticholinergic agent (e.g., atropine), (3) at least one vasodilator (e.g., phentolamine, caffeine), and (4) at least one COMT inhibitor (e.g., entacapone).

Example 106: In one embodiment, the pharmaceutical composition includes (1) 2-PAM, (2) at least one anticonvulsive agent (e.g., diazepam, lorazepam, midazolam), (3) at least one vasodilator (e.g., phentolamine, caffeine), and (4) at least one COMT inhibitor (e.g., entacapone).

Example 107: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one anticonvulsive agent (e.g., diazepam, lorazepam, midazolam).

Example 108: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 109: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 110: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), and (5) at least one vasodilator (e.g., phentolamine, caffeine).

Example 111: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), and (5) at least one COMT inhibitor (e.g., entacapone).

Example 112: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 113: In one embodiment, the pharmaceutical composition includes (1) 2-PAM, (2) at least one additional cholinesterase reactivator agent (e.g., obidoxime, pro-2-PAM), (3) at least one anticholinergic agent (e.g., atropine), (4) at least one anticonvulsive agent (e.g., diazepam, lorazepam, midazolam), and (5) at least one vasodilator (e.g., phentolamine, caffeine).

Example 114: In one embodiment, the pharmaceutical composition includes (1) 2-PAM, (2) at least one additional cholinesterase reactivator agent (e.g., obidoxime, pro-2-PAM), (3) at least one anticholinergic agent (e.g., atropine), (4) at least one anticonvulsive agent (e.g., diazepam, lorazepam, midazolam), and (5) at least one COMT inhibitor (e.g., entacapone).

Example 115: In one embodiment, the pharmaceutical composition includes (1) 2-PAM, (2) at least one additional cholinesterase reactivator agent (e.g., obidoxime, pro-2-PAM), (3) at least one anticholinergic agent (e.g., atropine), (4) at least one vasodilator (e.g., phentolamine, caffeine), and (5) at least one COMT inhibitor (e.g., entacapone).

Example 116: In one embodiment, the pharmaceutical composition includes (1) 2-PAM, (2) at least one additional cholinesterase reactivator agent (e.g., obidoxime, pro-2-PAM), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 117: In one embodiment, the pharmaceutical composition includes (1) 2-PAM, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), and (5) at least one vasodilator (e.g., phentolamine, caffeine).

Example 118: In one embodiment, the pharmaceutical composition includes (1) 2-PAM, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), and (5) at least one COMT inhibitor (e.g., entacapone).

Example 119: In one embodiment, the pharmaceutical composition includes (1) 2-PAM, (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 120: In one embodiment, the pharmaceutical composition includes (1) 2-PAM, (2) at least one vasoactive agent (e.g., epinephrine, vasopressin, phenylephrine, or a salt thereof), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 121: In one embodiment, the pharmaceutical composition includes (1) 2-PAM, (2) at least one anticholinergic agent (e.g., atropine), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 122: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), and (6) at least one vasodilator (e.g., phentolamine, caffeine).

Example 123: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), and (6) at least one COMT inhibitor (e.g., entacapone).

Example 124: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 125: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 126: In one embodiment, the pharmaceutical composition includes (1) 2-PAM, (2) at least one additional cholinesterase reactivator agent (e.g., obidoxime, pro-2-PAM), (3) at least one anticholinergic agent (e.g., atropine), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 127: In one embodiment, the pharmaceutical composition includes (1) 2-PAM, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 128: In one embodiment, the pharmaceutical composition includes (1) 2-PAM, (2) at least one additional cholinesterase reactivator agent (e.g., obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), (6) at least one vasodilator (e.g., phentolamine, caffeine), and (7) at least one COMT inhibitor (e.g., entacapone).

Example 129: In one embodiment, the pharmaceutical composition includes obidoxime.

Example 130: In one embodiment, the pharmaceutical composition includes (1) obidoxime and (2) at least one additional cholinesterase reactivator agent (e.g., 2-PAM, pro-2-PAM).

Example 131: In one embodiment, the pharmaceutical composition includes (1) obidoxime and (2) at least one vasoactive agent (e.g., epinephrine, vasopressin, phenylephrine, or a salt thereof).

Example 132: In one embodiment, the pharmaceutical composition includes (1) obidoxime and (2) at least one anticholinergic agent (e.g., atropine).

Example 133: In one embodiment, the pharmaceutical composition includes (1) obidoxime and (2) at least one anticonvulsive agent (e.g., diazepam, lorazepam, midazolam).

Example 134: In one embodiment, the pharmaceutical composition includes (1) obidoxime and (2) at least one vasodilator (e.g., phentolamine, caffeine).

Example 135: In one embodiment, the pharmaceutical composition includes (1) obidoxime and (2) at least one COMT inhibitor (e.g., entacapone).

Example 136: In one embodiment, the pharmaceutical composition includes (1) obidoxime, (2) at least one additional cholinesterase reactivator agent (e.g., 2-PAM, pro-2-PAM), and (3) at least one vasoactive agent (e.g., epinephrine, vasopressin, phenylephrine, or a salt thereof).

Example 137: In one embodiment, the pharmaceutical composition includes (1) obidoxime, (2) at least one additional cholinesterase reactivator agent (e.g., 2-PAM, pro-2-PAM), and (3) at least one anticholinergic agent (e.g., atropine).

Example 138: In one embodiment, the pharmaceutical composition includes (1) obidoxime, (2) at least one additional cholinesterase reactivator agent (e.g., 2-PAM, pro-2-PAM), and (3) at least one anticonvulsive agent (e.g., diazepam, lorazepam, midazolam).

Example 139: In one embodiment, the pharmaceutical composition includes (1) obidoxime, (2) at least one additional cholinesterase reactivator agent (e.g., 2-PAM, pro-2-PAM), and (3) at least one vasodilator (e.g., phentolamine, caffeine).

Example 140: In one embodiment, the pharmaceutical composition includes (1) obidoxime, (2) at least one additional cholinesterase reactivator agent (e.g., 2-PAM, pro-2-PAM), and (3) at least one COMT inhibitor (e.g., entacapone).

Example 141: In one embodiment, the pharmaceutical composition includes (1) obidoxime, (2) at least one vasoactive agent (e.g., epinephrine, vasopressin, phenylephrine, or a salt thereof), and (3) at least one anticholinergic agent (e.g., atropine).

Example 142: In one embodiment, the pharmaceutical composition includes (1) obidoxime, (2) at least one vasoactive agent (e.g., epinephrine, vasopressin, phenylephrine, or a salt thereof), and (3) at least one anticonvulsive agent (e.g., diazepam, lorazepam, midazolam).

Example 143: In one embodiment, the pharmaceutical composition includes (1) obidoxime, (2) at least one vasoactive agent (e.g., epinephrine, vasopressin, phenylephrine, or a salt thereof), and (3) at least one vasodilator (e.g., phentolamine, caffeine).

Example 144: In one embodiment, the pharmaceutical composition includes (1) obidoxime, (2) at least one vasoactive agent (e.g., epinephrine, vasopressin, phenylephrine, or a salt thereof), and (3) at least one COMT inhibitor (e.g., entacapone).

Example 145: In one embodiment, the pharmaceutical composition includes (1) obidoxime, (2) at least one anticholinergic agent (e.g., atropine), and (3) at least one anticonvulsive agent (e.g., diazepam, lorazepam, midazolam).

Example 146: In one embodiment, the pharmaceutical composition includes (1) obidoxime, (2) at least one anticholinergic agent (e.g., atropine), and (3) at least one vasodilator (e.g., phentolamine, caffeine).

Example 147: In one embodiment, the pharmaceutical composition includes (1) obidoxime, (2) at least one anticholinergic agent (e.g., atropine), and (3) at least one COMT inhibitor (e.g., entacapone).

Example 148: In one embodiment, the pharmaceutical composition includes (1) obidoxime, (2) at least one anticonvulsive agent (e.g., diazepam, lorazepam, midazolam), and (3) at least one vasodilator (e.g., phentolamine, caffeine).

Example 149: In one embodiment, the pharmaceutical composition includes (1) obidoxime, (2) at least one anticonvulsive agent (e.g., diazepam, lorazepam, midazolam), and (3) at least one COMT inhibitor (e.g., entacapone).

Example 150: In one embodiment, the pharmaceutical composition includes (1) obidoxime, (2) at least one vasodilator (e.g., phentolamine, caffeine), and (3) at least one COMT inhibitor (e.g., entacapone).

Example 151: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), and (4) at least one anticholinergic agent (e.g., atropine).

Example 152: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), and (4) at least one anticonvulsive agent (e.g., diazepam, lorazepam, midazolam).

Example 153: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), and (4) at least one vasodilator (e.g., phentolamine, caffeine).

Example 154: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), and (4) at least one COMT inhibitor (e.g., entacapone).

Example 155: In one embodiment, the pharmaceutical composition includes (1) obidoxime, (2) at least one additional cholinesterase reactivator agent (e.g., 2-PAM, pro-2-PAM), (3) at least one anticholinergic agent (e.g., atropine), and (4) at least one anticonvulsive agent (e.g., diazepam, lorazepam, midazolam).

Example 156: In one embodiment, the pharmaceutical composition includes (1) obidoxime, (2) at least one additional cholinesterase reactivator agent (e.g., 2-PAM, pro-2-PAM), (3) at least one anticholinergic agent (e.g., atropine), and (4) at least one vasodilator (e.g., phentolamine, caffeine) .

Example 157: In one embodiment, the pharmaceutical composition includes (1) obidoxime, (2) at least one additional cholinesterase reactivator agent (e.g., 2-PAM, pro-2-PAM), (3) at least one anticholinergic agent (e.g., atropine), and (4) at least one COMT inhibitor (e.g., entacapone).

Example 158: In one embodiment, the pharmaceutical composition includes (1) obidoxime, (2) at least one additional cholinesterase reactivator agent (e.g., 2-PAM, pro-2-PAM), (3) at least one anticonvulsive agent (e.g., diazepam, lorazepam, midazolam), and (4) at least one vasodilator (e.g., phentolamine, caffeine).

Example 159: In one embodiment, the pharmaceutical composition includes (1) obidoxime, (2) at least one additional cholinesterase reactivator agent (e.g., 2-PAM, pro-2-PAM), (3) at least one anticonvulsive agent (e.g., diazepam, lorazepam, midazolam), and (4) at least one COMT inhibitor (e.g., entacapone).

Example 160: In one embodiment, the pharmaceutical composition includes (1) obidoxime, (2) at least one additional cholinesterase reactivator agent (e.g., 2-PAM, pro-2-PAM), (3) at least one vasodilator (e.g., phentolamine, caffeine), and (4) at least one COMT inhibitor (e.g., entacapone).

Example 161: In one embodiment, the pharmaceutical composition includes (1) obidoxime, (2) at least one vasoactive agent (e.g., epinephrine, vasopressin, phenylephrine, or a salt thereof), (3) at least one anticholinergic agent (e.g., atropine), and (4) at least one anticonvulsive agent (e.g., diazepam, lorazepam, midazolam).

Example 162: In one embodiment, the pharmaceutical composition includes (1) obidoxime, (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 163: In one embodiment, the pharmaceutical composition includes (1) obidoxime, (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 164: In one embodiment, the pharmaceutical composition includes (1) obidoxime, (2) at least one vasoactive agent (e.g., epinephrine, vasopressin, phenylephrine, or a salt thereof), (3) at least one anticonvulsive agent (e.g., diazepam, lorazepam, midazolam), and (4) at least one vasodilator (e.g., phentolamine, caffeine).

Example 165: In one embodiment, the pharmaceutical composition includes (1) obidoxime, (2) at least one vasoactive agent (e.g., epinephrine, vasopressin, phenylephrine, or a salt thereof), (3) at least one anticonvulsive agent (e.g., diazepam, lorazepam, midazolam), and (4) at least one COMT inhibitor (e.g., entacapone).

Example 166: In one embodiment, the pharmaceutical composition includes (1) obidoxime, (2) at least one vasoactive agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 167: In one embodiment, the pharmaceutical composition includes (1) obidoxime, (2) at least one anticholinergic agent (e.g., atropine), (3) at least one anticonvulsive agent (e.g., diazepam, lorazepam, midazolam), and (4) at least one vasodilator (e.g., phentolamine, caffeine).

Example 168: In one embodiment, the pharmaceutical composition includes (1) obidoxime, (2) at least one anticholinergic agent (e.g., atropine), (3) at least one anticonvulsive agent (e.g., diazepam, lorazepam, midazolam), and (4) at least one COMT inhibitor (e.g., entacapone).

Example 169: In one embodiment, the pharmaceutical composition includes (1) obidoxime, (2) at least one anticholinergic agent (e.g., atropine), (3) at least one vasodilator (e.g., phentolamine, caffeine), and (4) at least one COMT inhibitor (e.g., entacapone).

Example 170: In one embodiment, the pharmaceutical composition includes (1) obidoxime, (2) at least one anticonvulsive agent (e.g., diazepam, lorazepam, midazolam), (3) at least one vasodilator (e.g., phentolamine, caffeine), and (4) at least one COMT inhibitor (e.g., entacapone).

Example 171: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), (4) at least one anticholinergic agent (e.g., atropine), and (5) at least one anticonvulsive agent (e.g., diazepam, lorazepam, midazolam).

Example 172: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 173: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 174: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), and (5) at least one vasodilator (e.g., phentolamine, caffeine).

Example 175: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), and (5) at least one COMT inhibitor (e.g., entacapone).

Example 176: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 177: In one embodiment, the pharmaceutical composition includes (1) obidoxime, (2) at least one additional cholinesterase reactivator agent (e.g., 2-PAM, pro-2-PAM), (3) at least one anticholinergic agent (e.g., atropine), (4) at least one anticonvulsive agent (e.g., diazepam, lorazepam, midazolam), and (5) at least one vasodilator (e.g., phentolamine, caffeine).

Example 178: In one embodiment, the pharmaceutical composition includes (1) obidoxime, (2) at least one additional cholinesterase reactivator agent (e.g., 2-PAM, pro-2-PAM), (3) at least one anticholinergic agent (e.g., atropine), (4) at least one anticonvulsive agent (e.g., diazepam, lorazepam, midazolam), and (5) at least one COMT inhibitor (e.g., entacapone).

Example 179: In one embodiment, the pharmaceutical composition includes (1) obidoxime, (2) at least one additional cholinesterase reactivator agent (e.g., 2-PAM, pro-2-PAM), (3) at least one anticholinergic agent (e.g., atropine), (4) at least one vasodilator (e.g., phentolamine, caffeine), and (5) at least one COMT inhibitor (e.g., entacapone).

Example 180: In one embodiment, the pharmaceutical composition includes (1) obidoxime, (2) at least one additional cholinesterase reactivator agent (e.g., 2-PAM, pro-2-PAM), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 181: In one embodiment, the pharmaceutical composition includes (1) obidoxime, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), and (5) at least one vasodilator (e.g., phentolamine, caffeine).

Example 182: In one embodiment, the pharmaceutical composition includes (1) obidoxime, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), and (5) at least one COMT inhibitor (e.g., entacapone).

Example 183: In one embodiment, the pharmaceutical composition includes (1) obidoxime, (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 184: In one embodiment, the pharmaceutical composition includes (1) obidoxime, (2) at least one vasoactive agent (e.g., epinephrine, vasopressin, phenylephrine, or a salt thereof), (3) at least one anticholinergic agent (e.g., diazepam, lorazepam, midazolam), (4) at least one vasodilator (e.g., phentolamine, caffeine), and (5) at least one COMT inhibitor (e.g., entacapone).

Example 185: In one embodiment, the pharmaceutical composition includes (1) obidoxime, (2) at least one anticholinergic agent (e.g., atropine), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 186: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), and (6) at least one vasodilator (e.g., phentolamine, caffeine).

Example 187: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), and (6) at least one COMT inhibitor (e.g., entacapone).

Example 188: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 189: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 190: In one embodiment, the pharmaceutical composition includes (1) obidoxime, (2) at least one additional cholinesterase reactivator agent (e.g., 2-PAM, pro-2-PAM), (3) at least one anticholinergic agent (e.g., atropine), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 191: In one embodiment, the pharmaceutical composition includes (1) obidoxime, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 192: In one embodiment, the pharmaceutical composition includes (1) obidoxime, (2) at least one additional cholinesterase reactivator agent (e.g., 2-PAM, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), (6) at least one vasodilator (e.g., phentolamine, caffeine), and (7) at least one COMT inhibitor (e.g., entacapone).

Example 193: In one embodiment, the pharmaceutical composition includes at least one anticonvulsive agent (e.g., diazepam, lorazepam, midazolam).

Example 194: In one embodiment, the pharmaceutical composition includes (1) at least one anticonvulsive agent (e.g., diazepam, lorazepam, midazolam) and (2) at least one cholinesterase reactivator agent (e.g., 2-PAM, obidoxime, pro-2-PAM).

Example 195: In one embodiment, the pharmaceutical composition includes (1) at least one anticonvulsive agent (e.g., diazepam, lorazepam, midazolam) and (2) at least one vasoactive agent (e.g., epinephrine, vasopressin, phenylephrine, or a salt thereof).

Example 196: In one embodiment, the pharmaceutical composition includes (1) at least one anticonvulsive agent (e.g., diazepam, lorazepam, midazolam) and (2) at least one anticholinergic agent (e.g., atropine).

Example 197: In one embodiment, the pharmaceutical composition includes (1) at least one anticonvulsive agent (e.g., diazepam, lorazepam, midazolam) and (2) at least one vasodilator (e.g., phentolamine, caffeine).

Example 198: In one embodiment, the pharmaceutical composition includes (1) at least one anticonvulsive agent (e.g., diazepam, lorazepam, midazolam) and (2) at least one COMT inhibitor (e.g., entacapone).

Example 199: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), and (3) at least one vasoactive agent (e.g., epinephrine, vasopressin, phenylephrine, or a salt thereof).

Example 200: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), and (3) at least one anticholinergic agent (e.g., atropine).

Example 201: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), and (3) at least one vasodilator (e.g., phentolamine, caffeine).

Example 202: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), and (3) at least one COMT inhibitor (e.g., entacapone).

Example 203: In one embodiment, the pharmaceutical composition includes (1) at least one anticonvulsive agent (e.g., diazepam, lorazepam, midazolam), (2) at least one vasoactive agent (e.g., epinephrine, vasopressin, phenylephrine, or a salt thereof), and (3) at least one anticholinergic agent (e.g., atropine).

Example 204: In one embodiment, the pharmaceutical composition includes (1) at least one anticonvulsive agent (e.g., diazepam, lorazepam, midazolam), (2) at least one vasoactive agent (e.g., epinephrine, vasopressin, phenylephrine, or a salt thereof), and (3) at least one vasodilator (e.g., phentolamine, caffeine).

Example 205: In one embodiment, the pharmaceutical composition includes (1) at least one anticonvulsive agent (e.g., diazepam, lorazepam, midazolam), (2) at least one vasoactive agent (e.g., epinephrine, vasopressin, phenylephrine, or a salt thereof), and (3) at least one COMT inhibitor (e.g., entacapone).

Example 206: In one embodiment, the pharmaceutical composition includes (1) at least one anticonvulsive agent (e.g., diazepam, lorazepam, midazolam), (2) at least one anticholinergic agent (e.g., atropine), and (3) at least one vasodilator (e.g., phentolamine, caffeine).

Example 207: In one embodiment, the pharmaceutical composition includes (1) at least one anticonvulsive agent (e.g., diazepam, lorazepam, midazolam), (2) at least one anticholinergic agent (e.g., atropine), and (3) at least one COMT inhibitor (e.g., entacapone).

Example 208: In one embodiment, the pharmaceutical composition includes (1) at least one anticonvulsive agent (e.g., diazepam, lorazepam, midazolam), (2) at least one vasodilator (e.g., phentolamine, caffeine), and (3) at least one COMT inhibitor (e.g., entacapone).

Example 209: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticholinergic agent (e.g., atropine).

Example 210: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one vasodilator (e.g., phentolamine, caffeine).

Example 211: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one COMT inhibitor (e.g., entacapone).

Example 212: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), (3) at least one anticholinergic agent (e.g., atropine), and (4) at least one vasodilator (e.g., phentolamine, caffeine).

Example 213: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), (3) at least one anticholinergic agent (e.g., atropine), and (4) at least one COMT inhibitor (e.g., entacapone).

Example 214: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), (3) at least one vasodilator (e.g., phentolamine, caffeine), and (4) at least one COMT inhibitor (e.g., entacapone).

Example 215: In one embodiment, the pharmaceutical composition includes (1) at least one anticonvulsive agent (e.g., diazepam, lorazepam, midazolam), (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 216: In one embodiment, the pharmaceutical composition includes (1) at least one anticonvulsive agent (e.g., diazepam, lorazepam, midazolam), (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 217: In one embodiment, the pharmaceutical composition includes (1) at least one anticonvulsive agent (e.g., diazepam, lorazepam, midazolam), (2) at least one vasoactive agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 218: In one embodiment, the pharmaceutical composition includes (1) at least one anticonvulsive agent (e.g., diazepam, lorazepam, midazolam), (2) at least one anticholinergic agent (e.g., atropine), (3) at least one vasodilator (e.g., phentolamine, caffeine), and (4) at least one COMT inhibitor (e.g., entacapone).

Example 219: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 220: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 221: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 222: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one COMT inhibitor (e.g., entacapone).

Example 223: In one embodiment, the pharmaceutical composition includes (1) at least one anticonvulsive agent (e.g., diazepam, lorazepam, midazolam), (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 224: In one embodiment, the pharmaceutical composition includes (1) at least one anticonvulsive agent (e.g., diazepam, lorazepam, midazolam), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 225: In one embodiment, the pharmaceutical composition includes at least one AMPA receptor antagonist (e.g., tezampanel, perampanel, selurampanel, talampanel, fanapanel, irampanel, kynurenic acid).

Example 226: In one embodiment, the pharmaceutical composition includes (1) at least one AMPA receptor antagonist (e.g., tezampanel, perampanel, selurampanel, talampanel, fanapanel, irampanel, kynurenic acid) and (2) at least cholinesterase reactivator agent (e.g., 2-PAM, obidoxime, pro-2-PAM).

Example 227: In one embodiment, the pharmaceutical composition includes (1) at least one AMPA receptor antagonist (e.g., tezampanel, perampanel, selurampanel, talampanel, fanapanel, irampanel, kynurenic acid) and (2) at least one vasoactive agent (e.g., epinephrine, vasopressin, phenylephrine, or a salt thereof).

Example 228: In one embodiment, the pharmaceutical composition includes (1) at least one AMPA receptor antagonist (e.g., tezampanel, perampanel, selurampanel, talampanel, fanapanel, irampanel, kynurenic acid) and (2) at least one anticholinergic agent (e.g., atropine).

Example 229: In one embodiment, the pharmaceutical composition includes (1) at least one AMPA receptor antagonist (e.g., tezampanel, perampanel, selurampanel, talampanel, fanapanel, irampanel, kynurenic acid) and (2) at least one anticonvulsive agent (e.g., diazepam, midazolam, lorazepam).

Example 230: In one embodiment, the pharmaceutical composition includes (1) at least one AMPA receptor antagonist (e.g., tezampanel, perampanel, selurampanel, talampanel, fanapanel, irampanel, kynurenic acid) and (2) at least one vasodilator (e.g., phentolamine, caffeine).

Example 231: In one embodiment, the pharmaceutical composition includes (1) at least one AMPA receptor antagonist (e.g., tezampanel, perampanel, selurampanel, talampanel, fanapanel, irampanel, kynurenic acid) and (2) at least one COMT inhibitor (e.g., entacapone).

Example 232: In one embodiment, the pharmaceutical composition includes (1) at least one AMPA receptor antagonist (e.g., tezampanel, perampanel, selurampanel, talampanel, fanapanel, irampanel, kynurenic acid) and (2) at least one NMDA receptor antagonist (e.g., memantine).

Example 233: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), and (3) at least one vasoactive agent (e.g., epinephrine, vasopressin, phenylephrine, or a salt thereof).

Example 234: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), and (3) at least one anticholinergic agent (e.g., atropine).

Example 235: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), and (3) at least one anticonvulsive agent (e.g., diazepam, midazolam, lorazepam).

Example 236: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), and (3) at least one vasodilator (e.g., phentolamine, caffeine).

Example 237: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), and (3) at least one COMT inhibitor (e.g., entacapone).

Example 238: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), and (3) at least one NMDA receptor antagonist (e.g., memantine).

Example 239: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), and (3) at least one anticholinergic agent (e.g., atropine).

Example 240: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), and (3) at least one anticonvulsive agent (e.g., diazepam, midazolam, lorazepam).

Example 241: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), and (3) at least one vasodilator (e.g., phentolamine, caffeine).

Example 242: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), and (3) at least one COMT inhibitor (e.g., entacapone).

Example 243: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), and (3) at least one NMDA receptor antagonist (e.g., memantine).

Example 244: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), and (3) at least one anticonvulsive agent (e.g., diazepam, midazolam, lorazepam).

Example 245: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), and (3) at least one vasodilator (e.g., phentolamine, caffeine).

Example 246: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), and (3) at least one COMT inhibitor (e.g., entacapone).

Example 247: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), and (3) at least one NMDA receptor antagonist (e.g., memantine).

Example 248: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticonvulsive agent (e.g., diazepam, midazolam, lorazepam), and (3) at least one vasodilator (e.g., phentolamine, caffeine).

Example 249: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticonvulsive agent (e.g., diazepam, midazolam, lorazepam), and (3) at least one COMT inhibitor (e.g., entacapone).

Example 250: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticonvulsive agent (e.g., diazepam, midazolam, lorazepam), and (3) at least one NMDA receptor antagonist (e.g., memantine).

Example 251: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasodilator (e.g., phentolamine, caffeine), and (3) at least one COMT inhibitor (e.g., entacapone).

Example 252: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasodilator (e.g., phentolamine, caffeine), and (3) at least one NMDA receptor antagonist (e.g., memantine).

Example 253: In one embodiment, the pharmaceutical composition includes (1) at least one AMPA receptor antagonist (e.g., tezampanel, perampanel, selurampanel, talampanel, fanapanel, irampanel, kynurenic acid), (2) at least one COMT inhibitor (e.g., entacapone), and (3) at least one NMDA receptor antagonist (e.g., memantine).

Example 254: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticholinergic agent (e.g., atropine).

Example 255: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticonvulsive agent (e.g., diazepam, midazolam, lorazepam).

Example 256: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one vasodilator (e.g., phentolamine, caffeine).

Example 257: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one COMT inhibitor (e.g., entacapone).

Example 258: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one NMDA receptor antagonist (e.g., memantine).

Example 259: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one anticholinergic agent (e.g., atropine), and (4) at least one anticonvulsive agent (e.g., diazepam, midazolam, lorazepam).

Example 260: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one anticholinergic agent (e.g., atropine), and (4) at least one vasodilator (e.g., phentolamine, caffeine).

Example 261: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticholinergic agent (e.g., atropine), and (4) at least one COMT inhibitor (e.g., entacapone).

Example 262: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticholinergic agent (e.g., atropine), and (4) at least one NMDA receptor antagonist (e.g., memantine).

Example 263: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticonvulsive agent (e.g., diazepam, midazolam, lorazepam), and (4) at least one vasodilator (e.g., phentolamine, caffeine).

Example 264: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticonvulsive agent (e.g., diazepam, midazolam, lorazepam), and (4) at least one COMT inhibitor (e.g., entacapone).

Example 265: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticonvulsive agent (e.g., diazepam, midazolam, lorazepam), and (4) at least one NMDA receptor antagonist (e.g., memantine).

Example 266: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one vasodilator (e.g., phentolamine, caffeine), and (4) at least one COMT inhibitor (e.g., entacapone).

Example 267: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one vasodilator (e.g., phentolamine, caffeine), and (4) at least one NMDA receptor antagonist (e.g., memantine).

Example 268: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one COMT inhibitor (e.g., entacapone), and (4) at least one NMDA receptor antagonist (e.g., memantine).

Example 269: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), and (4) at least one anticonvulsive agent (e.g., diazepam, midazolam, lorazepam).

Example 270: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 271: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 272: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), and (4) at least one NMDA receptor antagonist (e.g., memantine).

Example 273: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticonvulsive agent (e.g., diazepam, midazolam, lorazepam), and (4) at least one vasodilator (e.g., phentolamine, caffeine).

Example 274: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticonvulsive agent (e.g., diazepam, midazolam, lorazepam), and (4) at least one COMT inhibitor (e.g., entacapone).

Example 275: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticonvulsive agent (e.g., diazepam, midazolam, lorazepam), and (4) at least one NMDA receptor antagonist (e.g., memantine).

Example 276: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 277: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one vasodilator (e.g., phentolamine, caffeine), and (4) at least one NMDA receptor antagonist (e.g., memantine).

Example 278: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one COMT inhibitor (e.g., entacapone), and (4) at least one NMDA receptor antagonist (e.g., memantine).

Example 279: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), (3) at least one anticonvulsive agent (e.g., diazepam, midazolam, lorazepam), and (4) at least one vasodilator (e.g., phentolamine, caffeine).

Example 280: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), (3) at least one anticonvulsive agent (e.g., diazepam, midazolam, lorazepam), and (4) at least one COMT inhibitor (e.g., entacapone).

Example 281: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), (3) at least one anticonvulsive agent (e.g., diazepam, midazolam, lorazepam), and (4) at least one NMDA receptor antagonist (e.g., memantine).

Example 282: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), (3) at least one vasodilator (e.g., phentolamine, caffeine), and (4) at least one COMT inhibitor (e.g., entacapone).

Example 283: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), (3) at least one vasodilator (e.g., phentolamine, caffeine), and (4) at least one NMDA receptor antagonist (e.g., memantine).

Example 284: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), (3) at least one COMT inhibitor (e.g., entacapone), and (4) at least one NMDA receptor antagonist (e.g., memantine).

Example 285: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticonvulsive agent (e.g., diazepam, midazolam, lorazepam), (3) at least one vasodilator (e.g., phentolamine, caffeine), and (4) at least one COMT inhibitor (e.g., entacapone).

Example 286: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticonvulsive agent (e.g., diazepam, midazolam, lorazepam), (3) at least one vasodilator (e.g., phentolamine, caffeine), and (4) at least one NMDA receptor antagonist (e.g., memantine).

Example 287: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticonvulsive agent (e.g., diazepam, midazolam, lorazepam), (3) at least one COMT inhibitor (e.g., entacapone), and (4) at least one NMDA receptor antagonist (e.g., memantine).

Example 288: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasodilator (e.g., phentolamine, caffeine), (3) at least one COMT inhibitor (e.g., entacapone), and (4) at least one NMDA receptor antagonist (e.g., memantine).

Example 289: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one anticonvulsive agent (e.g., diazepam, midazolam, lorazepam).

Example 290: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 291: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 292: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one NMDA receptor antagonist (e.g., memantine).

Example 293: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., diazepam, midazolam, lorazepam), and (5) at least one vasodilator (e.g., phentolamine, caffeine).

Example 294: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one COMT inhibitor (e.g., entacapone).

Example 295: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one NMDA receptor antagonist (e.g., memantine).

Example 296: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 297: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one NMDA receptor antagonist (e.g., memantine).

Example 298: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one COMT inhibitor (e.g., entacapone), and (5) at least one NMDA receptor antagonist (e.g., memantine).

Example 299: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 300: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one COMT inhibitor (e.g., entacapone).

Example 301: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one NMDA receptor antagonist (e.g., memantine).

Example 302: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one COMT inhibitor (e.g., entacapone).

Example 303: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one NMDA receptor antagonist (e.g., memantine).

Example 304: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticholinergic agent (e.g., atropine), (4) at least one COMT inhibitor (e.g., entacapone), and (5) at least one NMDA receptor antagonist (e.g., memantine).

Example 305: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 306: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), and (5) at least one NMDA receptor antagonist (e.g., memantine).

Example 307: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one anticonvulsive agent (e.g., diazepam, midazolam, lorazepam), (4) at least one COMT inhibitor (e.g., entacapone), and (5) at least one NMDA receptor antagonist (e.g., memantine).

Example 308: In one embodiment, the pharmaceutical composition includes (1) at least one AMPA receptor antagonist (e.g., tezampanel, perampanel, selurampanel, talampanel, fanapanel, irampanel, kynurenic acid), (2) at least one cholinesterase reactivator agent (e.g., 2-PAM, obidoxime, pro-2-PAM), (3) at least one vasodilator (e.g., phentolamine, caffeine), (4) at least one COMT inhibitor (e.g., entacapone), and (5) at least one NMDA receptor antagonist (e.g., memantine).

Example 309: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 310: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one COMT inhibitor (e.g., entacapone).

Example 311: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one NMDA receptor antagonist (e.g., memantine).

Example 312: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 313: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one NMDA receptor antagonist (e.g., memantine).

Example 314: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), (4) at least one COMT inhibitor (e.g., entacapone), and (5) at least one NMDA receptor antagonist (e.g., memantine).

Example 315: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 316: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), and (5) at least one NMDA receptor antagonist (e.g., memantine).

Example 317: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticonvulsive agent (e.g., diazepam, midazolam, lorazepam), (4) at least one COMT inhibitor (e.g., entacapone), and (5) at least one NMDA receptor antagonist (e.g., memantine).

Example 318: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one vasodilator (e.g., phentolamine, caffeine), (4) at least one COMT inhibitor (e.g., entacapone), and (5) at least one NMDA receptor antagonist (e.g., memantine).

Example 319: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 320: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), (3) at least one anticonvulsive agent (e.g., diazepam, midazolam, lorazepam), (4) at least one vasodilator (e.g., phentolamine, caffeine), and (5) at least one NMDA receptor antagonist (e.g., memantine).

Example 321: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), (3) at least one anticonvulsive agent (e.g., diazepam, midazolam, lorazepam), (4) at least one COMT inhibitor (e.g., entacapone), and (5) at least one NMDA receptor antagonist (e.g., memantine).

Example 322: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), (3) at least one vasodilator (e.g., phentolamine, caffeine), (4) at least one COMT inhibitor (e.g., entacapone), and (5) at least one NMDA receptor antagonist (e.g., memantine).

Example 323: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticonvulsive agent (e.g., diazepam, midazolam, lorazepam), (3) at least one vasodilator (e.g., phentolamine, caffeine), (4) at least one COMT inhibitor (e.g., entacapone), and (5) at least one NMDA receptor antagonist (e.g., memantine).

Example 324: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one vasodilator (e.g., phentolamine, caffeine).

Example 325: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one COMT inhibitor (e.g., entacapone).

Example 326: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one NMDA receptor antagonist (e.g., memantine).

Example 327: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 328: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one NMDA receptor antagonist (e.g., memantine).

Example 329: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one COMT inhibitor (e.g., entacapone), and (6) at least one NMDA receptor antagonist (e.g., memantine).

Example 330: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 331: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), and (6) at least one NMDA receptor antagonist (e.g., memantine).

Example 332: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one COMT inhibitor (e.g., entacapone), and (6) at least one NMDA receptor antagonist (e.g., memantine).

Example 333: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), (5) at least one COMT inhibitor (e.g., entacapone), and (6) at least one NMDA receptor antagonist (e.g., memantine).

Example 334: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 335: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one NMDA receptor antagonist (e.g., memantine).

Example 336: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one COMT inhibitor (e.g., entacapone), and (6) at least one NMDA receptor antagonist (e.g., memantine).

Example 337: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), (5) at least one COMT inhibitor (e.g., entacapone), and (6) at least one NMDA receptor antagonist (e.g., memantine).

Example 338: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), (5) at least one COMT inhibitor (e.g., entacapone), and (6) at least one NMDA receptor antagonist (e.g., memantine).

Example 339: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 340: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one NMDA receptor antagonist (e.g., memantine).

Example 341: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one COMT inhibitor (e.g., entacapone), and (6) at least one NMDA receptor antagonist (e.g., memantine).

Example 342: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), (5) at least one COMT inhibitor (e.g., entacapone), and (6) at least one NMDA receptor antagonist (e.g., memantine).

Example 343: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), (5) at least one COMT inhibitor (e.g., entacapone), and (6) at least one NMDA receptor antagonist (e.g., memantine).

Example 344: In one embodiment, the pharmaceutical composition includes (1) at least one AMPA receptor antagonist (e.g., tezampanel, perampanel, selurampanel, talampanel, fanapanel, irampanel, kynurenic acid), (2) at least one anticholinergic agent (e.g., atropine), (3) at least one anticonvulsive agent (e.g., diazepam, midazolam, lorazepam), (4) at least one vasodilator (e.g., phentolamine, caffeine), (5) at least one COMT inhibitor (e.g., entacapone), and (6) at least one NMDA receptor antagonist (e.g., memantine).

Example 345: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), and (7) at least one COMT inhibitor (e.g., entacapone).

Example 346: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), and (7) at least one NMDA receptor antagonist (e.g., memantine).

Example 347: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one COMT inhibitor (e.g., entacapone), and (7) at least one NMDA receptor antagonist (e.g., memantine).

Example 348: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), (6) at least one COMT inhibitor (e.g., entacapone), and (7) at least one NMDA receptor antagonist (e.g., memantine).

Example 349: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one NMDA receptor antagonist (e.g., memantine).

Example 350: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one NMDA receptor antagonist (e.g., memantine).

Example 351: In one embodiment, the pharmaceutical composition includes (1) at least one AMPA receptor antagonist (e.g., tezampanel, perampanel, selurampanel, talampanel, fanapanel, irampanel, kynurenic acid), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one NMDA receptor antagonist (e.g., memantine).

Example 352: In one embodiment, the pharmaceutical composition includes (1) at least one AMPA receptor antagonist (e.g., tezampanel, perampanel, selurampanel, talampanel, fanapanel, irampanel, kynurenic acid), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), (7) at least one COMT inhibitor (e.g., entacapone), and (8) at least one NMDA receptor antagonist (e.g., memantine).

Example 353: In one embodiment, the pharmaceutical composition includes at least one noncompetitive nicotinic antagonist (e.g., MB327, MB399).

Example 354: In one embodiment, the pharmaceutical composition includes (1) at least one noncompetitive nicotinic antagonist (e.g., MB327, MB399) and (2) at least cholinesterase reactivator agent (e.g., 2-PAM, obidoxime, pro-2-PAM).

Example 355: In one embodiment, the pharmaceutical composition includes (1) at least one noncompetitive nicotinic antagonist (e.g., MB327, MB399) and (2) at least one vasoactive agent (e.g., epinephrine, vasopressin, phenylephrine, or a salt thereof).

Example 356: In one embodiment, the pharmaceutical composition includes (1) at least one noncompetitive nicotinic antagonist (e.g., MB327, MB399) and (2) at least one anticholinergic agent (e.g., atropine).

Example 357: In one embodiment, the pharmaceutical composition includes (1) at least one noncompetitive nicotinic antagonist (e.g., MB327, MB399) and (2) at least one anticonvulsive agent (e.g., diazepam, midazolam, lorazepam).

Example 358: In one embodiment, the pharmaceutical composition includes (1) at least one noncompetitive nicotinic antagonist (e.g., MB327, MB399) and (2) at least one vasodilator (e.g., phentolamine, caffeine).

Example 359: In one embodiment, the pharmaceutical composition includes (1) at least one noncompetitive nicotinic antagonist (e.g., MB327, MB399) and (2) at least one COMT inhibitor (e.g., entacapone).

Example 360: In one embodiment, the pharmaceutical composition includes (1) at least one noncompetitive nicotinic antagonist (e.g., MB327, MB399) and (2) at least one avermectin (e.g., ivermectin, selamectin, doramectin, eprinomectin, abamectin).

Example 361: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), and (3) at least one vasoactive agent (e.g., epinephrine, vasopressin, phenylephrine, or a salt thereof).

Example 362: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), and (3) at least one anticholinergic agent (e.g., atropine).

Example 363: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), and (3) at least one anticonvulsive agent (e.g., diazepam, midazolam, lorazepam).

Example 364: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), and (3) at least one vasodilator (e.g., phentolamine, caffeine).

Example 365: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), and (3) at least one COMT inhibitor (e.g., entacapone).

Example 366: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), and (3) at least one avermectin (e.g., ivermectin, selamectin, doramectin, eprinomectin, abamectin).

Example 367: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), and (3) at least one anticholinergic agent (e.g., atropine).

Example 368: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), and (3) at least one anticonvulsive agent (e.g., diazepam, midazolam, lorazepam).

Example 369: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), and (3) at least one vasodilator (e.g., phentolamine, caffeine).

Example 370: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), and (3) at least one COMT inhibitor (e.g., entacapone).

Example 371: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), and (3) at least one avermectin (e.g., ivermectin, selamectin, doramectin, eprinomectin, abamectin).

Example 372: In one embodiment, the pharmaceutical composition includes (1) at least one noncompetitive nicotinic antagonist (e.g., MB327, MB399), (2) at least one anticholinergic agent (e.g., atropine), and (3) at least one anticonvulsive agent (e.g., diazepam, midazolam, lorazepam).

Example 373: In one embodiment, the pharmaceutical composition includes (1) at least one noncompetitive nicotinic antagonist (e.g., MB327, MB399), (2) at least one anticholinergic agent (e.g., atropine), and (3) at least one vasodilator (e.g., phentolamine, caffeine).

Example 374: In one embodiment, the pharmaceutical composition includes (1) at least one noncompetitive nicotinic antagonist (e.g., MB327, MB399), (2) at least one anticholinergic agent (e.g., atropine), and (3) at least one COMT inhibitor (e.g., entacapone).

Example 375: In one embodiment, the pharmaceutical composition includes (1) at least one noncompetitive nicotinic antagonist (e.g., MB327, MB399), (2) at least one anticholinergic agent (e.g., atropine), and (3) at least one avermectin (e.g., ivermectin, selamectin, doramectin, eprinomectin, abamectin).

Example 376: In one embodiment, the pharmaceutical composition includes (1) at least one noncompetitive nicotinic antagonist (e.g., MB327, MB399), (2) at least one anticonvulsive agent (e.g., diazepam, midazolam, lorazepam), and (3) at least one vasodilator (e.g., phentolamine, caffeine).

Example 377: In one embodiment, the pharmaceutical composition includes (1) at least one noncompetitive nicotinic antagonist (e.g., MB327, MB399), (2) at least one anticonvulsive agent (e.g., diazepam, midazolam, lorazepam), and (3) at least one COMT inhibitor (e.g., entacapone).

Example 378: In one embodiment, the pharmaceutical composition includes (1) at least one noncompetitive nicotinic antagonist (e.g., MB327, MB399), (2) at least one anticonvulsive agent (e.g., diazepam, midazolam, lorazepam), and (3) at least one avermectin (e.g., ivermectin, selamectin, doramectin, eprinomectin, abamectin).

Example 379: In one embodiment, the pharmaceutical composition includes (1) at least one noncompetitive nicotinic antagonist (e.g., MB327, MB399), (2) at least one vasodilator (e.g., phentolamine, caffeine), and (3) at least one COMT inhibitor (e.g., entacapone).

Example 380: In one embodiment, the pharmaceutical composition includes (1) at least one noncompetitive nicotinic antagonist (e.g., MB327, MB399), (2) at least one vasodilator (e.g., phentolamine, caffeine), and (3) at least one avermectin (e.g., ivermectin, selamectin, doramectin, eprinomectin, abamectin).

Example 381: In one embodiment, the pharmaceutical composition includes (1) at least one noncompetitive nicotinic antagonist (e.g., MB327, MB399), (2) at least one COMT inhibitor (e.g., entacapone), and (3) at least one avermectin (e.g., ivermectin, selamectin, doramectin, eprinomectin, abamectin).

Example 382: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticholinergic agent (e.g., atropine).

Example 383: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticonvulsive agent (e.g., diazepam, midazolam, lorazepam).

Example 384: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one vasodilator (e.g., phentolamine, caffeine).

Example 385: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one COMT inhibitor (e.g., entacapone).

Example 386: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one avermectin (e.g., ivermectin, selamectin, doramectin, eprinomectin, abamectin).

Example 387: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), and (4) at least one anticonvulsive agent (e.g., diazepam, midazolam, lorazepam).

Example 388: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), and (4) at least one vasodilator (e.g., phentolamine, caffeine)
.

Example 389: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), and (4) at least one COMT inhibitor (e.g., entacapone).

Example 390: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-

PAM), (3) at least one anticholinergic agent (e.g., atropine), and (4) at least one avermectin (e.g., ivermectin, selamectin, doramectin, eprinomectin, abamectin).

Example 391: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticonvulsive agent (e.g., diazepam, midazolam, lorazepam), and (4) at least one vasodilator (e.g., phentolamine, caffeine).

Example 392: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticonvulsive agent (e.g., diazepam, midazolam, lorazepam), and (4) at least one COMT inhibitor (e.g., entacapone).

Example 393: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticonvulsive agent (e.g., diazepam, midazolam, lorazepam), and (4) at least one avermectin (e.g., ivermectin, selamectin, doramectin, eprinomectin, abamectin).

Example 394: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasodilator (e.g., phentolamine, caffeine), and (4) at least one COMT inhibitor (e.g., entacapone).

Example 395: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasodilator (e.g., phentolamine, caffeine), and (4) at least one avermectin (e.g., ivermectin, selamectin, doramectin, eprinomectin, abamectin).

Example 396: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one COMT inhibitor (e.g., entacapone), and (4) at least one avermectin (e.g., ivermectin, selamectin, doramectin, eprinomectin, abamectin).

Example 397: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), and (4) at least one anticonvulsive agent (e.g., diazepam, midazolam, lorazepam).

Example 398: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 399: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 400: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), and (4) at least one avermectin (e.g., ivermectin, selamectin, doramectin, eprinomectin, abamectin).

Example 401: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticonvulsive agent (e.g., diazepam, midazolam, lorazepam), and (4) at least one vasodilator (e.g., phentolamine, caffeine).

Example 402: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticonvulsive agent (e.g., diazepam, midazolam, lorazepam), and (4) at least one COMT inhibitor (e.g., entacapone).

Example 403: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticonvulsive agent (e.g., diazepam, midazolam, lorazepam), and (4) at least one avermectin (e.g., ivermectin, selamectin, doramectin, eprinomectin, abamectin).

Example 404: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 405: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one vasodilator (e.g., phentolamine, caffeine), and (4) at least one avermectin (e.g., ivermectin, selamectin, doramectin, eprinomectin, abamectin).

Example 406: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one COMT inhibitor (e.g., entacapone), and (4) at least one avermectin (e.g., ivermectin, selamectin, doramectin, eprinomectin, abamectin).

Example 407: In one embodiment, the pharmaceutical composition includes (1) at least one noncompetitive nicotinic antagonist (e.g., MB327, MB399), (2) at least one anticholinergic agent (e.g., atropine), (3) at least one anticonvulsive agent (e.g., diazepam, midazolam, lorazepam), and (4) at least one vasodilator (e.g., phentolamine, caffeine)
.

Example 408: In one embodiment, the pharmaceutical composition includes (1) at least one noncompetitive nicotinic antagonist (e.g., MB327, MB399), (2) at least one anticholinergic agent (e.g., atropine), (3) at least one anticonvulsive agent (e.g., diazepam, midazolam, lorazepam), and (4) at least one COMT inhibitor (e.g., entacapone).

Example 409: In one embodiment, the pharmaceutical composition includes (1) at least one noncompetitive nicotinic antagonist (e.g., MB327, MB399), (2) at least one anticholinergic agent (e.g., atropine), (3) at least one anticonvulsive agent (e.g., diazepam, midazolam, lorazepam), and (4) at least one avermectin (e.g., ivermectin, selamectin, doramectin, eprinomectin, abamectin).

Example 410: In one embodiment, the pharmaceutical composition includes (1) at least one noncompetitive nicotinic antagonist (e.g., MB327, MB399), (2) at least one anticholinergic agent (e.g., atropine), (3) at least one vasodilator (e.g., phentolamine, caffeine), and (4) at least one COMT inhibitor (e.g., entacapone).

Example 411: In one embodiment, the pharmaceutical composition includes (1) at least one noncompetitive nicotinic antagonist (e.g., MB327, MB399), (2) at least one anticholinergic agent (e.g., atropine), (3) at least one vasodilator (e.g., phentolamine, caffeine), and (4) at least one avermectin (e.g., ivermectin, selamectin, doramectin, eprinomectin, abamectin).

Example 412: In one embodiment, the pharmaceutical composition includes (1) at least one noncompetitive nicotinic antagonist (e.g., MB327, MB399), (2) at least one anticholinergic agent (e.g., atropine), (3) at least one COMT inhibitor (e.g., entacapone), and (4) at least one avermectin (e.g., ivermectin, selamectin, doramectin, eprinomectin, abamectin).

Example 413: In one embodiment, the pharmaceutical composition includes (1) at least one noncompetitive nicotinic antagonist (e.g., MB327, MB399), (2) at least one anticonvulsive agent (e.g., diazepam, midazolam, lorazepam), (3) at least one vasodilator (e.g., phentolamine, caffeine), and (4) at least one COMT inhibitor (e.g., entacapone).

Example 414: In one embodiment, the pharmaceutical composition includes (1) at least one noncompetitive nicotinic antagonist (e.g., MB327, MB399), (2) at least one anticonvulsive agent (e.g., diazepam, midazolam, lorazepam), (3) at least one vasodilator (e.g., phentolamine, caffeine), and (4) at least one avermectin (e.g., ivermectin, selamectin, doramectin, eprinomectin, abamectin).

Example 415: In one embodiment, the pharmaceutical composition includes (1) at least one noncompetitive nicotinic antagonist (e.g., MB327, MB399), (2) at least one anticonvulsive agent (e.g., diazepam, midazolam, lorazepam), (3) at least one COMT inhibitor (e.g., entacapone), and (4) at least one avermectin (e.g., ivermectin, selamectin, doramectin, eprinomectin, abamectin).

Example 416: In one embodiment, the pharmaceutical composition includes (1) at least one noncompetitive nicotinic antagonist (e.g., MB327, MB399), (2) at least one vasodilator (e.g., phentolamine, caffeine), (3) at least one COMT inhibitor (e.g., entacapone), and (4) at least one avermectin (e.g., ivermectin, selamectin, doramectin, eprinomectin, abamectin).

Example 417: In one embodiment, the pharmaceutical composition includes (1) at least one noncompetitive nicotinic antagonist (e.g., MB327, MB399), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one anticonvulsive agent (e.g., diazepam, midazolam, lorazepam).

Example 418: In one embodiment, the pharmaceutical composition includes (1) at least one noncompetitive nicotinic antagonist (e.g., MB327, MB399), (2) at least one cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 419: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 420: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one avermectin (e.g., ivermectin, selamectin, doramectin, eprinomectin, abamectin).

Example 421: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one vasodilator (e.g., phentolamine, caffeine).

Example 422: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one COMT inhibitor (e.g., entacapone).

Example 423: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one avermectin (e.g., ivermectin, selamectin, doramectin, eprinomectin, abamectin).

Example 424: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 425: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one avermectin (e.g., ivermectin, selamectin, doramectin, eprinomectin, abamectin).

Example 426: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-

PAM), (3) at least one vasoactive agent (e.g., epinephrine, vasopressin, phenylephrine, or a salt thereof), (4) at least one COMT inhibitor (e.g., entacapone), and (5) at least one avermectin (e.g., ivermectin, selamectin, doramectin, eprinomectin, abamectin).

Example 427: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 428: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one COMT inhibitor (e.g., entacapone).

Example 429: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one avermectin (e.g., ivermectin, selamectin, doramectin, eprinomectin, abamectin).

Example 430: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one COMT inhibitor (e.g., entacapone).

Example 431: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one avermectin (e.g., ivermectin, selamectin, doramectin, eprinomectin, abamectin).

Example 432: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), (4) at least one COMT inhibitor (e.g., entacapone), and (5) at least one avermectin (e.g., ivermectin, selamectin, doramectin, eprinomectin, abamectin).

Example 433: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 434: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), and (5) at least one avermectin (e.g., ivermectin, selamectin, doramectin, eprinomectin, abamectin).

Example 435: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticonvulsive agent (e.g., diazepam, midazolam, lorazepam), (4) at least one COMT inhibitor (e.g., entacapone), and (5) at least one avermectin (e.g., ivermectin, selamectin, doramectin, eprinomectin, abamectin).

Example 436: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasodilator (e.g., phentolamine, caffeine), (4) at least one COMT inhibitor (e.g., entacapone), and (5) at least one avermectin (e.g., ivermectin, selamectin, doramectin, eprinomectin, abamectin).

Example 437: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 438: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one COMT inhibitor (e.g., entacapone).

Example 439: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one avermectin (e.g., ivermectin, selamectin, doramectin, eprinomectin, abamectin).

Example 440: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 441: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one avermectin (e.g., ivermectin, selamectin, doramectin, eprinomectin, abamectin).

Example 442: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), (4) at least one COMT inhibitor (e.g., entacapone), and (5) at least one avermectin (e.g., ivermectin, selamectin, doramectin, eprinomectin, abamectin).

Example 443: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 444: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), and (5) at least one avermectin (e.g., ivermectin, selamectin, doramectin, eprinomectin, abamectin).

Example 445: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticonvulsive agent (e.g., diazepam, midazolam, lorazepam), (4) at least one COMT inhibitor (e.g., entacapone), and (5) at least one avermectin (e.g., ivermectin, selamectin, doramectin, eprinomectin, abamectin).

Example 446: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one vasodilator (e.g., phentolamine, caffeine), (4) at least one COMT inhibitor (e.g., entacapone), and (5) at least one avermectin (e.g., ivermectin, selamectin, doramectin, eprinomectin, abamectin).

Example 447: In one embodiment, the pharmaceutical composition includes (1) at least one noncompetitive nicotinic antagonist (e.g., MB327, MB399), (2) at least one anticholinergic agent (e.g., atropine), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 448: In one embodiment, the pharmaceutical composition includes (1) at least one noncompetitive nicotinic antagonist (e.g., MB327, MB399), (2) at least one anticholinergic agent (e.g., atropine), (3) at least one anticonvulsive agent (e.g., diazepam, midazolam, lorazepam), (4) at least one vasodilator (e.g., phentolamine, caffeine), and (5) at least one avermectin (e.g., ivermectin, selamectin, doramectin, eprinomectin, abamectin).

Example 449: In one embodiment, the pharmaceutical composition includes (1) at least one noncompetitive nicotinic antagonist (e.g., MB327, MB399), (2) at least one anticholinergic agent (e.g., atropine), (3) at least one anticonvulsive agent (e.g., diazepam, midazolam, lorazepam), (4) at least one COMT inhibitor (e.g., entacapone), and (5) at least one avermectin (e.g., ivermectin, selamectin, doramectin, eprinomectin, abamectin).

Example 450: In one embodiment, the pharmaceutical composition includes (1) at least one noncompetitive nicotinic antagonist (e.g., MB327, MB399), (2) at least one anticholinergic agent (e.g., atropine), (3) at least one vasodilator (e.g., phentolamine, caffeine), (4) at least one COMT inhibitor (e.g., entacapone), and (5) at least one avermectin (e.g., ivermectin, selamectin, doramectin, eprinomectin, abamectin).

Example 451: In one embodiment, the pharmaceutical composition includes (1) at least one noncompetitive nicotinic antagonist (e.g., MB327, MB399), (2) at least one anticonvulsive agent (e.g., diazepam, midazolam, lorazepam), (3) at least one vasodilator (e.g., phentolamine, caffeine), (4) at least one COMT inhibitor (e.g., entacapone), and (5) at least one avermectin (e.g., ivermectin, selamectin, doramectin, eprinomectin, abamectin).

Example 452: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one vasodilator (e.g., phentolamine, caffeine).

Example 453: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one COMT inhibitor (e.g., entacapone).

Example 454: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one avermectin (e.g., ivermectin, selamectin, doramectin, eprinomectin, abamectin).

Example 455: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 456: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one avermectin (e.g., ivermectin, selamectin, doramectin, eprinomectin, abamectin).

Example 457: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one COMT inhibitor (e.g., entacapone), and (6) at least one avermectin (e.g., ivermectin, selamectin, doramectin, eprinomectin, abamectin).

Example 458: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 459: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), and (6) at least one avermectin (e.g., ivermectin, selamectin, doramectin, eprinomectin, abamectin).

Example 460: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one COMT inhibitor (e.g., entacapone), and (6) at least one avermectin (e.g., ivermectin, selamectin, doramectin, eprinomectin, abamectin).

Example 461: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), (5) at least one COMT inhibitor (e.g., entacapone), and (6) at least one avermectin (e.g., ivermectin, selamectin, doramectin, eprinomectin, abamectin).

Example 462: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 463: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one avermectin (e.g., ivermectin, selamectin, doramectin, eprinomectin, abamectin).

Example 464: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one COMT inhibitor (e.g., entacapone), and (6) at least one avermectin (e.g., ivermectin, selamectin, doramectin, eprinomectin, abamectin).

Example 465: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), (5) at least one COMT inhibitor (e.g., entacapone), and (6) at least one avermectin (e.g., ivermectin, selamectin, doramectin, eprinomectin, abamectin).

Example 466: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), (5) at least one COMT inhibitor (e.g., entacapone), and (6) at least one avermectin (e.g., ivermectin, selamectin, doramectin, eprinomectin, abamectin).

Example 467: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 468: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one avermectin (e.g., ivermectin, selamectin, doramectin, eprinomectin, abamectin).

Example 469: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one COMT inhibitor (e.g., entacapone), and (6) at least one avermectin (e.g., ivermectin, selamectin, doramectin, eprinomectin, abamectin).

Example 470: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), (5) at least one COMT inhibitor (e.g., entacapone), and (6) at least one avermectin (e.g., ivermectin, selamectin, doramectin, eprinomectin, abamectin).

Example 471: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), (5) at least one COMT inhibitor (e.g., entacapone), and (6) at least one avermectin (e.g., ivermectin, selamectin, doramectin, eprinomectin, abamectin).

Example 472: In one embodiment, the pharmaceutical composition includes (1) at least one noncompetitive nicotinic antagonist (e.g., MB327, MB399), (2) at least one anticholinergic agent (e.g., atropine), (3) at least one anticonvulsive agent (e.g., diazepam, midazolam, lorazepam), (4) at least one vasodilator (e.g., phentolamine, caffeine), (5) at least one COMT inhibitor (e.g., entacapone), and (6) at least one avermectin (e.g., ivermectin, selamectin, doramectin, eprinomectin, abamectin).

Example 473: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), and (7) at least one COMT inhibitor (e.g., entacapone).

Example 474: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), and (7) at least one avermectin (e.g., ivermectin, selamectin, doramectin, eprinomectin, abamectin).

Example 475: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one COMT inhibitor (e.g., entacapone), and (7) at least one avermectin (e.g., ivermectin, selamectin, doramectin, eprinomectin, abamectin).

Example 476: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), (6) at least one COMT inhibitor (e.g., entacapone), and (7) at least one avermectin (e.g., ivermectin, selamectin, doramectin, eprinomectin, abamectin).

Example 477: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one avermectin (e.g., ivermectin, selamectin, doramectin, eprinomectin, abamectin).

Example 478: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one avermectin (e.g., ivermectin, selamectin, doramectin, eprinomectin, abamectin).

Example 479: In one embodiment, the pharmaceutical composition includes (1) at least one noncompetitive nicotinic antagonist (e.g., MB327, MB399), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one avermectin (e.g., ivermectin, selamectin, doramectin, eprinomectin, abamectin).

Example 480: In one embodiment, the pharmaceutical composition includes (1) at least one noncompetitive nicotinic antagonist (e.g., MB327, MB399), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), (7) at least one COMT inhibitor (e.g., entacapone), and (8) at least one avermectin (e.g., ivermectin, selamectin, doramectin, eprinomectin, abamectin).

Example 481: In one embodiment, the pharmaceutical composition includes at least one synthetic pregnane steroid (e.g., ganaxolone, alfadolone, alfaxolone, allopregnanolone, hydroxydione, minaxolone, pregnanolone, renanolone).

Example 482: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone) and (2) at least cholinesterase reactivator agent (e.g., 2-PAM, obidoxime, pro-2-PAM).

Example 483: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone) and (2) at least one vasoactive agent (e.g., epinephrine, vasopressin, phenylephrine, or a salt thereof).

Example 484: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone) and (2) at least one anticholinergic agent (e.g., atropine).

Example 485: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone) and (2) at least one anticonvulsive agent (e.g., diazepam, midazolam, lorazepam).

Example 486: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone) and (2) at least one vasodilator (e.g., phentolamine, caffeine).

Example 487: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone) and (2) at least one COMT inhibitor (e.g., entacapone).

Example 488: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), and (3) at least one vasoactive agent (e.g., epinephrine, vasopressin, phenylephrine, or a salt thereof).

Example 489: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), and (3) at least one anticholinergic agent (e.g., atropine).

Example 490: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), and (3) at least one anticonvulsive agent (e.g., diazepam, midazolam, lorazepam).

Example 491: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), and (3) at least one vasodilator (e.g., phentolamine, caffeine).

Example 492: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), and (3) at least one COMT inhibitor (e.g., entacapone).

Example 493: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), and (3) at least one anticholinergic agent (e.g., atropine).

Example 494: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), and (3) at least one anticonvulsive agent (e.g., diazepam, midazolam, lorazepam).

Example 495: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), and (3) at least one vasodilator (e.g., phentolamine, caffeine).

Example 496: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), and (3) at least one COMT inhibitor (e.g., entacapone).

Example 497: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one anticholinergic agent (e.g., atropine), and (3) at least one anticonvulsive agent (e.g., diazepam, midazolam, lorazepam).

Example 498: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one anticholinergic agent (e.g., atropine), and (3) at least one vasodilator (e.g., phentolamine, caffeine).

Example 499: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one anticholinergic agent (e.g., atropine), and (3) at least one COMT inhibitor (e.g., entacapone).

Example 500: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one anticonvulsive agent (e.g., diazepam, midazolam, lorazepam), and (3) at least one vasodilator (e.g., phentolamine, caffeine).

Example 501: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one anticonvulsive agent (e.g., diazepam, midazolam, lorazepam), and (3) at least one COMT inhibitor (e.g., entacapone).

Example 502: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasodilator (e.g., phentolamine, caffeine), and (3) at least one COMT inhibitor (e.g., entacapone).

Example 503: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticholinergic agent (e.g., atropine).

Example 504: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticonvulsive agent (e.g., diazepam, midazolam, lorazepam).

Example 505: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one vasodilator (e.g., phentolamine, caffeine).

Example 506: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one COMT inhibitor (e.g., entacapone).

Example 507: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one anticholinergic agent (e.g., atropine), and (4) at least one anticonvulsive agent (e.g., diazepam, midazolam, lorazepam).

Example 508: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one anticholinergic agent (e.g., atropine), and (4) at least one vasodilator (e.g., phentolamine, caffeine).

Example 509: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one anticholinergic agent (e.g., atropine), and (4) at least one COMT inhibitor (e.g., entacapone).

Example 510: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one anticonvulsive agent (e.g., diazepam, midazolam, lorazepam), and (4) at least one vasodilator (e.g., phentolamine, caffeine).

Example 511: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one anticonvulsive agent (e.g., diazepam, midazolam, lorazepam), and (4) at least one COMT inhibitor (e.g., entacapone).

Example 512: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasodilator (e.g., phentolamine, caffeine), and (4) at least one COMT inhibitor (e.g., entacapone).

Example 513: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), (3) at least one anticholinergic agent (e.g., atropine), and (4) at least one anticonvulsive agent (e.g., diazepam, midazolam, lorazepam).

Example 514: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 515: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 516: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), (3) at least one anticonvulsive agent (e.g., diazepam, midazolam, lorazepam), and (4) at least one vasodilator (e.g., phentolamine, caffeine).

Example 517: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), (3) at least one anticonvulsive agent (e.g., diazepam, midazolam, lorazepam), and (4) at least one COMT inhibitor (e.g., entacapone).

Example 518: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 519: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one anticholinergic agent (e.g., atropine), (3) at least one anticonvulsive agent (e.g., diazepam, midazolam, lorazepam), and (4) at least one vasodilator (e.g., phentolamine, caffeine).

Example 520: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one anticholinergic agent (e.g., atropine), (3) at least one anticonvulsive agent (e.g., diazepam, midazolam, lorazepam), and (4) at least one COMT inhibitor (e.g., entacapone).

Example 521: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one anticholinergic agent (e.g., atropine), (3) at least one vasodilator (e.g., phentolamine, caffeine), and (4) at least one COMT inhibitor (e.g., entacapone).

Example 522: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one anticonvulsive agent (e.g., diazepam, midazolam, lorazepam), (3) at least one vasodilator (e.g., phentolamine, caffeine), and (4) at least one COMT inhibitor (e.g., entacapone).

Example 523: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one anticonvulsive agent (e.g., diazepam, midazolam, lorazepam).

Example 524: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 525: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 526: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one vasodilator (e.g., phentolamine, caffeine).

Example 527: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one COMT inhibitor (e.g., entacapone).

Example 528: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 529: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 530: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one COMT inhibitor (e.g., entacapone).

Example 531: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one COMT inhibitor (e.g., entacapone).

Example 532: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 533: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 534: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one COMT inhibitor (e.g., entacapone).

Example 535: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 536: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 537: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one anticholinergic agent (e.g., atropine), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 538: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one vasodilator (e.g., phentolamine, caffeine).

Example 539: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one COMT inhibitor (e.g., entacapone).

Example 540: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 541: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 542: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 543: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 544: In one embodiment, the pharmaceutical composition includes (1) at least one synthetic pregnane steroid (e.g., ganaxolone, alfadolone, alfaxolone, allopregnanolone, hydroxydione, minaxolone, pregnanolone, renanolone), (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), and (7) at least one COMT inhibitor (e.g., entacapone).

Example 545: In one embodiment, the pharmaceutical composition includes amyl nitrite, sodium nitrite, and/or sodium thiosulfate.

Example 546: In one embodiment, the pharmaceutical composition includes (1) amyl nitrite, sodium nitrite, and/or sodium thiosulfate and (2) at least cholinesterase reactivator agent (e.g., 2-PAM, obidoxime, pro-2-PAM).

Example 547: In one embodiment, the pharmaceutical composition includes (1) amyl nitrite, sodium nitrite, and/or sodium thiosulfate and (2) at least one vasoactive agent (e.g., epinephrine, vasopressin, phenylephrine, or a salt thereof).

Example 548: In one embodiment, the pharmaceutical composition includes (1) amyl nitrite, sodium nitrite, and/or sodium thiosulfate and (2) at least one anticholinergic agent (e.g., atropine).

Example 549: In one embodiment, the pharmaceutical composition includes (1) amyl nitrite, sodium nitrite, and/or sodium thiosulfate and (2) at least one anticonvulsive agent (e.g., diazepam, midazolam, lorazepam).

Example 550: In one embodiment, the pharmaceutical composition includes (1) amyl nitrite, sodium nitrite, and/or sodium thiosulfate and (2) at least one vasodilator (e.g., phentolamine, caffeine).

Example 551: In one embodiment, the pharmaceutical composition includes (1) amyl nitrite, sodium nitrite, and/or sodium thiosulfate and (2) at least one COMT inhibitor (e.g., entacapone).

Example 552: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), and (3) at least one vasoactive agent (e.g., epinephrine, vasopressin, phenylephrine, or a salt thereof).

Example 553: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), and (3) at least one anticholinergic agent (e.g., atropine).

Example 554: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), and (3) at least one anticonvulsive agent (e.g., diazepam, midazolam, lorazepam).

Example 555: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), and (3) at least one vasodilator (e.g., phentolamine, caffeine).

Example 556: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), and (3) at least one COMT inhibitor (e.g., entacapone).

Example 557: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), and (3) at least one anticholinergic agent (e.g., atropine).

Example 558: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), and (3) at least one anticonvulsive agent (e.g., diazepam, midazolam, lorazepam).

Example 559: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), and (3) at least one vasodilator (e.g., phentolamine, caffeine).

Example 560: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), and (3) at least one COMT inhibitor (e.g., entacapone).

Example 561: In one embodiment, the pharmaceutical composition includes (1) amyl nitrite, sodium nitrite, and/or sodium thiosulfate, (2) at least one anticholinergic agent (e.g., atropine), and (3) at least one anticonvulsive agent (e.g., diazepam, midazolam, lorazepam).

Example 562: In one embodiment, the pharmaceutical composition includes (1) amyl nitrite, sodium nitrite, and/or sodium thiosulfate, (2) at least one anticholinergic agent (e.g., atropine), and (3) at least one vasodilator (e.g., phentolamine, caffeine).

Example 563: In one embodiment, the pharmaceutical composition includes (1) amyl nitrite, sodium nitrite, and/or sodium thiosulfate, (2) at least one anticholinergic agent (e.g., atropine), and (3) at least one COMT inhibitor (e.g., entacapone).

Example 564: In one embodiment, the pharmaceutical composition includes (1) amyl nitrite, sodium nitrite, and/or sodium thiosulfate, (2) at least one anticonvulsive agent (e.g., diazepam, midazolam, lorazepam), and (3) at least one vasodilator (e.g., phentolamine, caffeine).

Example 565: In one embodiment, the pharmaceutical composition includes (1) amyl nitrite, sodium nitrite, and/or sodium thiosulfate, (2) at least one anticonvulsive agent (e.g., diazepam, midazolam, lorazepam), and (3) at least one COMT inhibitor (e.g., entacapone).

Example 566: In one embodiment, the pharmaceutical composition includes (1) amyl nitrite, sodium nitrite, and/or sodium thiosulfate, (2) at least one vasodilator (e.g., phentolamine, caffeine), and (3) at least one COMT inhibitor (e.g., entacapone).

Example 567: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticholinergic agent (e.g., atropine).

Example 568: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticonvulsive agent (e.g., diazepam, midazolam, lorazepam).

Example 569: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one vasodilator (e.g., phentolamine, caffeine).

Example 570: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one COMT inhibitor (e.g., entacapone).

Example 571: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one anticholinergic agent (e.g., atropine), and (4) at least one anticonvulsive agent (e.g., diazepam, midazolam, lorazepam).

Example 572: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one anticholinergic agent (e.g., atropine), and (4) at least one vasodilator (e.g., phentolamine, caffeine).

Example 573: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one anticholinergic agent (e.g., atropine), and (4) at least one COMT inhibitor (e.g., entacapone).

Example 574: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one anticonvulsive agent (e.g., diazepam, midazolam, lorazepam), and (4) at least one vasodilator (e.g., phentolamine, caffeine).

Example 575: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one anticonvulsive agent (e.g., diazepam, midazolam, lorazepam), and (4) at least one COMT inhibitor (e.g., entacapone).

Example 576: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasodilator (e.g., phentolamine, caffeine), and (4) at least one COMT inhibitor (e.g., entacapone).

Example 577: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), (3) at least one anticholinergic agent (e.g., atropine), and (4) at least one anticonvulsive agent (e.g., diazepam, midazolam, lorazepam).

Example 578: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 579: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 580: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), (3) at least one anticonvulsive agent (e.g., diazepam, midazolam, lorazepam), and (4) at least one vasodilator (e.g., phentolamine, caffeine).

Example 581: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), (3) at least one anticonvulsive agent (e.g., diazepam, midazolam, lorazepam), and (4) at least one COMT inhibitor (e.g., entacapone).

Example 582: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 583: In one embodiment, the pharmaceutical composition includes (1) amyl nitrite, sodium nitrite, and/or sodium thiosulfate, (2) at least one anticholinergic agent (e.g., atropine), (3) at least one anticonvulsive agent (e.g., diazepam, midazolam, lorazepam), and (4) at least one vasodilator (e.g., phentolamine, caffeine).

Example 584: In one embodiment, the pharmaceutical composition includes (1) amyl nitrite, sodium nitrite, and/or sodium thiosulfate, (2) at least one anticholinergic agent (e.g., atropine), (3) at least one anticonvulsive agent (e.g., diazepam, midazolam, lorazepam), and (4) at least one COMT inhibitor (e.g., entacapone).

Example 585: In one embodiment, the pharmaceutical composition includes (1) amyl nitrite, sodium nitrite, and/or sodium thiosulfate, (2) at least one anticholinergic agent (e.g., atropine), (3) at least one vasodilator (e.g., phentolamine, caffeine), and (4) at least one COMT inhibitor (e.g., entacapone).

Example 586: In one embodiment, the pharmaceutical composition includes (1) amyl nitrite, sodium nitrite, and/or sodium thiosulfate, (2) at least one anticonvulsive agent (e.g., diazepam, midazolam, lorazepam), (3) at least one vasodilator (e.g., phentolamine, caffeine), and (4) at least one COMT inhibitor (e.g., entacapone).

Example 587: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one anticonvulsive agent (e.g., diazepam, midazolam, lorazepam).

Example 588: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 589: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 590: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one vasodilator (e.g., phentolamine, caffeine).

Example 591: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one COMT inhibitor (e.g., entacapone).

Example 592: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 593: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 594: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one COMT inhibitor (e.g., entacapone).

Example 595: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one COMT inhibitor (e.g., entacapone).

Example 596: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 597: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 598: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one COMT inhibitor (e.g., entacapone).

Example 599: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 600: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 601: In one embodiment, the pharmaceutical composition includes (1) amyl nitrite, sodium nitrite, and/or sodium thiosulfate, (2) at least one anticholinergic agent (e.g., atropine), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 602: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one vasodilator (e.g., phentolamine, caffeine).

Example 603: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one COMT inhibitor (e.g., entacapone).

Example 604: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 605: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 606: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 607: In one embodiment, the pharmaceutical composition includes (1) amyl nitrite, sodium nitrite, and/or sodium thiosulfate, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 608: In one embodiment, the pharmaceutical composition includes (1) amyl nitrite, sodium nitrite, and/or sodium thiosulfate, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), and (7) at least one COMT inhibitor (e.g., entacapone).

Example 609: In one embodiment, the pharmaceutical composition includes at least one 3-MP prodrug (e.g., sulfanegen or a pharmaceutically acceptable salt thereof).

Example 610: In one embodiment, the pharmaceutical composition includes (1) at least one 3-MP prodrug (e.g., sulfanegen or a pharmaceutically acceptable salt thereof) and (2) a Vitamin B12 analogue (e.g., cobinamide, hydroxocobalamin).

Example 611: In one embodiment, the pharmaceutical composition includes (1) at least one 3-MP prodrug (e.g., sulfanegen or a pharmaceutically acceptable salt thereof) and (2) at least one vasodilator (e.g., phentolamine, caffeine).

Example 612: In one embodiment, the pharmaceutical composition includes (1) at least one 3-MP prodrug (e.g., sulfanegen or a pharmaceutically acceptable salt thereof), (2) a Vitamin B12 analogue (e.g., cobinamide, hydroxoco-balamin), and (3) at least one vasodilator (e.g., phentolamine, caffeine).

Example 613: In one embodiment, the pharmaceutical composition includes galantamine.

Example 614: In one embodiment, the pharmaceutical composition includes (1) galantamine and (2) at least cho-linesterase reactivator agent (e.g., 2-PAM, obidoxime, pro-2-PAM).

Example 615: In one embodiment, the pharmaceutical composition includes (1) galantamine and (2) at least one vasoactive agent (e.g., epinephrine, vasopressin, phenyleph-rine, or a salt thereof).

Example 616: In one embodiment, the pharmaceutical composition includes (1) galantamine and (2) at least one anticholinergic agent (e.g., atropine).

Example 617: In one embodiment, the pharmaceutical composition includes (1) galantamine and (2) at least one anticonvulsive agent (e.g., diazepam, midazolam, loraze-pam).

Example 618: In one embodiment, the pharmaceutical composition includes (1) galantamine and (2) at least one vasodilator (e.g., phentolamine, caffeine).

Example 619: In one embodiment, the pharmaceutical composition includes (1) galantamine and (2) at least one COMT inhibitor (e.g., entacapone).

Example 620: In one embodiment, the pharmaceutical composition includes (1) galantamine and (2) at least one NMDA receptor antagonist (e.g., memantine).

Example 621: In one embodiment, the pharmaceutical composition includes (1) galantamine, (2) at least cholin-esterase reactivator agent (e.g., 2-PAM, obidoxime, pro-2-PAM), and (3) at least one vasoactive agent (e.g., epineph-rine, vasopressin, phenylephrine, or a salt thereof).

Example 622: In one embodiment, the pharmaceutical composition includes (1) galantamine, (2) at least cholin-esterase reactivator agent (e.g., 2-PAM, obidoxime, pro-2-PAM), and (3) at least one anticholinergic agent (e.g., atropine).

Example 623: In one embodiment, the pharmaceutical composition includes (1) galantamine, (2) at least cholin-esterase reactivator agent (e.g., 2-PAM, obidoxime, pro-2-PAM), and (3) at least one anticonvulsive agent (e.g., diazepam, midazolam, lorazepam).

Example 624: In one embodiment, the pharmaceutical composition includes (1) galantamine, (2) at least cholin-esterase reactivator agent (e.g., 2-PAM, obidoxime, pro-2-PAM), and (3) at least one vasodilator (e.g., phentolamine, caffeine).

Example 625: In one embodiment, the pharmaceutical composition includes (1) galantamine, (2) at least cholin-esterase reactivator agent (e.g., 2-PAM, obidoxime, pro-2-PAM), and (3) at least one COMT inhibitor (e.g., entaca-pone).

Example 626: In one embodiment, the pharmaceutical composition includes (1) galantamine, (2) at least cholin-esterase reactivator agent (e.g., 2-PAM, obidoxime, pro-2-PAM), and (3) at least one NMDA receptor antagonist (e.g., memantine).

Example 627: In one embodiment, the pharmaceutical composition includes (1) galantamine, (2) at least one vaso-active agent (e.g., epinephrine, vasopressin, phenylephrine, or a salt thereof), and (3) at least one anticholinergic agent (e.g., atropine).

Example 628: In one embodiment, the pharmaceutical composition includes (1) galantamine, (2) at least one vaso-active agent (e.g., epinephrine, vasopressin, phenylephrine, or a salt thereof), and (3) at least one anticonvulsive agent (e.g., diazepam, midazolam, lorazepam).

Example 629: In one embodiment, the pharmaceutical composition includes (1) galantamine, (2) at least one vaso-active agent (e.g., epinephrine, vasopressin, phenylephrine, or a salt thereof), and (3) at least one vasodilator (e.g., phentolamine, caffeine).

Example 630: In one embodiment, the pharmaceutical composition includes (1) galantamine, (2) at least one vaso-active agent (e.g., epinephrine, vasopressin, phenylephrine, or a salt thereof), and (3) at least one COMT inhibitor (e.g., entacapone).

Example 631: In one embodiment, the pharmaceutical composition includes (1) galantamine, (2) at least one vaso-active agent (e.g., epinephrine, vasopressin, phenylephrine, or a salt thereof), and (3) at least one NMDA receptor antagonist (e.g., memantine).

Example 632: In one embodiment, the pharmaceutical composition includes (1) galantamine, (2) at least one anti-cholinergic agent (e.g., atropine), and (3) at least one anti-convulsive agent (e.g., diazepam, midazolam, lorazepam).

Example 633: In one embodiment, the pharmaceutical composition includes (1) galantamine, (2) at least one anti-cholinergic agent (e.g., atropine), and (3) at least one vaso-dilator (e.g., phentolamine, caffeine).

Example 634: In one embodiment, the pharmaceutical composition includes (1) galantamine, (2) at least one anti-cholinergic agent (e.g., atropine), and (3) at least one COMT inhibitor (e.g., entacapone).

Example 635: In one embodiment, the pharmaceutical composition includes (1) galantamine, (2) at least one anti-cholinergic agent (e.g., atropine), and (3) at least one NMDA receptor antagonist (e.g., memantine).

Example 636: In one embodiment, the pharmaceutical composition includes (1) galantamine, (2) at least one anti-convulsive agent (e.g., diazepam, midazolam, lorazepam), and (3) at least one vasodilator (e.g., phentolamine, caffeine).

Example 637: In one embodiment, the pharmaceutical composition includes (1) galantamine, (2) at least one anti-convulsive agent (e.g., diazepam, midazolam, lorazepam), and (3) at least one COMT inhibitor (e.g., entacapone).

Example 638: In one embodiment, the pharmaceutical composition includes (1) galantamine, (2) at least one anti-convulsive agent (e.g., diazepam, midazolam, lorazepam), and (3) at least one NMDA receptor antagonist (e.g., memantine).

Example 639: In one embodiment, the pharmaceutical composition includes (1) galantamine, (2) at least one vaso-dilator (e.g., phentolamine, caffeine), and (3) at least one COMT inhibitor (e.g., entacapone).

Example 640: In one embodiment, the pharmaceutical composition includes (1) galantamine, (2) at least one vaso-dilator (e.g., phentolamine, caffeine), and (3) at least one NMDA receptor antagonist (e.g., memantine).

Example 641: In one embodiment, the pharmaceutical composition includes (1) galantamine, (2) at least one COMT inhibitor (e.g., entacapone), and (3) at least one NMDA receptor antagonist (e.g., memantine).

Example 642: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticholinergic agent (e.g., atropine).

Example 643: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticonvulsive agent (e.g., diazepam, midazolam, lorazepam).

Example 644: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one vasodilator (e.g., phentolamine, caffeine).

Example 645: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one COMT inhibitor (e.g., entacapone).

Example 646: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one NMDA receptor antagonist (e.g., memantine).

Example 647: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), and (4) at least one anticonvulsive agent (e.g., diazepam, midazolam, lorazepam).

Example 648: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), and (4) at least one vasodilator (e.g., phentolamine, caffeine)
.

Example 649: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), and (4) at least one COMT inhibitor (e.g., entacapone).

Example 650: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), and (4) at least one NMDA receptor antagonist (e.g., memantine).

Example 651: In one embodiment, the pharmaceutical composition includes (1) galantamine, (2) at least cholinesterase reactivator agent (e.g., 2-PAM, obidoxime, pro-2-PAM), (3) at least one anticonvulsive agent (e.g., diazepam, midazolam, lorazepam), and (4) at least one vasodilator (e.g., phentolamine, caffeine).

Example 652: In one embodiment, the pharmaceutical composition includes (1) galantamine, (2) at least cholinesterase reactivator agent (e.g., 2-PAM, obidoxime, pro-2-PAM), (3) at least one anticonvulsive agent (e.g., diazepam, midazolam, lorazepam), and (4) at least one COMT inhibitor (e.g., entacapone).

Example 653: In one embodiment, the pharmaceutical composition includes (1) galantamine, (2) at least cholinesterase reactivator agent (e.g., 2-PAM, obidoxime, pro-2-PAM), (3) at least one anticonvulsive agent (e.g., diazepam, midazolam, lorazepam), and (4) at least one NMDA receptor antagonist (e.g., memantine).

Example 654: In one embodiment, the pharmaceutical composition includes (1) galantamine, (2) at least cholinesterase reactivator agent (e.g., 2-PAM, obidoxime, pro-2-PAM), (3) at least one vasodilator (e.g., phentolamine, caffeine), and (4) at least one COMT inhibitor (e.g., entacapone).

Example 655: In one embodiment, the pharmaceutical composition includes (1) galantamine, (2) at least cholinesterase reactivator agent (e.g., 2-PAM, obidoxime, pro-2-PAM), (3) at least one vasodilator (e.g., phentolamine, caffeine), and (4) at least one NMDA receptor antagonist (e.g., memantine).

Example 656: In one embodiment, the pharmaceutical composition includes (1) galantamine, (2) at least cholinesterase reactivator agent (e.g., 2-PAM, obidoxime, pro-2-PAM), (3) at least one COMT inhibitor (e.g., entacapone), and (4) at least one NMDA receptor antagonist (e.g., memantine).

Example 657: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), and (4) at least one anticonvulsive agent (e.g., diazepam, midazolam, lorazepam).

Example 658: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 659: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 660: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), and (4) at least one NMDA receptor antagonist (e.g., memantine).

Example 661: In one embodiment, the pharmaceutical composition includes (1) galantamine, (2) at least one vasoactive agent (e.g., epinephrine, vasopressin, phenylephrine, or a salt thereof), (3) at least one anticonvulsive agent (e.g., diazepam, midazolam, lorazepam), and (4) at least one vasodilator (e.g., phentolamine, caffeine).

Example 662: In one embodiment, the pharmaceutical composition includes (1) galantamine, (2) at least one vasoactive agent (e.g., epinephrine, vasopressin, phenylephrine, or a salt thereof), (3) at least one anticonvulsive agent (e.g., diazepam, midazolam, lorazepam), and (4) at least one COMT inhibitor (e.g., entacapone).

Example 663: In one embodiment, the pharmaceutical composition includes (1) galantamine, (2) at least one vasoactive agent (e.g., epinephrine, vasopressin, phenylephrine, or a salt thereof), (3) at least one anticonvulsive agent (e.g., diazepam, midazolam, lorazepam), and (4) at least one NMDA receptor antagonist (e.g., memantine).

Example 664: In one embodiment, the pharmaceutical composition includes (1) galantamine, (2) at least one vaso-active agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 665: In one embodiment, the pharmaceutical composition includes (1) galantamine, (2) at least one vaso-active agent (e.g., epinephrine, vasopressin, phenylephrine, or a salt thereof), (3) at least one vasodilator (e.g., phentolamine, caffeine), and (4) at least one NMDA receptor antagonist (e.g., memantine).

Example 666: In one embodiment, the pharmaceutical composition includes (1) galantamine, (2) at least one vaso-active agent (e.g., epinephrine, vasopressin, phenylephrine, or a salt thereof), (3) at least one COMT inhibitor (e.g., entacapone), and (4) at least one NMDA receptor antagonist (e.g., memantine).

Example 667: In one embodiment, the pharmaceutical composition includes (1) pyridostigmine, (2) at least one anticholinergic agent (e.g., atropine), (3) at least one anti-convulsive agent (e.g., diazepam, midazolam, lorazepam), and (4) at least one vasodilator (e.g., phentolamine, caffeine).

Example 668: In one embodiment, the pharmaceutical composition includes (1) galantamine, (2) at least one anti-cholinergic agent (e.g., atropine), (3) at least one anticon-vulsive agent (e.g., diazepam, midazolam, lorazepam), and (4) at least one COMT inhibitor (e.g., entacapone).

Example 669: In one embodiment, the pharmaceutical composition includes (1) galantamine, (2) at least one anti-cholinergic agent (e.g., atropine), (3) at least one anticon-vulsive agent (e.g., diazepam, midazolam, lorazepam), and (4) at least one NMDA receptor antagonist (e.g., meman-tine).

Example 670: In one embodiment, the pharmaceutical composition includes (1) galantamine, (2) at least one anti-cholinergic agent (e.g., atropine), (3) at least one vasodilator (e.g., phentolamine, caffeine), and (4) at least one COMT inhibitor (e.g., entacapone).

Example 671: In one embodiment, the pharmaceutical composition includes (1) galantamine, (2) at least one anti-cholinergic agent (e.g., atropine), (3) at least one vasodilator (e.g., phentolamine, caffeine), and (4) at least one NMDA receptor antagonist (e.g., memantine).

Example 672: In one embodiment, the pharmaceutical composition includes (1) galantamine, (2) at least one anti-cholinergic agent (e.g., atropine), (3) at least one COMT inhibitor (e.g., entacapone), and (4) at least one NMDA receptor antagonist (e.g., memantine).

Example 673: In one embodiment, the pharmaceutical composition includes (1) galantamine, (2) at least one anti-convulsive agent (e.g., diazepam, midazolam, lorazepam), (3) at least one vasodilator (e.g., phentolamine, caffeine), and (4) at least one COMT inhibitor (e.g., entacapone).

Example 674: In one embodiment, the pharmaceutical composition includes (1) galantamine, (2) at least one anti-convulsive agent (e.g., diazepam, midazolam, lorazepam), (3) at least one vasodilator (e.g., phentolamine, caffeine), and (4) at least one NMDA receptor antagonist (e.g., memantine).

Example 675: In one embodiment, the pharmaceutical composition includes (1) galantamine, (2) at least one anti-convulsive agent (e.g., diazepam, midazolam, lorazepam), (3) at least one COMT inhibitor (e.g., entacapone), and (4) at least one NMDA receptor antagonist (e.g., memantine).

Example 676: In one embodiment, the pharmaceutical composition includes (1) galantamine, (2) at least one vaso-dilator (e.g., phentolamine, caffeine), (3) at least one COMT inhibitor (e.g., entacapone), and (4) at least one NMDA receptor antagonist (e.g., memantine).

Example 677: In one embodiment, the pharmaceutical composition includes (1) galantamine, (2) at least cholin-esterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one anticonvulsive agent (e.g., diazepam, midazolam, loraze-pam).

Example 678: In one embodiment, the pharmaceutical composition includes (1) galantamine, (2) at least cholin-esterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 679: In one embodiment, the pharmaceutical composition includes (1) galantamine, (2) at least cholin-esterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 680: In one embodiment, the pharmaceutical composition includes (1) galantamine, (2) at least cholin-esterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one NMDA receptor antagonist (e.g., memantine).

Example 681: In one embodiment, the pharmaceutical composition includes (1) galantamine, (2) at least cholin-esterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, loraze-pam), and (5) at least one vasodilator (e.g., phentolamine, caffeine).

Example 682: In one embodiment, the pharmaceutical composition includes (1) galantamine, (2) at least cholin-esterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, loraze-pam), and (5) at least one COMT inhibitor (e.g., entaca-pone).

Example 683: In one embodiment, the pharmaceutical composition includes (1) galantamine, (2) at least cholin-esterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, loraze-pam), and (5) at least one NMDA receptor antagonist (e.g., memantine).

Example 684: In one embodiment, the pharmaceutical composition includes (1) galantamine, (2) at least cholin-esterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 685: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one NMDA receptor antagonist (e.g., memantine).

Example 686: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one COMT inhibitor (e.g., entacapone), and (5) at least one NMDA receptor antagonist (e.g., memantine).

Example 687: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 688: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one COMT inhibitor (e.g., entacapone).

Example 689: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one NMDA receptor antagonist (e.g., memantine).

Example 690: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one COMT inhibitor (e.g., entacapone).

Example 691: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one NMDA receptor antagonist (e.g., memantine).

Example 692: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), (4) at least one COMT inhibitor (e.g., entacapone), and (5) at least one NMDA receptor antagonist (e.g., memantine).

Example 693: In one embodiment, the pharmaceutical composition includes (1) galantamine, (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 694: In one embodiment, the pharmaceutical composition includes (1) galantamine, (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), and (5) at least one NMDA receptor antagonist (e.g., memantine).

Example 695: In one embodiment, the pharmaceutical composition includes (1) galantamine, (2) at least cholinesterase reactivator agent (e.g., 2-PAM, obidoxime, pro-2-PAM), (3) at least one anticonvulsive agent (e.g., diazepam, midazolam, lorazepam), (4) at least one COMT inhibitor (e.g., entacapone), and (5) at least one NMDA receptor antagonist (e.g., memantine).

Example 696: In one embodiment, the pharmaceutical composition includes (1) galantamine, (2) at least cholinesterase reactivator agent (e.g., 2-PAM, obidoxime, pro-2-PAM), (3) at least one vasodilator (e.g., phentolamine, caffeine), (4) at least one COMT inhibitor (e.g., entacapone), and (5) at least one NMDA receptor antagonist (e.g., memantine).

Example 697: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 698: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one COMT inhibitor (e.g., entacapone).

Example 699: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one NMDA receptor antagonist (e.g., memantine).

Example 700: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 701: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one NMDA receptor antagonist (e.g., memantine).

Example 702: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), (4) at least one COMT inhibitor (e.g., entacapone), and (5) at least one NMDA receptor antagonist (e.g., memantine).

Example 703: In one embodiment, the pharmaceutical composition includes (1) galantamine, (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 704: In one embodiment, the pharmaceutical composition includes (1) galantamine, (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), and (5) at least one NMDA receptor antagonist (e.g., memantine).

Example 705: In one embodiment, the pharmaceutical composition includes (1) galantamine, (2) at least one vasoactive agent (e.g., epinephrine, vasopressin, phenylephrine, or a salt thereof), (3) at least one anticonvulsive agent (e.g., diazepam, midazolam, lorazepam), (4) at least one COMT inhibitor (e.g., entacapone), and (5) at least one NMDA receptor antagonist (e.g., memantine).

Example 706: In one embodiment, the pharmaceutical composition includes (1) galantamine, (2) at least one vasoactive agent (e.g., epinephrine, vasopressin, phenylephrine, or a salt thereof), (3) at least one vasodilator (e.g., phentolamine, caffeine), (4) at least one COMT inhibitor (e.g., entacapone), and (5) at least one NMDA receptor antagonist (e.g., memantine).

Example 707: In one embodiment, the pharmaceutical composition includes (1) galantamine, (2) at least one anticholinergic agent (e.g., atropine), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 708: In one embodiment, the pharmaceutical composition includes (1) galantamine, (2) at least one anticholinergic agent (e.g., atropine), (3) at least one anticonvulsive agent (e.g., diazepam, midazolam, lorazepam), (4) at least one vasodilator (e.g., phentolamine, caffeine), and (5) at least one NMDA receptor antagonist (e.g., memantine).

Example 709: In one embodiment, the pharmaceutical composition includes (1) galantamine, (2) at least one anticholinergic agent (e.g., atropine), (3) at least one anticonvulsive agent (e.g., diazepam, midazolam, lorazepam), (4) at least one COMT inhibitor (e.g., entacapone), and (5) at least one NMDA receptor antagonist (e.g., memantine).

Example 710: In one embodiment, the pharmaceutical composition includes (1) galantamine, (2) at least one anticholinergic agent (e.g., atropine), (3) at least one vasodilator (e.g., phentolamine, caffeine), (4) at least one COMT inhibitor (e.g., entacapone), and (5) at least one NMDA receptor antagonist (e.g., memantine).

Example 711: In one embodiment, the pharmaceutical composition includes (1) galantamine, (2) at least one anticonvulsive agent (e.g., diazepam, midazolam, lorazepam), (3) at least one vasodilator (e.g., phentolamine, caffeine), (4) at least one COMT inhibitor (e.g., entacapone), and (5) at least one NMDA receptor antagonist (e.g., memantine).

Example 712: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one vasodilator (e.g., phentolamine, caffeine).

Example 713: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one COMT inhibitor (e.g., entacapone).

Example 714: In one embodiment, the pharmaceutical composition includes (1) galantamine, (2) at least cholinesterase reactivator agent (e.g., 2-PAM, obidoxime, pro-2-

PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one NMDA receptor antagonist (e.g., memantine).

Example 715: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 716: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one NMDA receptor antagonist (e.g., memantine).

Example 717: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one COMT inhibitor (e.g., entacapone), and (6) at least one NMDA receptor antagonist (e.g., memantine).

Example 718: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 719: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), and (6) at least one NMDA receptor antagonist (e.g., memantine).

Example 720: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one COMT inhibitor (e.g., entacapone), and (6) at least one NMDA receptor antagonist (e.g., memantine).

Example 721: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), (5) at least one COMT inhibitor (e.g., entacapone), and (6) at least one NMDA receptor antagonist (e.g., memantine).

Example 722: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 723: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one NMDA receptor antagonist (e.g., memantine).

Example 724: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one COMT inhibitor (e.g., entacapone), and (6) at least one NMDA receptor antagonist (e.g., memantine).

Example 725: In one embodiment, the pharmaceutical composition includes (1) galantamine, (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), (5) at least one COMT inhibitor (e.g., entacapone), and (6) at least one NMDA receptor antagonist (e.g., memantine).

Example 726: In one embodiment, the pharmaceutical composition includes (1) galantamine, (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), (5) at least one COMT inhibitor (e.g., entacapone), and (6) at least one NMDA receptor antagonist (e.g., memantine).

Example 727: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 728: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one NMDA receptor antagonist (e.g., memantine).

Example 729: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one COMT inhibitor (e.g., entacapone), and (6) at least one NMDA receptor antagonist (e.g., memantine).

Example 730: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), (5) at least one COMT inhibitor (e.g., entacapone), and (6) at least one NMDA receptor antagonist (e.g., memantine).

Example 731: In one embodiment, the pharmaceutical composition includes (1) galantamine, (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), (5) at least one COMT inhibitor (e.g., entacapone), and (6) at least one NMDA receptor antagonist (e.g., memantine).

Example 732: In one embodiment, the pharmaceutical composition includes (1) agent (e.g., diazepam, midazolam, lorazepam), (4) at least one vasodilator (e.g., phentolamine, caffeine), (5) at least one COMT inhibitor (e.g., entacapone), and (6) at least one NMDA receptor antagonist (e.g., memantine).

Example 733: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), and (7) at least one COMT inhibitor (e.g., entacapone).

Example 734: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), and (7) at least one NMDA receptor antagonist (e.g., memantine).

Example 735: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one COMT inhibitor (e.g., entacapone), and (7) at least one NMDA receptor antagonist (e.g., memantine).

Example 736: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), (6) at least one COMT inhibitor (e.g., entacapone), and (7) at least one NMDA receptor antagonist (e.g., memantine).

Example 737: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one NMDA receptor antagonist (e.g., memantine).

Example 738: In one embodiment, the pharmaceutical composition includes (1) galantamine, (2) at least cholinesterase reactivator agent (e.g., 2-PAM, obidoxime, pro-2-

PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one NMDA receptor antagonist (e.g., memantine).

Example 739: In one embodiment, the pharmaceutical composition includes (1) galantamine, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one NMDA receptor antagonist (e.g., memantine).

Example 740: In one embodiment, the pharmaceutical composition includes (1) galantamine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), (7) at least one COMT inhibitor (e.g., entacapone), and (8) at least one NMDA receptor antagonist (e.g., memantine).

Example 741: In one embodiment, the pharmaceutical composition includes pyridostigmine.

Example 742: In one embodiment, the pharmaceutical composition includes (1) pyridostigmine and (2) at least cholinesterase reactivator agent (e.g., 2-PAM, obidoxime, pro-2-PAM).

Example 743: In one embodiment, the pharmaceutical composition includes (1) pyridostigmine and (2) at least one vasoactive agent (e.g., epinephrine, vasopressin, phenylephrine, or a salt thereof).

Example 744: In one embodiment, the pharmaceutical composition includes (1) pyridostigmine and (2) at least one anticholinergic agent (e.g., atropine).

Example 745: In one embodiment, the pharmaceutical composition includes (1) pyridostigmine and (2) at least one anticonvulsive agent (e.g., diazepam, midazolam, lorazepam).

Example 746: In one embodiment, the pharmaceutical composition includes (1) pyridostigmine and (2) at least one vasodilator (e.g., phentolamine, caffeine).

Example 747: In one embodiment, the pharmaceutical composition includes (1) pyridostigmine and (2) at least one COMT inhibitor (e.g., entacapone).

Example 748: In one embodiment, the pharmaceutical composition includes (1) pyridostigmine and (2) at least one alpha-adrenergic agonist (e.g., midodrine).

Example 749: In one embodiment, the pharmaceutical composition includes (1) pyridostigmine, (2) at least cholinesterase reactivator agent (e.g., 2-PAM, obidoxime, pro-2-PAM), and (3) at least one vasoactive agent (e.g., epinephrine, vasopressin, phenylephrine, or a salt thereof).

Example 750: In one embodiment, the pharmaceutical composition includes (1) pyridostigmine, (2) at least cholinesterase reactivator agent (e.g., 2-PAM, obidoxime, pro-2-PAM), and (3) at least one anticholinergic agent (e.g., atropine).

Example 751: In one embodiment, the pharmaceutical composition includes (1) pyridostigmine, (2) at least cholinesterase reactivator agent (e.g., 2-PAM, obidoxime, pro-2-PAM), and (3) at least one anticonvulsive agent (e.g., diazepam, midazolam, lorazepam).

Example 752: In one embodiment, the pharmaceutical composition includes (1) pyridostigmine, (2) at least cholinesterase reactivator agent (e.g., 2-PAM, obidoxime, pro-2-PAM), and (3) at least one vasodilator (e.g., phentolamine, caffeine).

Example 753: In one embodiment, the pharmaceutical composition includes (1) pyridostigmine, (2) at least cholinesterase reactivator agent (e.g., 2-PAM, obidoxime, pro-2-PAM), and (3) at least one COMT inhibitor (e.g., entacapone).

Example 754: In one embodiment, the pharmaceutical composition includes (1) pyridostigmine, (2) at least cholinesterase reactivator agent (e.g., 2-PAM, obidoxime, pro-2-PAM), and (3) at least one alpha-adrenergic agonist (e.g., midodrine).

Example 755: In one embodiment, the pharmaceutical composition includes (1) pyridostigmine, (2) at least one vasoactive agent (e.g., epinephrine, vasopressin, phenylephrine, or a salt thereof), and (3) at least one anticholinergic agent (e.g., atropine).

Example 756: In one embodiment, the pharmaceutical composition includes (1) pyridostigmine, (2) at least one vasoactive agent (e.g., epinephrine, vasopressin, phenylephrine, or a salt thereof), and (3) at least one anticonvulsive agent (e.g., diazepam, midazolam, lorazepam).

Example 757: In one embodiment, the pharmaceutical composition includes (1) pyridostigmine, (2) at least one vasoactive agent (e.g., epinephrine, vasopressin, phenylephrine, or a salt thereof), and (3) at least one vasodilator (e.g., phentolamine, caffeine).

Example 758: In one embodiment, the pharmaceutical composition includes (1) pyridostigmine, (2) at least one vasoactive agent (e.g., epinephrine, vasopressin, phenylephrine, or a salt thereof), and (3) at least one COMT inhibitor (e.g., entacapone).

Example 759: In one embodiment, the pharmaceutical composition includes (1) pyridostigmine, (2) at least one vasoactive agent (e.g., epinephrine, vasopressin, phenylephrine, or a salt thereof), and (3) at least one alpha-adrenergic agonist (e.g., midodrine).

Example 760: In one embodiment, the pharmaceutical composition includes (1) pyridostigmine, (2) at least one anticholinergic agent (e.g., atropine), and (3) at least one anticonvulsive agent (e.g., diazepam, midazolam, lorazepam).

Example 761: In one embodiment, the pharmaceutical composition includes (1) pyridostigmine, (2) at least one anticholinergic agent (e.g., atropine), and (3) at least one vasodilator (e.g., phentolamine, caffeine).

Example 762: In one embodiment, the pharmaceutical composition includes (1) pyridostigmine, (2) at least one anticholinergic agent (e.g., atropine), and (3) at least one COMT inhibitor (e.g., entacapone).

Example 763: In one embodiment, the pharmaceutical composition includes (1) pyridostigmine, (2) at least one anticholinergic agent (e.g., atropine), and (3) at least one alpha-adrenergic agonist (e.g., midodrine).

Example 764: In one embodiment, the pharmaceutical composition includes (1) pyridostigmine, (2) at least one anticonvulsive agent (e.g., diazepam, midazolam, lorazepam), and (3) at least one vasodilator (e.g., phentolamine, caffeine).

Example 765: In one embodiment, the pharmaceutical composition includes (1) pyridostigmine, (2) at least one anticonvulsive agent (e.g., diazepam, midazolam, lorazepam), and (3) at least one COMT inhibitor (e.g., entacapone).

Example 766: In one embodiment, the pharmaceutical composition includes (1) pyridostigmine, (2) at least one anticonvulsive agent (e.g., diazepam, midazolam, lorazepam), and (3) at least one alpha-adrenergic agonist (e.g., midodrine).

Example 767: In one embodiment, the pharmaceutical composition includes (1) pyridostigmine, (2) at least one vasodilator (e.g., phentolamine, caffeine), and (3) at least one COMT inhibitor (e.g., entacapone).

Example 768: In one embodiment, the pharmaceutical composition includes (1) pyridostigmine, (2) at least one vasodilator (e.g., phentolamine, caffeine), and (3) at least one alpha-adrenergic agonist (e.g., midodrine).

Example 769: In one embodiment, the pharmaceutical composition includes (1) pyridostigmine, (2) at least one COMT inhibitor (e.g., entacapone), and (3) at least one alpha-adrenergic agonist (e.g., midodrine).

Example 770: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticholinergic agent (e.g., atropine).

Example 771: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticonvulsive agent (e.g., diazepam, midazolam, lorazepam).

Example 772: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one vasodilator (e.g., phentolamine, caffeine).

Example 773: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one COMT inhibitor (e.g., entacapone).

Example 774: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one alpha-adrenergic agonist (e.g., midodrine).

Example 775: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), and (4) at least one anticonvulsive agent (e.g., diazepam, midazolam, lorazepam).

Example 776: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), and (4) at least one vasodilator (e.g., phentolamine, caffeine).

Example 777: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), and (4) at least one COMT inhibitor (e.g., entacapone).

Example 778: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), and (4) at least one alpha-adrenergic agonist (e.g., midodrine).

Example 779: In one embodiment, the pharmaceutical composition includes (1) pyridostigmine, (2) at least cholinesterase reactivator agent (e.g., 2-PAM, obidoxime, pro-2-PAM), (3) at least one anticonvulsive agent (e.g., diazepam, midazolam, lorazepam), and (4) at least one vasodilator (e.g., phentolamine, caffeine).

Example 780: In one embodiment, the pharmaceutical composition includes (1) pyridostigmine, (2) at least cholinesterase reactivator agent (e.g., 2-PAM, obidoxime, pro-2-PAM), (3) at least one anticonvulsive agent (e.g., diazepam, midazolam, lorazepam), and (4) at least one COMT inhibitor (e.g., entacapone).

Example 781: In one embodiment, the pharmaceutical composition includes (1) pyridostigmine, (2) at least cholinesterase reactivator agent (e.g., 2-PAM, obidoxime, pro-2-PAM), (3) at least one anticonvulsive agent (e.g., diazepam, midazolam, lorazepam), and (4) at least one alpha-adrenergic agonist (e.g., midodrine).

Example 782: In one embodiment, the pharmaceutical composition includes (1) pyridostigmine, (2) at least cholinesterase reactivator agent (e.g., 2-PAM, obidoxime, pro-2-PAM), (3) at least one vasodilator (e.g., phentolamine, caffeine), and (4) at least one COMT inhibitor (e.g., entacapone).

Example 783: In one embodiment, the pharmaceutical composition includes (1) pyridostigmine, (2) at least cholinesterase reactivator agent (e.g., 2-PAM, obidoxime, pro-2-PAM), (3) at least one vasodilator (e.g., phentolamine, caffeine), and (4) at least one alpha-adrenergic agonist (e.g., midodrine).

Example 784: In one embodiment, the pharmaceutical composition includes (1) pyridostigmine, (2) at least cholinesterase reactivator agent (e.g., 2-PAM, obidoxime, pro-2-PAM), (3) at least one COMT inhibitor (e.g., entacapone), and (4) at least one alpha-adrenergic agonist (e.g., midodrine).

Example 785: In one embodiment, the pharmaceutical composition includes (1) pyridostigmine, (2) at least one vasoactive agent (e.g., epinephrine, vasopressin, phenylephrine, or a salt thereof), (3) at least one anticholinergic agent (e.g., atropine), and (4) at least one anticonvulsive agent (e.g., diazepam, midazolam, lorazepam).

Example 786: In one embodiment, the pharmaceutical composition includes (1) pyridostigmine, (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 787: In one embodiment, the pharmaceutical composition includes (1) pyridostigmine, (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 788: In one embodiment, the pharmaceutical composition includes (1) pyridostigmine, (2) at least one vasoactive agent (e.g., epinephrine, vasopressin, phenylephrine, or a salt thereof), (3) at least one anticholinergic agent (e.g., atropine), and (4) at least one alpha-adrenergic agonist (e.g., midodrine).

Example 789: In one embodiment, the pharmaceutical composition includes (1) pyridostigmine, (2) at least one vasoactive agent (e.g., epinephrine, vasopressin, phenylephrine, or a salt thereof), (3) at least one anticonvulsive agent (e.g., diazepam, midazolam, lorazepam), and (4) at least one vasodilator (e.g., phentolamine, caffeine).

Example 790: In one embodiment, the pharmaceutical composition includes (1) pyridostigmine, (2) at least one vasoactive agent (e.g., epinephrine, vasopressin, phenylephrine, or a salt thereof), (3) at least one anticonvulsive agent (e.g., diazepam, midazolam, lorazepam), and (4) at least one COMT inhibitor (e.g., entacapone).

Example 791: In one embodiment, the pharmaceutical composition includes (1) pyridostigmine, (2) at least one vasoactive agent (e.g., epinephrine, vasopressin, phenylephrine, or a salt thereof), (3) at least one anticonvulsive agent (e.g., diazepam, midazolam, lorazepam), and (4) at least one alpha-adrenergic agonist (e.g., midodrine).

Example 792: In one embodiment, the pharmaceutical composition includes (1) pyridostigmine, (2) at least one vasoactive agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 793: In one embodiment, the pharmaceutical composition includes (1) pyridostigmine, (2) at least one vasoactive agent (e.g., epinephrine, vasopressin, phenylephrine, or a salt thereof), (3) at least one vasodilator (e.g., phentolamine, caffeine), and (4) at least one alpha-adrenergic agonist (e.g., midodrine).

Example 794: In one embodiment, the pharmaceutical composition includes (1) pyridostigmine, (2) at least one vasoactive agent (e.g., epinephrine, vasopressin, phenylephrine, or a salt thereof), (3) at least one COMT inhibitor (e.g., entacapone), and (4) at least one alpha-adrenergic agonist (e.g., midodrine).

Example 795: In one embodiment, the pharmaceutical composition includes (1) pyridostigmine, (2) at least one anticholinergic agent (e.g., atropine), (3) at least one anticonvulsive agent (e.g., diazepam, midazolam, lorazepam), and (4) at least one vasodilator (e.g., phentolamine, caffeine).

Example 796: In one embodiment, the pharmaceutical composition includes (1) pyridostigmine, (2) at least one anticholinergic agent (e.g., atropine), (3) at least one anticonvulsive agent (e.g., diazepam, midazolam, lorazepam), and (4) at least one COMT inhibitor (e.g., entacapone).

Example 797: In one embodiment, the pharmaceutical composition includes (1) pyridostigmine, (2) at least one anticholinergic agent (e.g., atropine), (3) at least one anticonvulsive agent (e.g., diazepam, midazolam, lorazepam), and (4) at least one alpha-adrenergic agonist (e.g., midodrine).

Example 798: In one embodiment, the pharmaceutical composition includes (1) pyridostigmine, (2) at least one anticholinergic agent (e.g., atropine), (3) at least one vasodilator (e.g., phentolamine, caffeine), and (4) at least one COMT inhibitor (e.g., entacapone).

Example 799: In one embodiment, the pharmaceutical composition includes (1) pyridostigmine, (2) at least one anticholinergic agent (e.g., atropine), (3) at least one vasodilator (e.g., phentolamine, caffeine), and (4) at least one alpha-adrenergic agonist (e.g., midodrine).

Example 800: In one embodiment, the pharmaceutical composition includes (1) pyridostigmine, (2) at least one anticholinergic agent (e.g., atropine), (3) at least one COMT inhibitor (e.g., entacapone), and (4) at least one alpha-adrenergic agonist (e.g., midodrine).

Example 801: In one embodiment, the pharmaceutical composition includes (1) pyridostigmine, (2) at least one anticonvulsive agent (e.g., diazepam, midazolam, lorazepam), (3) at least one vasodilator (e.g., phentolamine, caffeine), and (4) at least one COMT inhibitor (e.g., entacapone).

Example 802: In one embodiment, the pharmaceutical composition includes (1) pyridostigmine, (2) at least one anticonvulsive agent (e.g., diazepam, midazolam, lorazepam), (3) at least one vasodilator (e.g., phentolamine, caffeine), and (4) at least one alpha-adrenergic agonist (e.g., midodrine).

Example 803: In one embodiment, the pharmaceutical composition includes (1) pyridostigmine, (2) at least one anticonvulsive agent (e.g., diazepam, midazolam, lorazepam), (3) at least one COMT inhibitor (e.g., entacapone), and (4) at least one alpha-adrenergic agonist (e.g., midodrine).

Example 804: In one embodiment, the pharmaceutical composition includes (1) pyridostigmine, (2) at least one vasodilator (e.g., phentolamine, caffeine), (3) at least one COMT inhibitor (e.g., entacapone), and (4) at least one alpha-adrenergic agonist (e.g., midodrine).

Example 805: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one anticonvulsive agent (e.g., diazepam, midazolam, lorazepam).

Example 806: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 807: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 808: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one alpha-adrenergic agonist (e.g., midodrine).

Example 809: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one vasodilator (e.g., phentolamine, caffeine).

Example 810: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one COMT inhibitor (e.g., entacapone).

Example 811: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), and (5) at least one alpha-adrenergic agonist (e.g., midodrine).

Example 812: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 813: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one alpha-adrenergic agonist (e.g., midodrine).

Example 814: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one COMT inhibitor (e.g., entacapone), and (5) at least one alpha-adrenergic agonist (e.g., midodrine).

Example 815: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 816: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one COMT inhibitor (e.g., entacapone).

Example 817: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), and (5) at least one alpha-adrenergic agonist (e.g., midodrine).

Example 818: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one COMT inhibitor (e.g., entacapone).

Example 819: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one alpha-adrenergic agonist (e.g., midodrine).

Example 820: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), (4) at least one COMT inhibitor (e.g., entacapone), and (5) at least one alpha-adrenergic agonist (e.g., midodrine).

Example 821: In one embodiment, the pharmaceutical composition includes (1) pyridostigmine, (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 822: In one embodiment, the pharmaceutical composition includes (1) pyridostigmine, (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), and (5) at least one alpha-adrenergic agonist (e.g., midodrine).

Example 823: In one embodiment, the pharmaceutical composition includes (1) pyridostigmine, (2) at least cholinesterase reactivator agent (e.g., 2-PAM, obidoxime, pro-2-PAM), (3) at least one anticonvulsive agent (e.g., diazepam, midazolam, lorazepam), (4) at least one COMT inhibitor (e.g., entacapone), and (5) at least one alpha-adrenergic agonist (e.g., midodrine).

Example 824: In one embodiment, the pharmaceutical composition includes (1) pyridostigmine, (2) at least cholinesterase reactivator agent (e.g., 2-PAM, obidoxime, pro-2-PAM), (3) at least one vasodilator (e.g., phentolamine, caffeine), (4) at least one COMT inhibitor (e.g., entacapone), and (5) at least one alpha-adrenergic agonist (e.g., midodrine).

Example 825: In one embodiment, the pharmaceutical composition includes (1) pyridostigmine, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one vasodilator (e.g., phentolamine, caffeine).

Example 826: In one embodiment, the pharmaceutical composition includes (1) pyridostigmine, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one COMT inhibitor (e.g., entacapone).

Example 827: In one embodiment, the pharmaceutical composition includes (1) pyridostigmine, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), and (5) at least one alpha-adrenergic agonist (e.g., midodrine).

Example 828: In one embodiment, the pharmaceutical composition includes (1) pyridostigmine, (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 829: In one embodiment, the pharmaceutical composition includes (1) pyridostigmine, (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one alpha-adrenergic agonist (e.g., midodrine).

Example 830: In one embodiment, the pharmaceutical composition includes (1) pyridostigmine, (2) at least one vasoactive agent (e.g., epinephrine, vasopressin, phenylephrine, or a salt thereof), (3) at least one anticholinergic agent (e.g., atropine), (4) at least one COMT inhibitor (e.g., entacapone), and (5) at least one alpha-adrenergic agonist (e.g., midodrine).

Example 831: In one embodiment, the pharmaceutical composition includes (1) pyridostigmine, (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 832: In one embodiment, the pharmaceutical composition includes (1) pyridostigmine, (2) at least one vasoactive agent (e.g., epinephrine, vasopressin, phenylephrine, or a salt thereof), (3) at least one anticonvulsive agent (e.g., diazepam, midazolam, lorazepam), (4) at least one vasodilator (e.g., phentolamine, caffeine), and (5) at least one alpha-adrenergic agonist (e.g., midodrine).

Example 833: In one embodiment, the pharmaceutical composition includes (1) pyridostigmine, (2) at least one vasoactive agent (e.g., epinephrine, vasopressin, phenylephrine, or a salt thereof), (3) at least one anticonvulsive agent (e.g., diazepam, midazolam, lorazepam), (4) at least one COMT inhibitor (e.g., entacapone), and (5) at least one alpha-adrenergic agonist (e.g., midodrine).

Example 834: In one embodiment, the pharmaceutical composition includes (1) pyridostigmine, (2) at least one vasoactive agent (e.g., epinephrine, vasopressin, phenylephrine, or a salt thereof), (3) at least one vasodilator (e.g., phentolamine, caffeine), (4) at least one COMT inhibitor (e.g., entacapone), and (5) at least one alpha-adrenergic agonist (e.g., midodrine).

Example 835: In one embodiment, the pharmaceutical composition includes (1) pyridostigmine, (2) at least one anticholinergic agent (e.g., atropine), (3) at least one anticonvulsive agent (e.g., diazepam, midazolam, lorazepam), (4) at least one vasodilator (e.g., phentolamine, caffeine), and (5) at least one COMT inhibitor (e.g., entacapone).

Example 836: In one embodiment, the pharmaceutical composition includes (1) pyridostigmine, (2) at least one anticholinergic agent (e.g., atropine), (3) at least one anticonvulsive agent (e.g., diazepam, midazolam, lorazepam), (4) at least one vasodilator (e.g., phentolamine, caffeine), and (5) at least one alpha-adrenergic agonist (e.g., midodrine).

Example 837: In one embodiment, the pharmaceutical composition includes (1) pyridostigmine, (2) at least one anticholinergic agent (e.g., atropine), (3) at least one anticonvulsive agent (e.g., diazepam, midazolam, lorazepam), (4) at least one COMT inhibitor (e.g., entacapone), and (5) at least one alpha-adrenergic agonist (e.g., midodrine).

Example 838: In one embodiment, the pharmaceutical composition includes (1) pyridostigmine, (2) at least one anticholinergic agent (e.g., atropine), (3) at least one vasodilator (e.g., phentolamine, caffeine), (4) at least one COMT inhibitor (e.g., entacapone), and (5) at least one alpha-adrenergic agonist (e.g., midodrine).

Example 839: In one embodiment, the pharmaceutical composition includes (1) pyridostigmine, (2) at least one anticonvulsive agent (e.g., diazepam, midazolam, lorazepam), (3) at least one vasodilator (e.g., phentolamine, caffeine), (4) at least one COMT inhibitor (e.g., entacapone), and (5) at least one alpha-adrenergic agonist (e.g., midodrine).

Example 840: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one vasodilator (e.g., phentolamine, caffeine)
.

Example 841: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one COMT inhibitor (e.g., entacapone).

Example 842: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), and (6) at least one alpha-adrenergic agonist (e.g., midodrine).

Example 843: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 844: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one alpha-adrenergic agonist (e.g., midodrine).

Example 845: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one COMT inhibitor (e.g., entacapone), and (6) at least one alpha-adrenergic agonist (e.g., midodrine).

Example 846: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 847: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, loraze-pam), (5) at least one vasodilator (e.g., phentolamine, caffeine), and (6) at least one alpha-adrenergic agonist (e.g., midodrine).

Example 848: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, loraze-pam), (5) at least one COMT inhibitor (e.g., entacapone), and (6) at least one alpha-adrenergic agonist (e.g., midodrine).

Example 849: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), (5) at least one COMT inhibitor (e.g., entacapone), and (6) at least one alpha-adrenergic agonist (e.g., midodrine).

Example 850: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 851: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one alpha-adrenergic agonist (e.g., midodrine).

Example 852: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one COMT inhibitor (e.g., entacapone), and (6) at least one alpha-adrenergic agonist (e.g., midodrine).

Example 853: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), (4) at least one vasodilator (e.g., phentolamine, caffeine), (5) at least one COMT inhibitor (e.g., entacapone), and (6) at least one alpha-adrenergic agonist (e.g., midodrine).

Example 854: In one embodiment, the pharmaceutical composition includes (1) pyridostigmine, (2) at least cholinesterase reactivator agent (e.g., 2-PAM, obidoxime, pro-2-PAM), (3) at least one anticonvulsive agent (e.g., diazepam, midazolam, lorazepam), (4) at least one vasodilator (e.g., phentolamine, caffeine), (5) at least one COMT inhibitor (e.g., entacapone), and (6) at least one alpha-adrenergic agonist (e.g., midodrine).

Example 855: In one embodiment, the pharmaceutical composition includes (1) pyridostigmine, (2) at least one vasoactive agent (e.g., epinephrine, vasopressin, phenyleph-rine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one COMT inhibitor (e.g., entacapone).

Example 856: In one embodiment, the pharmaceutical composition includes (1) pyridostigmine, (2) at least one vasoactive agent (e.g., epinephrine, vasopressin, phenyleph-rine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), and (6) at least one alpha-adrenergic agonist (e.g., midodrine).

Example 857: In one embodiment, the pharmaceutical composition includes (1) pyridostigmine, (2) at least one vasoactive agent (e.g., epinephrine, vasopressin, phenyleph-rine, or a salt thereof), (3) at least one anticholinergic agent (e.g., atropine), (4) at least one anticonvulsive agent (e.g., diazepam, midazolam, lorazepam), (5) at least one COMT inhibitor (e.g., entacapone), and (6) at least one alpha-adrenergic agonist (e.g., midodrine).

Example 858: In one embodiment, the pharmaceutical composition includes (1) pyridostigmine, (2) at least one vasoactive agent (e.g., epinephrine, vasopressin, phenyleph-rine, or a salt thereof), (3) at least one anticholinergic agent (e.g., atropine), (4) at least one vasodilator (e.g., phen-tolamine, caffeine), (5) at least one COMT inhibitor (e.g., entacapone), and (6) at least one alpha-adrenergic agonist (e.g., midodrine).

Example 859: In one embodiment, the pharmaceutical composition includes (1) pyridostigmine, (2) at least one vasoactive agent (e.g., epinephrine, vasopressin, phenyleph-rine, or a salt thereof), (3) at least one anticonvulsive agent (e.g., diazepam, midazolam, lorazepam), (4) at least one vasodilator (e.g., phentolamine, caffeine), (5) at least one COMT inhibitor (e.g., entacapone), and (6) at least one alpha-adrenergic agonist (e.g., midodrine).

Example 860: In one embodiment, the pharmaceutical composition includes (1) pyridostigmine, (2) at least one anticholinergic agent (e.g., atropine), (3) at least one anti-convulsive agent (e.g., diazepam, midazolam, lorazepam), (4) at least one vasodilator (e.g., phentolamine, caffeine), (5) at least one COMT inhibitor (e.g., entacapone), and (6) at least one alpha-adrenergic agonist (e.g., midodrine).

Example 861: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anti-convulsive agent (e.g., diazepam, midazolam, lorazepam), (6) at least one vasodilator (e.g., phentolamine, caffeine), and (7) at least one COMT inhibitor (e.g., entacapone).

Example 862: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anti-convulsive agent (e.g., diazepam, midazolam, lorazepam), (6) at least one vasodilator (e.g., phentolamine, caffeine), and (7) at least one alpha-adrenergic agonist (e.g., mido-drine).

Example 863: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anti-convulsive agent (e.g., diazepam, midazolam, lorazepam),

US 12,616,807 B2

185

(6) at least one COMT inhibitor (e.g., entacapone), and (7) at least one alpha-adrenergic agonist (e.g., midodrine).

Example 864: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), (6) at least one COMT inhibitor (e.g., entacapone), and (7) at least one alpha-adrenergic agonist (e.g., midodrine).

Example 865: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one alpha-adrenergic agonist (e.g., midodrine).

Example 866: In one embodiment, the pharmaceutical composition includes (1) pyridostigmine, (2) at least cholinesterase reactivator agent (e.g., 2-PAM, obidoxime, pro-2-PAM), (3) at least one anticholinergic agent (e.g., atropine), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one alpha-adrenergic agonist (e.g., midodrine).

Example 867: In one embodiment, the pharmaceutical composition includes (1) pyridostigmine, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, midazolam, lorazepam), (5) at least one vasodilator (e.g., phentolamine, caffeine), (6) at least one COMT inhibitor (e.g., entacapone), and (7) at least one alpha-adrenergic agonist (e.g., midodrine).

Example 868: In one embodiment, the pharmaceutical composition includes (1) pyridostigmine, (2) at least cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, midazolam, lorazepam), (6) at least one vasodilator (e.g., phentolamine, caffeine), (7) at least one COMT inhibitor (e.g., entacapone), and (8) at least one alpha-adrenergic agonist (e.g., midodrine).

Example 869: In one embodiment, the pharmaceutical composition includes RS194B.

Example 870: In one embodiment, the pharmaceutical composition includes (1) RS194B and (2) at least one additional cholinesterase reactivator agent (e.g., 2-PAM, obidoxime, pro-2-PAM).

Example 871: In one embodiment, the pharmaceutical composition includes (1) RS194B and (2) at least one vasoactive agent (e.g., epinephrine, vasopressin, phenylephrine, or a salt thereof).

Example 872: In one embodiment, the pharmaceutical composition includes (1) RS194B and (2) at least one anticholinergic agent (e.g., atropine).

Example 873: In one embodiment, the pharmaceutical composition includes (1) RS194B and (2) at least one anticonvulsive agent (e.g., diazepam, lorazepam, midazolam).

Example 874: In one embodiment, the pharmaceutical composition includes (1) RS194B and (2) at least one vasodilator (e.g., phentolamine, caffeine).

Example 875: In one embodiment, the pharmaceutical composition includes (1) RS194B and (2) at least one COMT inhibitor (e.g., entacapone).

Example 876: In one embodiment, the pharmaceutical composition includes (1) RS194B, (2) at least one additional cholinesterase reactivator agent (e.g., 2-PAM, obidoxime, pro-2-PAM), and (3) at least one vasoactive agent (e.g., epinephrine, vasopressin, phenylephrine, or a salt thereof).

Example 877: In one embodiment, the pharmaceutical composition includes (1) RS194B, (2) at least one additional cholinesterase reactivator agent (e.g., 2-PAM, obidoxime, pro-2-PAM), and (3) at least one anticholinergic agent (e.g., atropine).

Example 878: In one embodiment, the pharmaceutical composition includes (1) RS194B, (2) at least one additional cholinesterase reactivator agent (e.g., 2-PAM, obidoxime, pro-2-PAM), and (3) at least one anticonvulsive agent (e.g., diazepam, lorazepam, midazolam).

Example 879: In one embodiment, the pharmaceutical composition includes (1) RS194B, (2) at least one additional cholinesterase reactivator agent (e.g., 2-PAM, obidoxime, pro-2-PAM), and (3) at least one vasodilator (e.g., phentolamine, caffeine).

Example 880: In one embodiment, the pharmaceutical composition includes (1) RS194B, (2) at least one additional cholinesterase reactivator agent (e.g., 2-PAM, obidoxime, pro-2-PAM), and (3) at least one COMT inhibitor (e.g., entacapone).

Example 881: In one embodiment, the pharmaceutical composition includes (1) RS194B, (2) at least one vasoactive agent (e.g., epinephrine, vasopressin, phenylephrine, or a salt thereof), and (3) at least one anticholinergic agent (e.g., atropine).

Example 882: In one embodiment, the pharmaceutical composition includes (1) RS194B, (2) at least one vasoactive agent (e.g., epinephrine, vasopressin, phenylephrine, or a salt thereof), and (3) at least one anticonvulsive agent (e.g., diazepam, lorazepam, midazolam).

Example 883: In one embodiment, the pharmaceutical composition includes (1) RS194B, (2) at least one vasoactive agent (e.g., epinephrine, vasopressin, phenylephrine, or a salt thereof), and (3) at least one vasodilator (e.g., phentolamine, caffeine).

Example 884: In one embodiment, the pharmaceutical composition includes (1) RS194B, (2) at least one vasoactive agent (e.g., epinephrine, vasopressin, phenylephrine, or a salt thereof), and (3) at least one COMT inhibitor (e.g., entacapone).

Example 885: In one embodiment, the pharmaceutical composition includes (1) RS194B, (2) at least one anticholinergic agent (e.g., atropine), and (3) at least one anticonvulsive agent (e.g., diazepam, lorazepam, midazolam).

Example 886: In one embodiment, the pharmaceutical composition includes (1) RS194B, (2) at least one anticholinergic agent (e.g., atropine), and (3) at least one vasodilator (e.g., phentolamine, caffeine).

Example 887: In one embodiment, the pharmaceutical composition includes (1) RS194B, (2) at least one anticholinergic agent (e.g., atropine), and (3) at least one COMT inhibitor (e.g., entacapone).

Example 888: In one embodiment, the pharmaceutical composition includes (1) RS194B, (2) at least one anticonvulsive agent (e.g., diazepam, lorazepam, midazolam), and (3) at least one vasodilator (e.g., phentolamine, caffeine).

Example 889: In one embodiment, the pharmaceutical composition includes (1) RS194B, (2) at least one anticonvulsive agent (e.g., diazepam, lorazepam, midazolam), and (3) at least one COMT inhibitor (e.g., entacapone).

Example 890: In one embodiment, the pharmaceutical composition includes (1) RS194B, (2) at least one vasodilator (e.g., phentolamine, caffeine), and (3) at least one COMT inhibitor (e.g., entacapone).

Example 891: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticholinergic agent (e.g., atropine).

Example 892: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticonvulsive agent (e.g., diazepam, lorazepam, midazolam).

Example 893: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one vasodilator (e.g., phentolamine, caffeine).

Example 894: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one COMT inhibitor (e.g., entacapone).

Example 895: In one embodiment, the pharmaceutical composition includes (1) RS194B, (2) at least one additional cholinesterase reactivator agent (e.g., 2-PAM, obidoxime, pro-2-PAM), (3) at least one anticholinergic agent (e.g., atropine), and (4) at least one anticonvulsive agent (e.g., diazepam, lorazepam, midazolam).

Example 896: In one embodiment, the pharmaceutical composition includes (1) RS194B, (2) at least one additional cholinesterase reactivator agent (e.g., 2-PAM, obidoxime, pro-2-PAM), (3) at least one anticholinergic agent (e.g., atropine), and (4) at least one vasodilator (e.g., phentolamine, caffeine).

Example 897: In one embodiment, the pharmaceutical composition includes (1) RS194B, (2) at least one additional cholinesterase reactivator agent (e.g., 2-PAM, obidoxime, pro-2-PAM), (3) at least one anticholinergic agent (e.g., atropine), and (4) at least one COMT inhibitor (e.g., entacapone).

Example 898: In one embodiment, the pharmaceutical composition includes (1) RS194B, (2) at least one additional cholinesterase reactivator agent (e.g., 2-PAM, obidoxime, pro-2-PAM), (3) at least one anticonvulsive agent (e.g., diazepam, lorazepam, midazolam), and (4) at least one vasodilator (e.g., phentolamine, caffeine).

Example 899: In one embodiment, the pharmaceutical composition includes (1) RS194B, (2) at least one additional cholinesterase reactivator agent (e.g., 2-PAM, obidoxime, pro-2-PAM), (3) at least one anticonvulsive agent (e.g., diazepam, lorazepam, midazolam), and (4) at least one COMT inhibitor (e.g., entacapone).

Example 900: In one embodiment, the pharmaceutical composition includes (1) RS194B, (2) at least one additional cholinesterase reactivator agent (e.g., 2-PAM, obidoxime, pro-2-PAM), (3) at least one vasodilator (e.g., phentolamine, caffeine), and (4) at least one COMT inhibitor (e.g., entacapone).

Example 901: In one embodiment, the pharmaceutical composition includes (1) RS194B, (2) at least one vasoactive agent (e.g., epinephrine, vasopressin, phenylephrine, or a salt thereof), (3) at least one anticholinergic agent (e.g., atropine), and (4) at least one anticonvulsive agent (e.g., diazepam, lorazepam, midazolam).

Example 902: In one embodiment, the pharmaceutical composition includes (1) RS194B, (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 903: In one embodiment, the pharmaceutical composition includes (1) RS194B, (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 904: In one embodiment, the pharmaceutical composition includes (1) RS194B, (2) at least one vasoactive agent (e.g., epinephrine, vasopressin, phenylephrine, or a salt thereof), (3) at least one anticonvulsive agent (e.g., diazepam, lorazepam, midazolam), and (4) at least one vasodilator (e.g., phentolamine, caffeine).

Example 905: In one embodiment, the pharmaceutical composition includes (1) RS194B, (2) at least one vasoactive agent (e.g., epinephrine, vasopressin, phenylephrine, or a salt thereof), (3) at least one anticonvulsive agent (e.g., diazepam, lorazepam, midazolam), and (4) at least one COMT inhibitor (e.g., entacapone).

Example 906: In one embodiment, the pharmaceutical composition includes (1) RS194B, (2) at least one vasoactive agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 907: In one embodiment, the pharmaceutical composition includes (1) RS194B, (2) at least one anticholinergic agent (e.g., atropine), (3) at least one anticonvulsive agent (e.g., diazepam, lorazepam, midazolam), and (4) at least one vasodilator (e.g., phentolamine, caffeine).

Example 908: In one embodiment, the pharmaceutical composition includes (1) RS194B, (2) at least one anticholinergic agent (e.g., atropine), (3) at least one anticonvulsive agent (e.g., diazepam, lorazepam, midazolam), and (4) at least one COMT inhibitor (e.g., entacapone).

Example 909: In one embodiment, the pharmaceutical composition includes (1) RS194B, (2) at least one anticholinergic agent (e.g., atropine), (3) at least one vasodilator (e.g., phentolamine, caffeine), and (4) at least one COMT inhibitor (e.g., entacapone).

Example 910: In one embodiment, the pharmaceutical composition includes (1) RS194B, (2) at least one anticonvulsive agent (e.g., diazepam, lorazepam, midazolam), (3) at least one vasodilator (e.g., phentolamine, caffeine), and (4) at least one COMT inhibitor (e.g., entacapone).

Example 911: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one anticonvulsive agent (e.g., diazepam, lorazepam, midazolam).

Example 912: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 913: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 914: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), and (5) at least one vasodilator (e.g., phentolamine, caffeine).

Example 915: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), and (5) at least one COMT inhibitor (e.g., entacapone).

Example 916: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 917: In one embodiment, the pharmaceutical composition includes (1) RS194B, (2) at least one additional cholinesterase reactivator agent (e.g., 2-PAM, obidoxime, pro-2-PAM), (3) at least one anticholinergic agent (e.g., atropine), (4) at least one anticonvulsive agent (e.g., diazepam, lorazepam, midazolam), and (5) at least one vasodilator (e.g., phentolamine, caffeine).

Example 918: In one embodiment, the pharmaceutical composition includes (1) RS194B, (2) at least one additional cholinesterase reactivator agent (e.g., 2-PAM, obidoxime, pro-2-PAM), (3) at least one anticholinergic agent (e.g., atropine), (4) at least one anticonvulsive agent (e.g., diazepam, lorazepam, midazolam), and (5) at least one COMT inhibitor (e.g., entacapone).

Example 919: In one embodiment, the pharmaceutical composition includes (1) RS194B, (2) at least one additional cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one COMT inhibitor (e.g., entacapone).

Example 920: In one embodiment, the pharmaceutical composition includes (1) RS194B, (2) at least one additional cholinesterase reactivator agent (e.g., 2-PAM, obidoxime, pro-2-PAM), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 921: In one embodiment, the pharmaceutical composition includes (1) RS194B, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), and (5) at least one vasodilator (e.g., phentolamine, caffeine).

Example 922: In one embodiment, the pharmaceutical composition includes (1) RS194B, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), and (5) at least one COMT inhibitor (e.g., entacapone).

Example 923: In one embodiment, the pharmaceutical composition includes (1) RS194B, (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 924: In one embodiment, the pharmaceutical composition includes (1) RS194B, (2) at least one vasoactive agent (e.g., epinephrine, vasopressin, phenylephrine, or a salt thereof), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 925: In one embodiment, the pharmaceutical composition includes (1) RS194B, (2) at least one anticholinergic agent (e.g., atropine), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 926: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), and (6) at least one vasodilator (e.g., phentolamine, caffeine).

Example 927: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), and (6) at least one COMT inhibitor (e.g., entacapone).

Example 928: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 929: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 930: In one embodiment, the pharmaceutical composition includes (1) RS194B, (2) at least one additional cholinesterase reactivator agent (e.g., 2-PAM, obidoxime, pro-2-PAM), (3) at least one anticholinergic agent (e.g., atropine), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 931: In one embodiment, the pharmaceutical composition includes (1) RS194B, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 932: In one embodiment, the pharmaceutical composition includes (1) RS194B, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), (6) at least one vasodilator (e.g., phentolamine, caffeine), and (7) at least one COMT inhibitor (e.g., entacapone).

Example 933: In one embodiment, the pharmaceutical composition includes huperizine A.

Example 934: In one embodiment, the pharmaceutical composition includes (1) huperizine A and (2) at least one additional cholinesterase reactivator agent (e.g., 2-PAM, obidoxime, pro-2-PAM).

Example 935: In one embodiment, the pharmaceutical composition includes (1) huperizine A and (2) at least one vasoactive agent (e.g., epinephrine, vasopressin, phenylephrine, or a salt thereof).

Example 936: In one embodiment, the pharmaceutical composition includes (1) huperizine A and (2) at least one anticholinergic agent (e.g., atropine).

Example 937: In one embodiment, the pharmaceutical composition includes (1) huperizine A and (2) at least one anticonvulsive agent (e.g., diazepam, lorazepam, midazolam).

Example 938: In one embodiment, the pharmaceutical composition includes (1) huperizine A and (2) at least one vasodilator (e.g., phentolamine, caffeine).

Example 939: In one embodiment, the pharmaceutical composition includes (1) huperizine A and (2) at least one COMT inhibitor (e.g., entacapone).

Example 940: In one embodiment, the pharmaceutical composition includes (1) huperizine A, (2) at least one additional cholinesterase reactivator agent (e.g., 2-PAM, obidoxime, pro-2-PAM), and (3) at least one vasoactive agent (e.g., epinephrine, vasopressin, phenylephrine, or a salt thereof).

Example 941: In one embodiment, the pharmaceutical composition includes (1) huperizine A, (2) at least one additional cholinesterase reactivator agent (e.g., 2-PAM, obidoxime, pro-2-PAM), and (3) at least one anticholinergic agent (e.g., atropine).

Example 942: In one embodiment, the pharmaceutical composition includes (1) huperizine A, (2) at least one additional cholinesterase reactivator agent (e.g., 2-PAM, obidoxime, pro-2-PAM), and (3) at least one anticonvulsive agent (e.g., diazepam, lorazepam, midazolam).

Example 943: In one embodiment, the pharmaceutical composition includes (1) huperizine A, (2) at least one additional cholinesterase reactivator agent (e.g., 2-PAM, obidoxime, pro-2-PAM), and (3) at least one vasodilator (e.g., phentolamine, caffeine).

Example 944: In one embodiment, the pharmaceutical composition includes (1) huperizine A, (2) at least one additional cholinesterase reactivator agent (e.g., 2-PAM, obidoxime, pro-2-PAM), and (3) at least one COMT inhibitor (e.g., entacapone).

Example 945: In one embodiment, the pharmaceutical composition includes (1) huperizine A, (2) at least one vasoactive agent (e.g., epinephrine, vasopressin, phenylephrine, or a salt thereof), and (3) at least one anticholinergic agent (e.g., atropine).

Example 946: In one embodiment, the pharmaceutical composition includes (1) huperizine A, (2) at least one vasoactive agent (e.g., epinephrine, vasopressin, phenylephrine, or a salt thereof), and (3) at least one anticonvulsive agent (e.g., diazepam, lorazepam, midazolam).

Example 947: In one embodiment, the pharmaceutical composition includes (1) huperizine A, (2) at least one vasoactive agent (e.g., epinephrine, vasopressin, phenylephrine, or a salt thereof), and (3) at least one vasodilator (e.g., phentolamine, caffeine).

Example 948: In one embodiment, the pharmaceutical composition includes (1) huperizine A, (2) at least one vasoactive agent (e.g., epinephrine, vasopressin, phenylephrine, or a salt thereof), and (3) at least one COMT inhibitor (e.g., entacapone).

Example 949: In one embodiment, the pharmaceutical composition includes (1) huperizine A, (2) at least one anticholinergic agent (e.g., atropine), and (3) at least one anticonvulsive agent (e.g., diazepam, lorazepam, midazolam).

Example 950: In one embodiment, the pharmaceutical composition includes (1) huperizine A, (2) at least one anticholinergic agent (e.g., atropine), and (3) at least one vasodilator (e.g., phentolamine, caffeine).

Example 951: In one embodiment, the pharmaceutical composition includes (1) huperizine A, (2) at least one anticholinergic agent (e.g., atropine), and (3) at least one COMT inhibitor (e.g., entacapone).

Example 952: In one embodiment, the pharmaceutical composition includes (1) huperizine A, (2) at least one anticonvulsive agent (e.g., diazepam, lorazepam, midazolam), and (3) at least one vasodilator (e.g., phentolamine, caffeine).

Example 953: In one embodiment, the pharmaceutical composition includes (1) huperizine A, (2) at least one anticonvulsive agent (e.g., diazepam, lorazepam, midazolam), and (3) at least one COMT inhibitor (e.g., entacapone).

Example 954: In one embodiment, the pharmaceutical composition includes (1) huperizine A, (2) at least one vasodilator (e.g., phentolamine, caffeine), and (3) at least one COMT inhibitor (e.g., entacapone).

Example 955: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticholinergic agent (e.g., atropine).

Example 956: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one anticonvulsive agent (e.g., diazepam, lorazepam, midazolam). Example 957: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one vasodilator (e.g., phentolamine, caffeine).

Example 958: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), and (4) at least one COMT inhibitor (e.g., entacapone).

Example 959: In one embodiment, the pharmaceutical composition includes (1) huperizine A, (2) at least one additional cholinesterase reactivator agent (e.g., 2-PAM, obidoxime, pro-2-PAM), (3) at least one anticholinergic agent (e.g., atropine), and (4) at least one anticonvulsive agent (e.g., diazepam, lorazepam, midazolam).

Example 960: In one embodiment, the pharmaceutical composition includes (1) huperizine A, (2) at least one additional cholinesterase reactivator agent (e.g., 2-PAM, obidoxime, pro-2-PAM), (3) at least one anticholinergic agent (e.g., atropine), and (4) at least one vasodilator (e.g., phentolamine, caffeine).

Example 961: In one embodiment, the pharmaceutical composition includes (1) huperizine A, (2) at least one additional cholinesterase reactivator agent (e.g., 2-PAM, obidoxime, pro-2-PAM), (3) at least one anticholinergic agent (e.g., atropine), and (4) at least one COMT inhibitor (e.g., entacapone).

Example 962: In one embodiment, the pharmaceutical composition includes (1) huperizine A, (2) at least one additional cholinesterase reactivator agent (e.g., 2-PAM, obidoxime, pro-2-PAM), (3) at least one anticonvulsive agent (e.g., diazepam, lorazepam, midazolam), and (4) at least one vasodilator (e.g., phentolamine, caffeine).

Example 963: In one embodiment, the pharmaceutical composition includes (1) huperizine A, (2) at least one additional cholinesterase reactivator agent (e.g., 2-PAM, obidoxime, pro-2-PAM), (3) at least one anticonvulsive agent (e.g., diazepam, lorazepam, midazolam), and (4) at least one COMT inhibitor (e.g., entacapone).

Example 964: In one embodiment, the pharmaceutical composition includes (1) huperizine A, (2) at least one additional cholinesterase reactivator agent (e.g., 2-PAM, obidoxime, pro-2-PAM), (3) at least one vasodilator (e.g., phentolamine, caffeine), and (4) at least one COMT inhibitor (e.g., entacapone).

Example 965: In one embodiment, the pharmaceutical composition includes (1) huperizine A, (2) at least one vasoactive agent (e.g., epinephrine, vasopressin, phenylephrine, or a salt thereof), (3) at least one anticholinergic agent (e.g., atropine), and (4) at least one anticonvulsive agent (e.g., diazepam, lorazepam, midazolam).

Example 966: In one embodiment, the pharmaceutical composition includes (1) huperizine A, (2) at least one vasoactive agent (e.g., epinephrine, vasopressin, phenylephrine, or a salt thereof), (3) at least one anticholinergic agent (e.g., atropine), and (4) at least one vasodilator (e.g., phentolamine, caffeine).

Example 967: In one embodiment, the pharmaceutical composition includes (1) huperizine A, (2) at least one vasoactive agent (e.g., epinephrine, vasopressin, phenylephrine, or a salt thereof), (3) at least one anticholinergic agent (e.g., atropine), and (4) at least one COMT inhibitor (e.g., entacapone).

Example 968: In one embodiment, the pharmaceutical composition includes (1) huperizine A, (2) at least one vasoactive agent (e.g., epinephrine, vasopressin, phenylephrine, or a salt thereof), (3) at least one anticonvulsive agent (e.g., diazepam, lorazepam, midazolam), and (4) at least one vasodilator (e.g., phentolamine, caffeine).

Example 969: In one embodiment, the pharmaceutical composition includes (1) huperizine A, (2) at least one vasoactive agent (e.g., epinephrine, vasopressin, phenylephrine, or a salt thereof), (3) at least one anticonvulsive agent (e.g., diazepam, lorazepam, midazolam), and (4) at least one COMT inhibitor (e.g., entacapone).

Example 970: In one embodiment, the pharmaceutical composition includes (1) huperizine A, (2) at least one vasoactive agent (e.g., epinephrine, vasopressin, phenylephrine, or a salt thereof), (3) at least one vasodilator (e.g., phentolamine, caffeine), and (4) at least one COMT inhibitor (e.g., entacapone).

Example 971: In one embodiment, the pharmaceutical composition includes (1) huperizine A, (2) at least one anticholinergic agent (e.g., atropine), (3) at least one anticonvulsive agent (e.g., diazepam, lorazepam, midazolam), and (4) at least one vasodilator (e.g., phentolamine, caffeine).

Example 972: In one embodiment, the pharmaceutical composition includes (1) huperizine A, (2) at least one anticholinergic agent (e.g., atropine), (3) at least one anticonvulsive agent (e.g., diazepam, lorazepam, midazolam), and (4) at least one COMT inhibitor (e.g., entacapone).

Example 973: In one embodiment, the pharmaceutical composition includes (1) huperizine A, (2) at least one anticholinergic agent (e.g., atropine), (3) at least one vasodilator (e.g., phentolamine, caffeine), and (4) at least one COMT inhibitor (e.g., entacapone).

Example 974: In one embodiment, the pharmaceutical composition includes (1) huperizine A, (2) at least one anticonvulsive agent (e.g., diazepam, lorazepam, midazolam), (3) at least one vasodilator (e.g., phentolamine, caffeine), and (4) at least one COMT inhibitor (e.g., entacapone).

Example 975: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one anticonvulsive agent (e.g., diazepam, lorazepam, midazolam).

Example 976: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one vasodilator (e.g., phentolamine, caffeine).

Example 977: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), and (5) at least one COMT inhibitor (e.g., entacapone).

Example 978: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), and (5) at least one vasodilator (e.g., phentolamine, caffeine).

Example 979: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), and (5) at least one COMT inhibitor (e.g., entacapone).

Example 980: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one vasodilator (e.g., phentolamine, caffeine), and (5) at least one COMT inhibitor (e.g., entacapone).

Example 981: In one embodiment, the pharmaceutical composition includes (1) huperizine A, (2) at least one additional cholinesterase reactivator agent (e.g., 2-PAM, obidoxime, pro-2-PAM), (3) at least one anticholinergic agent (e.g., atropine), (4) at least one anticonvulsive agent (e.g., diazepam, lorazepam, midazolam), and (5) at least one vasodilator (e.g., phentolamine, caffeine).

Example 982: In one embodiment, the pharmaceutical composition includes (1) huperizine A, (2) at least one additional cholinesterase reactivator agent (e.g., 2-PAM, obidoxime, pro-2-PAM), (3) at least one anticholinergic agent (e.g., atropine), (4) at least one anticonvulsive agent (e.g., diazepam, lorazepam, midazolam), and (5) at least one COMT inhibitor (e.g., entacapone).

Example 983: In one embodiment, the pharmaceutical composition includes (1) huperizine A, (2) at least one additional cholinesterase reactivator agent (e.g., 2-PAM, obidoxime, pro-2-PAM), (3) at least one anticholinergic agent (e.g., atropine), (4) at least one vasodilator (e.g., phentolamine, caffeine), and (5) at least one COMT inhibitor (e.g., entacapone).

Example 984: In one embodiment, the pharmaceutical composition includes (1) huperizine A, (2) at least one additional cholinesterase reactivator agent (e.g., 2-PAM, obidoxime, pro-2-PAM), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 985: In one embodiment, the pharmaceutical composition includes (1) huperizine A, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), and (5) at least one vasodilator (e.g., phentolamine, caffeine).

Example 986: In one embodiment, the pharmaceutical composition includes (1) huperizine A, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), and (5) at least one COMT inhibitor (e.g., entacapone).

Example 987: In one embodiment, the pharmaceutical composition includes (1) huperizine A, (2) at least one vasoactive agent (e.g., epinephrine, vasopressin, phenylephrine, or a salt thereof), (3) at least one anticholinergic agent (e.g., atropine), (4) at least one vasodilator (e.g., phentolamine, caffeine), and (5) at least one COMT inhibitor (e.g., entacapone).

Example 988: In one embodiment, the pharmaceutical composition includes (1) huperizine A, (2) at least one vasoactive agent (e.g., epinephrine, vasopressin, phenylephrine, or a salt thereof), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 989: In one embodiment, the pharmaceutical composition includes (1) huperizine A, (2) at least one anticholinergic agent (e.g., atropine), (3) at least one anticonvulsive agent (e.g., diazepam, lorazepam, midazolam), (4) at least one vasodilator (e.g., phentolamine, caffeine), and (5) at least one COMT inhibitor (e.g., entacapone).

Example 990: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), and (6) at least one vasodilator (e.g., phentolamine, caffeine).

Example 991: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), and (6) at least one COMT inhibitor (e.g., entacapone).

Example 992: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one vasodilator (e.g., phentolamine, caffeine), and (6) at least one COMT inhibitor (e.g., entacapone).

Example 993: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 994: In one embodiment, the pharmaceutical composition includes (1) huperizine A, (2) at least one additional cholinesterase reactivator agent (e.g., 2-PAM, obidoxime, pro-2-PAM), (3) at least one anticholinergic agent (e.g., atropine), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 995: In one embodiment, the pharmaceutical composition includes (1) huperizine A, (2) at least one vasoactive agent (e.g., epinephrine, vasopressin, phenylephrine, or a salt thereof), (3) at least one anticholinergic agent (e.g., atropine), (4) at least one anticonvulsive agent (e.g., diazepam, lorazepam, midazolam), (5) at least one vasodilator (e.g., phentolamine, caffeine), and (6) at least one COMT inhibitor (e.g., entacapone).

Example 996: In one embodiment, the pharmaceutical composition includes (1) huperizine A, (2) at least one additional cholinesterase reactivator agent (e.g., 2-PAM, obidoxime, pro-2-PAM), (3) at least one vasoactive agent (e.g., epinephrine, vasopressin, phenylephrine, or a salt thereof), (4) at least one anticholinergic agent (e.g., atropine), (5) at least one anticonvulsive agent (e.g., diazepam, lorazepam, midazolam), (6) at least one vasodilator (e.g., phentolamine, caffeine), and (7) at least one COMT inhibitor (e.g., entacapone).

Example 997: In one embodiment, the pharmaceutical composition includes at least one triptan (e.g., sumatriptan, rizatriptan, naratriptan, eletriptan, donitriptan, almotriptan, frovatriptan, avitriptan, zolmitriptan).

Example 998: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan) and (2) at least one vasodilator (e.g., phentolamine, caffeine).

Example 999: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan) and (2) acetylsalicylic acid and/or acetaminophen.

Example 1000: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan) and (2) ibuprofen.

Example 1001: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan) and (2) lidocaine.

Example 1002: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan), (2) at least one vasodilator (e.g., phentolamine, caffeine), and (3) acetylsalicylic acid and/or acetaminophen.

Example 1003: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan), (2) at least one vasodilator (e.g., phentolamine, caffeine), and (3) ibuprofen.

Example 1004: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan), (2) at least one vasodilator (e.g., phentolamine, caffeine), and (3) lidocaine.

Example 1005: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan), (2) acetaminophen, and (3) ibuprofen.

Example 1006: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan), (2) acetylsalicylic acid and/or acetaminophen, and (3) lidocaine.

Example 1007: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan), (2) ibuprofen, and (3) lidocaine.

Example 1008: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan), (2) at least one vasodilator (e.g., phentolamine, caffeine), (3) acetaminophen, and (4) ibuprofen.

Example 1009: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan), (2) at least one vasodilator (e.g., phentolamine, caffeine), (3) acetylsalicylic acid and/or acetaminophen, and (4) lidocaine.

Example 1010: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan), (2) at least one vasodilator (e.g., phentolamine, caffeine), (3) ibuprofen, and (4) lidocaine.

Example 1011: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan), (2) acetaminophen, (3) ibuprofen, and (4) lidocaine.

Example 1012: In one embodiment, the pharmaceutical composition includes (1) at least one triptan (e.g., sumatriptan, rizatriptan, naratriptan, eletriptan, donitriptan, almotriptan, frovatriptan, avitriptan, zolmitriptan), (2) at least one vasodilator (e.g., phentolamine, caffeine), (3) acetaminophen, (4) ibuprofen, and (5) lidocaine.

Example 1013: In one embodiment, the pharmaceutical composition includes lidocaine.

Example 1014: In one embodiment, the pharmaceutical composition includes (1) lidocaine and (2) at least one vasodilator (e.g., phentolamine, caffeine).

Example 1015: In one embodiment, the pharmaceutical composition includes (1) lidocaine and (2) acetylsalicylic acid and/or acetaminophen.

Example 1016: In one embodiment, the pharmaceutical composition includes (1) lidocaine and (2) ibuprofen.

Example 1017: In one embodiment, the pharmaceutical composition includes (1) lidocaine, (2) at least one vasodilator (e.g., phentolamine, caffeine), and (3) acetylsalicylic acid and/or acetaminophen.

Example 1018: In one embodiment, the pharmaceutical composition includes (1) lidocaine, (2) at least one vasodilator (e.g., phentolamine, caffeine), and (3) ibuprofen.

Example 1019: In one embodiment, the pharmaceutical composition includes (1) lidocaine, (2) acetaminophen, and (3) ibuprofen.

Example 1020: In one embodiment, the pharmaceutical composition includes (1) lidocaine, (2) at least one vasodilator (e.g., phentolamine, caffeine), (3) acetaminophen, and (4) ibuprofen.

Example 1021: In one embodiment, the pharmaceutical composition includes acetylsalicylic acid.

Example 1022: In one embodiment, the pharmaceutical composition includes (1) acetylsalicylic acid and (2) at least one vasodilator (e.g., phentolamine, caffeine).

Example 1023: In one embodiment, the pharmaceutical composition includes (1) acetylsalicylic acid and (2) acetaminophen.

Example 1024: In one embodiment, the pharmaceutical composition includes (1) acetylsalicylic acid, (2) at least one vasodilator (e.g., phentolamine, caffeine), and (3) acetaminophen.

Example 1025: In one embodiment, the pharmaceutical composition includes acetaminophen.

Example 1026: In one embodiment, the pharmaceutical composition includes (1) acetaminophen and (2) at least one vasodilator (e.g., phentolamine, caffeine).

In one embodiment, the intranasal dry powder compositions and/or unit doses of Examples 1-1026 further include at least one enabling agent and/or at least one carrier and/or excipient.

The at least one enabling agent in Examples 1-1026 includes, but is not limited to, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent in Examples 1-1026 includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient in Examples 1-1026 includes at least one cellulose derivative and/or starch. In one embodiment, the at least one carrier and/or excipient includes lactose and/or sodium carboxymethylcellulose. In one embodiment, the at least one carrier and/or excipient includes sodium chloride and/or a polysorbate (e.g., polysorbate 80). In one embodiment, the at least one carrier and/or excipient includes sodium chloride, a polysorbate (e.g., polysorbate 80), lactose, and/or sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Location data is created in the present invention using one or more hardware and/or software components. By way of example and not limitation, location data is created using the Global Positioning System (GPS), low energy BLUETOOTH based systems such as beacons, wireless networks such as WIFI, Radio Frequency (RF) including RF Identification (RFID), Near Field Communication (NFC), magnetic positioning, and/or cellular triangulation. By way of example, location data is determined via an Internet Protocol (IP) address of a device connected to a wireless network. A wireless router is also operable to determine identities of devices connected to the wireless network through the router, and thus is operable to determine the locations of these devices through their presence in the connection range of the wireless router.

Figure 6:
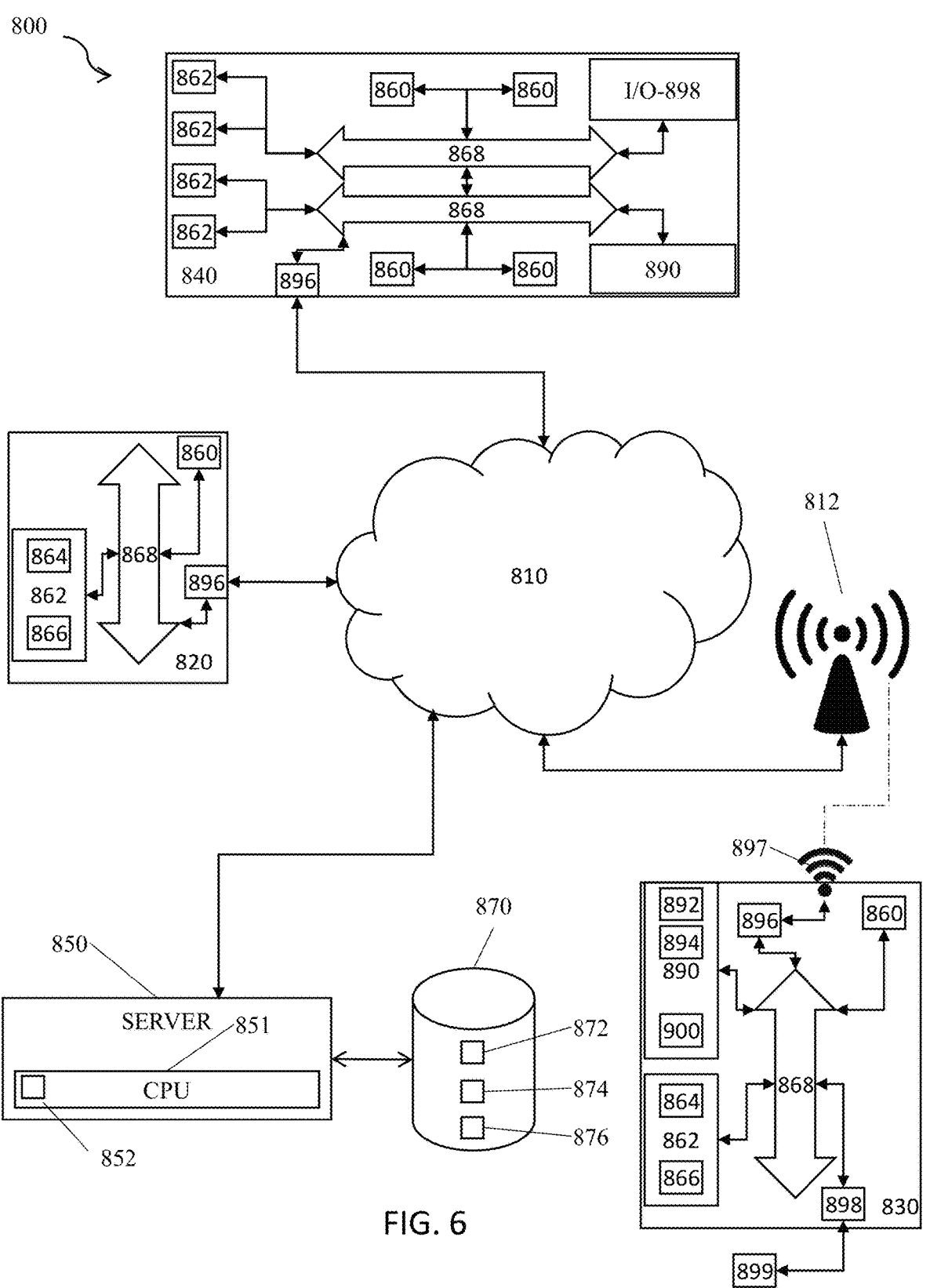
FIG. 6 is a schematic diagram of a system of the present invention.

FIG. 6 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 6, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 6, is operable to include other components that are not explicitly shown in FIG. 6, or is operable to utilize an architecture completely different than that shown in FIG. 6. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

The invention claimed is:

1. A device for intranasal administration of a pharmaceutical composition comprising:

a reservoir and a means for discharging one or more doses of the pharmaceutical composition, wherein the reservoir contains a quantity of the pharmaceutical composition;

wherein the pharmaceutical composition is a dry powder comprising:

galantamine or a pharmaceutical salt thereof, wherein the pharmaceutical composition provides a dose of about 5 mg to about 75 mg of the galantamine or the pharmaceutical salt thereof;

sodium chloride, wherein the pharmaceutical composition comprises about 0.01 mg to about 5 mg of the sodium chloride; and a carrier;

wherein the pharmaceutical composition does not include chitosan.

2. The device of claim 1, wherein the device includes a nasal probe, and wherein the nasal probe is constructed and configured to be replaced between discharges.

3. The device of claim 1, wherein the pharmaceutical composition further comprises a vasoactive agent, wherein the vasoactive agent is epinephrine or a pharmaceutically acceptable salt thereof, wherein the pharmaceutical composition provides a dose of about 0.01 mg to about 10 mg of the epinephrine or the pharmaceutically acceptable salt thereof.

4. The device of claim 1, wherein the pharmaceutical composition further comprises an anti-convulsant agent, wherein the anti-convulsant agent is diazepam or a pharmaceutically acceptable salt thereof, wherein the pharmaceutical composition provides a dose of about 0.1 mg to about 20 mg of the diazepam or the pharmaceutically acceptable salt thereof.

5. The device of claim 1, wherein the pharmaceutical composition further comprises at least one anticholinergic agent, wherein the at least one anticholinergic agent is atropine or a pharmaceutically acceptable salt thereof, wherein the pharmaceutical composition provides a dose of about 0.1 mg to about 10 mg of the atropine or the pharmaceutically acceptable salt thereof.

6. The device of claim 1, wherein the pharmaceutical composition further comprises a cholinesterase reactivator, wherein the cholinesterase reactivator is 2-pyridine aldoxime methyl chloride or a pharmaceutically acceptable salt thereof, wherein the pharmaceutical composition provides a dose of about 1 mg to about 1000 mg of the pyridine aldoxime methyl chloride or the pharmaceutically acceptable salt thereof.

7. The device of claim 1, wherein the pharmaceutical composition further comprises a vasodilator, wherein the vasodilator is phentolamine or a pharmaceutically acceptable salt thereof, wherein the pharmaceutical composition provides a dose of about 0.01 mg to about 10 mg of the phentolamine or the pharmaceutically acceptable salt thereof.

8. The device of claim 1, wherein the pharmaceutical composition further comprises a catechol-o-methyl transferase (COMT) inhibitor, wherein the COMT inhibitor is entacapone or a pharmaceutically acceptable salt thereof, wherein the pharmaceutical composition provides a dose of about 5 mg to about 20 mg of the entacapone or the pharmaceutically acceptable salt thereof.

9. The device of claim 1, wherein the pharmaceutical composition further comprises an N-Methyl-D-aspartate (NMDA) receptor antagonist, wherein the NMDA receptor antagonist is memantine, wherein the pharmaceutical composition provides a dose of about 1 mg to about 40 mg of the memantine.

10. The device of claim 1, wherein the pharmaceutical composition further comprises a chelator.

11. The device of claim 1, wherein the pharmaceutical composition further comprises one or more agents selected from a group consisting of a mucosal permeation or penetration enhancer, a mucoadhesive, a mucosal transit slowing agent, a mucosal transport enhancer, or any combination thereof.

12. The device of claim 1, wherein the device has 360° functionality and is constructed and configured to dispense a dose from any position.

13. The device of claim 1, wherein the pharmaceutical composition is a spray-dried powder.

14. The device of claim 1, wherein the device further includes a sensor that is adapted to detect a displacement or a deformation of a portion of the delivery device when the dose is dispensed.

15. The device of claim 1, wherein the device further includes a display, a power supply, a timer, a clock, and/or a printed circuit board, wherein the display is constructed and configured to display a time of dose dispensation.

16. The device of claim 1, wherein the device further includes a communications interface, wherein the communications interface is constructed and configured to transmit data wirelessly to at least one remote device.

17. A kit for intranasal administration of a pharmaceutical composition comprising:
   at least one device, wherein each of the at least one device includes a reservoir and a means for discharging one or more doses of the pharmaceutical composition, wherein the reservoir contains a quantity of the pharmaceutical composition; and
   a pouch and/or a hard case;
   wherein the pharmaceutical composition is a dry powder comprising:
      galantamine or a pharmaceutical salt thereof, wherein the pharmaceutical composition provides a dose of about 5 mg to about 75 mg of the galantamine or the pharmaceutical salt thereof;
      sodium chloride, wherein the pharmaceutical composition comprises about 0.01 mg to about 5 mg of the sodium chloride; and
      a carrier;
      wherein the pharmaceutical composition does not include chitosan.

18. The kit of claim 17, wherein the hard case includes a desiccant plastic, wherein the desiccant plastic includes a base polymer, a channeling agent, and a desiccant.

19. The kit of claim 17, wherein the pouch and/or the hard case incorporates a pouch attachment ladder system (PALS).

20. A device for intranasal administration of a pharmaceutical composition comprising:
   a reservoir and a means for discharging one or more doses of the pharmaceutical composition, wherein the reservoir contains a quantity of the pharmaceutical composition;
   wherein the pharmaceutical composition is a dry powder comprising:
      galantamine or a pharmaceutical salt thereof, wherein the pharmaceutical composition provides a dose of the galantamine or the pharmaceutical salt thereof;
      memantine, wherein the pharmaceutical composition provides a dose of about 1 mg to about 30 mg of the memantine;
      sodium chloride, wherein the pharmaceutical composition comprises about 0.01 mg to about 5 mg of the sodium chloride; and
      a carrier;
      wherein the pharmaceutical composition does not include chitosan.

* * * * *